(12) United States Patent
Piepenburg et al.

(10) Patent No.: US 10,329,603 B2
(45) Date of Patent: *Jun. 25, 2019

(54) RECOMBINASE POLYMERASE AMPLIFICATION

(71) Applicant: Alere San Diego Inc., San Diego, CA (US)

(72) Inventors: Olaf Piepenburg, Suffron Walden (GB); Colin H. Williams, Chiswick (GB); Niall A. Armes, Helions Bumpstead (GB); Derek L. Stemple, St. Albans (GB)

(73) Assignee: ALERE SAN DIEGO INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/496,756

(22) Filed: Apr. 25, 2017

(65) Prior Publication Data

US 2017/0321262 A1 Nov. 9, 2017

Related U.S. Application Data

(60) Continuation of application No. 14/989,499, filed on Jan. 6, 2016, now Pat. No. 9,663,820, which is a continuation of application No. 14/610,915, filed on Jan. 30, 2015, now Pat. No. 9,309,502, which is a continuation of application No. 13/851,711, filed on Mar. 27, 2013, now Pat. No. 8,945,845, which is a continuation of application No. 13/212,361, filed on Aug. 18, 2011, now Pat. No. 8,426,134, which is a continuation of application No. 12/660,117, filed on Feb. 19, 2010, now Pat. No. 8,030,000, which is a division of application No. 11/628,179, filed as application No. PCT/IB2005/001560 on Apr. 11, 2005, now Pat. No. 7,666,598, and a continuation-in-part of application No. 10/931,916, filed on Sep. 1, 2004, now Pat. No. 7,399,590, and a continuation-in-part of application No. 10/371,641, filed on Feb. 21, 2003, now Pat. No. 7,270,981.

(60) Provisional application No. 60/576,148, filed on Jun. 1, 2004, provisional application No. 60/576,162, filed on Jun. 1, 2004, provisional application No. 60/622,291, filed on Oct. 26, 2004, provisional application No. 60/632,746, filed on Dec. 2, 2004,
(Continued)

(51) Int. Cl.
| | |
|---|---|
| *C12P 19/34* | (2006.01) |
| *C12Q 1/6844* | (2018.01) |
| *C12Q 1/6806* | (2018.01) |
| *C12N 9/12* | (2006.01) |
| *B01L 7/00* | (2006.01) |
| *C12Q 1/6818* | (2018.01) |
| *G01N 33/53* | (2006.01) |

(52) U.S. Cl.
CPC .............. *C12Q 1/6844* (2013.01); *B01L 7/52* (2013.01); *C12N 9/1252* (2013.01); *C12Q 1/6806* (2013.01); *C12Q 1/6818* (2013.01); *C12Y 207/07007* (2013.01); *G01N 33/5308* (2013.01); *B01L 2200/10* (2013.01); *B01L 2300/0627* (2013.01); *B01L 2300/18* (2013.01)

(58) Field of Classification Search
USPC ................................................ 435/6.12, 91.2
See application file for complete search history.

(56) References Cited

U.S. PATENT DOCUMENTS

| 4,683,195 A | 7/1987 | Mullis et al. |
| 4,965,188 A | 10/1990 | Mullis et al. |

(Continued)

FOREIGN PATENT DOCUMENTS

| CA | 2444649 | 10/2002 |
| CA | 2476481 | 9/2003 |

(Continued)

OTHER PUBLICATIONS

Efim I. Golub et al., "Joints formed by RecA protein from oligonucleotides and duplex DNA block initiation and elongation of transcription," Nucleic Acids Research, 20(12):3121-3125 (1992).

(Continued)

*Primary Examiner* — Kenneth R Horlick
(74) *Attorney, Agent, or Firm* — Casimir Jones S.C.; Thomas Isenbarger

(57) ABSTRACT

This disclosure describes related novel methods for Recombinase-Polymerase Amplification (RPA) of a target DNA that exploit the properties of recombinase and related proteins, to invade double-stranded DNA with single stranded homologous DNA permitting sequence specific priming of DNA polymerase reactions. The disclosed methods have the advantage of not requiring thermocycling or thermophilic enzymes, thus offering easy and affordable implementation and portability relative to other amplification methods. Further disclosed are conditions to enable real-time monitoring of RPA reactions, methods to regulate RPA reactions using light and otherwise, methods to determine the nature of amplified species without a need for gel electrophoresis, methods to improve and optimize signal to noise ratios in RPA reactions, methods to optimize oligonucleotide primer function, methods to control carry-over contamination, and methods to employ sequence-specific third 'specificity' probes. Further described are novel properties and approaches for use of probes monitored by light in dynamic recombination environments.

19 Claims, 80 Drawing Sheets

Specification includes a Sequence Listing.

Related U.S. Application Data provisional application No. 60/553,999, filed on Mar. 16, 2004, provisional application No. 60/358,563, filed on Feb. 21, 2002.

(56) References Cited

U.S. PATENT DOCUMENTS

| | | | |
|---|---|---|---|
| 5,223,414 | A | 6/1993 | Zarling et al. |
| 5,273,881 | A | 12/1993 | Sena et al. |
| 5,326,692 | A | 7/1994 | Brinkley et al. |
| 5,326,962 | A | 7/1994 | Brinkley et al. |
| 5,354,668 | A | 10/1994 | Auerbach |
| 5,418,149 | A | 5/1995 | Gelfand et al. |
| 5,430,136 | A | 7/1995 | Urdea et al. |
| 5,455,166 | A | 10/1995 | Walker |
| 5,536,649 | A | 7/1996 | Fraiser et al. |
| 5,556,751 | A | 9/1996 | Stefano |
| 5,591,609 | A | 1/1997 | Auerbach |
| 5,614,389 | A | 3/1997 | Auerbach |
| 5,635,347 | A | 6/1997 | Link et al. |
| 5,639,599 | A * | 6/1997 | Ryder .......... C12Q 1/6806 435/5 |
| 5,656,430 | A | 8/1997 | Chirikjian |
| 5,665,572 | A | 9/1997 | Ikeda et al. |
| 5,670,316 | A | 9/1997 | Sena et al. |
| 5,705,366 | A | 1/1998 | Backus |
| 5,712,124 | A | 1/1998 | Walker |
| 5,731,150 | A | 3/1998 | Sandhu et al. |
| 5,733,733 | A | 3/1998 | Auerbach |
| 5,744,311 | A | 4/1998 | Fraiser et al. |
| 5,792,607 | A | 8/1998 | Backman et al. |
| 5,834,202 | A | 11/1998 | Auerbach |
| 5,849,547 | A | 12/1998 | Cleuziat |
| 5,858,652 | A | 1/1999 | Laffler et al. |
| 5,916,779 | A | 6/1999 | Pearson et al. |
| 5,942,391 | A | 8/1999 | Zhang et al. |
| 5,985,561 | A | 11/1999 | Kimberly et al. |
| 6,087,112 | A | 7/2000 | Dale |
| 6,140,054 | A | 10/2000 | Wittwer et al. |
| 6,153,412 | A | 11/2000 | Park |
| 6,165,793 | A | 12/2000 | Stemmer |
| 6,251,600 | B1 | 6/2001 | Winger et al. |
| 6,379,899 | B1 | 4/2002 | Ullman |
| 6,387,621 | B1 | 5/2002 | Wittwer |
| 6,448,065 | B2 | 9/2002 | Laugharn, Jr. et al. |
| 6,509,157 | B1 | 1/2003 | Martinez |
| 6,566,103 | B2 | 5/2003 | Wijnhoven et al. |
| 6,699,693 | B1 | 3/2004 | Marians et al. |
| 6,929,915 | B2 | 8/2005 | Benkovic et al. |
| 7,112,423 | B2 | 9/2006 | Van Ness et al. |
| 7,252,940 | B2 | 8/2007 | Kutyavin et al. |
| 7,270,981 | B2 | 9/2007 | Armes et al. |
| 7,282,328 | B2 | 10/2007 | Kong |
| 7,399,590 | B2 | 7/2008 | Piepenburg et al. |
| 7,435,561 | B2 | 10/2008 | Piepenburg et al. |
| 7,485,428 | B2 | 2/2009 | Armes et al. |
| 7,666,598 | B2 | 2/2010 | Piepenburg et al. |
| 7,763,427 | B2 | 7/2010 | Piepenburg et al. |
| 7,777,958 | B2 | 8/2010 | Shimmo et al. |
| 8,017,339 | B2 | 9/2011 | Piepenburg et al. |
| 8,030,000 | B2 | 10/2011 | Piepenburg et al. |
| 8,062,850 | B2 | 11/2011 | Piepenburg et al. |
| 8,071,308 | B2 | 12/2011 | Piepenburg et al. |
| 8,426,134 | B2 | 4/2013 | Piepenburg et al. |
| 8,431,347 | B2 | 4/2013 | Millar et al. |
| 8,574,846 | B2 | 11/2013 | Piepenburg et al. |
| 8,809,021 | B2 | 8/2014 | Armes et al. |
| 8,945,845 | B2 | 2/2015 | Piepenburg et al. |
| 8,962,255 | B2 | 2/2015 | Piepenburg et al. |
| 9,057,097 | B2 | 6/2015 | Piepenburg et al. |
| 10,036,057 | B2 | 7/2018 | Piepenburg et al. |
| 2001/0044111 | A1 | 11/2001 | Carr et al. |
| 2002/0039783 | A1 | 4/2002 | McMillan et al. |
| 2002/0061530 | A1 | 5/2002 | Belotserkovskii et al. |
| 2002/0155573 | A1 | 10/2002 | Lanes et al. |
| 2003/0082565 | A1 | 5/2003 | Jang |
| 2003/0082590 | A1 | 5/2003 | Van Ness et al. |
| 2003/0108936 | A1 | 6/2003 | Wagner |
| 2003/0138800 | A1 | 7/2003 | Van Ness et al. |
| 2003/0143525 | A1 | 7/2003 | Benkovic et al. |
| 2003/0219784 | A1 | 11/2003 | Hon et al. |
| 2003/0219792 | A1 | 11/2003 | Armes et al. |
| 2003/0228611 | A1 | 12/2003 | Chruch et al. |
| 2004/0038213 | A1 | 2/2004 | Kwon |
| 2004/0058378 | A1 | 3/2004 | Kong et al. |
| 2004/0091864 | A1 | 5/2004 | French et al. |
| 2004/0101893 | A1 | 5/2004 | Kutyavin et al. |
| 2004/0137456 | A1 | 7/2004 | Yokota et al. |
| 2004/0224336 | A1 | 11/2004 | Wagner |
| 2005/0003395 | A1 | 1/2005 | Gellibolian et al. |
| 2005/0059003 | A1 | 3/2005 | Enoki et al. |
| 2005/0112631 | A1 | 5/2005 | Piepenburg et al. |
| 2005/0136443 | A1 | 6/2005 | Shigemori |
| 2006/0110765 | A1 | 5/2006 | Wang |
| 2006/0154286 | A1 | 7/2006 | Kong et al. |
| 2007/0031869 | A1 | 2/2007 | McCoy et al. |
| 2007/0042427 | A1 | 2/2007 | Gerdes et al. |
| 2007/0054296 | A1 | 3/2007 | Piepenburg |
| 2007/0154914 | A1 | 7/2007 | Gelfand et al. |
| 2007/0259348 | A1 | 11/2007 | Phadke et al. |
| 2008/0076160 | A1 | 3/2008 | Armes et al. |
| 2008/0293045 | A1 | 11/2008 | Piepenburg et al. |
| 2009/0017453 | A1 | 1/2009 | Maples et al. |
| 2009/0017462 | A1 | 1/2009 | Piepenburg et al. |
| 2009/0029421 | A1 | 1/2009 | Piepenburg et al. |
| 2009/0081670 | A1 | 3/2009 | Maples et al. |
| 2009/0269813 | A1 | 10/2009 | Piepenburg et al. |
| 2009/0325165 | A1 | 12/2009 | Armes et al. |
| 2010/0234245 | A1 | 9/2010 | McGee et al. |
| 2010/0311127 | A1 | 12/2010 | Piepenburg et al. |
| 2011/0053153 | A1 | 3/2011 | Piepenburg et al. |
| 2011/0059506 | A1 | 3/2011 | Piepenburg et al. |
| 2011/0065106 | A1 | 3/2011 | Armes et al. |
| 2012/0015367 | A1 | 1/2012 | Piepenburg et al. |
| 2012/0021462 | A1 | 1/2012 | Armes et al. |
| 2012/0058517 | A1 | 3/2012 | Piepenburg et al. |
| 2012/0082990 | A1 | 4/2012 | Piepenburg et al. |
| 2012/0129173 | A1 | 5/2012 | Piepenburg et al. |
| 2014/0099674 | A1 | 4/2014 | Piepenburg et al. |
| 2014/0141434 | A1 | 5/2014 | Armes et al. |
| 2014/0234846 | A1 | 8/2014 | Piepenburg et al. |
| 2014/0295436 | A1 | 10/2014 | Piepenburg et al. |
| 2016/0032374 | A1 | 2/2016 | Piepenburg et al. |
| 2016/0083780 | A1 | 3/2016 | Piepenburg et al. |

FOREIGN PATENT DOCUMENTS

| | | |
|---|---|---|
| EP | 0 624 643 | 4/1994 |
| EP | 0 702 090 | 3/1996 |
| EP | 0 810 436 | 12/1997 |
| EP | 1403379 | 3/2004 |
| EP | 1 420 069 | 5/2004 |
| EP | 1 564 306 | 8/2005 |
| JP | 08-103300 | 4/1996 |
| JP | 2000-500981 | 2/2000 |
| JP | 2002-512044 | 4/2002 |
| JP | 2003-38180 | 7/2003 |
| JP | 2004-512843 | 4/2004 |
| JP | 2005-518215 | 6/2006 |
| JP | 2008-515447 | 5/2008 |
| JP | 2009-502161 | 1/2009 |
| JP | 2011-505127 | 2/2011 |
| WO | WO 91/17267 | 11/1991 |
| WO | WO 93/05178 | 3/1993 |
| WO | WO 97/20078 | 6/1997 |
| WO | WO 98/08975 | 3/1998 |
| WO | WO 99/60158 | 11/1999 |
| WO | WO 00/41524 | 7/2000 |
| WO | WO 00/46408 | 8/2000 |
| WO | WO 02/086167 | 10/2002 |
| WO | WO 03/027640 | 4/2003 |
| WO | WO 03/038053 | 5/2003 |
| WO | WO 03/072805 | 9/2003 |
| WO | WO 04/007078 | 1/2004 |
| WO | WO 04/027025 | 4/2004 |

(56) References Cited

FOREIGN PATENT DOCUMENTS

| WO | WO 04/090169 | 10/2004 |
|---|---|---|
| WO | WO 05/118853 | 12/2005 |
| WO | WO 06/040187 | 4/2006 |
| WO | WO 07/096702 | 8/2007 |
| WO | WO 2008035205 | 3/2008 |
| WO | WO 2008090340 A2 | 7/2008 |
| WO | WO 2010141940 | 12/2010 |
| WO | WO 2013185081 | 12/2013 |

OTHER PUBLICATIONS

Menetski and Kowalczykowski, "Enhancement of *Escherichia coli* RecA Protein Enzymatic Function by dATP," Biochemistry 1989, 28, 5871-5881.
Riddles and Lehman, "The Formation of Paranemic and Plectonemic Joints between DNA Molecules by the recA and Single-stranded DNA-binding Proteins of *Escherichia coli*\*," The Journal of Biological Chemistry, 260(1):165-169 (1985).
Steffen and Bryant, "Reevaluation of the Nucelotide Cofactor Specificity of the RecA Protein from Bacillus subtilis\*," The Journal of Biological Chemistry, 274(37):25990-25994 (1999).
Toshihiro Horii et al., "Organization of the recA gene of *Escherichia coli*," Proc. Natl. Acad. Sci. USA., 77(1):313-317 (1980).
Thomas Kodadek "Functional Interactions Between Phage T4 and *E. coli* DNA-Binding Proteins During the Presynapsis Phase of Homologous Recombination," Biochemical and Biophysical Research Communications, 172(2):804-810 (1990).
Crannell et al., "Quantification of HIV-1 DNA Using Real-Time Recombinase Polymerase Amplification," American Chemical Society 2014, 86, 5615-5619.
Canadian Office Action, for the corresponding Canada Application No. 2569512, dated Jan. 4, 2013.
English Translation of Japanese Office Action, for the corresponding Japanese Patent Application No. 2011-044524, dated Oct. 30, 2012 (dated Nov. 1, 2012).
Barnes and Rowlyk, "Magnesium precipitate hot start method for PCR," Mol. and Cell. Probes, 16(3):167-171, 2002.
Crowe et al., "Is Trehalose Special for Preserving Dry Biomaterials?," Biophys. J., 71(4):2087-2093, 1996.
Mannarelli and Kurtzman, "Rapid Identification of Candida albicans and Other Human Pathogenic Yeasts by Using Short Oligonucleotides in a PCR," J. Clin. Microbiol., 36(6):1634-1641, 1998.
Ramos et al., "Stabilization of Enzymes against Thermal Stress and Freeze-Drying by Mannosylglycerate," Appl. and Env. Microbiol., 63(10):4020-4025, 1997.
English translation of Japan Office Action, for Japanese Application No. 2009-278020, dated Oct. 1, 2012 (dated Oct. 3, 2012).
EP Office Action for EP Application No. 08012222.9, dated Sep. 28, 2012.
European Office Action, for corresponding EP Application No. 10180482.1, dated Sep. 21, 2012.
European Office Action, for EP Application No. 10180775.8, dated Sep. 24, 2012.
European Search Report for EP Application No. 11184367.8, dated Oct. 9, 2012.
Kim and Chae, "Optimized protocols for the detection of porcine circovirus 2 DNA from formalin-fixed paraffin-embedded tissues using nested polymerase chain reaction and comparison of nested PCR with in situ hybridization," J. Vir. Methods, 92:105-111, 2001.
Miyamoto et al., "Development of a New Seminested PCR Method for Detection of *Legionella* Species and Its Application to Surveillance of Legionellae in Hospital Cooling Tower Water," Applied and Environmental Microbiology, 63(7):2489-2494, 1997.
Monis and Saint, "Development of a Nested-PCR Assay for the Detection of Cryptosporidium Parvum in Finished Water," Wat. Res., 35(7):1641-1648, 2001.
Ozbas et al., "Development of a multiplex and semi-nested PCR assay for detection of Yersinia enterocolitica and Aeromonas hydrophila in raw milk" Food Microbiology, 17:197-203, 2000.

English translation of Japanese Office Action, for the corresponding Japanese Patent Application No. 2008-096623, dated Jul. 25, 2012 (dated Jul. 27, 2012).
Australian Office Action, for AU Application No. 2011-202896, dated May 9, 2012.
"UvsX RecA-like recombination protein [Enterobacteria phage RB69]", online NCBI, http://www.ncbi.nlm.nih.gov/protein/32350347?sat=13&satkey=7100722, Apr. 5, 2005 (retrieved on Aug. 22, 2012).
"UvsX [Aeromonas phage Aehl]", online NCBI, http://www.ncbi.nlm.nih.gov/protein/38639939?sat=12&satkey=851579, Mar. 30, 2006 (retrieved on Aug. 22, 2012).
Desplats and Krisch, "The diversity and evolution of the T4-type bacteriophages," Res. Microbiol, 154(4):259-267, 2003.
Miller et al., "Complete Genome Sequence of the Broad-Host-Range vibriophage KVP40: Comparative Genomics of a T4-Related Bacteriophage," J. Bacteriol., 185(17):5220-5233, 2003.
Canadian Office Action, for Canada Application No. 2476481, dated May 29, 2012.
Canadian Office Action, for the corresponding Canada Application No. 2569512, dated Jun. 19, 2012.
Accession: NP_861734 [GI: 32453528], Definition: UvsX RecA-like recombination protein [Enterobacteria phage RB69]. NCBI Sequence Revision History [online]; Mar. 30, 2006 uploaded, NCBI, <URL: http://www.ncbi.nlm.nih.gov/protein/32453528?sat=12&satkey=7706006> [retrieved on Aug. 30, 2011].
Accession: NP_861890 [GI: 32453681], Definition: UvsY recombination, repair and ssDNA binding protein [Enterobacteria phage RB69]. NCBI Sequence Revision History [online]; Mar. 30, 2006 uploaded, NCBI, <URL: http://www.ncbi.nlm.nih.gov/protein/32453681?sat=12&satkey=7706006> [retrieved on Aug. 30, 2011].
Adams et al., "Dissociation of RecA filaments from duplex DNA by the RuvA and RuvB DNA repair proteins," Proc. Natl. Acad. Sci. USA 91:9901-9905, 1994.
Alexseyev et al., "Genetic Characteristics of New recA Mutants of *Escherichia coli* K-12," J. Bacteriol., 178:2018-2024, 1996.
Amasino, "Acceleration of Nucleic Acid Hybridization Rate by Polyethylene Glycol," Anal. Biochem., 152:304-307, 1986.
Bains and Smith, "A Novel Method for Nucleic Acid Sequence Determination," J. Theor. Biol., 135:303-307, 1988.
Bar-Ziv and Libchaber, "Effects of DNA sequence and structure on binding of RecA to single-stranded DNA," PNAS USA, 98(16):9068-9073.
Baumann et al., "Purification of human Rad51 protein by selective spermidine precipitation," Mutat. Res., 384:65-72, 1997.
Benedict and Kowalczykowski, "Increase of the DNA Strand Assimilation Activity of recA Protein by Removal of the C Terminus and Structure-Function Studies of the Resulting Protein Fragment," J. Biol. Chem., 263(30):15513-15520, 1988.
Benkovic et al., "Replisome-Mediated DNA Replication," Annu. Rev. Biochem., 70:181-208, 2001.
Bennett and Holloman, "A RecA Homologue in Ustilago maydis That Is Distinct and Evolutionarily Distant from Rad51 Actively Promotes DNA Pairing Reactions in the Absence of Auxiliary Factors," Biochemistry, 40:2942-2953, 2001.
Better and Helinski, "Isolation and Characterization of the recA Gene of Rhizobium meliloti," J. Bacteriol, 155:311-316, 1983.
Bianco and Weinstock, "Interaction of the RecA protein of *Escherichia coli* with single-stranded oligodeoxyribonucleotides," Nucleic Acids Research, 24(24):4933-4939, 1996.
Bianco et al., "DNA Strand Exchange Proteins: A Biochemical and Physical Comparison," Frontiers in Bioscience, 3:D570-D603, 1998.
Borjac-Natour et al., "Divergence of the mRNA targets for the Ssb proteins of bacteriophages T4 and RB69," Virology J., 1(4):1-14, 2004.
Bork et al., "The RecOR proteins modulate RecA protein function at 5' ends of single-stranded DNA," EMBO J., 20:7313-7322, 2001.
Bork et al., "RecA Protein Filaments Disassemble in the 5' to 3' Direction on Single-stranded DNA," J. Biol. Chem., 276:45740-45743, 2001.
Butler et al., "Investigating Structural Changes Induced by nucleotide Binding to RecA Using Difference FTIR," Biophysical J., 82(4):2198-2210, 2002.

(56) References Cited

OTHER PUBLICATIONS

Byrd and Raney, "Protein displacement by an assembly of helicase molecules aligned along single-stranded DNA," Nat. Struct. Mol. Biol., 11(6):531-538, 2004.
Cai, "An inexpensive and simple nucleic acid dipstick for rapid pathogen detection," LAUR #05-9067 of Los Alamos National Laboratory, Aug. 22, 2006.
Chan et al., "Effects of Polyethylene Glycol on Reverse Transcriptase and Other polymerase Activities," Biochim. Biophys. Acta., 606(2):353-361, 1980.
Compton, "Nucleic acid sequence-based amplification," Nature, 350:91-92, 1991.
Conklin and Drake, "Isolation and Characterization of conditional Alleles of bacteriophage T4 Genes uvsX and uvsY," Genetics, 107:505-523, 1984.
Cox et al., "The importance of repairing stalled replication forks," Nature, 404:37-41, 2000.
Cox et al., "A Simple and Rapid Procedure for the Large Scale Purification of the recA protein of Escherichia coli," J. Biol. Chem., 256:4676-4678, 1981.
Cromie and Leach, "Control of Crossing Over," Mol. Cell., 6:815-826. 2000.
Decker et al., "In Vitro Initiation of DNA Replication in Simian Virus 40 Chromosomes," J. Biol. Chem., 262(22):10863-10872, 1987.
Demidov, "Rolling-circle amplification in DNA diagnostics: the power of simplicity," Expert Rev. Mol. Diagn., 2(6):89-95, 2002.
Digard et al., "The Extreme C Terminus of Herpes Simplex Virus DNA Polymerase Is Crucial for Functional Interaction with Processivity Factor UL42 and for Viral Replication," J. Virol., 67(1):398-406, 1993.
Dillingham and Kowalczykowski, "A Step Backward in Advancing DNA Replication: Rescue of Stalled Replication Forks by RecG," Mol. Cell., 8:734-736, 2001.
Dong et al., "A coupled complex of T4 DNA replication helicase (gp41) and polymerase (gp43) can perform rapid and processive DNA strand-displacement synthesis," Proc. Natl. Acad. Sci. USA, 93:14456-14461, 1996.
Drmanac, et al., "Sequencing of Megabase Plus DNA by Hybridization: Theory of the Method," Genomics, 4:114-128, 1989.
Edwards et al., "Genetic Variation at Five Trimeric and Tetrameric Tandem Repeat Loci in Four Human Population Groups," Genomics, 12:241-253, 1992.
Eggler et al., "The C Terminus of the Escherichia coli RecA Protein Modulates the DNA Binding Competition with Single-stranded DNA-binding Protein," J. Biol. Chem., 278:16389-16396, 2003.
Eggleston and West, "Cleavage of Holliday Junctions by the Escherichia coli RuvABC Complex," J. Biol. Chem., 275:26467-26476, 2000.
Elias-Arnanz and Salas, "Bacteriophage ø29 DNA replication arrest caused by codirectional collisions with the transcription machinery," EMBO J., 16:5775-5783, 1997.
Ellis, "Macromolecular crowding: obvious but underappreciated," Trends in Biochem. Sci., 26(10):597-604, 2001.
Ellouze et al., "Evidence for elongation of the helical pitch of the RecA filament upon ATP and ADP binding using small-angle neutron scattering," Eur. J. Biochem., 23392):579-583, 1995.
Enright et al., The evolutionary history of methicillin-resistant Staphylococcus aureus (MRSA), Proc. Natl. Acad. Sci. USA, 99:7687-7692, 2002.
Fahy et al., "Self-sustained sequence replication (3SR): an isothermal transcription-based amplification system alternative to PCR," Genome Res, 1:25-33, 1991.
Ferrari et al., "Co-operative Binding of Escherichia coli SSB Tetramers to Single-stranded DNA in the $(SSB)_{35}$ Binding Mode," J. Mol. Biol, 236:106-123, 1994.
Formosa et al., "Affinity purification of bacteriophage T4 proteins essential for DNA replication and genetic recombination," Proc. Natl. Acad. Sci. USA, 80:2442-2446, 1983.
Formosa and Alberts, "Purification and Characterization of the T4 Bacteriophage uvsX Protein," J. Biol. Chem., 261:6107-6118, 1986.

Formosa and Alberts, "DNA Synthesis Dependent on Genetic Recombination: Characterization of a Reaction Catalyzed by Purified Bacteriophage T4 Proteins," Cell, 47:793-806, 1986.
Fu et al., "Dynamics of DNA-tracking by two sliding-clamp proteins," EMBO J., 15(16):4414-4422, 1996.
Fuller et al., "Enzymatic replication of the origin of the Escherichia coli chromosome," Proc. Natl. Acad. Sci. USA, 78(12):7370-7374, 1981.
Giedroc et al., "The Function of Zinc in Gene 32 Protein from T4," Biochem., 26:5251-5259, 1987.
Giedroc et al., "Zn(II) Coordination Domain Mutants of T4 Gene 32 protein," Biochem., 31:765-774, 1992.
Ginocchio, "Life Beyond PCR: Alternative Target Amplification Technologies for the Diagnosis of Infectious Diseases, Part II," Clin. Microbiol. Newsletter, 26(17):129-136, 2004.
Glover and McHenry, "The DNA Polymerase III Holoenzyme: An Asymmetric Dimeric Replicative Complex with Leading and Lagging Strand Polymerases," Cell., 105:925-934.
Goodman et al., "Cloning and expression in Escherichia coli of a recA-like gene from Bacteroides fragilis," Gene, 58:265-271, 1987.
Hacker and Alberts, "Overexpression, Purification, Sequence Analysis, and Characterization of the T4 Bacteriophage dda DNA Helicase," J. Biol. Chem., 267:20674-20681, 1992.
Hammond et al., "Evaluation of 13 Short Tandem Repeat Loci for Use in Personal Identification Applications," Am. J. Hum. Genetics, 55:175-189, 1994.
Harris and Griffith, "UvsY Protein of Bacteriophage T4 is an Accessory Protein for in Vitro Catalysis of Strand Exchange," J. Mol. Biol., 206:19-27, 1989.
Harris and Griffith, "Visualization of the Homologous Pairing of DNA Catalyzed by the Bacteriophage T4 UvsX Protein," J. Biol. Chem., 262:9285-9292, 1987.
Harris and Griffith, "Formation of D Loops by the UvsX Protein of T4 Bacteriophage: A Comparison of the Reaction Catalyzed in the Presence or Absence of Gene 32 Protein," Biochem., 27:6954-6959, 1988.
Harvey et al., "Characterization and applications of CataCleave probe in real-time detection assays," Anal. Biochem., 333(2):246-255, 2004.
Heid et al., "Real time quantitative PCR," Genome Res., 6(10):986-994, 1996.
Heyer and Kolodner, "Purification and Characteirzation of a Protein from Saccharomyces cerevisiae That Binds Tightly to Single-Stranded DNA and Stimulates a cognate Strand Exchange Protein," Biochem. 28:2856-2862, 1989.
Hickson et al., "A Temperature Sensitive RecA Protein of Escherichia coli," Mol. Gen. Genet., 184:68-72, 1981.
Hopp et al., "A Short Polypeptide Marker Sequence Useful for Recombinant Protein Identification and Purification," Biotech., 6:1204-1210, 1988.
Hsieh et al., "The synapsis event in the homologous pairing of DNAs: RecA recognizes and pairs less than one helical repeat of DNA," Proc. Natl. Acad. Sci. USA, 89:6492-6496, 1992.
Huang et al., "Relationship between Bacteriophage T4 and T6 DNA Topoisomerases," J. Biol. Chem., 260(15):8973-8977, 1985.
Huletsky et al., "New Real-Time PCR Assay for Rapid Detection of Methicillin-Resistant Staphylococcus aureus Directly from Specimens Containing a Mixturre of Staphylococci," J. Clin. Microbiol., 42:1875-1884, 2004.
Ischenko and Saparbaev, "Alternative nucleotide incision repair pathway for oxidative DNA damage," Nature, 415(6868):183-187, 2002.
Ishmael et al., "Protein-Protein Interactions in the Bacteriophage T4 Replisome," J. Biol. Chem., 278(5):3145-3152, 2003.
Jarvis et al., "'Macromolecular Crowding': Thermodynamic Consequences for Protein-Protein Interactions with in the T4 DNA Replication Complex," J. Biol. Chem., 265(25):15160-15167, 1990.
Kaboord and Benkovic, "Rapid assembly of the bacteriophage T4 core replication complex on a linear primer/template construct," Proc. Natl. Acad. Sci. USA, 90:10881-10885, 1993.
Kaiser et al., "A Comparison of Eubacterial and Archaeal Structure-specific 5'-Exonucleases," J. Biol. Chem., 274(30):21387-21394, 1999.

(56) References Cited

OTHER PUBLICATIONS

Kato and Kuramitsu, "RecA Protein from an Extremely Thermophilic Bacterium, Thermus thermophiles HB8," J. Biochem., 114:926-929, 1993.
Katz and Bryant, "Interdependence of the Kinetics of NTP Hydrolysis and the Stability of the RecA-ssDNA Complex," Biochem., 40:11082-11089, 2001.
Kelman and O'Donnell, "DNA Polymerase III Holoenzyme: Structure and Function of a Chromosomal Replicating Machine," Annu. Rev. Biochem., 64:171-2000.
Khrapko et al., "An oligonucleotide hybridization approach to DNA sequencing," FEBS Lett., 256:118-122, 1989.
Komori et al., "Both RadA and RadB are Involved in Homologous Recombination in *Pyrococcus furiosus*," J. Biol. Chem., 275:33782-33790, 2000.
Kool, "Replacing the Nucleobases in DNA with Designer Molecules," Acc. Chem. Res., 35:936-943, 2002.
Kowalczykowski et al., "Effects of the *Escherichia coli* SSB Protein on the Binding of *Escherichia coli* RecA Protein to Single-stranded DNA—Demonstration of Competitive Binding and the Lack of a Specific Protein-Protein Interaction," J. Mol. Biol., 193:81-95, 1987.
Kreader, "Relief of amplification inhibition in PCR with bovine serum albumin or T4 gene 32 protein," Appl. Env. Microbiol., 62:1102-1106, 1996.
Kuil et al., "The internal dynamics of gene 32 protein-DNA complexes studied by quasi-elastic light scattering," Biophys. Chem., 32:211-227, 1988.
Kuil et al., "A Refined Calculation of the Solution Dimensions of the Complex Between gene 32 Protein and Single Stranded DNA Based on Estimates of the Bending Persistence Length," J. Biomol. Struct. Dyn. 7(4):943-957, 1990.
Kuramitsu et al., "A Large-Scale Preparation and Some Physicochemical Properties of RecA Protein," J. Biochem., 90:1033-1045, 1981.
Kurumizaka et al., "A Chimeric RecA Protein Exhibits Altered Double-stranded DNA Binding," J. Biol. Chem., 269:3068-3075, 1994.
Lavery and Kowalczykowski, "Enhancement of recA Protein-promoted DNA Strand Exchange Activity by Volume-occupying Agents," J. Biol. Chem., 267:9301-9314, 1992.
Lavery and Kowalczykowski, "A Postsynaptic Role for Single-stranded DNA-binding Protein in recA Protein-promoted DNA Strand Exchange," J. Biol. Chem., 267(13):9315-9320, 1992.
LeBowitz and McMacken, "The bacteriophage λ O and P protein initiators promote the replication of single-stranded DNA," 12(7):1-20, 1984.
Lerman, "A Transition to a Compact Form of DNA in Polymer Solutions," Proc. Nat. Acad. Sci. USA, 68(8):1886-1890, 1971.
Levin et al., "Homogeneous *Escherichia coli* Endonuclease IV," J. Biol. Chem., 263:8066-8071, 1988.
Liu et al., "The Ordered Assembly of the øX174-type Primosome," J. Biol. Chem., 271:15656-15661, 1996.
Lohman and Ferrari, "*Escherichia coli* Single-Stranded DNA-Binding Protein: Multiple DNA-Binding Modes and Cooperativities," Annu. Rev. Biochem., 63:527-570, 1994.
Lovett and Roberts, "Purification of a RecA Protein Analogue from *Bacillus subtilis*," J. Biol. Chem., 260:3305-3313, 1985.
Lusetti et al., "Magnesium Ion-dependent Activation of the RecA Protein Involves the C Terminus," J. Biol. Chem., 278(18):16381-16388, 2003.
Lutz-Freyermuth et al., "Quantitative determination that one of two potential RNA-binding domains of the A protein component of the U1 small nuclear ribonucleoprotein complex binds with high affinity to stem-loop II of U1 RNA," Proc. Natl. Acad. Sci. USA, 87:6393-6397, 1990.
Lysov et al., "Establishing Nucleotide Sequence of DNA using Oligonucleotide Hydridization. Novel Method," SSSR 303:1508-1511, 1988 (English translation).
Maeshima et al., "Purification and characterization of XRad51.1 protein, Xenopus RAD51 homologue: recombinant XRad51.1 promotes strand exchange reaction," Genes Cells, 1:1057-1068, 1996.
Maki et al., "DNA Polymerase III Holoenzyme of *Escherichia coli*," J. Biol. Chem., 263(14):6570-6578, 1988.
Malkov and Camerini-Otero, Photocross-links between Single-stranded DNA and *Escherichia coli* RecA Protein Map to Loops L1 (Amino Acid Residues 157-164) and L2 (Amino Acid Residues 195-209),: J. Biol. Chem., 270(50):30230-30233, 1995.
Marians, "Prokaryotic DNA Replication," Annu. Rev. Biochem., 61:673-719, 1992.
Marians, "PriA: At the Crossroads of DNA Replication and Recombination," Prog. Nucleic Acid Res. Mol. Biol., 63:39-67, 1999.
Marras et al., "Multiplex detection of single-nucleotide variations using molecular beacons," Genet. Anal. Biomolec. Eng., 14:151-156, 1999.
Martin et al., "GAP Domains Responsible for Ras p21-Dependent Inhibition of Muscarinic Atrial K+ $^C$hannel Currents," Science, 255:192-194, 1992.
Maxam and Gilbert, "A new method for sequencing DNA," Proc. Natl. Acad. Sci. USA, 74:560-564, 1877.
Mazin and Kowalczykowski, "The function of the secondary DNA-binding site of RecA protein during DNA strand exchange," Proc. Natl. Acad. Sci. USA, 74:560-564, 1977.
McGlynn and Lloyd, "RecG helicase activity at three- and four-strand DNA structures," Nucl. Acid Res., 27:3049-3056, 1999.
McGlynn et al., "Characterisation of the catalytically active form of RecG helicase," Nucl. Acid Res., 28:2324-2332, 2000.
Minton, "The Influence of Macromolecular Crowding and Macromolecular Confinement on Biochemical Reactions in Physiological Media," J. Biol. Chem., 276(14):10577-10580, 2001.
Mitra and Church, "In situ localized amplification and contact replication of many individual DNA molecules," Nucl. Acids Res., 27(24):e34i-e34vi.
Mizuuchi, "In Vitro Transposition of Bacteriophage Mu: A Biochemical Approach to a Novel Replication Reaction," Cell, 35:785-794, 1983.
Morel et al., "Recombination-dependent Repair of DNA Double-strand Breaks with Purified Proteins from *Escherichia coli*," J. Biol. Chem., 272:17091-17096, 1997.
Morrical et al., "Amplification of Snap-back DNA Synthesis Reactions by the uvsX Recombinase of Bacteriophage T4," J. Biol. Chem., 266:14031-14038, 1991.
Morrical and Alberts, "The UvsY Protein of Bacteriophage T4 Modulates Recombination-dependent DNA Synthesis in Vitro," J. Biol. Chem., 265:15096-15103, 1990.
Morris and Raney, "DNA Helicases Displace Streptavidin from Biotin-Labeled Oligonucleotides," Biochem., 38(16):5164-5171, 1999.
Morrison et al., "Quantificationo f Low-Copy Transcripts by Continuous SYBR Green I Monitoring during Amplification," BioTechniques, 24:954-962, 1998.
Mosig et al., "Two recombination-dependent DNA replication pathways of bacteriophage T4, and their roles in mutagenesis and horizontal gene transfer," Proc. Natl. Acad. Sci. USA, 98:8306-8311, 2011.
Nadler et al., "A Novel Function for Zinc(II) in a Nucleic Acid-binding Protein," J. Biol. Chem., 265(18):10389-10394, 1990.
Nadeau et al., "Real-Time, Sequence-Specific Detection of Nucleic Acids during Strand Displacement Amplification," Anal. Biochem., 276(2):177-187, 1999.
Nagai et al., "Additive Effects of Bovine Serum Albumin, Dithiothreitol, and Glycerol in PCR," 44:157-163, 1998.
Naimushin et al., "Effect of Polyethylene Glycol on the Supercoiling Free Energy of DNA," Biopolymers, 58(2):204-217, 2001.
Ng and Marians, "The Ordered Assembly of the øX174-type Primosome," J. Biol. Chem., 271:15642-15648, 1996.
Ng and Marians, "The Ordered Assembly of the øX174-type Primosome," J. Biol. Chem., 271:15649-15655, 1996.
Okazaki and Kornberg, "Enzymatic Synthesis of Deoxyribonucleic Acid," J. Biol. Chem., 239:259-268, 1964.

(56) References Cited

OTHER PUBLICATIONS

Paulus and Bryant, "Time-Dependent Inhibition of recA Protein-Catalyzed ATPHydrolysis by ATPyS: Evidence for a Rate-Determining Isomerization of the recA-ssDNA Complex," Biochem., 36:7832-7838, 1997.
Petrov et al., "Plasticity of the Gene Functions for DNA Replication in the T4-like Phages," J. Mol. Biol., 361:46-68, 2006.
Pevzner, "1-Tuple DNA Sequencing: Computer Analysis," J. Biomol. Struct. Dyn., 7:63-73, 1989.
Pham et al., "A model for SOS-lesion-targeted mutations in *Escherichia coli*," Nature, 409:366-370, 2001.
Piepenburg et al., "DNA Detection Using Recombination Proteins," PLOS Biology, 4(7):1115-1121, 2006.
Pierre and Paoletti, "Purification and Characterization of recA Protein from *Salmonella typhimurium*," J. Biol. Chem., 258:2870-2874, 1983.
Podust et al., "Replication Factor C Disengages from Proliferating Cell Nuclear Antigen (PCNA) upon Sliding Clamp Formation, and PCNA Itself Tethers DNA Polymerase δ to DNA," J. Biol. Chem., 273(48):31992-31999, 1998.
Pomp and Medrano, "Organic Solvents as Facilitators of Polymerase chain Reaction," Biotechniques, 10(1):58-59, 1991.
Qiu and Giedroc, "Effects of Substitution of Proposed Zn(II) Ligand $His^{81}$ or $His^{64}$ in Phage T4 Gene 32 Protein: Spectroscopic Evidence for a Novel Zinc Coordination Complex," Biochem., 33(26):8139-8148, 1994.
Raap, "Advances in fluorescence in situ hybridization," Mutation Research, 400:287-298, 1998.
Raap et al., "Synthesis and Proton-NMR Studies of Oligonucleotides Containing and Apurinic (AP) Site," J. Biom. Structure & Dynamics, 5(2):219-247, 1987.
Rashid et al., "RecA/Rad51 Homolog from *Thermococcus kodakaraensis* KOD1," Methods Enzymol., 334:261-270, 2001.
Reddy et al., "Assembly of a functional replication complex without ATP hydrolysis: A direct interaction of bacteriophage T4 gp45 with T4 DNA polymerase," Proc. Natl. Acad. Sci. USA, 90:3211-3215, 1993.
Reddy et al., "Using Macromolecular Crowding Agents to Identify Weak Interactions within DNA Replication Complexes," Methods Enzymol., 262:466-476, 1995.
Riddles and Lehman, "The Formation of Plectonemic Joints by the recA Protein of *Escherichia coli*," J. Biol. Chem., 260:170-173, 1985.
Rivas et al., "Life in a crowded world—Workshop on the Biological Implications of Macromolecular Crowding," EMBO Reports, 5(1):23-27, 2004.
Ronaghi et al., "A Sequencing Method Based on Real-Time Pyrophosphate," Science, 281:363-365, 1998.
Rosselli and Stasiak, "Energetics of RecA-mediated Recombination Reactions Without ATP Hydrolysis RecA Can Mediate Polar Strand Exchange But Is Unable to Recycle," J. Mol. Biol., 216:335-352, 1990.
Roux, "Optimization and troubleshooting in PCR," Genome Res., 4:S185-S194, 1995.
Saiki et al., "Primer-Directed Enzymatic Amplification of DNA with a Thermostable DNA Polymerase," Science, 239:487-491, 1988.
Salinas et al., "Homology Dependence of UvsX Protein-catalyzed Joint Molecule Formation," J. Biol. Chem., 270:5181-5186.
Salinas and Benkovic, "Characterization of bacteriophage T4-coordinated leading- and lagging-strand synthesis on a minicircle substrate," PNAS, 97(13):7196-7201, 2000.
Sanders et al., "Use of a macromolecular crowding agent to dissect interactions and define functions in transcriptional activation by a DNA-tracking protein: Bacteriphage T4 gene 45 protein and late transcription," Proc. Natl. Acad. Sci. USA, 91:7703-7707, 1994.
Sanders et al., "Dual targets of a transcriptional activator that tracks on DNA," EMBO J., 16(11):3124-3132, 1997.
Sanger et al., "DNA sequencing with chain-terminating inhibitors," Proc. Natl. Acad. Sci. USA, 75:5463-5467, 1977.
Sawa and Pearl, "Cloning and Expression of the Uracil-DNA Glycosylase Inhibitor (UGI) From Bacteriophage PBS-1 and Crystallization of a Uracil-DNA Glycosylase-UGI Complex," Proteins, 22(3):287-289, 1995.
Scheerhagen et al., "Binding Stoichiometry of the Gene 32 Protein of Phage T4 in the Complex with Single Stranded DNA Deduced from Boundary Sedimentation," J. Biomol. Struct. Dyn., 3:887-898, 1986.
Scheerhagen et al., "Hydrodynamic studies of a DNA-protein complex—Dimensions of the complex of single-stranded 145 base DNA with gene 32 protein of phage T4 deduced from quasi-elastic light scattering," FEBS Lett., 184(2):221-225, 1985.
Shan et al., "RecA Protein Filaments: End-dependent Dissociation from ssDNA and Stabilization by RecO and RecR Proteins," J. Mol. Biol., 265:519-540, 1997.
Shibata et al., "Purified *Escherichia coli* recA protein catalyzes homologous pairing of superhelical DNA and single-stranded fragments," Proc. Natl. Acad. Sci. USA, 76:1638-1642, 1979.
Shibata et al., "Homologous pairing in genetic recombination: Formation of D loops by combined action of recA protein and a helix-destabilizing protein," Proc. Natl. Acad. Sci. USA, 77:2606-2610, 1980.
Shibata et al, "Homologous pairing in genetic recombination: Complexes of recA protein and DNA," Proc. Natl. Acad. Sci. USA, 76(10):5100-5104, 1979.
Singleton et al., "Structural Analysis of DNA Replication Fork Reversal by RecG," Cell, 107:79-89, 2001.
Skinner et al., "Use of the Glu-Glu-Phe C-terminal Epitope for Rapid Purification of the Catalytic Domain of Normal and Mutant ras GTPase-activating Proteins," J. Biol. Chem., 266:14163-14166, 1991.
Southern et al., "Analyzing and Comparing Nucleic Acid sequences by Hybridization to Arrays of Oligonucleotides: Evaluation Using Experimental Models," Genomics, 13:1008-1017, 1992.
Spies et al., "The RadA protein from a hyperthennophilic archaeon *Pyrobaculum islandicum* is a DNA-dependent ATPase that exhibits two disparate catalytic modes, with a transition temperature at 75° C.," Eur. J. Biochem., 267:1125-1137, 2000.
Steffen and Bryant, "Purification and Characterization of the RecA Protein from *Streptococcus pneumoniae*," Arch. Biochem. Biophys., 382:303-309, 2000.
Story et al., "Structural Relationship of Bacterial RecA Proteins to Recombination Proteins from Bacteriophage T4 and Yeast," Science, 259(5103):1892-1896, 1993.
Sun and Shamoo, "Biochemical characterization of Interactions between DNA Polymerase and Single-stranded DNA-binding Protein in Bacteriophage RB69," J. Biol. Chem., 278(6):3876-3881.
Takeshita et al., "Oligodeoxynucleotides Containing Synthetic Abasic Sites," J. Biol. Chem., 262:10171-10179, 1987.
Tang et al., "Roles of *E. coli*DNA polymerases IV and V in lesion-targeted and untargeted SOS mutagenesis," Nature, 404:1014-1018, 2000.
Tinker-Kulberg et al., "A direct interaction between a DNA-tracking protein and a promoter recognition protein: implications for searching DNA sequence," EMBO J., 15(18):5032-5039, 1996.
Tissier et al., "Purification and Characterization of a DNA Strand Transferase from Broccoli," Plant Physiol., 108:379-386, 1995.
Tracy and Kowalczykowski, "In vitro selection of preferred DNA pairing sequences by the *Escherichia coli* RecA protein," Genes Dev., 10:1890-1903, 1996.
Tsurimoto and Matsubara, "Replication of λ dv plasmid in vitro promoted by purified λ O and P proteins," Proc. Natl. Acad. Sci. USA, 79:7639-7643, 1982.
Tyagi et al., "Multicolor molecular beacons for allele discrimination," Nature Biotechnol., 16:49-53, 1998.
Van Ness et al., "Isothermal reactions for the amplification of oligonucleotides," Proc. Natl. Acad. Sci. USA, 100(8):4504-4509, 2003.
Villemain et al., "Mutations in the N-terminal Cooperativity Domain of Gene 32 protein Alter Properties of the T4 DNA Replication and Recombination Systems," J. Biol. Chem., 275:31496-31504, 2000.
Vincent et al., "Helicase-dependent isothermal DNA amplification," EMBO Rep., 5:795-800, 2004.

(56) References Cited

OTHER PUBLICATIONS

Volodin and Camerini-Otero, "Influence of DNA Sequence on the Positioning of RecA Monomers in RecA-DNA Cofilaments," J. Biol. Chem., 277(2):1614-1618, 2002.
Volodin et al., "Phasing of RecA monomers on quasi-random DNA sequences," FEBS Letters, 546:203-208, 2003.
Voloshin et al., "Homologous DNA Pairing Promoted by a 20-Amino Acid Peptide Derived from RecA," Science, 272:868-872, 1996.
Voloshin et al., "The Homologous Pairing Domain of RecA also Mediates the Allosteric Regulation of DNA Binding and ATP Hydrolysis: A Remarkable Concentration of Functional Residues," J. Mol. Biol., 303(5):709-720, 2000.
Waidner, et al., "Domain effects on the DNA-interactive properties of bacteriophage T4 gene 32 protein," J. Biol. Chem., 276:2509-16 (2001).
Walker et al., "Isothermal in vitro amplification of DNA by a restriction enzyme/DNA polymerase system," Proc. Natl. Acad. Sci. USA, 89:392-396, 1992.
Walker, "Empirical aspects of strand displacement amplification," Genome Res., 3:1-6, 1993.
Walker et al., "Distantly related sequences in the α- and β-subunits of ATP synthase, myosin, kinases and other ATP-requiring enzymes and a common nucleotide binding fold," EMBO J., 1:945-951, 1982.
Wang et al., "Modular Organization of T4 DNA Polymerase," J. Biol. Chem., 270(44):26558-26564, 1995.
Wang and Mosbaugh, "Uracil-DNA Glycosylase Inhibitor of Bacteriophage PBS2: Cloning and Effects of Expression of the Inhibitor Gene in *Escherichia coli*," J. Bacteriol., 170(3):1082-1091, 1988.
Webb et al., "An Interaction between the *Escherichia coli* RecF and RecR Proteins Dependent on ATP and Double-stranded DNA," J. Biol. Chem., 270:31397-31404, 1995.
Webb et al., "Recombinational DNA Repair: The RecF and RecR Proteins Limit the Extension of RecA Filaments beyond Single-Strand DNA Gaps," Cell, 91:347-356, 1997.
Webb et al., "ATP Hydrolysis and DNA Binding by the *Escherichia coli* RecF Protein," J. Biol. Chem., 274:15367-15374, 1999.
West et al., "Purification and Properties of the recA Protein of *Proteus mirabilis*," J. Biol. Chem., 258:4648-4654, 1983.
Wetmur et al, "Cloning, Sequencing, and Expressionf RecA Proteins from Three Distantly Related Thermophilic Eubacteria," J. Biol. Chem., 269:25928-25935, 1994.
Wittwer et al., "Continuous Fluorescence Monitoring of Rapid Cycle DNA Amplification," Biotechniques, 22(1):130-1, 134-138, 1997.
Xu and Marians, "A Dynamic RecA Filament Permits DNA Polymerase-catalyzed Extension of the Invading Strand in Recombination Intermediates," J. Biol. Chem., 277:14321-14328, 2002.
Yang et al., "Comparison of Bacteriophage T4 and UvsX and Human Rad51 Filaments Suggests that RecA-like Polymers May Have Evolved Independently," J. Mol. Biol., 312(5):999-1009, 2001.
Yeh et al., "Divergence of a DNA Replication Gene Cluster in the T4-Related Bacteriophage RB69," J. Bacteriol., 180(8):2005-2013, 1998.
Yonesaki et al., "Purification and some of the functions of the product of bacteriophage T4 recombination genes, uvsX and uvsY ," Eur. J. Biochem., 148:127-134, 1985.
Young et al., "The Kinetic Mechanism of Formation of the Bacteriophage T4 DNA polymerase Sliding Clamp," J. Mol. Biol., 264:440-452, 1996.
Zhang et al., "Ramification Amplification: A Novel Isothermal DNA Amplification Method," Mol. Diagn., 6:141-150, 2001.
Zimmerman and Trach, "Macromolecular crowding extends the range of conditions under which DNA polymerase is functional," Biochim. Biophys. Acta., 949:297-304, 1988.
Zimmerman and Minton, "Macromolecular Crowding: Biochemical, Biophysical, and Physiological Consequences," Annu. Rev. Biophys. Biomol. Struct., 22:27-65, 1993.
Zimmerman and Harrison, "Macromolecular crowding increases binding of DNA polymerase to DNA: An adaptive effect," Proc. Natl. Acad. Sci. USA, 84(7):1871-1875, 1987.
Zinchenko and Yoshikawa, "$Na^+$ Shows a Markedly Higher Potential than $K^+$ in DNA Compaction in a Crowded Environment," Biophysical Journal, 88:4118-4123, 2005.
International Search Report, for the corresponding PCT Application No. PCT/US03/05492, dated Oct. 14, 2003.
International Search Report, for the corresponding PCT Application No. PCT/IB2005/001560, dated May 2, 2006.
Partial European Search Report for EP 08012222.9, 3 pgs., dated Nov. 12, 2008.
Office Action for U.S. Appl. No. 12/151,741, dated Dec. 24, 2008, 9 pgs.
EP search report for corresponding EP Application No. 08012222.9, dated Feb. 17, 2009.
Office Action for U.S. Appl. No. 10/813,693 (U.S. counterpart to WO 00/41524—Foreign Patent Document No. 56 above), dated May 28, 2009 (with pending claims attached).
Australian Office Action, for the corresponding Australia Application No. 2005250233, filed Apr. 11, 2005, dated Dec. 9, 2009.
Canadian Office Action, for the corresponding Canada Application No. 2476481, dated Aug. 2, 2010.
English Translation and Japanese Office Action for corresponding Japanese Application No. 2007-514201, dated Nov. 30, 2010.
English Translation and Japanese Office Action for corresponding Japanese Application No. 2008-096623, dated Nov. 30, 2010.
Response to the Canadian Examination Report dated Aug. 2, 2010, for corresponding Canadian application Serial No. 2,476,481, as filed on Feb. 1, 2011.
Response to Australian Office Action, for the corresponding Australia Application No. 2005250233, as filed Feb. 2, 2011.
EP Search Report for counterpart EP Application No. EP 10180775.8, dated Mar. 4, 2011, (9 pages).
Reply to Office Action in corresponding EP Application No. 08012222.9, filed Feb. 21, 2003, dated Mar. 4, 2011.
European Office Action, for the corresponding EP Application No. 05741662.0, filed Apr. 11, 2005, dated Jun. 1, 2011.
EP Search Report, for the corresponding EP Application No. 10180482, dated Jun. 8, 2011.
EP Search Report, for the corresponding EP Application No. 10180775, dated Jun. 9, 2011.
Canadian Office Action for the corresponding Canada Application No. 2,476,481, dated Jul. 15, 2011.
EP Office Action for corresponding EP Application No. 08012222.9, dated Oct. 10, 2011.
English Translation of Japanese Office Action, for the corresponding Japanese Patent Application No. 2008-096623, dated Dec. 5, 2011 (dated Dec. 7, 2011).
Reply to Office Action in corresponding EP Application No. 05741662.0, filed Apr. 11, 2005, dated Dec. 7, 2011.
Response to Office Action for the corresponding Canadian Application No. 2,476,481, dated Jan. 11, 2012.
European Office Action, for the corresponding EP Application No. 05741662.0, dated Feb. 16, 2012.
Office action in corresponding Canadian application 2,476,481, dated May 16, 2013, 9 pages.
Reply to Office Action in EP Application No. 11184367.8, dated Aug. 21, 2013.
Peter W. Riddles and I.R. Lehman, "The Formation of Paranemic and Plectonemic Joints between DNA Molecules by the recA and Single-stranded DNA-binding Proteins of *Escherichia coli*\*," The Journal of Biological Chemistry, 260(1):165-169 (1985).
Office Action in EP Application No. 11184367.8, dated Oct. 23, 2013.
Gunna Christiansen et al., "Visualization of the paranemic joining of homologous DNA molecules catalyzed by the RecA protein of *Escherichia coli*," PNAS, 83:2066-2070 (1986).
Marco Bianchi et al., "Synapsis and the Formation of Paranemic Joints by *E. coli* RecA Protein," Cell, 34:931-939 (1983).
Gill et al., "Nucleic acid isothermal amplification technologies: a review," Nucleosides Nucleotides Nucleic Acids 2008 27:224-243.

(56) References Cited

OTHER PUBLICATIONS

Mukai et al., "Highly efficient isothermal DNA amplification system using three elements of 5'-DNA-RNA-3' chimeric primers, RNaseH and strand-displacing DNA polymerase," 2007, J. Biochem. 142:273-281.
Tan et al., "Isothermal DNA amplification coupled with DNA nanosphere-based colorimetric detection," Anal. Chem. 2005, 77:7984-7992.
Lizard et al., Nature Biotech. 1998, 6:1197-1202.
Mori et al., "Loop-mediated isothermal amplification (LAMP): a rapid, accurate, and cost-effective diagnostic method for infectious diseases," J. Infect. Chemother. 2009 15:62-69.
Kurn et al., "Novel isothermal, linear nucleic acid amplification systems for highly multiplexed applications," Clin. Chem. 2005, 51:10, 1973-1981.
Piekarowicz et al., "Characterization of the dsDNA prophage sequences in the genome of Neisseria gonorrhoeae and visualization of productive bacteriophage," 2007, BMC Microbiol., 7:66.
Liu et al., 2005, "Rapid identification of Streptococcus pyogenes with PCR primers from a putative transcriptional regulator gene," Res. Microbiol., 156:564-567.
Podbielski et al., Molecular characterization of the cfb gene encoding group B streptococcal CAMP-factor, 1994, Med. Microbiol. Immunol., 183:239-256.
Schoenmakers et al., 1992, Biotechniques, 12:870-874.
Fujishiro et al., 1995, Comput. Biol. Med., 25:61-80.
Bahador et al., 2005, Res. J. Agr. Biol. Sci. 1;142-145.
International Search Report and Written Opinion in corresponding Application No. PCT/US13/44796, dated Nov. 8, 2013, pp. 1-8.
El-Harakany AA et al., "Dissociation Constants and Related Thermodynamic Quantities of the Protonated Acid Form of Tris-(Hydroxymethyl)-Aminomethane in Mixtures of 2-Methoxyethanol and Water at Different Temperatures," Journal of Electroanalytical Chemistry:162:285-305 & 296 (1984).
Granholm K. et al., "Desorption of Metal Ions from Kraft Pulps. Part 1. Chelation of Hardwood and Softwood Kraft Pulp With EDTA," Bioresources:5(1)206-226 (2010).
Office Action in corresponding EP Application No. 10180482.1, dated May 30, 2014, pp. 1-5.
Response to the Article 94 in EP Application No. 11184367.8, dated Oct. 23, 2013, pp. 1-12.
Reddy et al., Joints Made by RecA Protein in the Interior of Linear Duplex DNA: Effects of Single-Stranded Ends, Length of Homology, and Dynamic State, *Biochemistry*, 33:11486-11492 (1994).
Notice of Reasons for Rejection in corresponding Application No. JP2012-209422, dated Mar. 3, 2015, pp. 1-15.
Tetart et al., "Phylogeny of the Major Head and Tail Genes of the Wide-Ranging T4-Type Bacteriophages," Journal of Bacteriology, vol. 183(1):358-366 (2001).
Office Action from corresponding Japanese Patent Application No. 2013-029664, dated May 8, 2015, pp. 1-7.
Jill S. Bleuit et al., "Mediator proteins orchestrate enzyme-ssDNA assembly during T4 recombination-dependent DNA replication and repair," PNAS:98(15):8298-8305, Jul. 17, 2001.
Beernink and Morrical, "RMPs: recombination/replication mediator proteins," TIBS Oct. 24, 1999:385-389.
Kozer et al., "Effect of Crowding on Protein-Protein Association Rates: Fundamental Differences between Low and High Mass Crowding Agents," J. Mol. Biol. (2004) 336, 763-774.
Kadyrov et al., "Properties of Bacteriophage T4 Proteins Deficient in Replication Repair," The Journal of Biological Chemistry, 276(27):25247-25255, 2003.
Transmittal of 3$^{rd}$ Party Observations in Application No. 10180482.1, dated Dec. 3, 2015, p. 1.
Third Party Observations under Article 115 EPC in Application No. 10180482, pp. 1-8, dated Nov. 27, 2015.
Third Party Observation for Application No. EP20100180482, pp. 1-2, dated Nov. 27, 2015 16:42.
Third Party Observation for Application No. EP20100180482, pp. 1-2, dated Nov. 27, 2015 16:46.
Third Party Observation for Application No. EP20100180482, pp. 1-2, dated Nov. 27, 2015 16:49.
Third Party Observation in corresponding European Application No. 10180482.1, dated Sep. 19, 2016, pp. 1-8.
Response to Office Action dated Mar. 1, 2016, in corresponding European Application No. 10180482.1, dated Aug. 17, 2016, pp. 1-10.
Office Action in corresponding European Application No. 10180482.1, dated Jan. 17, 2017, pp. 1-7.

\* cited by examiner

Target A Oligonucleotide ——
Target B Oligonucleotide ----
RecA ∿∿∿
SSB ⊂⊃
RecO, RecR ⊙

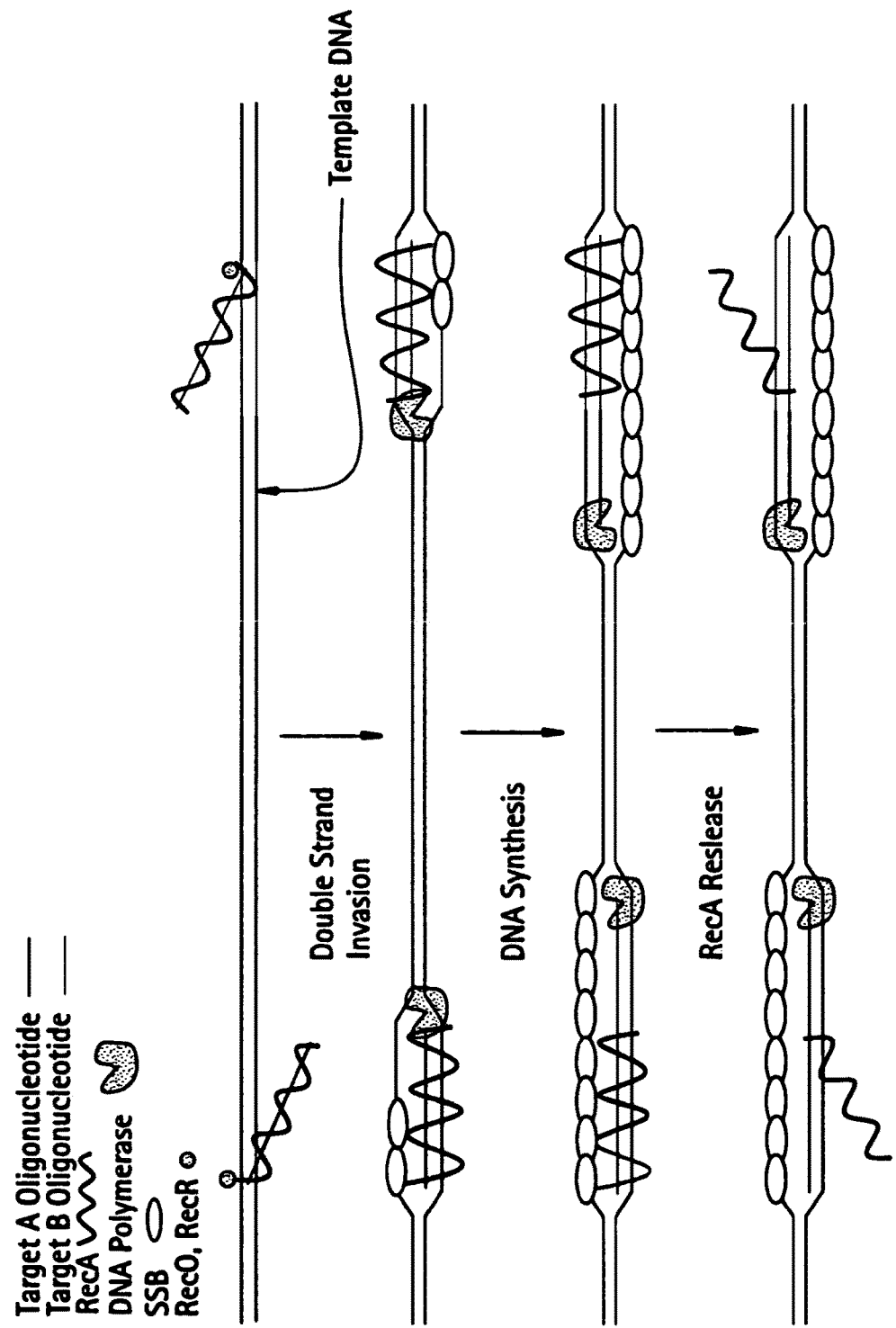

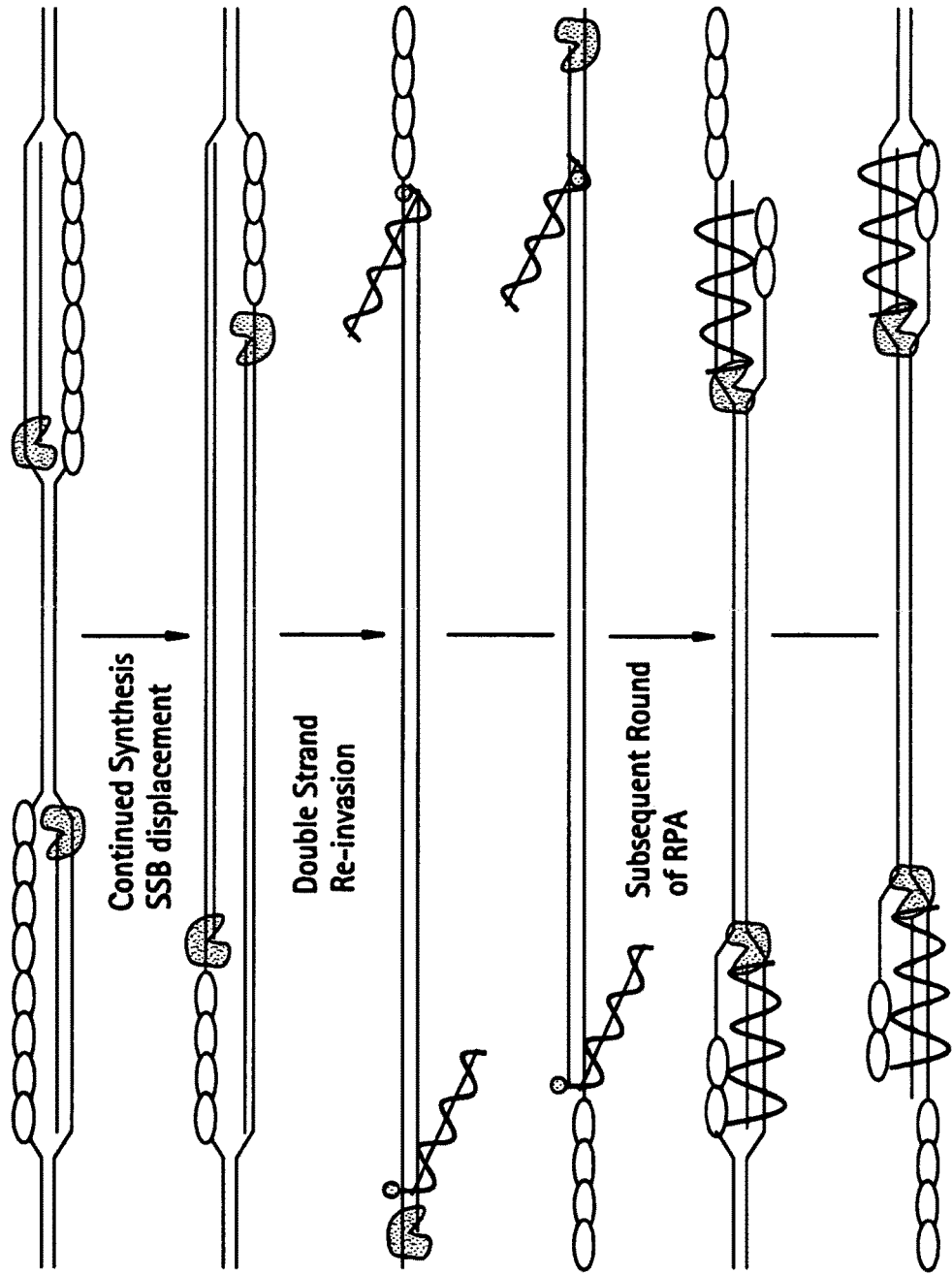

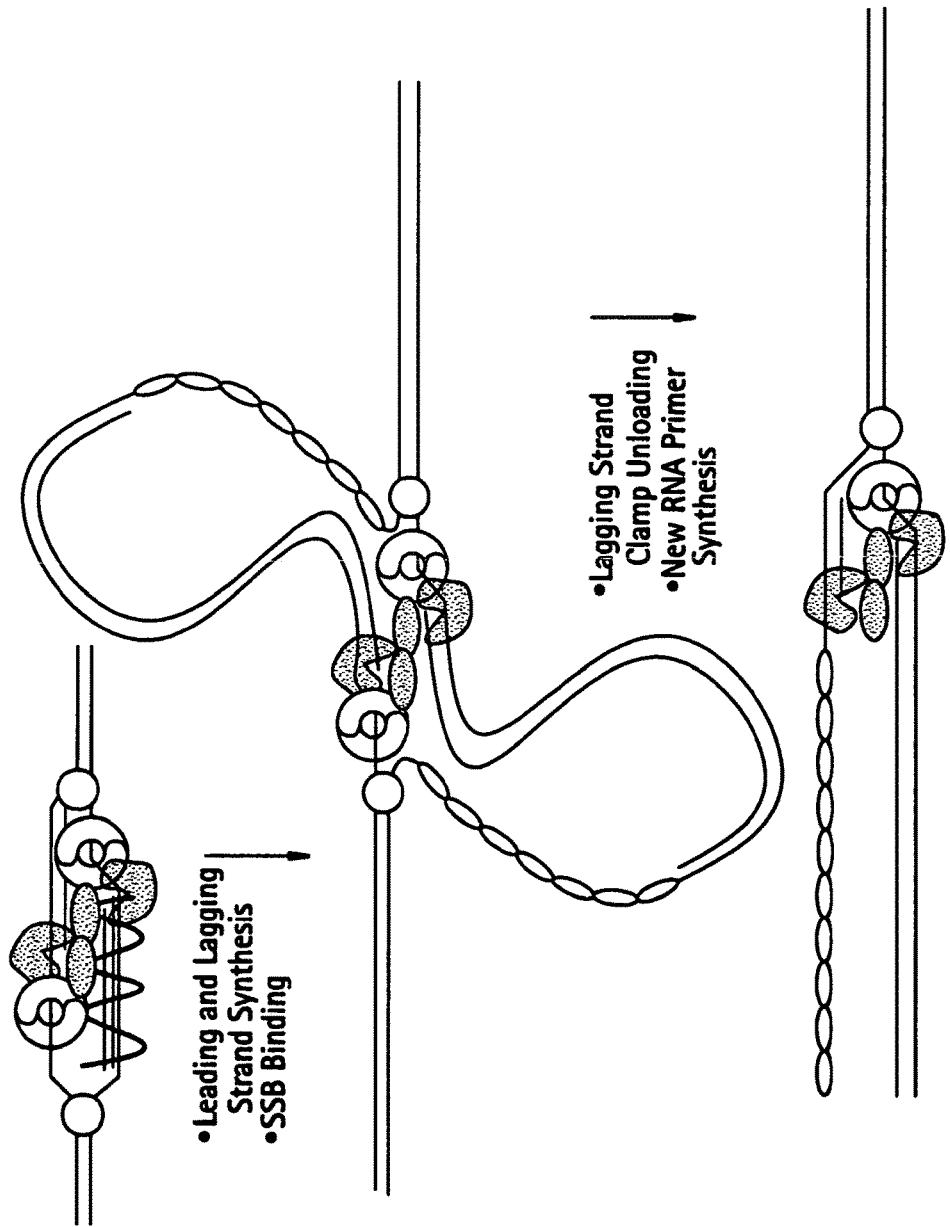

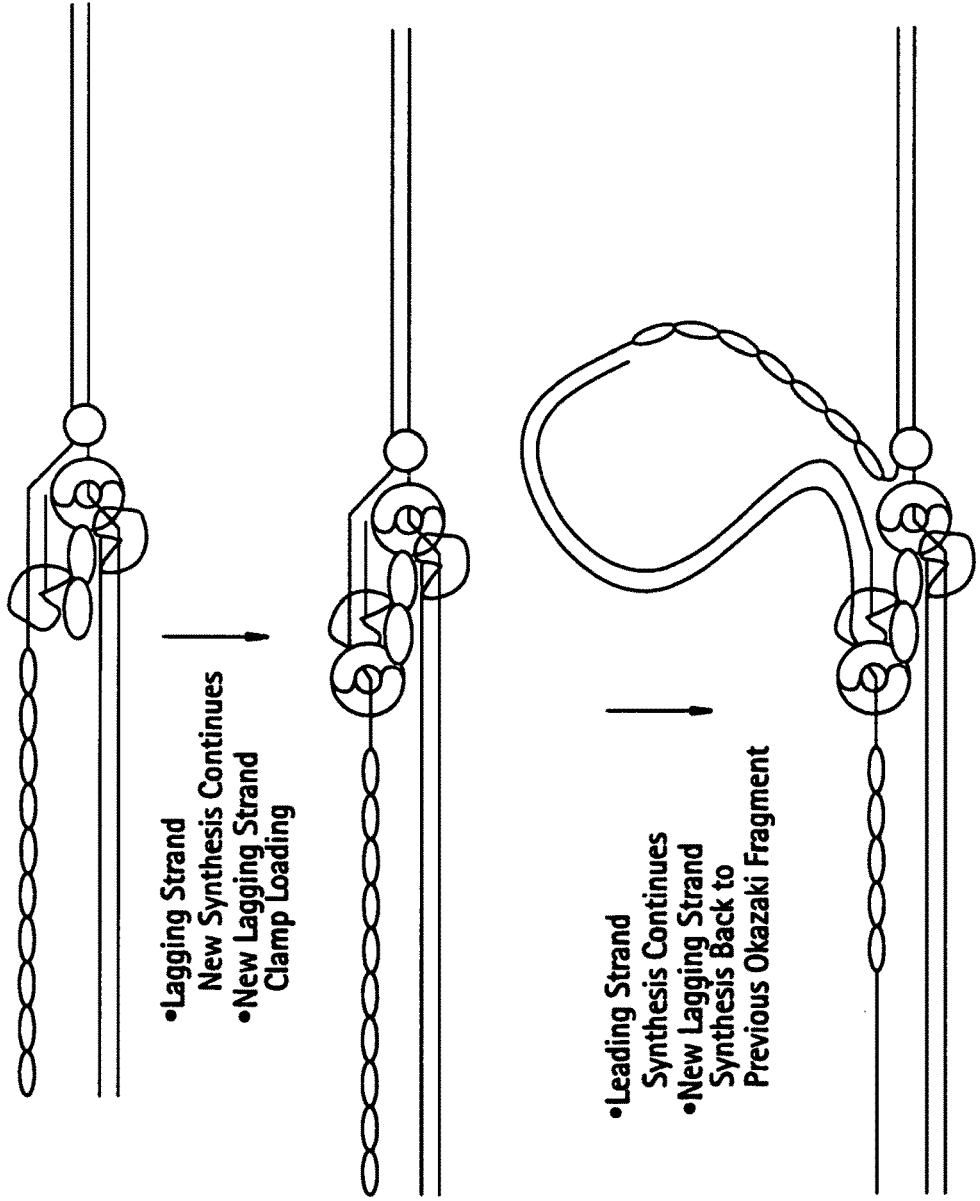

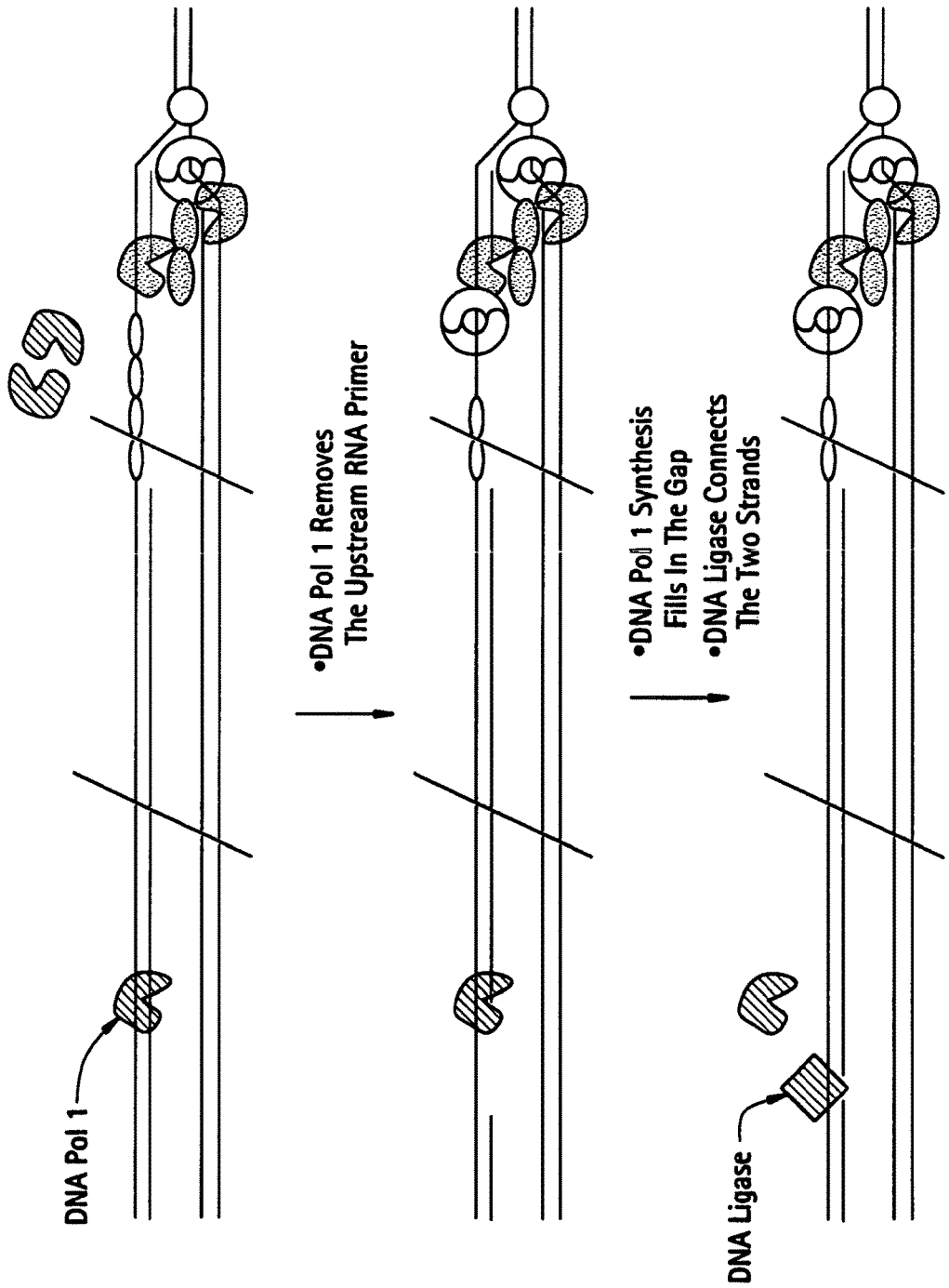

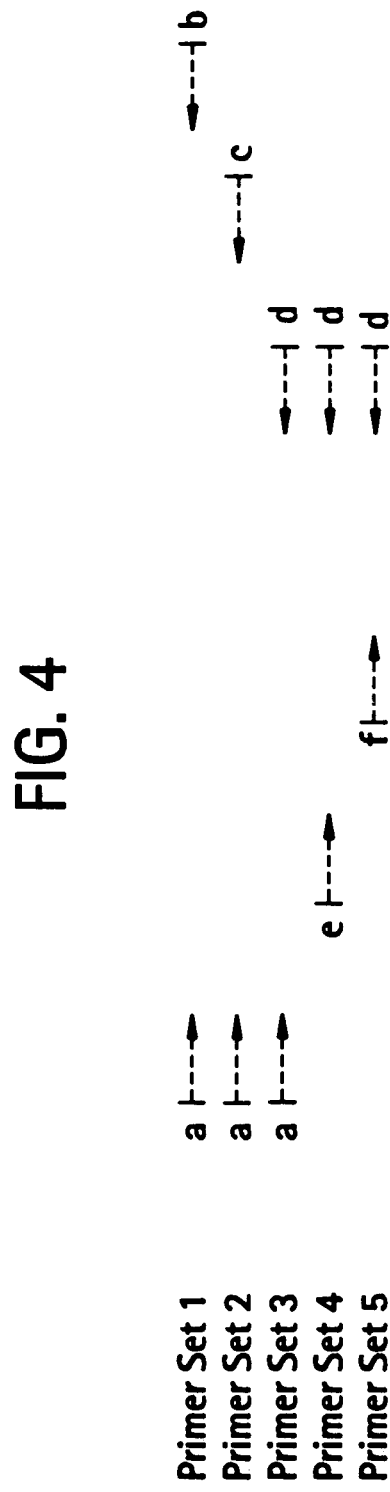

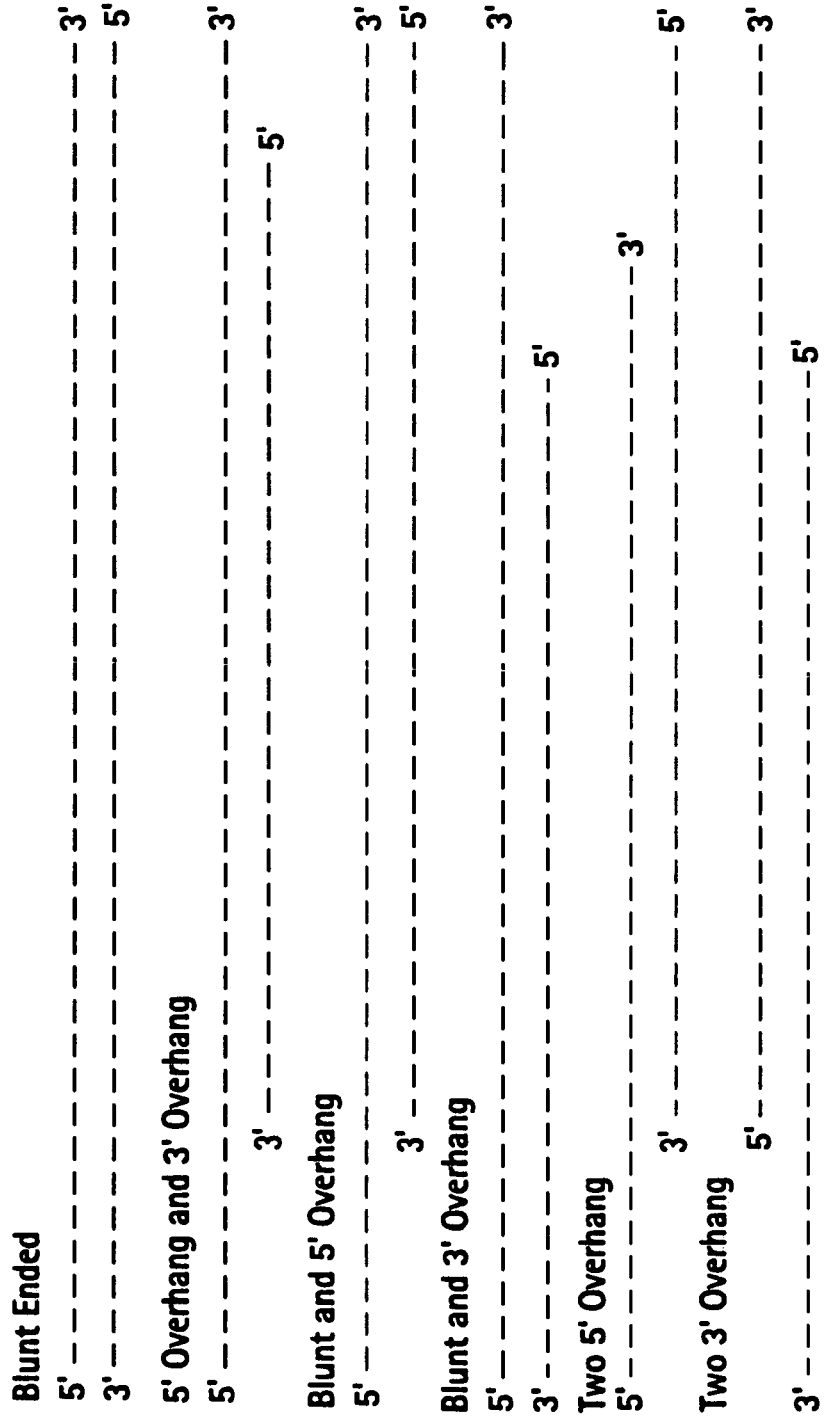

Orientation of nucleic acid primer pairs.

RPA Reaction in Progress

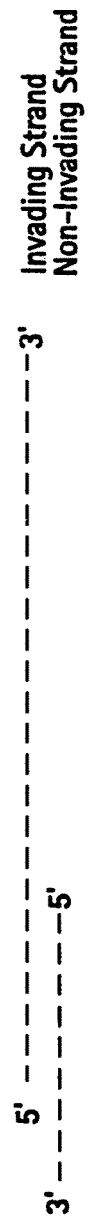
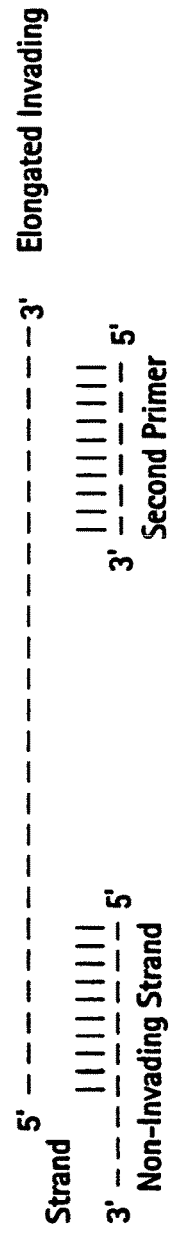
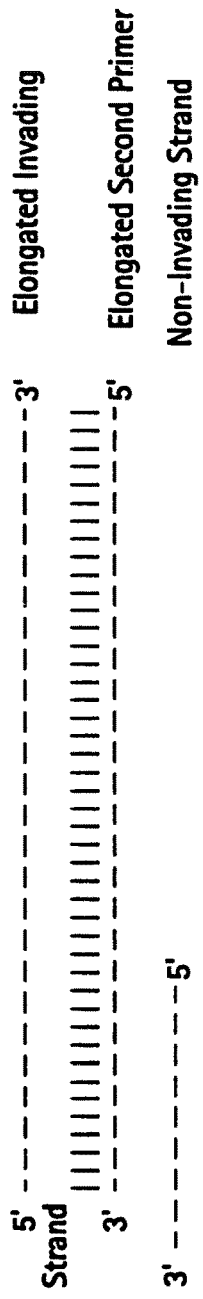
FIG. 8A
FIG. 8B
FIG. 8C

*E.coli* SSB and T4 phage gr32(N) both recombination/extension reactions

Schematic structure of gp32 proteins used in this study

Titration of untagged gp32, and requirement for uvsY

FIG. 34 Methods to limit primer noise

Deliberate use of 'hairpin' oligonucleotides can lead to self-priming of displaced strands FIG. 43 Theoretical consideration of primer noise origin

FIG. 44
Oligonucleotide design strategies
1. Length
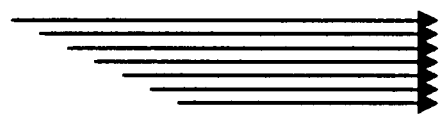
2. Inclusion of LNA bases, or other modified sugars.
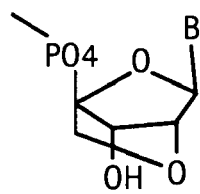
3. Addition of sequences to 5' end of oligo.
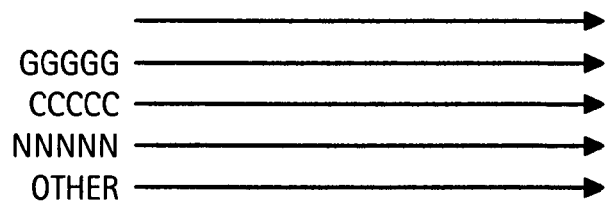

FIG. 46
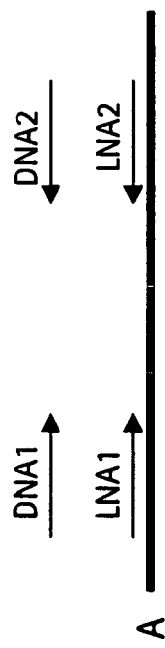
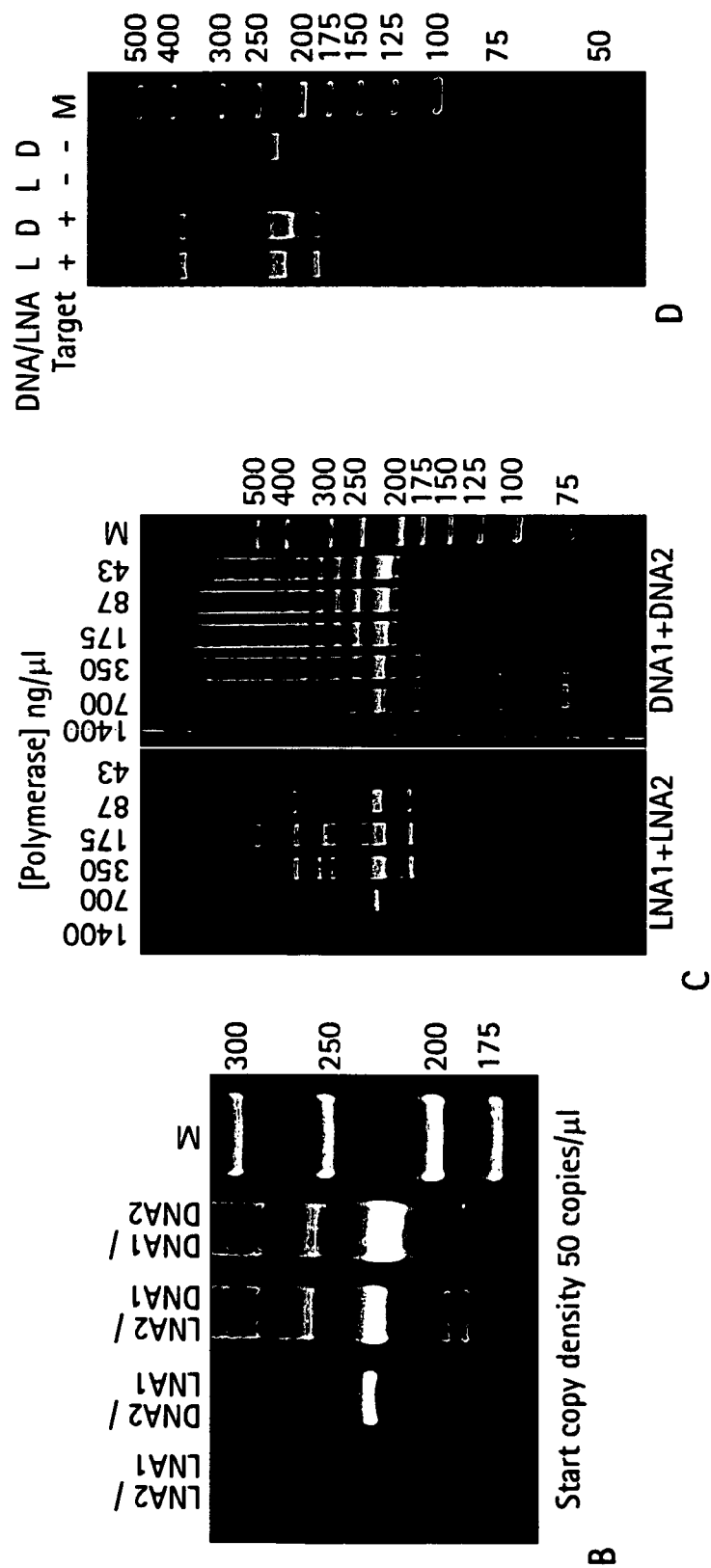

Betaine can regulate signal to noise ratio

Detection strategies

FIG. 52
Bead Capture: Results
- A short oligo can be used for capture but does not support efficient amplification
- Significant quantities of specific products are captured onto beads
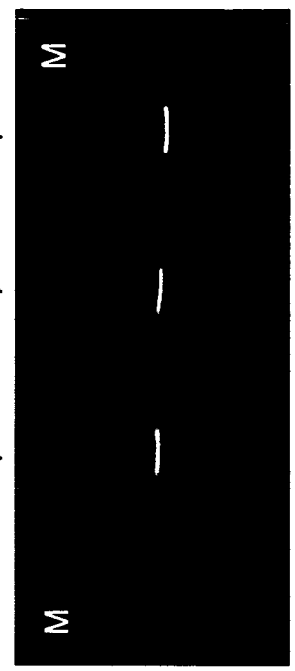
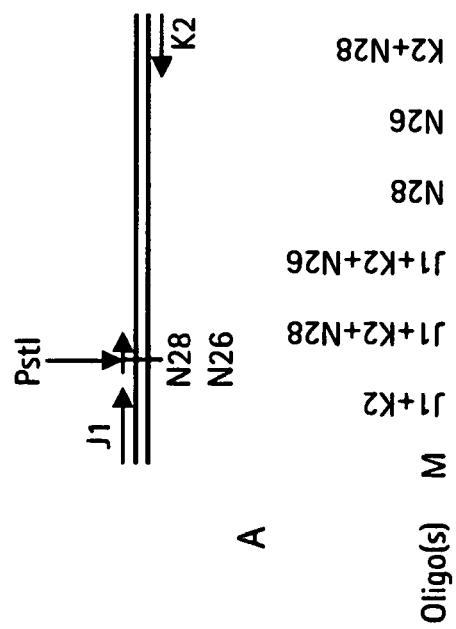
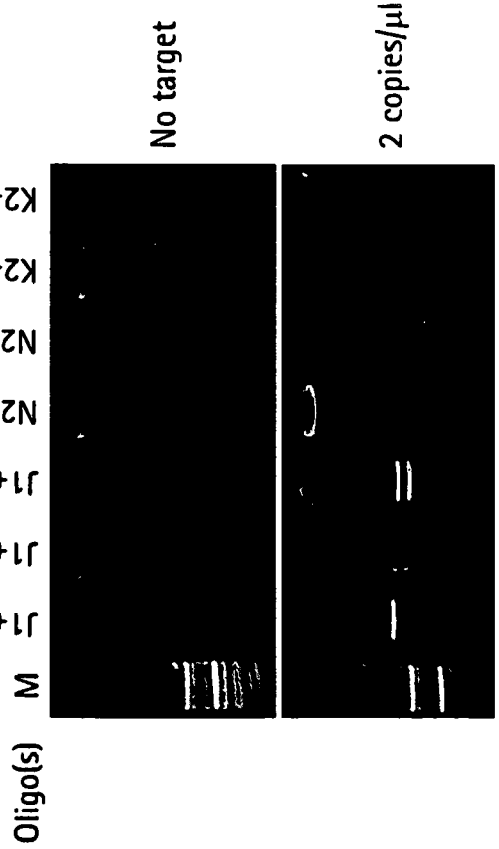

Lyophilization

- Complete RPA reactions were lyophilized under a variety of conditions (A-D).
- Reconstitution with buffer and incubation with template yields good product generation after 3, 6 and 10 days of storage at room temperature.

RPA Is Not Inhibited by blood

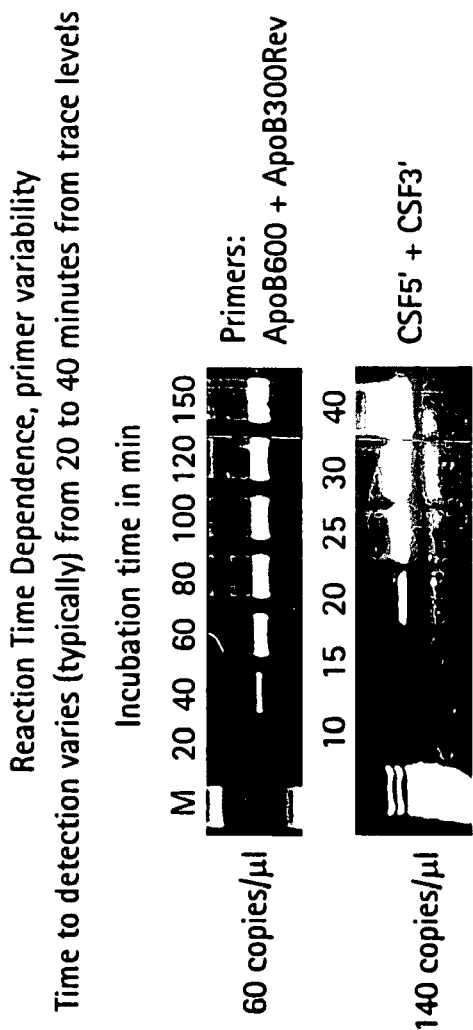

FIG. 67

Reaction Time Dependence, primer variability
Time to detection varies (typically) from 20 to 40 minutes from trace levels Incubation time in min

M  20  40  60  80  100  120  150

60 copies/μl

Primers:
ApoB600 + ApoB300Rev 10  15  20  25  30  40

140 copies/μl

CSF5' + CSF3'

|  | G | A | T | C | T/C |
|---|---|---|---|---|---|
| ApoB600   GCTCACTGTTCTGCATCTGGTCAATGGTTCTG | 25% | 12.5% | 37.5% | 25% | 62.5% |
| ApoB300Rev CTATCCAAGATTGGGCTAAACGTATGAAAGCA | 22% | 37.5% | 22% | 18.5% | 40.5% |
| CSF5'     AGACTCTTCCACACACCTGGCCATCTTCAGC | 12% | 24% | 21% | 42.5% | 63.5 |
| CSF3'     GTTGCTAACCACCCTGTGTCTCAGTTTTCCTAC | 15% | 15% | 36% | 33% | 70% |

Composition hypotheses:
1. High pyrimidine content?
2. High C, low G ?
3. Distribution features important?

Observations:
1. Fast pair have paucity of G.
2. Fast pair have high C content
3. A/T content correlation less clear.

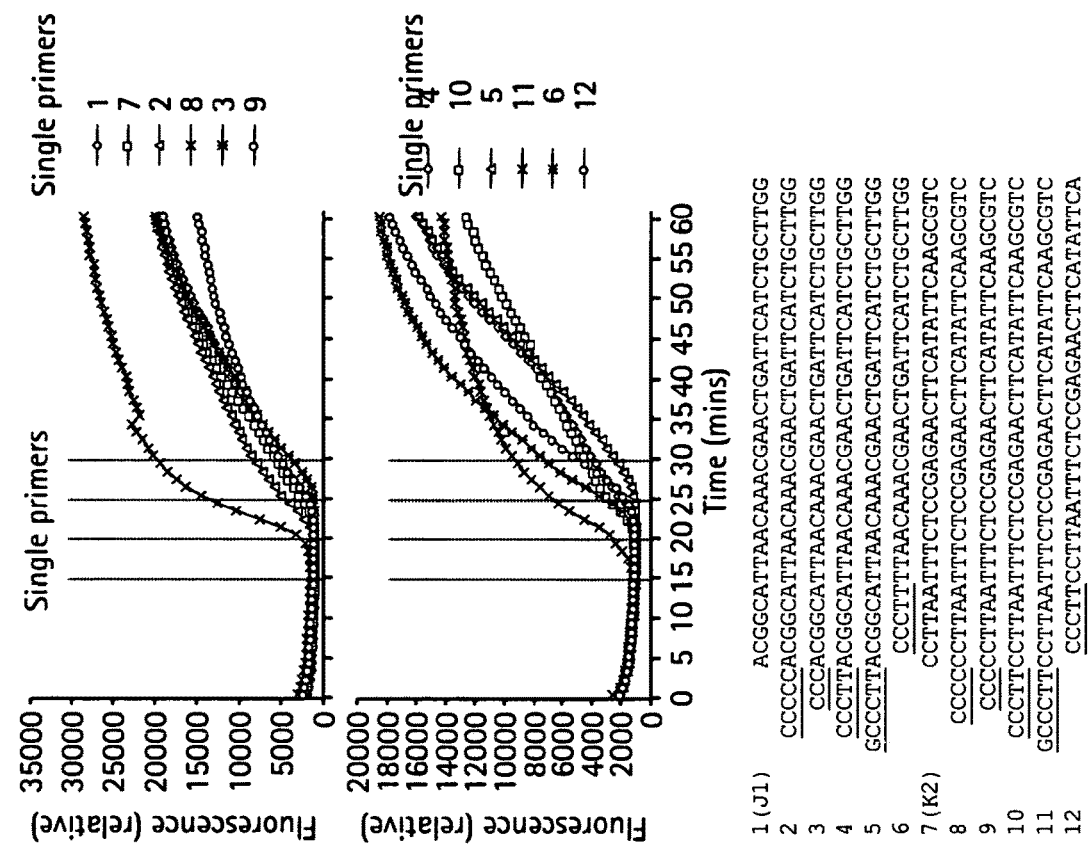
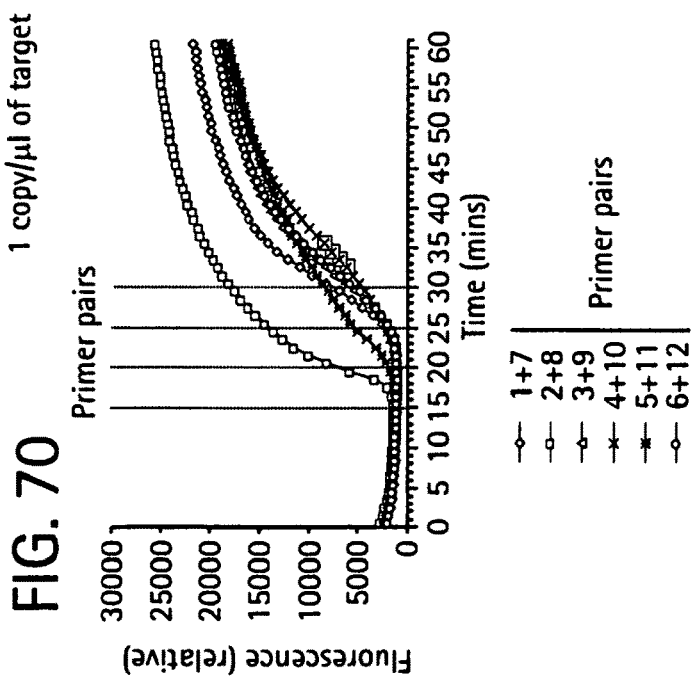
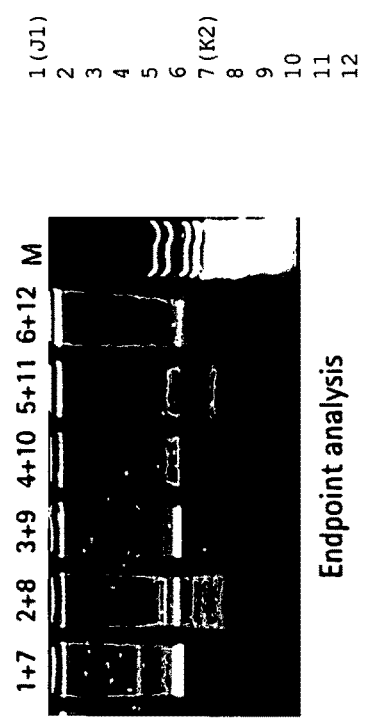
FIG. 70

FIG. 71

Third probes in real-time

Use wide repertoire of nucleases that can discriminate probe/target hybrids

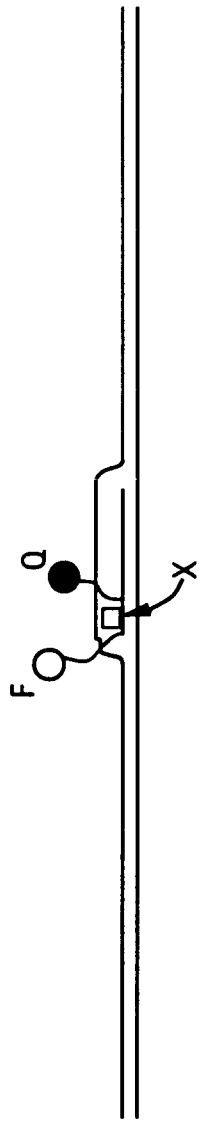

Where probe is DNA and X=
8-oxoguanine and is cut by fpg
Thymine glycol and is cut by Nth
Abasic mimic (tetrahydrofuranyl) and is cut by Nfo Or probe is RNA and RNase H is employed
Or amplification primers are 5'LNA-protected and T7 exo is used
Or 'backfire' probe is used and restriction endonuclease is used Example of probes for RPA using Nfo enzyme cutting

SEQUENCE LISTING

<160> NUMBER OF SEQ ID NOS: 121

<210> SEQ ID NO 1
<211> LENGTH: 327
<212> TYPE: DNA
<213> ORGANISM: Escherichia coli

<400> SEQUENCE: 1

```
atcatgattg gtgaaggtcc ggcggcacgc tccattaaaa ttgatttgcc gccgtttacc    60
ctgattggtg caaccacgcg cgcaggttcg ctgacatcac cgttgcgcga ccgttttggt   120
attgtgcaac gtctggagtt ttatcaggtg ccggatctgc aatatatcgt cagtcgcagc   180
gcacgcttta tggggcttga gatgagtgat gacggcgcgc tggaagttgc tcgtcgcgct   240
cgcggtacgc cgcgcattgc caaccgtctg ctgcgtcgag tgcgtgattt cgccgaagtg   300
aagcacgatg gcaccatctc ggcagat                                      327
```

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

```
ctagcgatgg tgccatcgta cagaattccc tcagcatctg ccga                    44
```

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3

```
ctcactatac ctcagcatca tgattggtga aggtccggcg gcac                    44
```

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Biotin-g

<400> SEQUENCE: 4

```
gctaatacga ctcactatac ctcagcatca tgattggtga aggtccggcg gcac         54
```

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (1)..(1)
<223> OTHER INFORMATION: Biotin-c

<400> SEQUENCE: 5
ctcactatac ctcagcatca tgattggtga aggtccggcg gcac            44

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctatgcgaat tcagcgaacc tgcgcgcgtg gttgcaccaa tcaggg          46

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctatgcgaat tcggtgatgt cagcgaacct gcgcgcgtgg ttgca            45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctatgcgaat tctccagacg ttgcacaata ccaaaacggt cgcgc            45

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ctatgcgaat tccgtgcgct gcgactgacg atatattgca gatcc            45

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Biotin-a

<400> SEQUENCE: 10
atctgccgag atggtgcc                                          18

<210> SEQ ID NO 11
```

```
<211> LENGTH: 158
<212> TYPE: DNA
<213> ORGANISM: Homo sapiens

<400> SEQUENCE: 11
aaccaactcc gccccgggcc acggcctcgc tctgctccag gtactttgtc agcttcatca        60
tccagttcca gttccacgag gcactgtgcc aggcagctgg ccacacgggc cccctgcaca       120
agtgtgacat ctaccagtcc aaggaggccg ggcagcgc                               158

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
attcgtcagc ctcgctctgc tccaggtact ttgtcagctt catc                         44

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcctccttgg actggtagat gtcacacttg tgc                                     33

<210> SEQ ID NO 14
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gcgctgcccg gcctccttgg actggtagat gtcacacttg tgc                          43

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tatgcgaatt gcctccttgg actggtagat gtcacacttg tgc                          43

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Biotin-g

<400> SEQUENCE: 16
```
gcctccttgg actggtagat gtcacacttg tg					32

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ggccacggcc tcgctctgct ccaggtactt tgtcagcttc atc					43

<210> SEQ ID NO 18
<211> LENGTH: 791
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
ggtaccactt tgccggaaga tgtagcagat cgcgccattc gccccaaatt actggaagag					60 tatgttggtc agccgaggtt cgttcacaga tggagttttt catcaaagca gcgaaactgc					120 gcggcgatgc cctcgatcat ttgttgattt ttggtcctcc ggggttgggt aaaactacgc					180 ttgccaacat tgtcgccaat gaaatgggcg ttaatttacg cacgacttct ggtccggtgc					240 tggaaaaggc gggcgatttg gctgcgatgc tcactaacct tgaaccgcat gacgtgctgt					300 ttattgatga gatccaccgt ctatcgccag ttgttgaaga agtgctgtac ccggcaatgg					360 aagactacca actggatatc atgattggtg aaggtccggc ggcacgctcc attaaaattg					420 atttgccgcc gtttaccctg attggtgcaa ccacgcgcgc aggttcgctg acatcaccgt					480 tgcgcgaccg ttttggtatt gtgcaacgtc tggagtttta tcaggtgccg gatctgcaat					540 atatcgtcag tcgcagcgca cgcttttatg ggcttgagat gagtgatgac ggcgcgctgg					600 aagttgctcg tcgcgctcgc ggtacgccgc gcattgccaa ccgtctgctg cgtcgagtgc					660 gtgatttcgc cgaagtgaag cacgatggca ccatctcggc agatatcgct gctcaggcgc					720 tggatatgtt gaatgtcgat gctgaaggtt tcgattatat ggaccgcaaa ttgttgctgg					780 cggtaatcga t					791

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Biotin-c

<400> SEQUENCE: 19
ctcactatac ctcagcatca tgattggtga aggtccggcg gcac					44

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagtgtatct ggaaagccta caggacacca aaa                          33

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgctttcata cgtttagccc aatcttggat ag                           32

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tggtaaacgg aagtctggca gggtgattct cg                           32

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caattgtgtg tgagatgtgg ggaagctgga at                           32

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaggtggttc cattccctat gtcagcattt gc                           32

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gggtttgaga gttgtgcatt tgcttgaaaa tc                           32

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ttgaatttca agtttagaaa agttgaggga gccag        35

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaagctgtaa ctctaagtat cagtgtgaaa c        31

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gttgtccagt tgcacttcgc tgcagagtac c        31

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ttgggcactt ggatatgatg gaactggcac        30

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acagaaagct attaaagcaa ctgacggtgt gg        32

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccatcttcag agaacgcttt aacagcaatc c        31

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gttgctaacc accctgtgtc tcagttttcc tac                                  33

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33 agatcttcc acacaccact ggccatcttc agc                                   33

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaacacttgt catagtttag aacgaactaa cg                                   32

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaattataac gattccacat ttatcctcat tgac                                 34

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttgctggaca tggtatcaca gaagtctggg atg                                  33

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccataggcag cccaaaaaga cagacagaaa ga                                   32

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aaacaaaggc agatcccaag ctcttcctct tcc                           33

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ataccattta cgtttgtgtg tgcatctgta agc                           33

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggtggacatg ttggcttctc tctgttctta ac                            32

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggtggcacgt gcctgtagtc tcagctactt gc                            32

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tacacagggc ttccggtgca ggtcacaggg a                             31

<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccttcccagg ctctagcagc agctcatggt gg                            32

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
actggcacag aacaggcact tagggaaccc                               30

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggaggaactg ggaaccacac aggttaatta                                        30

<210> SEQ ID NO 46
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gctcactgtt ctgcatctgg tcaatggttc tg                                     32

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctatccaaga ttgggctaaa cgtatgaaag ca                                     32

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
atggtaaatt ctggtgtgga aaacctggat gg                                     32

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
taaattctgg tgtggaaaac ctggatgg                                          28

<210> SEQ ID NO 50
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
attctggtgt ggaaaacctg gatgg                                             25

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctatccaaga ttgggctaaa cgtatgaaag ca                                    32

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccaagattgg gctaaacgta tgaaagca                                         28

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agattgggct aaacgtatga aagca                                            25

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggtggacatg ttggcttctc tctgttctta ac                                    32

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gacatgttgg cttctctctg ttcttaac                                         28

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
atgttggctt ctctctgttc ttaac                                            25

```
<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ggtggcacgt gcctgtagtc tcagctactt gc                                     32

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcacgtgcct gtagtctcag ctacttgc                                          28

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cgtgcctgta gtctcagcta cttgc                                             25

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aaagctgtaa ctctaagtat cagtgtgaaa c                                      31

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gctgtaactc taagtatcag tgtgaaac                                          28

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gtaactctaa gtatcagtgt gaaac                                             25

<210> SEQ ID NO 63
```

-continued

```
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gttgtccagt tgcacttcgc tgcagagtac c                                    31

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gtccagttgc acttcgctgc agagtacc                                        28

<210> SEQ ID NO 65
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cagttgcact tcgctgcaga gtacc                                           25

<210> SEQ ID NO 66
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acggcattaa caaacgaact gattcatctg cttgg                                35

<210> SEQ ID NO 67
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ataaccattt cttcaatcat ttcaaagaca cggtc                                35

<210> SEQ ID NO 68
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tatagacgca aagcacgaat caaagctctc aaacc                                35

<210> SEQ ID NO 69
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ccttaatttc tccgagaact tcatattcaa gcgtc                               35

<210> SEQ ID NO 70
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
atatgaagtt ctcggagaaa ttaaggattt gtcgg                               35

<210> SEQ ID NO 71
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
aatcagctgt ctgtcaggat gatccgtttg aagcg                               35

<210> SEQ ID NO 72
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cattaacaaa cgaactgatt catctgcttg g                                   31

<210> SEQ ID NO 73
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acagatgaaa cagctttctc atcagtttcg                                     30

<210> SEQ ID NO 74
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gctccttgga ctggtagatg tcacacttgt g                                   31

<210> SEQ ID NO 75
<211> LENGTH: 32
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 75
gccttggctc tgctgtgcgc atgtgactta gc                                   32

<210> SEQ ID NO 76
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ggatgaataa gctgcagctg attaaagg                                        28

<210> SEQ ID NO 77
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
atgaataagc tgcagctgat taaagg                                          26

<210> SEQ ID NO 78
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ttccgactgc gagcttattg ttaaggcaat g                                    31

<210> SEQ ID NO 79
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cttaagtaag caattgctgt aaagtcgtca c                                    31

<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)..(1)
<223> OTHER INFORMATION: Biotin-c
<220> FEATURE:
<221> NAME/KEY: modified_base
<222> LOCATION: (25)..(25)
<223> OTHER INFORMATION: tetrahydrofuran abasic site
<220> FEATURE:
<221> NAME/KEY: modified_base
```

```
<222> LOCATION: (39)..(39)
<223> OTHER INFORMATION: c-DIG

<400> SEQUENCE: 80
catgattgga tgaataagct gcagntgatt aaaggaaac                              39

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 81

His His His His His His
1               5

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Gln Lys Leu Ile Ser Glu Glu Asp Leu
1               5                   10

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asp Tyr Lys Asp Asp Asp Asp Lys
1               5

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Asp Gln Val Asp Pro Arg Leu Ile Asp Gly Lys
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Glu Glu Thr Ala Arg Phe Gln Pro Gly Tyr Arg Ser
1               5                   10

<210> SEQ ID NO 86
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Lys Pro Ile Pro Asn Pro Leu Leu Gly Leu Asp Ser Thr
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Tyr Thr Asp Ile Glu Met Asn Arg Leu Gly Lys
1               5                   10

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Leu Tyr Asp Asp Asp Asp Lys
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Tyr Pro Tyr Asp Val Pro Asp Tyr Ala
1               5

<210> SEQ ID NO 90
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Biotin-c

<400> SEQUENCE: 90
ctcactatac ctcagcatca tgattggtga aggtccggcg gcacgctcc            49

<210> SEQ ID NO 91
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 91
ctatgcgaat tc                                                          12

<210> SEQ ID NO 92
<211> LENGTH: 453
<212> TYPE: DNA
<213> ORGANISM: Bacillus subtilis

<400> SEQUENCE: 92
aaaaatcaag aagaaaatat aagcgacacg gcattaacaa acgaactgat tcatctgctt      60
ggccattccc ggcatgattg gatgaataag ctgcagctga ttaaaggaaa cttaagctta     120
cagaagtatg accgtgtctt tgaaatgatt gaagaaatgg ttatagacgc aaagcacgaa     180
tcaaagctct caaacctgaa acaccgcat ttggcgtttg attttcttac gtttaattgg      240
aaaacccatt atatgacgct tgaatatgaa gttctcggag aaattaagga tttgtcggct     300
tatgatcaaa agctggcgaa actgatgaga aagctgtttc atctgtttga tcaagcagtc     360
agcagagaga gtgaaaatca tttaacggtt tcgcttcaaa cggatcatcc tgacagacag     420
ctgattctgt accttgattt tcacggcgcc ttt                                  453

<210> SEQ ID NO 93
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
acgataggct tatgtgtacg gctagacatg g                                     31

<210> SEQ ID NO 94
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
acgataggct tatgtgtacg gctagacatg gtctagccgt acacataagc ctatcgt         57

<210> SEQ ID NO 95
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
acgataggct tatgtgtacg gctagacatg gctagccgta cacataagcc tatcgt          56

<210> SEQ ID NO 96
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96

```
acgatggctt atgtgtacgg ctagacatgg tctagccgta cacataagcc atcgt          55
```

<210> SEQ ID NO 97
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97

```
acgatggctt atgtgtacgg ctagacatgg tctagccgta cacataagcc tatcgt         56
```

<210> SEQ ID NO 98
<211> LENGTH: 109
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98

```
acgataggct tatgtgtacg gctagacatg gtctagccgt acacataagc ctatcgtagg     60
cttatgtgta cggctagacc atgtctagcc gtacacataa gcctatcgt               109
```

<210> SEQ ID NO 99
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99

```
cccccacggc attaacaaac gaactgattc atctgcttgg                           40
```

<210> SEQ ID NO 100
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100

```
ggggacggc attaacaaac gaactgattc atctgcttgg                            40
```

<210> SEQ ID NO 101
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101

```
ccccccttaa tttctccgag aacttcatat tcaagcgtc                            39
```

<210> SEQ ID NO 102
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gggggcctta atttctccga gaacttcata ttcaagcgtc    40

<210> SEQ ID NO 103
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103 tttttttacgg cattaacaaa cgaactgatt catctgcttg g    41

<210> SEQ ID NO 104
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tcttctacgg cattaacaaa cgaactgatt catctgcttg g    41

<210> SEQ ID NO 105
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ctctctacgg cattaacaaa cgaactgatt catctgcttg g    41

<210> SEQ ID NO 106
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106 tttttttcctt aatttctccg agaacttcat attcaagcgt c    41

<210> SEQ ID NO 107
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
tcttctcctt aatttctccg agaacttcat attcaagcgt c    41

<210> SEQ ID NO 108
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108 ctctctccttt aatttctccg agaacttcat attcaagcgt c        41

<210> SEQ ID NO 109
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cccacggcat taacaaacga actgattcat ctgcttgg        38

<210> SEQ ID NO 110
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
cccttacggc attaacaaac gaactgattc atctgcttgg        40

<210> SEQ ID NO 111
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gcccttacgg cattaacaaa cgaactgatt catctgcttg g        41

<210> SEQ ID NO 112
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cccttttaac aaacgaactg attcatctgc ttgg        34

<210> SEQ ID NO 113
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
cccccttaat ttctccgaga acttcatatt caagcgtc        38

<210> SEQ ID NO 114
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cccttcctta atttctccga gaacttcata ttcaagcgtc        40

<210> SEQ ID NO 115
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gcccttcctt aatttctccg agaacttcat attcaagcgt c                          41

<210> SEQ ID NO 116
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
cccttcctta atttctccga gaacttcata ttca                                  34

<210> SEQ ID NO 117
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: FAM-a

<400> SEQUENCE: 117
aaagctgtaa ctctaagtat cagtgtgaaa c                                     31

<210> SEQ ID NO 118
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: FAM-a
<220> FEATURE:
<221> NAME/KEY: modified_base
<222> LOCATION: (15)..(15)
<223> OTHER INFORMATION: g-BHQ1

<400> SEQUENCE: 118
atgcggtgtt ttcag                                                       15

<210> SEQ ID NO 119
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: FAM-a
<220> FEATURE:
<221> NAME/KEY: modified_base

```
<222> LOCATION: (10)..(10)
<223> OTHER INFORMATION: t-BHQ1

<400> SEQUENCE: 119
atgcggtgtt                                                              10

<210> SEQ ID NO 120
<211> LENGTH: 42
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (28)..(28)
<223> OTHER INFORMATION: tetrahydrofuran abasic site

<400> SEQUENCE: 120
catgattgga tgaataagct gcagctgntt aaaggaaact ta                           42

<210> SEQ ID NO 121
<211> LENGTH: 37
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (33)..(33)
<223> OTHER INFORMATION: tetrahydrofuran abasic site

<400> SEQUENCE: 121
catgattgga tgaataagct gcagctgatt aanggaa                                 37
```

RECOMBINASE POLYMERASE AMPLIFICATION

RELATED APPLICATIONS

This application is a continuation of U.S. application Ser. No. 14/989,499, filed Jan. 6, 2016, now U.S. Pat. No. 9,663,820, which is a continuation of U.S. application Ser. No. 14/610,915, filed Jan. 30, 2015, now U.S. Pat. No. 9,309,502, which is a continuation of U.S. application Ser. No. 13/851,711, filed Mar. 27, 2013, now U.S. Pat. No. 8,945,845, which is a continuation of U.S. application Ser. No. 13/212,361, filed Aug. 18, 2011, now U.S. Pat. No. 8,426,134, which is a continuation of U.S. application Ser. No. 12/660,117, filed Feb. 19, 2010, now U.S. Pat. No. 8,030,000, which is a divisional of U.S. application Ser. No. 11/628,179, filed Aug.30, 2007, now U.S. Pat. No. 7,666,598, which is a National Stage of International Application No. PCT/IB2005/001560, filed Apr. 11, 2005, which claims the benefit of priority to Provisional Application No. 60/576,148, filed Jun. 1, 2004, Provisional Application No. 60/576,162, filed Jun. 1, 2004, Provisional Application No. 60/622,291, filed Oct. 26, 2004, Provisional Application No. 60/632,746, filed Dec. 2, 2004, and is also a continuation-in-part of U.S. application Ser. No. 10/931,916, filed Sep. 1, 2004, now U.S. Pat. No. 7,399,590, which claims the benefit of priority to Provisional Application No. 60/553,999, filed Mar. 16, 2004. U.S. application Ser. No. 10/931,916 is also a continuation-in-part of U.S. application Ser. No. 10/371,641, filed Feb. 21, 2003, now U.S. Pat. No. 7,270,981, which claims the benefit of priority to Provisional Application No. 60/358,563, filed Feb. 21, 2002. All of the foregoing applications are incorporated by reference herein.

BACKGROUND OF THE INVENTION

The ability to amplify DNA lies at the heart of modern biological and medical research. This is because most molecular biology techniques rely on samples containing many identical molecules to increase the sensitivity of an assay or to prepare enough material for further processing. Among the various nucleic acid amplification techniques, polymerase chain reaction (PCR) is the most common because of its sensitivity and efficiency at amplifying short nucleic acid sequences.

While PCR is of great utility, it is also limited in a number of ways. The first limitation of PCR is that it relies on multiple cycles of thermal melting (denaturing) at high temperatures followed by hybridization and elongation at a reduced temperature. To maximize efficiency and to minimize noise, complex temperature control of multiple reactions is required. This necessitates the use of a thermocycler controllable rapid heating/cooling block made with exotic material (e.g., gold plated silver blocks), or a robotic mechanism to move samples between temperature-controlled zones. Because of the high-temperature required to melt DNA in physiological salt conditions, PCR technology requires either the addition of fresh polymerase per cycle or the use of thermostable polymerases. The approach of adding fresh polymerase has not been automated and is thus labor intensive and prone to errors (e.g., contamination, dropped tubes, labeling errors). Furthermore, the need to add enzymes and to mix each reaction individually presents serious drawbacks that have limited adaptation of enzyme-addition PCR methods to the small scale.

Compared to methods involving the addition of fresh polymerase, the use of thermostable polymerases in PCR is the most widely practiced. This approach suffers from the fact that thermostable polymerases are found in a limited number of organisms, and the replication mechanisms used by thermophilic organisms are poorly understood. The available repertoire of thermostable polymerases is limited to single polypeptide polymerase enzymes involved in DNA repair, and/or lagging strand synthesis. DNA repair and/or lagging strand polymerases are poor choices for DNA amplification because they exhibit poor processivity (distributive synthesis). In part as a consequence of using repair and/or lagging strand polymerases (e.g. Taq, Pfu, Vent polymerases), and due to the formation of inhibitory secondary or tertiary nucleic acid structures following thermal melting, current PCR protocols do not readily amplify sequences longer than several thousands of base pairs. Reliable synthesis (and amplification) of longer templates will rely on polymerases and auxiliary enzymatic complexes collectively exhibiting much higher levels of processivity, strand displacement, and secondary structure resolution, as well as limiting the formation of inhibitory higher order nucleic acid structures that may form on cooling heat-denatured DNA.

A second limitation of PCR is that it relies on solution hybridization between oligonucleotides (PCR primers) and denatured template DNA (i.e., the DNA to be amplified) in an aqueous environment. To be effective, PCR reactions are performed in a short time because the thermostable polymerases have a rapidly declining activity at PCR temperatures. Further, for effective hybridization in a short time, a feature critical to rapid turnaround, it is necessary to perform PCR in an environment with high concentrations of oligonucleotides. The high oligonucleotide concentration also ensures rapid interaction of target sequences with the oligonucleotides in competition with the heat-denatured complementary strand still present in solution. High oligonucleotide primer concentrations can cause problems, particularly when the copy number of the target sequence is low and present in a complex mixture of DNA molecules. This would be the case, for example, in a PCR of a genome to determine the genetic polymorphism in one locus.

One problem with using high oligonucleotide concentrations is that it enhances the degree of false priming at only partly matched sequences in the complex DNA mixture. False priming refers to the hybridization of a primer to a template DNA in PCR even when the primer sequence is not completely complementary to the template nucleic acid, which can lead to non-specific amplification of nucleic acids. Noise, due to false priming, increases with the oligonucleotide concentration and the complexity of total starting DNA. In addition, the possibility of false priming increases as the copy number of target sequences decreases. Where the conditions for false priming are favorable (i.e., high oligonucleotide concentration, high complexity, low copy number), errant amplified sequences can become a dominant reaction product. Consequently it can be difficult to identify conditions, and oligonucleotides, for clean amplification of target sequences from a sample DNA without an excess of false priming background. Thus a further disadvantage of using PCR is the limited success at cleanly amplifying rare target DNAs from complex sequences mixtures.

One solution to the problems of specificity and template-melting problem incurred by PCR is to employ methods that rely on the biological properties of the bacterial RecA recombinase protein, or its prokaryotic and eukaryotic relatives. These proteins coat single-stranded DNA (ssDNA) to form filaments, which then scan double-stranded DNA (dsDNA) for regions of sequence homology. When homologous sequences are located, the nucleoprotein filament strand invades the dsDNA creating a short hybrid and a displaced strand bubble known as a D-loop. The free 3'-end of the filament strand in the D-loop can be extended by DNA polymerases to synthesize a new complementary strand. The complementary strand displaces the originally paired strand as it elongates. By utilizing pairs of oligonucleotides in a manner similar to that used in PCR it should be possible to amplify target DNA sequences in an analogous fashion but without any requirement for thermal melting (thermocycling). This has the advantage both of allowing the use of heat labile polymerases previously unusable in PCR, and increasing the fidelity and sensitivity by template scanning and strand invasion instead of hybridization.

Although the use of RecA and its homologues for in vitro amplification of nucleic acids has been previously described (U.S. Pat. No. 5,223,414 to Zarling et al., referred to herein as "Zarling"), the method and results are limited. Zarling's method has critical failings that limit its ability to achieve exponential amplification of double-stranded DNA. The failure of the Zarling method to achieve exponential amplification may be due to its specification for the use of ATPγS rather than ATP. The Zarling method urges the use of ATPγS, instead of ATP, in the assembly of RecA nucleoprotein filaments because it results in a more stable RecA/ssDNA filament structure. Normally, filaments are assembled in a 5' to 3' direction and will spontaneously disassemble in the same 5' to 3' direction as RecA hydrolyzes ATP. This process is dynamic in that assembly and disassembly occurs at the same time and the amount of assembled filaments is at equilibrium. If the non-hydrolyzable ATP analog, ATPγS, is used, hydrolysis of the ATPγS and the 5' to 3' disassembly of the filaments are inhibited. The great stability of RecA/ATPγS filaments, both before and after strand exchange, while helpful in the method of targeting (i.e., the Zarling method) is detrimental and unpractical for DNA amplification.

In the Zarling method, RecA protein involved in strand invasion will remain associated with the double-stranded portion of the exchanged material after strand exchange. This interaction occurs because the newly formed duplex is bound in the high-affinity site of RecA. The displaced strand occupies a different low-affinity site, unless it is bound to another single-stranded DNA binding protein (SSB), such as *E. coli* SSB. If ATP had been utilized to generate the exchange structure, spontaneous 5' to 3' disassembly might occur, although the exchange complex can be quite stable and may require additional factors to stimulate ATP-dependent disassembly. Regardless of whether spontaneous or stimulated, in the presence of ATPγS, 5' to 3' disassembly of the RecA filament is inhibited (Paulus, B. F. and Bryant, F. R. (1997). Biochemistry 36, 7832-8; Rosselli, W. and Stasiak, A. (1990). J Mol Biol 216, 335-52; Shan, Q. et al., (1997). J Mol Biol 265, 519-40).

These RecA/dsDNA complexes are precisely the sites targeted by the RecA/ssDNA primer complexes used to initiate subsequent rounds of invasion and synthesis. Indeed, with the RecA bound, the intermediate may not be accessible to polymerase, and certainly the dsDNAs can no longer be invaded by RecA/ssDNA primer complexes and are therefore not amplifiable from this point. Further synthesis from these templates might occur if initiated at the other end of the template, which is free of RecA, and this might eventually lead to physical displacement of the bound RecA. It is not clear, however, whether many polymerases can displace RecA in this manner. Moreover, the initiation site for that synthetic round will now be 'blocked' instead. In such a situation, amplification is only linear with time, and will predominately generate single-stranded DNA amplification products.

Thus, the described Zarling method, at best, is likely to generate little more than small quantities of ssDNA copies from each template. The linear amplification potentially given by the Zarling method will only occur in the presence of SSB, since the displaced strand will continue to bind to the second interaction site on RecA, and single-stranded DNA will not be released (Mazin, A. V. and Kowalczykowski, S. C. (1998). EMBO J 17, 1161-8). This probably explains why the Zarling method observed additional faster-migrating fragments when they included SSB. These additional fragments were most likely displaced single-stranded fragments. Hence, in the Zarling method only linear amplification of single-stranded DNA will occur at best. There is, therefore, a need in the art for an improved recombinase-dependent DNA amplification method.

This invention utilizes two new amplification strategies that avoid any requirement for thermal melting of DNA or thermostable components. These strategies also overcome the inefficiencies of the Zarling method. As with the Zarling strategy, these methods rely on the biological properties of the bacterial RecA protein, or its prokaryotic and eukaryotic relatives, in particular, the phage T4 uvsX protein. However, in contrast to the Zarling method, these methods are devised to achieve exponential amplification of dsDNA. They achieve this by permitting rapid regeneration of targetable sequences in the target nucleic acid in the presence of dynamic recombinase/DNA filaments, rather than ATPγS loaded non-dynamic filaments, and in an environment that concomitantly succeeds in maintaining high recombination activity. Furthermore, and critically, while the concept of elongating from recombination intermediates has been visited earlier in concept, and limited practice, both in the Zarling approach, and also in the Alberts laboratory (Formosa and Alberts, 1996; Morrical and Alberts, 1990; Morrical, Wong, and Alberts 1991) and elsewhere (Salinas, Jiang, and Kodadek, 1995; Morel, Cherney, Ehrlich, and Cassuto, 1997; International patent application WO 02/086167, Benkovic and Salinas), none of the descriptions to date teaches a practical method to allow exquisitely specific, sensitive exponential DNA amplification with a capacity for amplification up to 10 to the power of 12 fold. This is because establishing this necessary environment which supports high recombinase/filament activity, but in the presence of large quantities of the necessary single-stranded DNA binding proteins in an in vitro environment has proved extremely challenging, and this environment is entirely dependant on a strict combination of components. This includes, most critically and unexpectedly, very specific crowding agents which alter the behaviour of the in vitro system in a remarkable, and essentially unpredictable way. This remarkable and largely unpredictable alteration of system behaviour with specific volume-occupying agents presumably reflects their capacity to engender fractal-like kinetics, phase separation effects, or other additional properties on the biochemical system. By identifying such precise conditions to enable rapid and highly geometric DNA amplification, as well as conditions for driving high persistent and dynamic recombination activity in vitro for other uses, this invention enables a new generation of in vitro molecular techniques. We refer to the described amplification method performed under these enabling conditions as Recombinase Polymerase Amplification (RPA). We envision herein yet further methods based upon this high activity, persistent, yet dynamic recombination environment, which will likely become practiced in due course. This invention enables this new generation of approaches, and should be contrasted to the current circumstance in which, despite decades of research, no other widely used application of recombinases for in vitro technology has appeared apart from a very limited number dependant on the use of ATPγS.

In this invention we go further and demonstrate that RPA reactions can be fully integrated with dynamic detection of reaction products. This validates that RPA reactions achieve two general criteria for real-time analysis. First a biochemical sensor, such as sensing dye like SYBR green or 'third' probe, is compatible with the RPA reaction environment. Such compatibility is not a trivial assumption because RPA employs saturating quantities of DNA binding proteins, which might interfere with dye or probe binding behaviour. Conversely the binding of dyes or probes to nucleic acids might have interfered with the activity of the DNA binding proteins. Secondly to be employed in real-time quantitative applications RPA would need to demonstrate exponential DNA amplification of target DNA over a significant range of starting template quantities, and be able to maintain exponential amplification up to concentrations easily within the detection range of the overall sensor system.

Also in this invention we disclose approaches to control, and potentially synchronise aspects of, RPA reactions. In current configurations of RPA there is no temporal separation between the DNA targeting and DNA synthesis phases. For RPA, it is difficult to ensure that all reactions in RPA are initiated at exactly the same moment unless a rate-limiting reagent is supplied to all samples simultaneously, or the reactions are assembled at a non-permissive temperature. We suggest approaches by which RPA reactions may be initiated, and individual 'rounds' of priming activity may be regulated, by limiting invasion to well-spaced short bursts. Such approaches to limit recombinase activity to short limited bursts could improve amplification. One way to control DNA invasion in RPA may be by regulating the concentration of free ATP. In the absence of sufficient ATP, or an excess of ADP, recombinase/DNA filaments disassemble and recombination halts. Caged ATP does not support recA loading, but subsequently uncaged material does [Butler B C, Hanchett R H, Rafailov H, MacDonald G (2002) Investigating Structural Changes Induced By Nucleotide Binding to RecA Using Difference FTIR. Biophys J 82(4): 2198-2210]. Thus the use of caged ATP analogues in RPA reactions, which can be deprotected in pulses by light thus permitting bursts of recombinase activity, should be an effective means to control the invasion phase of an RPA reaction. Alternatively ATP concentration could be cyclically controlled by alternative methods such as periodic addition of ATP to the reaction from an external source, or by establishing a biochemical oscillator capable of generating periodic increases of ATP in the reaction.

In this invention we extend the knowledge of how to attain ideal recombinase/ssDNA loading by virtue of 5' sequence design, and widen the repertoire of contexts in which this key stable dynamic recombination environment can be employed in addition to DNA amplification reactions. We describe how this unique composition may be used to replace classical hybridisation steps in any process that otherwise would require thermal or chemical melting, or other duplex targeting approach, in a variety of molecular applications. In particular the use of stable dynamic recombination environments in the presence of synthetic oligonucleotides will be useful in combination with other enzyme systems than the polymerase systems previously described, due to the lack of need for thermal or chemical melting, and the concomitant capacity to employ a wider range of enzymes and avoid thermal cycling equipment.

SUMMARY OF THE INVENTION

The invention provides a method of DNA amplification, termed RPA, which comprises the following steps. First, a recombinase agent is contacted with a first and a second nucleic acid primer to form a first and a second nucleoprotein primer. Second, the first and second nucleoprotein primers are contacted to a double stranded target sequence to form a first double stranded structure at a first portion of said first strand and form a double stranded structure at a second portion of said second strand so the 3' ends of said first nucleic acid primer and said second nucleic acid primer are oriented towards each other on a given template DNA molecule. Third, the 3' end of said first and second nucleoprotein primers are extended by DNA polymerases to generate first and second double stranded nucleic acids, and first and second displaced strands of nucleic acid. Finally, the second and third steps are repeated until a desired degree of amplification is reached.

The invention also provides for a method of nested RPAs. In a nested RPA, a first region of nucleic acid is amplified by RPA to form a first amplified region. Then a second region of nucleic acid that is completely within the first amplified region is amplified using RPA to form a second amplified region. This process may be repeated as often as necessary. For example, a third region of nucleic acid, which is completely within the second region, may be amplified from the second amplified region by RPA. In addition to the one, two and three rounds of RPA discussed above, the invention contemplates at least 4, and preferably at least 5 rounds of nested RPAs also.

The invention also provides for methods of detecting a genotype using RPA. This method is useful for genotyping, for detecting a normal or diseased condition, a predisposition, or a lack of a disposition for a diseased condition. Further, RPA can be used for detecting the presence of a genome, such as for example, a genome of a pathogen. In this use, the method is useful for diagnosis and detection.

The invention also details the nature and concentrations of recombinases, single-stranded binding proteins, polymerases, and nucleotides necessary to establish an effective amplification reaction. The invention further provides detailed enablement on the nature of the target DNA, the length, and composition of targeting oligonucleotides, and the inter-oligonucleotide length optimal for amplification under various conditions. The invention provides for the inclusion of additional components, or the use of modified components, that contribute to establishing a recombination-polymerase amplification system that is sensitive, robust, and with optimal signal-to-noise properties. In particular the use of more than one species of recombinase is demonstrated, and the utility of engineered and modified analogues of the recombinases *E. coli* recA and T4 bacteriophage uvsX, of polymerases including the *E. coli* DNA polymerase I Klenow fragment, Bst polymerase, Phi-29 polymerase, *Bacillus subtilis* Pol I (Bsu), as well as single-stranded DNA binding proteins from *E. coli* and T4 (the gp32 protein) is detailed.

The utility of forms of gp32 with altered cooperativity and/or strand assimilation properties is demonstrated. Also shown is the use of T4 uvsY protein, and most particularly of molecular crowding agents especially PEG compound (also known as Carbowax 20M), to aid in establishing an optimal reaction environment. Further the present invention details effects and the possible use of other enzymes involved in DNA metabolism including toposiomerases, helicases and nucleases, in order to improve the amplification behaviour. The present invention also includes the use of optimised conditions for repeated invasion/extension of a primer targeted to a supercoiled or linear template to generate a linear amplification, and the use of this method for DNA sequencing. The present invention also describes the use of a recombinase in detection of a specific amplified product of a reaction by directing oligonucleotides labeled in some manner to the specific product species and measuring a change in the appearance or property of the reactants as a consequence.

This invention also provides data and approaches to improve the implementation of the RPA method, notably for diagnostic applications. Careful design of oligonucleotide length, base composition, and use of modified backbone sugar residues underpin strategies for high sensitivity and specificity tests. We also disclose approaches to combine oligonucleotides with distinct activities as nucleoprotein filaments to improve signal-to-noise ratios. Also disclosed are methods of product detection that obviate gel electrophoresis, in some cases employing 'third' specific oligonucleotides. We disclose the constitution of an active lyophilizate that can be stored at ambient temperature for at least 10 days and retain amplification activity when reconstituted with buffered sample only.

This invention also discloses enabling data to permit the use of the RPA method in quantitative real-time applications. We show that appropriate dilutions of SYBR green or SYBR gold fluorescent nucleic acid binding dyes are compatible with RPA reactions and permit the monitoring of the accumulation of products. Products continue to accumulate in an apparently exponential fashion for sufficient time to permit quantification after threshold detection levels are achieved. We show experimentally that using this approach RPA is quantitative over at least four or five orders of magnitude of starting template quantity. Simultaneous initiation of many parallel reactions is achieved by establishing reaction mixes on ice then simultaneously shifting the samples to reaction temperatures (33-39° C.). Alternatively parallel RPA reactions might be simultaneously initiated by other means, such as light-driven uncaging of ATP, or of caged oligonucleotide primers. We detail other product-specific real-time monitoring approaches that may be compatible with the RPA system. We also describe the overall composition of a real-time RPA device composed of low power solid state components which could enable cheap portable implementation in both laboratory and non-laboratory contexts.

This invention also discloses method to control RPA reactions, achieved by controlling the presence of the necessary supporting nucleoside triphosphate cofactors such as ATP, to limited periods during the reaction. If chemically caged nucleotide triphosphates are used, pulses of free ATP may be generated by illumination with a defined burst of light corresponding to the uncaging wavelength of the photoprotecting group. The released ATP will then allow the binding of recombinase proteins to single-stranded DNA (ssDNA), and the subsequent homology searching and strand exchange activity of the recombinase-ssDNA complexes. Alternatively, ATP may be periodically added to the reaction. Over time, the concentration of ATP will decrease as a consequence of hydrolysis, either recombinase hydrolysis or hydrolysis by other reaction components specifically added to hydrolyse excess ATP, and ADP. Consequently after a period of time defined by the decreases in ATP concentration and/or an increase in the ADP concentration, recombinase molecules will cease to function and dissociate from DNA. Subsequent pulses of light at the uncaging wavelength can be delivered to release fresh ATP, or fresh ATP can be added to re-initiate recombinase activity. In this manner a series of controlled periods of homology searching and priming are enabled so that initiation of elongation can be phased.

As a second method to control the invasion phase of RPA reactions, we describe an approach to separate the activity driven by one primer from the other. This method utilises recombinase-mediated invasion at one primer target site and the completion of synthesis from that primer. This will generate a single-stranded displaced DNA, which can then be used as a template for a second facing primer that is modified and thus unable to support recombinase-mediated initiation of synthesis. This will possibly avoid conflicts arising through collision of polymerases.

This invention also discloses approaches to assess the polymorphic nature of amplified products without a need for size fractionation. Amplification reaction products are permitted to form duplex hybrids with immobilized probes of either initially single or double stranded character by the action of recombinases and/or single-stranded DNA binding proteins and other accessory molecules. Methods to destabilize imperfect hybrids formed between products and probes are described, occurring in a dynamic environment of recombinase action, and supportive of the activity of a wide variety of additional enzymatic components. Productive hybrids are detected by one of many standard approaches used to reveal the presence of absence of a molecular interaction.

This invention also describes the combination of the determined in vitro conditions which support a stable persistent dynamic recombination environment with other enzymatic activities, thus permitting strand invasion and pairing between ssDNAs and duplexes to occur continuously and in the presence of other metabolic enzymes, especially those non-thermophilic enzymes that would be necessitated in conventional approaches, as well as other processes that are not equivalent, or attainable, in a system employing thermal or chemical melting. We also describe findings that improve the design of oligonucleotides to permit high activity in stable dynamic recombination systems by virtue of including optimised sequences within, and particularly at the 5' end of desired sequences.

Other embodiments, objects, aspects, features, and advantages of the invention will be apparent from the accompanying description and claims.

BRIEF DESCRIPTION OF THE DRAWINGS

FIGS. 2A-2B depict a schematic of succeeding steps, shown in panels (A) and (B), of Leading Strand Recombinase Polymerase Amplification (lsRPA). RecA/primer nucleoprotein filaments invade double stranded template DNA preferentially associating with homologous target sites. As D-loops are formed and synthesis proceeds displaced single stranded DNA becomes coated with SSB. RecA release from double-stranded DNA can occur via ATP hydrolysis in a 5'-3' direction or as a result of helicase/resolvase or polymerase activity. As synthesis continues, polymerases encounter SSB bound, displaced, single-stranded template. Double-stranded target site are re-invaded by RecA/primer nucleoprotein filaments. Subsequent rounds of lsRPA proceed from re-invaded sites.

FIGS. 3A-3D depict a schematic of succeeding steps, shown in panels (A), (B), (C), and (D), of Leading and Lagging Strand Recombinase Polymerase Amplification. First, the primosome loads onto the D-loop formed by RecA nucleoprotein filament invasion The primosome synthesizes a stretch of RNA primer. Finally. primosome recruits the clamp loader, which recruits both the sliding clamp dimer and the asymmetric DNA polymerase core. Synthesis occurs simultaneously in both the leading and lagging directions. Eventually lagging strand synthesis stops and the lagging strand clamp is unloaded. Synthesis of the leading strand continues until a new site of lagging strand synthesis is formed. While leading strand synthesis continues a new site of lagging strand synthesis is formed. Lagging strand synthesis continues back to the previous Okazaki fragment where the lagging strand clamp is unloaded. DNA Polymerase I removes the RNA primer, and fills in the gap while DNA ligase connects the two Okazaki fragments forming a continuous lagging strand.

FIG. 4 depicts an example of nested primers chosen for nested RPA.

FIG. 5 depicts examples of suitable double stranded template nucleic acids.

FIGS. 8A-8C depict (A) examples of double stranded primers; (B) double stranded primers after elongation and after annealing of the second member of a primer pair; (C) after the elongation of the second member of a primer pair with the non-invading strand displaced.

FIG. 43 (A) discloses SEQ ID NO: 93; (B) discloses SEQ ID NO: 93; (C) discloses SEQ ID NO: 94; (D) discloses SEQ ID NOS 93 and 95, respectively, in order of appearance; (E) discloses SEQ ID NO: 95; (F) discloses SEQ ID NO: 96; (G) discloses SEQ ID NO: 97; (H) discloses SEQ ID NO: 98; (I) discloses SEQ ID NOS 98 and 93, respectively, in order of appearance; and (J) discloses SEQ ID NO: 98.

FIG. 44 Oligonucleotide improvement strategies—overview of three general schemes.

FIG. 46 Locked nucleic acids can function in RPA and exhibit significant differences in product accumulation, noise accumulation, and polymerase concentration requirement.

FIG. 52 Bead capture II. Experimental results demonstrating that a low activity nucleoprotein filament immobilized on a solid support can participate as a third primer and separate target amplicons from primer noise.

FIG. 64A depicts that RPA is capable of amplification from whole human blood. Expected amplicon is indicated by arrow. FIG. 64B depicts that template yield is enhanced by treatment of whole blood with a simple lysis buffer. For each of the experimental samples we expect the total possible number of genome copies to be ~1750. This is compared to ~500 genome copies of purified DNA used as control.

FIG. 67 Primer sequences (SEQ ID NOS 46-47, 33 and 32, respectively, in order of appearance) affect amplification rate behaviour—preliminary analysis suggests that 'fast' primers may be associated with low G content, and high C or C/T content.

FIG. 70 Utility of real-time RPA analysis in optimising reaction environment; heterologous 5' sequences appended to oligonucleotides influence reaction behaviour—not all pyrimidine-rich 5' sequences drive excellent kinetic behaviour. Figure discloses SEQ ID NOS 66, 99, 109-112, 69, 101 and 113-116, respectively, in order of appearance.

FIG. 71 So-called 'third probes' may be employed to monitor RPA reactions and increase specificity. Candidate enzymes for processing specific duplexes containing the target and probe.

DETAILED DESCRIPTION OF THE INVENTION

Figure 1:
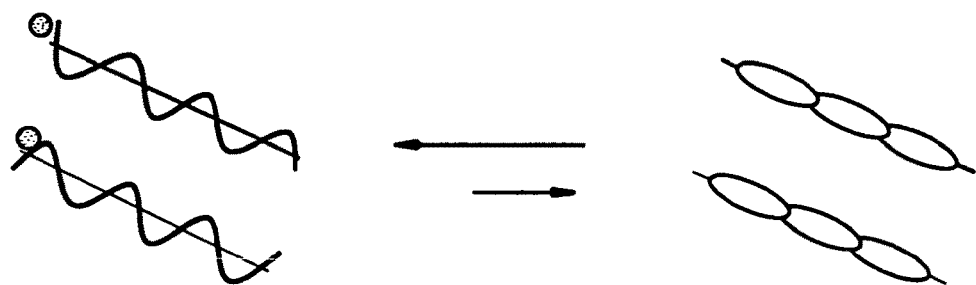
FIG. 1 depicts a schematic representation of RecA/Primer Loading. Prior to the addition of template DNA and/or Polymerase, RecA and SSB-will compete for binding to single-stranded oligonucleotide primers. In the presence of a RecR and RecO, RecA is selectively stabilized onto the single-stranded primers forming RecA nucleoprotein filaments in a complex with RecO and RecR. This complex is competent to invade double-stranded DNA to form a D-loop at sites homologous to the oligonucleotide primers. Alternatively, RecA, RecO and RecR can be pre-loaded onto oligonucleotide primers prior to the introduction of SSB to the reaction mixture.

The present invention provides for Recombinase-Polymerase Amplification (RPA)—a method for the amplification of target nucleic acid polymers. It also provides for a general in vitro environment in which high recombinase activity is maintained in a highly dynamic recombination environment, supported by ATP. One benefit of RPA is that it may be performed without the need for thermal melting of double-stranded templates. Therefore, the need for expensive thermocyclers is also eliminated. The present invention describes two related strategies by which RPA can be configured to permit exponential amplification of target nucleic acid polymers.

Throughout this specification, various patents, published patent applications and scientific references are cited to describe the state and content of the art. Those disclosures, in their entireties, are hereby incorporated into the present specification by reference.

Leading Strand Recombinase-Polymerase Amplification (lsRPA)

In leading strand Recombinase-polymerase Amplification (lsRPA) single-stranded, or partially single-stranded, nucleic acid primers are targeted to homologous double-stranded, or partially double-stranded, sequences using recombinase agents, which would form D-loop structures. The invading single-stranded primers, which are part of the D-loops, are used to initiate polymerase synthesis reactions. A single primer species will amplify a target nucleic acid sequence through multiple rounds of double-stranded invasion followed by synthesis. If two opposing primers are used, amplification of a fragment—the target sequence—can be achieved. LsRPA is described briefly in FIGS. 1 and 2.

The target sequence to be amplified, in any of the methods of the invention, is preferably a double stranded DNA. However, the methods of the invention are not limited to double stranded DNA because other nucleic acid molecules, such as a single stranded DNA or RNA can be turned into double stranded DNA by one of skill in the arts using known methods. Suitable double stranded target DNA may be a genomic DNA or a cDNA. An RPA of the invention may amplify a target nucleic acid at least 10 fold, preferably at least 100 fold, more preferably at least 1,000 fold, even more preferably at least 10,000 fold, and most preferably at least 1,000,000 fold.

The target sequence is amplified with the help of recombinase agents. A recombinase agent is an enzyme that can coat single-stranded DNA (ssDNA) to form filaments, which can then scan double-stranded DNA (dsDNA) for regions of sequence homology. When homologous sequences are located, the nucleoprotein filament (comprising the recombinase agent) strand invades the dsDNA creating a short hybrid and a displaced strand bubble known as a D-loop. Suitable recombinase agents include the *E. coli* RecA protein, the T4 uvsX protein, or any homologous protein or protein complex from any phyla. Eukaryotic RecA homologues are generally named Rad51 after the first member of this group to be identified. Other non-homologous recombinase agents may be utilized in place of RecA, for example as RecT or RecO. Recombinase agents generally require the presence of ATP, ATPγS, or other nucleoside triphosphates and their analogs. It is preferred that recombinase agents are used in a reaction environment in which regeneration of targeting sites can occur shortly following a round of D-loop stimulated synthesis. Completed recombination events involving recombinase disassembly will avoid a stalling of amplification or very inefficient linear amplification of ssDNA caused by oscillating single-sided synthesis from one end to the other.

Naturally, any derivatives and functional analogs of the recombinase agent above may also function itself as a recombinase agent and these derivatives and analogs are also contemplated as embodiments of the invention. For example, a small peptide from recA, which has been shown to retain some aspects of the recombination properties of recA, may be used. This peptide comprises residues 193 to 212 of E. coli recA and can mediate pairing of single stranded oligos (Oleg N. Voloshin, Lijang Wang, R. Daniel Camerini-Otero, Homologous DNA pairing Promoted by a 20-amino Acid Peptide Derived from RecA. Science Vol. 272 10 May 1996).

Since the use of ATPγS results in the formation of stable Recombinase-agent/dsDNA complexes that are likely incompatible with efficient amplification, it is preferable to use ATP and auxiliary enzymes to load and maintain the Recombinase-agent/ssDNA primer complexes. Alternatively, the limitations of the use of ATPγS may be overcome by the use of additional reaction components capable of stripping recA bound to ATPγS from exchange complexes. This role might be played by helicases such as the RuvA/RuvB complex.

The terms 'nucleic acid polymer' or 'nucleic acids' as used in this description can be interpreted broadly and include DNA and RNA as well as other hybridizing nucleic-acid-like molecules such as those with substituted backbones e.g. peptide nucleic acids (PNAs), morpholino backboned nucleic acids, locked nucleic acid or other nucleic acids with modified bases and sugars.

Structurally similar to RNA, LNA monomers are bicyclic compounds that bear a methylene linker that connects the nucleotide sugar ring's 2'-oxygen to its 4'-carbon. LNA polymers obey standard base-pairing rules, but their physical properties make them suitable for mismatch discrimination applications. LNA are available from Exiqon (Denmark) or Proligo (USA, Colorado).

One embodiment of the invention is directed to a method of performing RPA. The method comprises two steps. In the first step, the following reagents are combined in a reaction: (1) at least one recombinase; (2) at least one single stranded DNA binding protein; (3) at least one DNA polymerase; (4) dNTPs or a mixture of dNTPs and ddNTPs; (5) a crowding agent; (6) a buffer; (7) a reducing agent; (8) ATP or ATP analog; (9) at least one recombinase loading protein; (10) a first primer and optionally a second primer; and (11) a target nucleic acid molecule. In the second step, the reagents are incubated until a desired degree of amplification is achieved.

The recombinase may be uvsX, recA or a combination of both. The recombinase may also comprise a C terminal deletion of acidic residues to improve its activity. While any recombinase concentration disclosed in the specification may be used, preferred recombinase concentrations may be, for example, in the range of 0.2-12 µM, 0.2-1 µM, 1-4 µM, 4-6 µM, and 6-12 µM.

Figure 13:
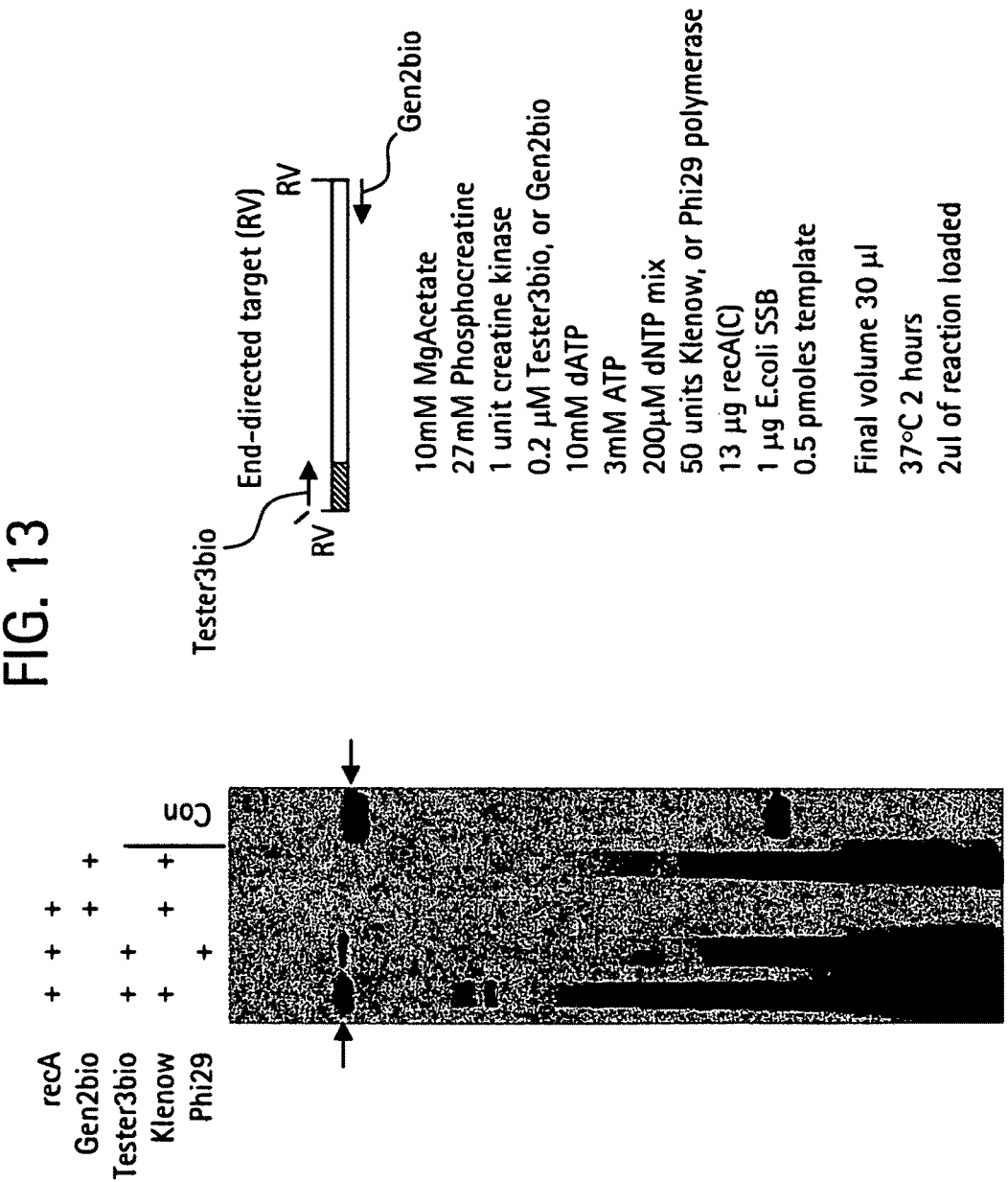
FIG. 13 depicts the requirement for a minimal oligonucleotide length or overhang for invasion and elongation during end targeting of linear templates. When the invading oligonucleotide is targeted at ends of a linearized template a minimal oligonucleotide length, or an overhang is needed for invasion/elongation to occur.

The single stranded DNA binding protein may be the E. coli SSB or the T4 gp32 or a derivative or a combination of these proteins. gp32 derivative may include, at least, gp32 (N), gp32(C), gp32(C)K3A, gp32(C)R4Q, gp32(C)R4T, gp32K3A, gp32R4Q, gp32R4T and a combination thereof (See FIG. 13). The DNA binding protein may be present at a concentration of between 1 µM and 30 µM.

The DNA polymerase may be a eukaryotic polymerase. Examples of eukaryotic polymerases include pol-α, pol-β, pol-δ, pol-ε and derivatives and combinations thereof. Examples of prokaryotic polymerase include E. coli DNA polymerase I Klenow fragment, bacteriophage T4 gp43 DNA polymerase, Bacillus stearothermophilus polymerase I large fragment, Phi-29 DNA polymerase, T7 DNA polymerase, Bacillus subtilis Pol I, E. coli DNA polymerase I, E. coli DNA polymerase II, E. coli DNA polymerase III, E. coli DNA polymerase IV, E. coli DNA polymerase V and derivatives and combinations thereof. In a preferred embodiment, the DNA polymerase is at a concentration of between 10,000 units/ml to 10 units/ml, such as between 5000 units/ml to 500 units/ml. In another preferred embodiment, the DNA polymerase lacks 3'-5' exonuclease activity. In yet another preferred embodiment, the DNA polymerase contains strand displacing properties.

Any of the proteins mentioned in the methods of the invention is understood to also include its derivative. These proteins includes at least the following: recombinases, polymerase, recombinase loading protein, single stranded DNA binding protein, accessory agents, RecA/ssDNA nucleoprotein filaments stabilizing agent and the like. The derivative of these proteins include, at least, a fusion protein comprising a C terminus tag, N terminus tag, or C and N terminus tags. Non-limiting examples of suitable sequence tags include 6-histidine (6×-His; HHHHHH; SEQ ID NO: 81), c-myc epitope (EQKLISEEDL; SEQ ID NO: 82), FLAG® octapeptide (DYKDDDDK; SEQ ID NO: 83), Protein C (EDQVDPRLIDGK; SEQ ID NO: 84), Tag-100 (EETARFQPGYRS; SEQ ID NO: 85), V5 epitope (GKPIPNPLL-GLDST; SEQ ID NO: 86), VSV-G (YTDIEMNRLGK; SEQ ID NO: 87), Xpress (DLYDDDDK; SEQ ID NO: 88), and hemagglutinin (YPYDVPDYA; SEQ ID NO: 89). Non-limiting examples of suitable protein tags include β-galactosidase, thioredoxin, His-patch thioredoxin, IgG-binding domain, intein-chitin binding domain, T7 gene 10, glutathione-S-transferase (GST), green fluorescent protein (GFP), and maltose binding protein (MBP). It will be understood by those in the art that sequence tags and protein tags can be used interchangeably, e.g., for purification and/or identification purposes. Accordingly, as used herein, the terms "His tag" and "hexahistidine tag" encompass all suitable sequence tags and protein tags as known in the art and indicated in this paragraph.

The dNTPs includes, for example, dATP, dGTP, dCTP, and dTTP. In leading and lagging strand RPA, ATP, GTP, CTP, and UTP may also be included for synthesis of RNA primers. In addition, ddNTPs (ddATP, ddTTP, ddGTP and ddGTP) may be used to generate fragment ladders. The dNTP may be used at a concentration of between 1 µM to 200. µM of each NTP species. A mixture of dNTP and ddNTP may be used with ddNTP concentrations at 1/100 to 1/1000 of that of the dNTP (1 µM to 200 µM).

The crowding agents used in the RPA include polyethylene glycol (PEG), dextran and ficoll. The crowding agent may be at a concentration of between 1% to 12% by volume or 1% to 12% by weight of the reaction. While all PEGs are useful, preferred PEGs include PEG1450, PEG3000, PEG8000, PEG10000, PEG compound molecular weight 15000-to 20,000 (also known as Carbowax 20M), and a combination thereof.

The buffer solution in a an RPA may be a Tris-HCl buffer, a Tris-Acetate buffer, or a combination thereof. The buffers may be present at a concentration of between 10 to 100 mM.

The buffered pH may be between 6.5 to 9.0. The buffer may further contain Mg ions (e.g., in the form of Mg Acetate) at a concentration between 1 to 100 mM with a concentration of between 5 to 15 mM being preferred. One preferred Mg concentration is 10 mM (Mg concentration or Mg Acetate concentration).

Reducing agents to be used include DTT. The DTT concentration may be between 1 mM and 10 mM.

The ATP or ATP analog may be any of ATP, ATP-γ-S, ATP-β-S, ddATP or a combination thereof. A preferred ATP or ATP analog concentration is between 1 and 10 mM.

Recombinase loading protein may include, for example, T4uvsY, E. coli recO, E. coli recR and derivatives and combinations of these proteins. One preferred concentration of these proteins is between 0.2 and 8 µM.

The primers used may be made from DNA, RNA, PNA, LNA, morpholino backbone nucleic acid, phosphorothiorate backbone nucleic acid and a combination thereof. Combinations thereof in this can refers to a single nucleic acid molecules which may contain one or more of one base connected to one of more of another base. Preferred concentration of these molecules may be in the range of between 25 nM to 1000 nM. In one preferred embodiment, the primers may contain a non-phosphate linkage between the two bases at its 3' end and is resistant to 3' to 5' nuclease activity. In another embodiment, the primers may contain a locked nucleic acid at its 3' ultimate base or 3' penultimate base. For example, in a nucleic acid of the sequence 5'-AGT-3', the T is the 3' ultimate base and the G is the 3' penultimate base. The primers may be at least 20 bases in length or at least 30 bases in length. In one preferred embodiment, the primers are between 20 to 50 bases in length. In another preferred embodiment, the primers are between 20 to 40 bases in length such as between 30 to 40 bases in length.

The primers may contain additional 5' sequence that is not complementary to the target nucleic acid. These 5' sequence may contain, for example a restriction endonuclease recognition site. The primers may be partly double stranded with a single stranded 3' end.

In addition, any nucleic acid of any of the methods of the invention may be labeled with a detectable label. A detectable label include, for example, a fluorochrome, an enzyme, a fluorescence quencher, an enzyme inhibitor, a radioactive label and a combination thereof.

The target nucleic acid may be single stranded or double stranded. It is known that single stranded nucleic acids would be converted to double stranded nucleic acid in the methods of the invention. The target nucleic acid may be supercoiled or linear. The sequence to be amplified (target nucleic acid) may be in between other sequences. The sequence to be amplified may also be at one end of a linear nucleic acid. In one embodiment, the target nucleic acid is linear and not connected to non-target nucleic acids. In other words, where the target nucleic acid is linear, it can be in any of the following formats:

1. [non-target nucleic acid]-[target nucleic acid]-[non-target nucleic acid]
2. [non-target nucleic acid]-[target nucleic acid]
3. [target nucleic acid]-[non-target nucleic acid]
4. [target nucleic acid]

It should be noted that the arrangement above is intended to represent both single stranded nucleic acids and double stranded nucleic acids. "1" may be described as a target nucleic acid molecule which is linear with two ends and wherein both ends are linked to a non-target nucleic acid molecule. "2" may be described as a target nucleic acid molecule which is linear with two ends and wherein one end is linked to a non-target nucleic acid molecule. "3" may be described as a target nucleic acid molecule which is a linear nucleic acid molecule (with no non-target nucleic acid).

In another embodiment, the target nucleic acid may be a single-stranded nucleic acid which is converted to a double stranded nucleic acid by a polymerase or a double stranded nucleic acid denatured by the action of heat or chemical treatment.

The target nucleic acid may be of any concentration such as less than 10,000 copies, less than 1000 copies, less than 100 copies, less than 10 copies or 1 copy in a reaction. A reaction volume may be 5 µl, 10 µl, 20 µl, 30 µl, 50 µl, 75 µl, 100 µl, 300 µl, 1 ml, 3 ml, 10 ml, 30 ml, 50 ml or 100 ml.

The reaction may be incubated between 5 minutes and 16 hours, such as between 15 minutes and 3 hours or between 30 minutes and 2 hours. The incubation may be performed until a desired degree of amplification is achieved. The desired degree of amplification may be 10 fold, 100 fold, 1000 fold, 10,000 fold, 100,000 fold or 1000000 fold amplification. Incubation temperature may be between 20° C. and 50° C., between 20° C. and 40° C., such as between 20° C. and 30° C. One advantage of the methods of the invention is that the temperature is not critical and precise control, while preferred, is not absolutely necessary. For example, in a field environment, it is sufficient to keep the RPA at room temperature, or close to body temperature (35° C. to 38° C.) by placing the sample in a body crevice. Furthermore, the RPA may be performed without temperature induced melting of the template nucleic acid.

In another embodiment of the invention, the RPA further comprise accessory agents. These accessory agents includes helicase, topoisomerase, resolvase and a combination thereof which possess unwinding, relaxing, and resolving activities respectively on DNA. The accessory agents may also include RuvA, RuvB, RuvC, RecG, PriA, PriB, PriC, DnaT, DnaB, DnaC, DnaG, DnaX clamp loader, polymerase core complex, DNA ligase and a sliding clamp and a combination thereof. The sliding claim may be E. coli β-dimer sliding clamp, the eukaryotic PCNA sliding clamp, or the T4 sliding clamp gp45 and a combination thereof. The accessory agents may include, in addition, DNA Polymerase III holoenzyme complex consisting of β-Clamp, DnaX Clamp Loader, and the Polymerase Core Complex. These latter accessory agents would allow the performance of leading and lagging RPA.

In another embodiment, the RPA may be performed in the presence of a RecA/ssDNA nucleoprotein filaments stabilizing agent. Examples of such stabilizing include RecR, RecO, RecF and a combination thereof. These stabilizing agents may be present at a concentration of between 0.01 µM to 20 µM. Other examples of stabilizing agents include the T4 uvsY protein which stabilizes uvsX/ssDNA nucleoproteiun complexes.

Other components of RPA include a system for ATP regeneration (convert ADP to ATP). Such system may be, for example, phosphocreatine and creatine kinase.

The RPA reaction may also include a system to regenerate ADP from AMP and a to convert pyrophosphate to phosphate (pyrophosphate).

In one preferred embodiment, the RPA reaction as listed above are performed with E. coli components completely by using recA, SSB, recO, recR and E. coli polymerase.

In another preferred embodiment, the RPA reaction is performed with T4 components by using uvsX, gp32, uvxY, and T4 polymerase.

In one preferred embodiment, RPA may be performed by combining the following reagents: (1) a uvsX recombinase at a concentration of between 0.2 to 12 µM; (2) a gp32 single stranded DNA binding protein at a concentration between 1 to 30 µM; (3) a *Bacillus subtilis* DNA polymerase I large fragment (Bsu polymerase) at a concentration between 500 to 5000 units per ml; (4) dNTPs or a mixture of dNTPs and ddNTPs at a concentration of between 1-300 µM; (5) polyethylene glycol at a concentration of between 1% to 12% by weight or by volume; (6) Tris-acetate buffer at a concentration of between 1 mM to 60 mM; (7) DTT at a concentration of between 1 mM-10 mM; (8) ATP at a concentration of between 1 mM-10 mM; (9) uvsY at a concentration of between 0.2 µM-8 µM; (10) a first primer and optionally a second primer, wherein said primers are at a concentration of between 50 nM to 1 µM; and (11) a target nucleic acid molecule of at least one copy. After the reaction is assembled, it is incubated until a desired degree of amplification is achieved. This is usually within 2 hours, preferably within 1 hour, such as, for example, in 50 minutes.

One advantage of the invention is that the reagents for RPA, with the possible exception of the crowding agent and buffer, may be freeze dried (i.e., lyophilzed) before use. Freezed dried reagent offer the advantage of not requiring refrigeration to maintain activity. For example, a tube of RPA reagents may be stored at room temperature. This advantage is especially useful in field conditions where access to refrigeration is limited.

In one embodiment, the RPA reagents may be freeze dried onto the bottom of a tube, or on a bead (or another type of solid support). To perform an RPA reaction, the reagents are reconstituted in a buffer solution and with a crowding reagent, or simply a buffered solution or water, dependant on the composition of the freeze-dried reagents. Then a target nucleic acid, or a sample suspected to contain a target nucleic acid is added. The reconstitution liquid may also contain the sample DNA. The reconstituted reaction is incubated for a period of time and the amplified nucleic acid, if present, is detected.

Detection may be performed using any method, such as, for example, using electrophoresis on an agarose or PAGE gel followed by ethidium bromide staining.

In any of the methods of the invention, the reagents that can be freeze dried before use would include, at least, the recombinase, the single stranded DNA binding protein, the DNA polymerase, the dNTPs or the mixture of dNTPs and ddNTPs, the reducing agent, the ATP or ATP analog, the recombinase loading protein, and the first primer and optionally a second primer or a combination of any of these.

In one preferred embodiment, the reagents are assembled by combining the reagents such that when constituted, they will have the following concentrations: (1) a uvsX recombinase at a concentration of between 0.2 to 12 µM; (2) a gp32 single stranded DNA binding protein at a concentration between 1 to 30 µM; (3) a T4 gp43 DNA polymerase or Bsu polymerase at a concentration between 500 to 5000 units per ml; (4) dNTPs or a mixture of dNTPs and ddNTPs at a concentration of between 1-300 µM; (5) DTT at a concentration of between 1 mM-10 mM; (6) ATP at a concentration of between 1 mM-10 mM; (7) uvsY at a concentration of between 0.2 µM. Optionally, a first primer and optionally a second prime may be added where their concentration would be between 50 nM to 1 µM when reconstituted. The reagents are freeze dried before use. Stabilizing agents such as trehalose sugar may be included in the freeze dried mixture, for example at 20 mM to 200 mM and most optimally 40 mM to 80 mM in the reconstituted reaction, in order to improve freeze-drying performance and shelf life. If desired, the freeze dried reagents may be stored for 1 day, 1 week, 1 month or 1 year or more before use.

In use, the reagents are reconstituted with buffer (a) Tris-acetate buffer at a concentration of between 1 mM to 60 mM; and (b) polyethylene glycol at a concentration of between 1% to 12% by weight or by volume, or (c) with water. If the primers were not added before freeze drying, they can be added at this stage. Finally, a target nucleic acid, or a sample suspected of containing a target nucleic acid is added to begin the reaction. The target, or sample, nucleic acid may be contained within the reconstitution buffer as a consequence of earlier extraction or processing steps. The reaction is incubated until a desired degree of amplification is achieved.

Any of the RPA reaction conditions discussed anywhere in this specification may be freeze dried. For example, the following reagents can be assembled by combining each reagent such that when constituted, they will have the following concentrations: (1) 100-200 ng/µl uvsX recombinase; (2) 600 ng/µl gp32; (3) 20 ng/µl Bsu polymerase or T4 polymerase; (4) 200 µM dNTPs; (5) 1 mM DTT (6) 3 mM ATP or an ATP analog; (7) 16 ng/µl to 60 ng/µl uvsY; (8) 50 nM to 300 nM of a first primer and 50 nM to 300 nM of a second primer; (9) 80 mM Potassium acetate; (10) 10 mM Magnesium acetate; (11) 20 mM Phosphocreatine; (12) 50 ng/µl to 100 ng/µl Creatine kinase. The reagents may be freeze dried onto the bottom of a tube or in a well of a multi-well container. The reagent may be dried or attached onto a mobile solid support such as a bead or a strip, or a well.

In use, the tube with the reagent may be reconstituted with (1) Tris-acetate buffer at a concentration of between 1 mM to 60 mM and polyethylene glycol at a concentration of between 1% to 12% by weight or by volume. If the reagents were dried or attached to a mobile solid support, the support may be dropped in a tube and reconstituted. As discussed above, the primers may be dried as part of the reagent or added after reconstitution. Finally, a target nucleic acid, or a sample suspected of containing a target nucleic acid is added to begin the reaction. The reaction is incubated until a desired degree of amplification is achieved.

As another example, the following reagents can be assembled by combining each reagent such that when constituted, they will have the following concentrations: (1) 100-200 ng/µl uvsX recombinase; (2) 300-1000 ng/µl gp32; (3) 10-50 ng/µl Bsu polymerase or T4 polymerase; (4) 50-500 µM dNTPs; (5) 0.1 to 10 mM DTT; (6) 3 mM ATP or an ATP analog; (7) 16 ng/µl to 60 ng/µl uvsY; (8) 50 nM to 1000 nM of a first primer and 50 nM to 1000 nM of a second primer; (9) 40 mM to 160 mM Potassium acetate; (10) 5 mM to 20 mM Magnesium acetate; (11) 10 mM to 40 mM Phosphocreatine; (12) 50 ng/µl to 200 ng/µl Creatine kinase. These reagents are freeze dried and stored. In use, the reagents are reconstituted with Tris-acetate buffer at a concentration of between 1 mM to 60 mM and polyethylene glycol at a concentration of between 1% to 12% by weight or by volume. The primers, item 8 above, may be omitted before freeze drying and added after reconstitution. To initiate the RPA, a target nucleic acid, or a sample suspected of containing a target nucleic acid is added. The reaction is incubated until a desired degree of amplification is achieved.

Another embodiment of the invention comprises a kit for performing RPA. The kit may comprise any of the reagents discussed above for RPA in the concentrations described above. The reagents of the kit may be freeze dried. For example, the kit may contain (1) 100-200 ng/µl uvsX recombinase; (2) 300 ng/µl to 1000 ng/µl gp32; (3) 10 ng/µl to 50 ng/µl Bsu polymerase or T4 polymerase; (4) 50 µM to 500 µM dNTPs; (5) 0.1 to 10 mM DTT; (6) 1 mM to 5 mM ATP or an ATP analog; (7) 16 ng/µl to 60 ng/µl uvsY; (8) 50 nM to 1000 nM of a first primer and 50 nM to 1000 nM of a second primer (optional); (9) 40 mM to 160 mM Potassium acetate; (10) 5 mM to 20 mM Magnesium acetate; (11) 10 mM to 40 mM Phosphocreatine; (12) 50 ng/µl to 200 ng/µl Creatine kinase.

In a preferred embodiment, RPA is performed with several auxiliary enzymes that can promote efficient disassembly of Recombinase-agent/dsDNA complexes after DNA synthesis initiation. These auxiliary enzymes include those that are capable of stimulating 3' to 5' disassembly and those capable of supporting 5' to 3' disassembly.

Auxiliary enzymes include several polymerases that can displace RecA in the 3' to 5' direction and can stimulate 3' to 5' disassembly of Recombinase-agent/dsDNA complexes (Pham et al., 2001). These DNA polymerase include E. coli PolV and homologous polymerase of other species. Normally in the life of E. coli, displacement of RecA in the 3' to 5' direction occurs as part of SOS-lesion-targeted synthesis in concert with SSB, sliding clamps and DNA polymerase. The polymerase essential for this activity in E. coli is PolV, a member of the recently discovered superfamily of polymerases including UmuC, DinB, Rad30, and Rev1, whose function in vivo is to copy DNA lesion templates. Critical to RPA, the in vitro 3' to 5' disassembly of RecA filaments cannot be catalyzed by PolI, PolIII, or PolIV alone. Only PolV, in concert with SSB, has measurable ATP-independent 3' to 5' RecA/dsDNA disassembly activity. In effect, PolV pushes and removes RecA from DNA in a 3' to 5' direction ahead of the polymerase (Pham et al., 2001; Tang et al., 2000). Inclusion of PolV or a functional homologue may improve the amplification efficiency.

Other auxiliary enzymes include a class of enzymes called helicases that can be used to promote the disassembly of RecA from dsDNA. These promote disassembly in both the 5' to 3' and 3' to 5' directions. Helicases are essential components of the recombination process in vivo and function to move the branch points of recombination intermediates from one place to another, to separate strands, and to disassemble and recycle components bound to DNA. After the first round of invasion/synthesis has occurred in RPA, two new DNA duplexes are "marked" by the presence of RecA bound over the site to which primers must bind for additional rounds of synthesis. In such a situation dsDNA tends to occupy the high affinity site in RecA, or homologs, until it is actively displaced, either by ATP hydrolysis-dependent dissociation in the 5' to 3' direction, which may be limiting, or by 3' to 5' dissociation by some other active process. An ideal helicase complex for stimulating disassembly of RecA from intermediates consists of the E. coli proteins RuvA and RuvB. The RuvAB complex promotes branch migration, and dissociates the RecA protein, allowing RecA to be recycled (Adams et al., 1994). Normally, the RuvAB complex is targeted to recombination intermediates, particularly Holliday junction-like structures. As it works the RuvAB complex encircles DNA and forces RecA from the DNA in an ATP-driven translocation (Cromie and Leach, 2000; Eggleston and West, 2000). This RecA dissociation activity has been demonstrated using supercoiled dsDNA bound with RecA, which does not even possess Holliday junctions (Adams et al., PNAS 1994). The RuvAB complex can recognize branched structures within the RecA coated DNA. Incorporation of RuvAB into the RPA mixture will promote the dissociation of RecA from dsDNA following strand exchange and displacement, allowing renewed synthesis of the duplicated template from the same site. Additionally, the RuvAB complex can act in concert with RuvC, which finally cuts and resolves Holliday junctions. With RuvC added to the RPA reaction mixture, complicated structures such as Holliday junctions formed at invasion sites, can be resolved. Resolvase activity, such as that provided by RuvC, is particularly important when the targeting oligonucleotides are partially double-stranded. In such situations reverse branch migration can generate Holliday junctions, which can then be resolved by the RuvABC complex, to generate clean separated amplification products.

Still other auxiliary enzymes include the E. coli RecG protein. RecG can stimulate disassembly of branch structures. In vivo this protein functions to reverse replication forks at sites of DNA damage by unwinding both leading and lagging strands driving the replication fork back to generate a 4-way junction (Cox et al., 2000; Dillingham and Kowalczykowski, 2001; Singleton et al., 2001). In vivo such junctions function as substrates for strand switching to allow lesion bypass. In vitro RecG will bind to D-loops, and will lead to a decrease in D-loop structures by driving reverse branch migration. RecG prefers a junction with double-stranded elements on either side, hence partly double-stranded targeting oligonucleotides, homologous to the targeting site in both single-stranded and double-stranded regions, would be ideal. This would stimulate reverse branch migration and formation of a Holliday junction, which can be resolved by the RuvABC complex. In vivo RecG and RuvAB may compete to give different outcomes of recombination since branch migration will be driven in both directions (McGlynn and Lloyd, 1999; McGlynn et al., 2000). In both cases the proteins target junction DNA coated with RecA, and disassemble it in an active manner.

Other auxiliary enzymes useful in an RPA reaction mixture are those that allow continual generation of RecA nucleoprotein filaments in the presence of ATP and SSB. In order to allow removal of RecA at the appropriate moments, it is preferred to use ATP rather than ATPγS in an RPA reaction. Unfortunately RecA/ssDNA filaments formed with ATP spontaneously depolymerize in the 5' to 3' direction, and in the presence of SSB, as required here, repolymerization will not occur at significant rates. The solution to this problem is the use of the RecO, RecR, and possibly RecF proteins. Alternatively the uvsY protein may be employed to stabilize the T4 uvsX nucleoprotein filaments in a similar manner. In the presence of SSB and ATP, RecA/ssDNA filaments dissociate (Bork et al., 2001; Webb et al., 1995; Webb et al., 1997; Webb et al., 1999). If RecA/ssDNA is incubated in the presence of RecO and RecR proteins this dissociation does not occur. Indeed the RecR protein remains associated with the filament and stabilizes the structure indefinitely. Even if ssDNA is bound by SSB, in the presence of RecR and RecO, filaments of RecA can reassemble displacing SSB. In the T4 phage system similar properties are attributed to the uvsY protein. Thus it is possible to obviate the use of ATPγS, if necessary, by using ATP in the presence of RecO and RecR to maintain RecA/ssDNA filament integrity, or uvsY to maintain the uvsX/ssDNA filament integrity. The RecF protein interacts with the RecO and RecR system in a seemingly opposing manner. RecF competes with RecR tending to drive filament disassembly in vitro. It is likely that all three components in vivo function together to control the generation of invading structures, while limiting the extent of RecA coating of ssDNA. In another preferred embodiment, RecF is included in RPA reactions at an appropriate concentration to recapitulate the dynamics of the in vivo processes. In addition, RecF may facilitate dissociation of RecA-coated intermediates after invasion has occurred.

As described, the use of ATP rather than ATPγS, and/or the use of displacing polymerases and helicases (e.g. the RuvA/RuvB complex), RecO, RecR and RecF, or alternatively the T4 uvsX recombinase with the uvsY protein, should permit exponential amplification of double-stranded DNA by driving continual regeneration of targeting sites. This method, however, remains responsive to differences in initiation rate that might occur at the two opposing targeting sites. Such differences may lead to a decrease in amplification efficiency, and to the production of some single-stranded DNA. The PCR method largely avoids these complications because temperature cycling leads to coordinated synthesis from either side. In another embodiment, a situation analogous to the PCR condition just described may be induced by using temperature sensitive (ts) mutants of RecA that are non-functional at 42° C., but function at lower temperatures in the range 25 to 37° C. (Alexseyev et al., 1996; Hickson et al., 1981). In this case, synthesis from either end can be synchronized by periodic lowering to the permissive temperature and then raising the reaction to a temperature non-permissive for the mutant RecA protein function, but permissive for the other components. By performing RPA with tsRecA mutants in combination with cycling of reaction temperatures, the number of molecules of DNA produced can be controlled. While this will require some mechanism to provide temperature cycling, the temperatures are well below those that would require the use of thermophile-derived proteins. Indeed, a simple chemical-based or portable low-power temperature-cycling device may be sufficient to control such reaction cycles.

RPA, as all other present-day nucleic acid amplification methods, employs polymerases to generate copies of template nucleic acid molecules. It is a necessity of most nucleic acid polymerases that incorporation requires a free 3'-hydroxyl moiety on the terminal sugar of a short stretch of double-stranded nucleic acid adjacent to the site of new synthesis. This stretch of double-stranded nucleic acid is typically formed on a template by a short complementary sequence, called a primer, which serves as an initiation site for the polymerase synthesis reaction. In some cases a 3' modification, such as a sulfhydryl, may utilized to prime the synthesis reaction. The primer nucleic acid, which is base-paired with the template and extended by the polymerase, can be RNA or DNA. In vivo during genomic DNA replication, RNA primer sequences are synthesized de novo onto template DNA by primase enzymes. Typically, for in vitro reactions the primer is supplied as a short, often chemically synthesized, single-stranded DNA (or modified DNA or RNA), and is usually referred to as an oligonucleotide primer. The primer is often of a specific sequence, although random primers can also be used. The primer is targeted to complementary sequences by virtue of its specific base-pairing capacity. Formation of hybrids between the oligonucleotide primer and target nucleic acid are typically formed by incubation of the two in solution under conditions of salt, pH, and temperature that allow spontaneous annealing.

In the case of the PCR the oligonucleotide primer is usually in vast excess for two main reasons. First, the high concentration will drive rapid annealing. Second, as the reaction proceeds through rounds of melting, annealing and extension the primer is consumed and becomes limiting. PCR targeted nucleic acids are often initially double-stranded in character, and if not, become double stranded following the first synthetic cycle. Such double-stranded molecules cannot anneal new oligonucleotides at temperature and solvent conditions appropriate for the catalytic activity and stability of most prokaryotic and eukaryotic proteins. Consequently, in order to allow cycles of amplification the original template and the newly synthesized strands must be first separated before annealing can occur once again. In practice this is achieved by thermal melting. For PCR, temperatures of at least 80° C. are required for thermal melting of most double-stranded nucleic acid molecules of lengths greater than 100 base pairs. In most PCR protocols a temperature of 90 to 100° C. is applied to melt the DNA. Such temperatures allow only rare thermostable enzymes to be used. These polymerases are typically derived from thermophilic prokaryotes.

The advantage of RPA is that it allows the formation of short stretches of double-stranded nucleic acids bearing a free 3'-OH for extension from double-stranded templates without thermal melting. This is achieved by using the RecA protein from *E. coli* (or a RecA relative from other phyla including the T4 uvsX protein). In the presence of ATP, dATP, ddATP, UTP, ATPγS, and possibly other types of nucleoside triphosphates and their analogs, RecA or uvsX will form a nucleoprotein filament around single-stranded DNA. This filament will then scan double-stranded DNA. When homologous sequences are located the recombinase will catalyze a strand invasion reaction and pairing of the oligonucleotide with the homologous strand of the target DNA. The original pairing strand is displaced by strand invasion leaving a bubble of single stranded DNA in the region.

RecA protein can be obtained from commercial sources. Alternatively it can be purified according to standard protocols e.g. (Cox et al., 1981; Kuramitsu et al., 1981). RecA homologues have been purified from thermophilic organisms including *Thermococcus kodakaraensis* (Rashid et al., 2001), *Thermotoga maritima* (Wetmur et al., 1994), *Aquifex pyrophilus* (Wetmur et al., 1994), *Pyrococcus furiosus* (Komori et al., 2000), *Thermus aquaticus* (Wetmur et al., 1994), *Pyrobaculum islandicum* (Spies et al., 2000), and *Thermus thermophilus* (Kato and Kuramitsu, 1993). RecA has also been purified from other prokaryotes e.g. *Salmonella typhimurium* (Pierre and Paoletti, 1983), *Bacillus subtilis* (Lovett and Roberts, 1985), *Streptococcus pneumoniae* (Steffen and Bryant, 2000), *Bacteroides fragilis* (Goodman et al., 1987), *Proteus mirabilis* (West et al., 1983), *Rhizobium meliloti* (Better and Helinski, 1983), *Pseudomonas aeruginosa* (Kurumizaka et al., 1994), from eukaryotes e.g. *Saccharomyces cerevisiae* (Heyer and Kolodner, 1989), *Ustilago maydis* (Bennett and Holloman, 2001), including vertebrates e.g. Human Rad51 (Baumann et al., 1997) and *Xenopus laevis* (Maeshima et al., 1996), as well as plants including broccoli (Tissier et al., 1995). We here also show that *E. coli* recA, and T4 uvsX protein, can be purified from overexpression cultures using a hexahistidine tag at the C terminus, and remain biologically active. This is of great utility for the production of recombinant protein.

For clarity of description, leading strand Recombinase-Polymerase Amplification method (lsRPA) can be divided into four phases.

1) Sequence Targeting

RPA is initiated by targeting sequences using synthetic oligonucleotides coated with RecA, or a functional homologue such as the T4 uvsX protein. In order to permit exponential amplification two such synthetic oligonucleotides would be employed in a manner such that their free 3'-ends are orientated toward one another. Nucleoprotein filaments comprising these oligonucleotides and recombinase protein will identify targets in complex DNA rapidly and specifically. Once targeted the recombinase protein catalyses strand exchange such that D-loop structures are formed. It may be necessary to use ATP rather than ATPγS in the procedure for efficient amplification. If ATP is used, RecO, RecR, and/or RecF, molecules may prove essential for efficient amplification, or uvsY protein if uvsX recombinase is employed.

2) Initiation of DNA Synthesis

DNA polymerases will detect and bind to the hybrid between the invading oligonucleotides and the template DNA and initiate DNA synthesis from the free 3'-hydroxyl exposed in the hybrid. Exposure of this 3'-hydroxyl, and subsequent DNA synthesis, will likely require disassembly of recombinase protein from the double-stranded hybrid formed by strand exchange. To attain this disassembly it will probably be necessary to employ ATP, which can support spontaneous disassembly of recombinase from invasion complexes. Additionally disassembly can be stimulated/enhanced by the use of other proteins contained within the reaction mixture such as RuvA, RuvB, RuvC, recG, other helicases, or other stimulatory components, which can act to strip recombinase from the strand exchange product.

3) Strand Displacement DNA Synthesis and Replicon Separation.

As the DNA polymerases synthesize complementary copies of template DNAs using the free 3'-hydroxyls of invading oligonucleotides, or their partly extended products, the polymerases displace single-stranded DNAs, which may be coated with single strand binding proteins (SSB) included in the reaction. In an ideal configuration, invasion of oligonucleotides at both ends of the target nucleic acid sequence will occur in similar timeframes, such that two polymerases on the same template nucleic acid will initially progress toward one another. When these extending complexes meet one another, the original template should simply fall apart, and the polymerases will continue to synthesize without a need for strand displacement, now copying SSB-bound ssDNA template. Because of steric hinderance, polymerases may become dissociated from the template temporarily when the polymerases meet to permit the separation of the two template strands 4) Completion of Synthesis and Re-Invasion.

Once the template strands have separated, polymerases can complete the extension to the end of the template (or past the sequence acting as the second, facing, targeting site if the initial template is longer than the desired product). To permit exponential amplification it is necessary for new products to be targeted and replicated in a manner similar to the original templates, that is from both targeted ends. The newly synthesized targeted site will be freely available to targeting recombinase/oligonucleotide filaments. The site initially used to prime synthesis should also have been freed as a consequence of the use of conditions in the reaction that favor disassembly of recombinase from strand exchange products. Providing the re-invasion at this latter site occurs in less time than it takes the polymerase to synthesize past the second targeting site, be primed at that second site, and return to the first site, then single-stranded DNA will not be the primary product and exponential amplification will occur. Having multiple synthetic complexes operating on the same template raises the possibility that very short amplification times can be achieved.

Recombinase-Polymerase Amplification (RPA) Using Simultaneous Leading and Lagging Strand Synthesis In our description of (leading strand RPA) lsRPA we detail a multi-component system with the capacity to regenerate targeting sequences thus permitting exponential amplification of double-stranded DNA. Unlike the Zarling method, lsRPA avoids the linear production of single-stranded DNA. There is another approach to solving this problem that completely avoids the possibility of single-stranded products and a requirement for simultaneous end initiation. This method necessarily involves a more complex reaction mixture. Nevertheless all of the required components are now well understood and should be amenable to assembly into a single system. This system will recapitulate events occurring during the normal replication cycle of cells to permit coupled leading and lagging strand synthesis. This method, leading/lagging strand RPA is described briefly in FIGS. 1 and 3.

During normal replication in vivo, double-stranded DNA is simultaneously separated into 2 strands and both are copied to give 2 new molecules of double-stranded DNA by a replication machine. This 'machine' couples conventional 5' to 3' leading strand synthesis with lagging strand synthesis, in which short RNA primers are synthesized onto template nucleic acids by primase enzymes. During lagging strand synthesis, short fragments of DNA are produced, called Okazaki fragments, which are ligated together to form contiguous lagging strands. This simultaneous leading-strand/lagging-strand synthesis is responsible for duplication of the entire genome of prokaryotic and eukaryotic organisms alike. The essential components of this system have been identified and characterized biochemically. The components can be assembled in vitro to achieve a more efficient amplification than possible using only leading-strand synthesis.

The essential components of the replication 'machine' are now well characterized for *E. coli* and certain other organisms such as T4 phage. This machine comprises the PolIII holoenzyme (Glover and McHenry, 2001; Kelman and O'Donnell, 1995) and the primosome (Benkovic et al., 2001; Marians, 1999). The PolIII holoenzyme is made up of ten polypeptide components. Each holoenzyme contains two, asymmetrically oriented, core structures, each consisting of a polymerase (α subunit) and two additional core components the ε subunit, which possesses 3' to 5' exonuclease activity, and the θ subunit. In addition to the core complex another set of polypeptides provide the holoenzyme with processivity and couple leading and lagging strand synthesis. The β-dimer sliding clamp encircles the template DNA affixing the complex to the template with extremely high affinity. The sliding clamp loaded onto DNA by the DnaX clamp loader comprising the τ2γδδ'χψpolypeptide subunits.

For clarity of description, the RPA method can be divided into four phases. In reality all phases will occur simultaneously in a single reaction.

1) Sequence Targeting

RPA is initiated by targeting sequences using synthetic oligonucleotides coated with RecA, or T4 uvsX, or a functional homologue. Such nucleoprotein filaments will identify targets in complex DNA rapidly and specifically. Once targeted, the RecA or uvsX protein catalyses strand exchange such that a D-loop structure is formed. It may be necessary to use ATP rather than ATPγS in the procedure for efficient amplification. The linkage of leading and lagging strand syntheses however may obviate the requirement for very rapid recombinase stripping after initiation of synthesis. If ATP is used, RecO, RecR, and RecF may need to be employed with bacterial recA recombinase, or the T4 uvsY, proteins may prove essential for efficient amplification with T4 uvsX protein.

2) Primosome Assembly

Primosomes can be assembled at D-loops. Normally, in *E. coli*, D-loop structures are formed by RecA as part of the mechanism to rescue damaged DNA in vivo, or during other forms of recombination. The purpose of the combined action of RecA-mediated strand exchange and primosome assembly is to generate a replication fork. A replication fork is the nucleoprotein structure comprising the separated template DNA strands and the replisome. The replisome consists of the polymerase holoenzyme complex, the primosome, and other components needed to simultaneously replicate both strands of template DNA. Primosomes provide both the DNA unwinding and the Okazaki fragment priming functions required for replication fork progression. Similar primosome assembly occurs at recombination intermediates in T4 phage directed by gp59 and gp41 protein.

Primosome assembly has been studied intensively through genetic and biochemical analysis in *E. coli*. The minimal set of polypeptides required for this process is well known and exist as purified components. The primosome assembly proteins are PriA, PriB, PriC, DnaT, DnaC, DnaB, and DnaG. These proteins have been shown sufficient to assemble a primosome complex on bacteriophage .PHI.X174 DNA in vitro (Kornberg and Baker, 1992; Marians, 1992). PriA binds to the primosome assembly site (PAS) on the .PHI.X174 chromosome. Then PriB, DnaT, and PriC bind sequentially to the PriA-DNA complex. PriB appears to stabilize PriA at the PAS and facilitate the binding of DnaT (Liu et al., 1996). PriC is only partially required for the full assembly reaction. Omission of PriC from the reaction will lower priming 3 to 4 fold (Ng and Marians, 1996a; Ng and Marians, 1996b). The function of PriC in the bacterium is genetically redundant to PriB. DnaC then loads DnaB into the complex in an ATP-dependent fashion. This PriABC-DnaBT complex is competent to translocate along the chromosome. The DnaG primase can interact transiently with the complex to synthesize RNA primers.

During replication in *E. coli*, DnaB and DnaG function as a helicase and primase respectively. These two components are continually required in association with the PolIII holoenzyme to synthesize primers for the Okazaki fragments. Hence, DnaB and DnaG are the core components of the mobile primosome associated with the replication fork. The other primosome components described are essential for assembly of the primosome onto DNA, and for associating a dimeric polymerase. The primosome assembly proteins are required for the re-establishment of replication forks at recombination intermediates formed by RecA and strand exchange. PriA can initiate assembly of a replisome, competent for DNA synthesis, on recombination intermediates. It is possible to target D-loops in vitro with a mixture of PriA, PriB, and DnaT, which are then competent to incorporate DnaB and DnaC. Once a primosome has been formed at the D-loop, all that remains to initiate replication is to load a holoenzyme complex to the site. Alternatively in the phage T4 system the gp59 helicase loader protein recruits and assembles the gp41 replicative helicase to D-loop structures 3) Fork Assembly and Initiation of DNA Synthesis Replication forks will assemble at the site of primosome assembly. In *E. coli* the presence of a free 3'-end on the invading strand of the D-loop stimulates the DnaX clamp loader complex detailed earlier to assemble a β-dimer at this site to act as a sliding clamp. The holoenzyme and 2 core units are joined together by the scaffold τ subunit. The τ subunit also has interaction surfaces for the β-dimer, for the clamp loader, and for the DnaB helicase component of the primosome. These multiple interactions are necessary to coordinate synthesis of both leading and lagging strands using the 2 asymmetrically joined core polymerase complexes. In T4 phage the gp59/41 proteins with uvsY and gp32 proteins, and with other components coordinate assembly of the sliding clamp gp45 aided by gp44 and gp62 proteins initiates replisome assembly.

In *E. coli* the primosomal primase, DnaG, synthesizes a short RNA primer onto the unwound lagging strand DNA template. In the presence of the holoenzyme, the clamp loader recognizes the RNA/DNA duplex and loads a second β-dimer clamp onto this site. The presence of an active primosome and the interaction of the τ subunit with DnaB are critical to ensure simultaneous leading/lagging strand synthesis. Without this interaction the polymerase will move away from the primosome site without coupling.

A replication fork is now assembled. Synthesis of both leading and lagging strand will now occur simultaneously, and the DnaB helicase will separate template strands ahead of the oncoming holoenzyme. The lagging strand holoenzyme core will generate Okazaki fragments of 1 to 2 kilobases in length. Once the lagging strand polymerase encounters the previous RNA primer, it dissociates from the β-clamp and synthesis is initiated from a newly assembled clamp loaded in the vicinity of the front of the leading strand. The same lagging strand holoenzyme core will be re-used since it is physically tethered to leading strand core.

There is a dynamic interaction between β-dimer clamps, core subunits, and clamp loaders. Their affinities can switch depending upon the physical circumstances. The β-dimer that has been ' abandoned' at the end of the Okazaki fragments may be recycled via active removal by clamp loaders, or excess δ subunit that may be present.

The RNA primers at the ends of Okazaki fragments are removed by the 5' to 3' exonuclease activity of DNA polymerase I. DNA ligase then joins the Okazaki fragments together forming a continuous lagging strand.

4) Fork Meeting and Termination

In RPA, replication is initiated at two distant sites and the replication forks are oriented toward each other. As replication forks converge the two original template strands will dissociate from one another as they become separated entirely both behind, and in front, of each fork. The leading strand core of each fork will then complete synthesis, the remaining RNA primers will be processed, and the final products will be two double-stranded molecules. We can reasonably expect to amplify DNA's on the order of several Megabases (Mb) by such an approach. In this disclosure, megabase also encompasses megabasepairs. Based on the known synthetic rate of the PolIII holoenzyme we can expect the replication forks to proceed at a rate of approximately 1 Mb/1000 seconds, i.e., approximately 15 to 20 minutes per cycle for a 1 Mb fragment.

The final consideration is the mechanism by which rapid exponential amplification of DNA will be achieved. The key to this process will be to allow efficient reinvasion of the targeting sites by the use of mixtures of helicases, resolvases and the RecO, RecR, and RecF proteins. Under appropriate conditions reinvasion and primosome assembly should be possible shortly after a holoenzyme has moved away from the fork-assembly site. Continual invasions should present no problems since the DNA will simply become branched at many points. Each branch will naturally resolve as it encounters the oncoming fork. Under these conditions it may be possible to achieve enormous amplification in times similar to the time taken to replicate the DNA only once. It may be critical however to limit the concentrations of targeting oligonucleotides to avoid nucleotide depletion prior to the completion of synthesis.

In addition to the holoenzyme complex, the replication machine employs another complex known as the primosome, which synthesizes the lagging strand and moves the replication fork forwards. The primosome complex comprises a helicase encoded by DnaB and a primase encoded by DnaG. Finally, in addition to the proteins of the holoenzyme and primosome, replication requires the activity of single-stranded DNA binding protein (SSB), E. coli DNA polymerase I and DNA ligase. These latter two components are required to process Okazaki fragments.

Nested RPA

In another embodiment, RPA amplification may be performed in a process referred to herein as "nested RPA." A difficulty in detecting a rare sequence is that there can be a high ratio of non-target to target sequence. The ability of a RPA to discriminate between target and non-target DNA and amplify only target sequences is a key aspect of improved sensitivity. Discrimination between non-target and target is a reflection of the specificity of the primers and reaction conditions. The more specific a reaction is the greater the relative amount of the specific target sequence that is produced and the easier that product is to detect. An increase in specificity can, therefore, increase sensitivity as well.

The need for improved sensitivity and specificity can be addressed by using nested RPA. The nested RPA involves a first RPA of a first region of DNA. Then the reaction mixture is diluted, for example, by 10, 20, 30, 40, 50, 75, or 100 fold or more to reduce the concentration of the first primer pair, and a second primer pair is introduced into the reaction mixture and RPA repeated. According to one embodiment of the invention, the second primer pair is designed to be internal to the first primer pair to amplify a subsequence of the first RPA product. The method increases specific amplification, i.e., reduces non-specific background amplification products and therefore increases sensitivity. Such non-specific amplification products, although they arise by virtue of fortuitous partial homology to the flanking primers, are unlikely to also have sufficient homology to the nested primers to continue to amplify. Detection and specificity of RPA may be further improved by labeling one or both of the second primer pair such that only primers amplified with one or both of the second primer pair is detected.

Nested RPA is not limited to the use of two sets of primer. Naturally, more sets of primers may be used to increase specificity or sensitivity. Thus, three, four, or five pairs of primers may be used. Furthermore, the different sets of primers, as another embodiment of the invention, may share common primers as illustrated in FIG. 4.

In FIG. 4, the primer sets are designed to be used sequentially. For example, a first RPA is performed with primer set 1, a second RPA using the amplified product of the first RPA is performed with a primer set 2, a third RPA using the amplified product of the second RPA is performed with a primer set 3, a fourth RPA using the amplified sequence of the third RPA is performed with a primer set 4, and finally, a fifth RPA is performed using the amplified product of the fourth RPA is performed with a primer set 5. In this case, primer set 1, 2, and 3, share a common primer-primer (a). Primer 3, 4, and 5 share a common primer-primer (b).

Nested RPA may be performed using any of the two RPA methods described as well as a combination of the two methods in any particular order. That is, RPA may be performed solely by leading strand RPA, solely by leading and lagging strand RPA, or a combination of leading strand RPA and leading and lagging strand RPA in any particular order.

One benefit of any of the RPA methods of the invention is the size of the amplified product. While current methods of amplification such as PCR are limited to an upper limit of about 10 Kb, RPA methods are capable of amplifying regions of nucleic acids of up to hundreds of megabases. For leading/lagging strand RPA, the sizes of a target sequence to be amplified can be hundreds of megabases, such as, for example, less than 500 megabases, less than 300 megabase, less than 100 megabase, less than 70 megabase, less than 50 megabase, less than 25 megabase, less than 10 megabase, less than 5 megabase, less than 2 megabases, less than one megabase, less than 500 kb, less than 200 kb, less than 100 kb, less than 50 kb, less than 25 kb, or less than 10 kb, less than 5 kb, less than 2 kb, less than 1 kb. For lsRPA, the sizes of a target sequence can be in the megabase range such as, less than 5 megabase, less than 2 megabases, less than one megabase, less than 500 kb, less than 200 kb, less than 100 kb, less than 50 kb, less than 25 kb, or less than 10 kb, less than 5 kb, less than 2 kb, less than 1 kb.

General Considerations for Reconstituting and Enabling Recombinase-Mediated Amplification Reactions Both lsRPA and leading/lagging RPA rely on similar use of recombinase proteins to target oligonucleotide primers, however they differ in the mode by which the new daughter duplexes are formed during amplification. In leading/lagging RPA a full replication fork is established that simultaneously synthesizes leading and lagging strands so that two new duplexes are concomitantly formed. In leading strand RPA (lsRPA), only leading strand synthesis occurs so that synthesis generates one duplex and one displaced single-stranded DNA as products.

In RPA DNA synthesis initiated after strand exchange is accomplished by a polymerase. During extension of the newly synthesised strand the polymerase must be able to displace the outgoing strand, either alone or in combination with a helicase capable of mediating outgoing strand displacement. Extension of the invading primer results eventually in the release of the outgoing strand as a single-stranded DNA. To ensure that geometric amplification occurs, and that the reaction produces a vast majority of double-stranded DNA, it is necessary for this displaced single-stranded DNA to serve as template for DNA synthesis from the opposite direction. This is a central consideration for amplification using lsRPA. Two other central considerations are the polymerase species used, and the existence of a stable, dynamic, recombinase system that functions efficiently in the presence saturating levels of single-strand binding proteins. These considerations are important for both the leading/lagging RPA and lsRPA.

A) Ensuring Generation of Double-Stranded DNA from the Displaced Strand

The generation of the second strand of DNA in lsRPA can be achieved in one of several ways:

1) The displaced single-stranded DNA can simply hybridise to the complementary strand which has been displaced from invasion and extension of a second 'facing' targeting oligonucleotide. Alternatively the displaced single-stranded DNA can hybridise directly with the second 'facing' oligonucleotide. Such hybridisation events may occur spontaneously, or may be mediated by the strand assimilating activities of DNA binding proteins such as recombinases or single-stranded DNA binding proteins. Following hybridisation a polymerase will extend from the free 3' end to generate a double-stranded product. Note that for this to occur efficiently the reaction environment must enable hybridisation of complementary single-stranded DNAs, a situation not always compatible with the other aspects of the RPA reaction. In some circumstances a hybridising oligonucleotide with a modified backbone, unable to interact with most DNA binding protein, could be used.

2) If strand-displacement synthesis begins simultaneously from opposing oligonucleotide primer on the same template then the two converging replication complexes will eventually meet somewhere in the middle of the template. Provided that these converging complexes are able to pass one another the template strands will separate and each complex will complete replication by copying a single-stranded rather than double-stranded template with no further need for strand displacement.

3) If the outgoing strand possesses the capacity to form a hairpin then self-priming second strand synthesis may occur. This activity would result in a covalently linked duplex with a hairpin at one end, which could become a target for further invasion/extension reactions. This situation is not ideal for many applications, as it will generate products with variable lengths and structures. This may, however, be acceptable for detection assays, such as some diagnostic tests. Furthermore it may be possible to engineer primers such that after the first few rounds of invasion/extension most outgoing strands are capable of self-priming. This mode of duplex DNA formation may be very efficient.

Which of these three general processes dominate in an lsRPA reaction will depend on many factors. The most important factors are the distance separating the two oligonucleotides primers in the target, the invasion rate, and the sequence of the oligonucleotides and template.

In the second general format of RPA, leading/lagging RPA, the generation of substantial single-stranded DNA is avoided by establishing a full replication fork at the invasion site. A full replication fork permits the simultaneous copying of both leading and lagging strands (which would be equivalent to the outgoing strand). Leading/lagging RPA is elegant in its avoidance of the generation of single-stranded DNA, however a larger number of distinct proteins is required to generate full replication forks. Nevertheless most aspects of optimisation for RPA reactions apply to both lsRPA and leading/lagging RPA.

B) Choice of Polymerase, or Polymerase/Helicase System

The lsRPA method is similar in some respects to PCR. Both processes use of pairs of oligonucleotide primers orientated with 3' ends pointed toward one another in the target DNA and both methods achieve geometric amplification through the use of reaction products as targets for subsequent rounds of DNA synthesis. There are, however, fundamental differences in the reaction configurations. For example, in RPA target DNA is double-stranded prior to synthesis, whereas in PCR it is single-stranded after thermal separation of strands. In RPA, DNA synthesis must necessarily use DNA polymerases or polymerase complexes capable of strand displacement. Furthermore, because partially copied strands are physically associated with displaced strand through the template, there is a risk that if the polymerase dissociates temporarily from the template the 3' end of the new strand, and eventually the whole new strand, will be lost by the action of branch migration or another phenomenon known as bubble migration. This suggests that ideally processive polymerases will be used for RPA reactions. It is also important to consider that if converging replication complexes cannot readily pass one another without polymerase dissociation then some processive polymerases may inhibit the RPA reaction on some templates. In summary the ideal choice of polymerase will depend on the precise format and objective of the particular RPA reaction, in particular the size of the product to be amplified.

C) Establishment of a Stable Persistent Active Recombinase Activity in a Noise-Suppressed Environment A third consideration is how to establish a stable, but dynamic, recombinase activity, while silencing the noise generated by aberrant primer annealing seen at low temperatures. This means establishing a reaction environment that balances several seemingly incompatible requirements. For efficient RPA recombinase proteins must remain active while assembled into oligonucleotide/recombinase filaments scanning for target double-stranded DNAs. These complexes must also disassemble after completing strand exchanges to permit DNA synthesis. This must happen in an environment rich in single-stranded DNA proteins. These proteins are needed to stimulate recombination and DNA synthesis while preventing aberrant oligonucleotide behaviour by melting secondary structures. Fundamentally, the recombinases and single-stranded binding proteins are in competition for oligonucleotide binding. While the single-strand binding proteins are necessary to enable efficient strand displacement during synthesis, they suppress recombination activity because they have a higher affinity for single-stranded DNA and bind with more cooperativity than do recombinases.

Establishment of a functional recombinase/replication reaction environment requires nucleotide cofactors. RecA, and other recombinases, require nucleotide co-factors, such as ATP, to assemble filaments onto single-stranded DNA, perform homology searches, and complete strand exchange. We have surmised that non-hydrolysable analogues such as ATP-$\gamma$-S would be incompatible with RPA because the extremely high stability of the 3-stranded DNA/recA intermediate formed in the presence of with ATP-$\gamma$-S would prevent reinvasion at primer targets and would thus prevent efficient amplification. They may even prevent any useful access of polymerase to the recombination intermediate. Earlier attempts to amplify DNA using *E. coli* recA (Zarling et al) were probably limited by the ATP-$\gamma$-S in the described reactions.

The requirement for ATP in the reaction and the fact that recombinase-complexes will be dynamically forming and disassembling introduces additional complexities, primarily due to complex interactions and competition between key reaction components. In particular single-stranded binding proteins, such as the *E. coli* single-stranded binding proteins, such as *E. coli* SSB or T4 phage gp32 protein, are necessary to stimulate recombination by recA and homologues, due both to their capacity to collect the outgoing strand, and to melt secondary structures in single-stranded DNAs thus enhancing recombinase loading. In RPA it is likely that single-stranded binding proteins will further stimulate DNA synthesis by binding and stabilising the displaced DNA strand, preventing undesirable branch migration.

Despite the clear requirement for single-stranded binding proteins, these proteins generally have a considerably higher affinity for single-stranded DNA than recombinases such as recA, or uvsX, and can inhibit nucleation of recombinase/DNA filaments. Moreover, as filaments formed in the presence of ATP undergo end-dependant disassembly (Bork, Cox and Inman J Biol Chem. 2001 Dec. 7; 276(49):45740-3), such filaments are likely to be rapidly saturated with single-stranded binding proteins and inactivated soon after initiation of the reaction. Thus for efficient RPA conditions that prevent inactivation of the reaction components are key in establishing robust amplification.

We have predicted a potentially stable reaction composition using *E. coli* recA protein in the presence of ATP and the *E. coli* single-stranded binding protein SSB, or the T4 uvsX protein in the presence of gp32. We suggested the presence of recO, recR, and possibly recF proteins (Bork, Cox and Inman EMBO J. 2001 Dec. 17; 20(24):7313-22), could lead to an environment in which pre-loaded recA filaments were stabilised, and in which recA could nucleate successfully onto SSB-bound oligonucleotides. A similar recombinase loading system has been described in other organisms including the recombination/replication/repair system of bacteriophage T4. The T4 recombinase uvsX can be loaded onto single-stranded DNA coated with the T4 single-stranded DNA binding protein gp32 by the action of a third component, the uvsY protein (Morrical and Alberts J Biol Chem. 1990 Sep. 5; 265(25):15096-103). Interestingly a principal role of this recombination system in vivo is to permit recombination-dependant DNA synthesis by assembling replication components at recombination intermediates such as D-loops (Formosa and Alberts Cell. 1986 Dec. 5; 47(5):793-806). This process is similar to what should happen in RPA driven from D-loops made by the invasion of synthetic oligonucleotides. In addition to interactions between the three components uvsX, uvsY, and gp32, there are also interactions between these components and the replication machinery such as the polymerase, clamp loader, primase/helicase, and dda helicase (Reddy, Weitzel and Von Hippel, Proc Natl Acad Sci USA. 1993 Apr. 15; 90(8):3211-5, Hacker and Alberts, J Biol Chem. 1992 Oct. 15; 267(29): 20674-81). Taken together these facts suggest that the components of the T4 recombination/replication machinery would perhaps be even more ideal for RPA than the *E. coli* equivalents.

In addition to the use of recombinase loading proteins, such as recO and recR, or uvsY, there are other ways to create an appropriate balance between recombinase activity and the activity of single-stranded DNA binding proteins. The DNA binding and/or cooperativity behaviour of recombinases and single-stranded DNA binding proteins can be modulated by mutation. In addition, recombinases from different sources have distinct properties (Eggler, Lusetti and Cox, J Biol Chem. 2003 May 2; 278(18):16389-96. Epub 2003 Feb. 20, Villemain et al., J Biol Chem. 2000 Oct. 6; 275(40):31496-504). This suggests that a range of recombinase and single-strand DNA binding protein activities could be explored. The use of mutated proteins or proteins from different species, in a set of optimisation experiments could lead to the identification of an optimal ratio of the competing recombinase and single-stranded binding activities. Ultimately the activities would be balanced such that DNA association/dissociation for the two DNA-binding species permits sufficient recombinase activity together with sufficient DNA melting activity of the single-strand DNA binding protein to perform its necessary functions also. In addition, reduction of noise due to mispriming may be achieved through the optimisation of such parameters as oligonucleotide sequence design, reaction buffer, the use of partly modified oligonucleotides, the use of part duplex oligonucleotides or the addition of other specific reaction components detailed below.

Here we provide the results of experiments that validate the RPA method. In particular, we provide a description and demonstration of reaction compositions capable of supporting DNA amplification. We demonstrate that relatively short synthetic oligonucleotides can be used to target specific sequences and support initiation of DNA synthesis. We describe the requirements for particular types and concentrations of certain recombinases, single-stranded binding proteins, ATP, and oligonucleotide concentrations. We further describe the optimisation and modulation of the reaction environment, which supports an active and dynamic recombination system with desired rate behaviour, through the inclusion of crowding agents (such as polyethylene glycols), recombinase loading factors and/or mutated proteins with altered biochemical activities. We establish that in the presence of distributive polymerases at least (e.g. the *E. coli* DNA polymerase I Klenow fragment), there are substantial improvements in amplification efficiency when the distance between the amplification priming sites is optimised. We establish that a balance between polymerase exonuclease activity and oligonucleotide protecting agents must be employed to avoid non-specific degradation of oligonucleotide primers. We show that amplification of sequences embedded within linear (or relaxed) DNA substrates is relatively inefficient (at least with very distributive polymerases such as Klenow), whereas amplification reactions directed toward the ends of linear DNA substrates are most effective. We provide methods to prepare target DNA to be more efficiently amplified in an lsRPA reaction, including the methods of thermal or chemical melting or restriction enzyme digestion. We also provide evidence that the nature of the single-stranded binding protein is critical to establish efficient RPA reactions, and provide a rationale for this. Furthermore we suggest improvements and novel approaches to reduce noise and optimise amplification reactions performed at relatively low, or ambient, temperatures by the use of part-double-stranded oligonucleotides, or oligonucleotide wholly or partly lacking a phosphate backbone. We also provide evidence that other enzymes and proteins involved in DNA metabolism can influence RPA reactions, and some may be configured to improve reaction efficiency and specificity. These include topoisomerases, which can relax recombination/replication intermediates and may aid targeting of embedded sequences, as well as helicases such as T4 dda helicase or T4 gp41 which can improve the polymerase initiation and elongation efficiency, particularly if non-strand displacing polymerases are used. Finally we show that priA and the ruvA/B helicases have activities that might be used to optimise amplification efficiency.

Selection of RPA Reagents and Reaction Parameters

The details of leading strand RPA, leading and lagging strand RPA, and nested RPA were listed above. This section will describe the selection of reagents and parameter for any of the three methods discussed above.

One benefit of RPA is that the amplified product of RPA is double stranded DNA that could be used for other molecular biology procedures. Thus, RPA may be combined with other methods in molecular biology. For example, the starting material for RPA may be a PCR amplified fragment. Alternatively, the product of an RPA may be used for PCR.

If necessary, the RPA products in any of the methods of the invention may be purified. For example, in the nested RPA method, the amplified product may be purified after each RPA step before a subsequent RPA step. Methods of purification of nucleic acids are known in the art and would include, at least, phenol extraction, nucleic acid precipitation (e.g., with salt and ethanol), column chromatography (e.g., size exclusion, ionic column, affinity column and the like) or any combination of these techniques.

As discussed, the primers used in RPA may be "double stranded" or "capable of forming double stranded structures." These terms refer to DNA molecules that exist in a double stranded condition in a reaction solution such as a RPA reaction solution or a PCR reaction solution. The composition of a PCR solution is known. The composition of a RPA reaction is listed in this detailed description section and in the Examples.

The primers may have a single stranded region for hybridization to the target DNA in the presence of a recombinase agent. The single stranded region may be, for example, about 10 bases about 15 bases, about 20 bases, about 25 bases, about 30 bases, about 40 bases, and about 50 bases. Even longer regions such as about 75 bases, about 100 bases, about 150 bases or more may be used but it is not necessary. The choice of single stranded regions will depend on the complexity of the starting nucleic acid so that for example, a human genome may require a longer primer while a plasmid may require a much shorter primer.

The two strands of nucleic acid in a double stranded DNA need not be completely complementary. For example, the double-stranded region of a double-stranded DNA may differ by up to 1% in sequence. That is, the sequence of two strands of nucleic acid may differ by one base in one hundred bases and would still exist in a double stranded condition in solution. Nucleic acids with 1% difference in their complementary sequence are contemplated as double stranded DNA for the purposes of this disclosure.

In addition, the target nucleic acid (i.e., the nucleic acid to be amplified by the RPA methods of the invention) may be partially double stranded and partially single stranded. For example, nucleic acid in any of the configuration of FIG. 5 would be suitable as a target nucleic acid of the invention. As discussed, the target nucleic acid may be RNA. RNA can be converted to double-stranded cDNA using known methods and the double-stranded cDNA may be used as the target nucleic acid. As shown if FIG. 5, the template nucleic acid may have any combination of ends selected from 3' overhang, 5' overhang, or blunt ends.

The lsRPA method of the invention comprises at least the following steps. First, a recombinase agent is contacted to two nucleic acid primers (referred to herein as a first and a second primer) to form two nucleoprotein primers (referred to herein as a first nucleoprotein primer and a second nucleoprotein primer).

Figure 6A:
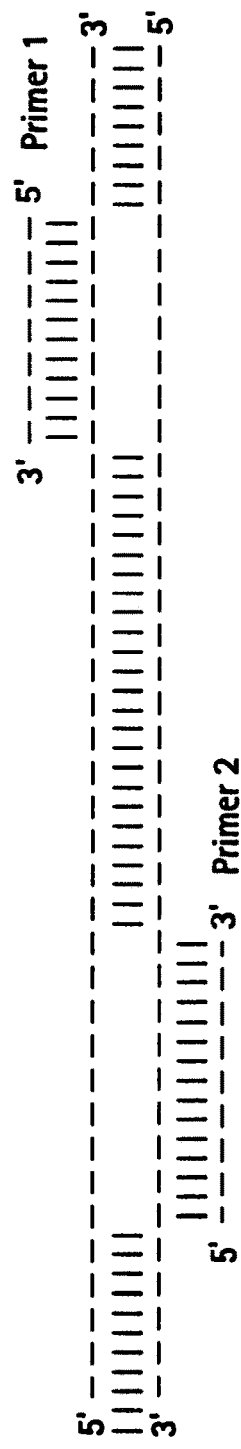
FIGS. 6A-6B depict in panels (a) and (b) the various orientations of the RPA primer pairs in hybridization with the target nucleic acid.
Figure 6B:
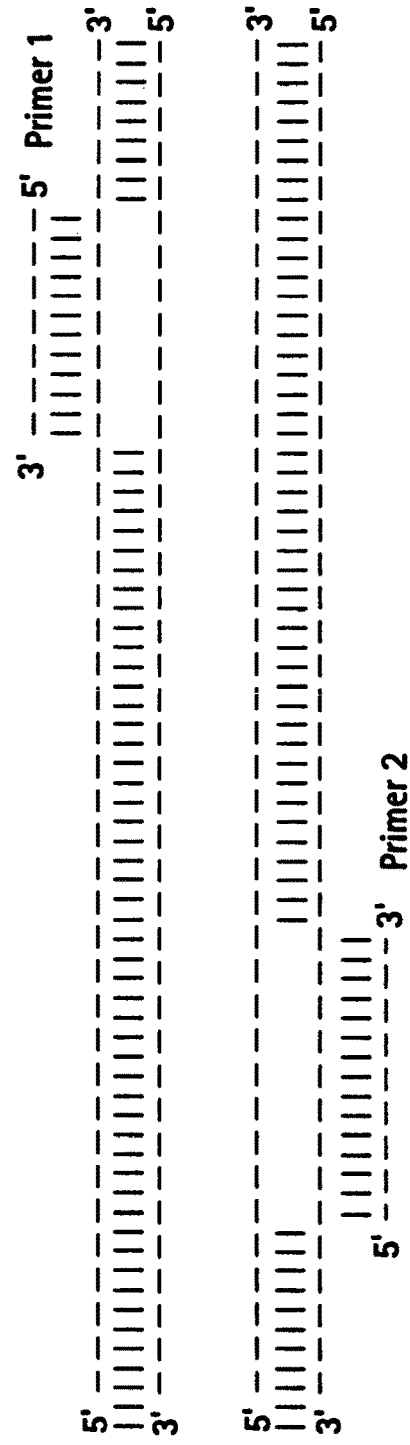

Second, the first and second nucleoprotein primers are contacted to the template nucleic acid to form a double stranded structure at a first portion of the first strand and a second double stranded structure at a second portion of the second strand. The two primers are designed so that when hybridized, they are pointed at each other as illustrated in FIG. 6A. Alternatively, primer 1 and primer 2 may hybridize different target nucleic acids as illustrated in FIG. 6B.

Figure 7A:
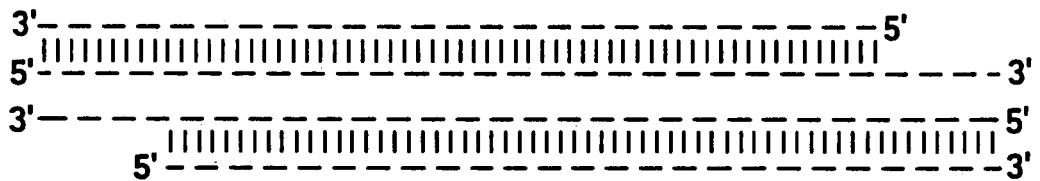
FIGS. 7A-7C in panels (A), (B), and (C) depict a schematic representation of an RPA reaction in progress.
Figure 7B:
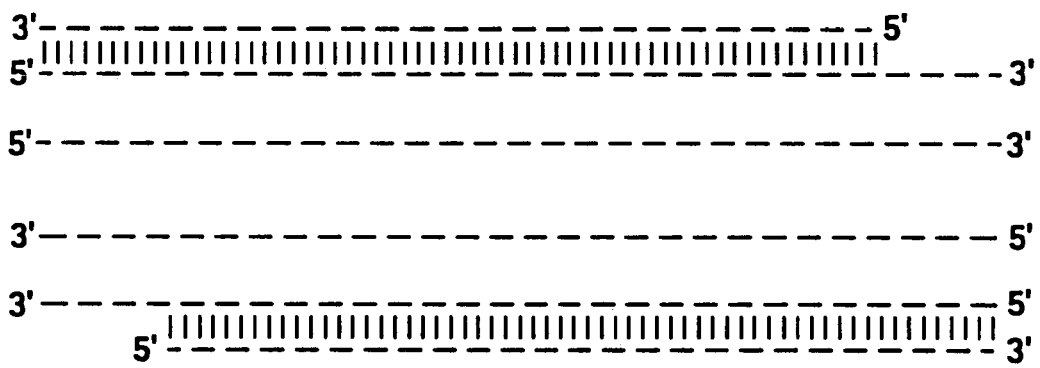
Figure 7C:
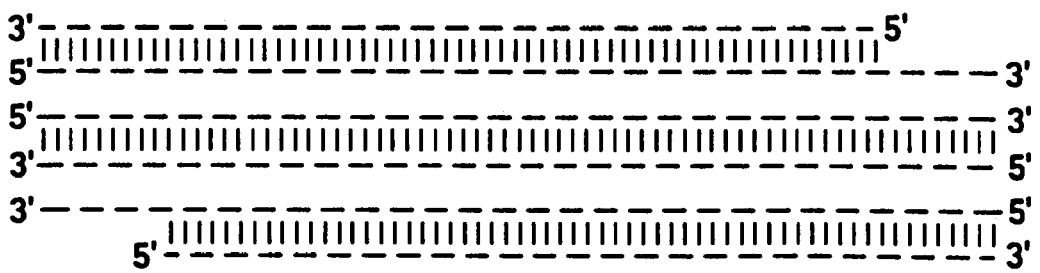

Third, the nucleoprotein primers are extended at their 3' ends to generate a first and a second double stranded nucleic acid (FIG. 7A). Where the primers are hybridized to different target nucleic acids, the elongation of the primers will generate displaced strands (FIG. 7B). In this case, the two displaced strands that result from primer elongation may hybridize and form a new double stranded template nucleic acid (FIG. 7C).

Step two and three are repeated until the desired degree of amplification is reached. The process is a dynamic process in that primer hybridization to the target nucleic acid and elongation are allowed to proceed continuously. One advantage of this invention is that the amplification is performed continuously without the need for temperature cycling or enzyme addition after initiation of the reaction.

In an embodiment, steps two and three are repeated at least 5 times. Preferably, it is repeated at least 10 times. More preferably, it is repeated at least 20 times, such as at least 30 times. Most preferably, the two steps are repeated at least 50 times. For multiple repetitions of the amplification step (e.g., step 2 and 3) a RPA of the invention is preferably started with a primer to target nucleic acid ration of at least 100 to 1, preferably at least 300 to 1, and most preferably at least 1000 to 1. That is, there are at least 100, 300 or 1000 copies of the primer per copy of a target nucleic acid.

In an optional step, after a sufficient round of amplification, additional components may be added to the reaction after a period of time to enhance the overall amplification efficiency. In one embodiment, the additional components may be one or more of the following: recombinase agents, one or more primers, polymerase, and one or more of the additional agents (discussed in a separate section below).

In a preferred embodiment, a small fraction of a first RPA reaction is used as a supply of template DNA for subsequent rounds or RPA amplification. In this method, a first RPA amplification reaction is performed on a target nucleic acid. After the first RPA reaction, a small fraction of the total reaction is used as a substitute of the target nucleic acid for a subsequent round of RPA reaction. The fraction may be, for example, less than about 10% of the first reaction. Preferably, the fraction may be less than about 5% of the first reaction. More preferably, the fraction may be less than 2% of the first reaction. Most preferably, the fraction may be less than 1% of the initial reaction.

The primer used in RPA is preferably DNA although PNA, and RNA are also suitable for use as primers. It is noted that in fact, in DNA replication, DNA polymerases elongate genomic DNA from RNA primers.

Synthetic oligonucleotides may serve as DNA primer and can be used as substrates for formation of nucleoprotein filaments with RecA or its homologues. Sequences as short as 15 nucleotides are capable of targeting double-stranded DNA (Hsieh et al., 1992). Such oligonucleotides can be synthesized according to standard phosphoroamidate chemistry, or otherwise. Modified bases and/or linker backbone chemistries may be desirable and functional in some cases. Additionally oligonucleotides may be modified at their ends, either 5' or 3', with groups that serve various purposes e.g. fluorescent groups, quenchers, protecting (blocking) groups (reversible or not), magnetic tags, proteins etc. In some cases single-stranded oligonucleotides may be used for strand invasion, in others only partly single stranded nucleic acids may be used, the 5' stretch of sequence of an invading nucleic acid being already hybridized to an oligonucleotide.

In another embodiment of the invention, the primers may comprise a 5' region that is not homologous to the target nucleic acid. It should be noted that the processes of the invention should be functional even if the primers are not completely complementary to the target nucleic acid. The primers may be noncomplementary by having additional sequences at their 5' end. These additional sequences may be, for example, the sequence for a restriction endonuclease recognition site or the sequence that is complementary to a sequencing primer. The restriction endonuclease recognition site may be useful for subsequent cleavage of the amplified sequence. The use of restriction endonuclease that cleaves nucleic acid outside the restriction endonuclease recognition site is also contemplated. The sequence that is complementary for a sequencing primer may allow rapid DNA sequencing of the amplified product using commercially available primers or commercially available sequencing apparatus.

Formation of nucleoprotein filaments can be performed by incubation of the primer (oligonucleotides) with RecA protein or its homologues in the presence of ATP, and auxiliary proteins such as RecO, RecR and RecF, or uvsY in the case of T4 proteins. When incubated at 37° C. in RecA buffer (20 mM Tris-HCl pH 7.5, 10 mM MgCl$_2$, 2 mM ATP, 2 mM DTT and 100 µg/ml Bovine Serum Albumin), RecA will form helical filaments on ssDNA with 6 protomers per turn. The DNA is located within the interior of the protein helix. In the presence of dsDNA, the RecA/ssDNA nucleoprotein filament can scan DNA at rates of at least $10^7$ bp per hour. The mode of scanning is unclear but it is at a speed (>$10^3$ bp per second) that it may involve only the initial few base pairs that can be easily accessed along one face of the major groove. Successful binding may result in a transition to a triple-helical intermediate, which is then followed by strand invasion and displacement to form a D-loop. Such joint molecules can be formed under similar condition to those described above for formation of helical filaments, and hence in the presence of ssDNA, the homologous dsDNA, RecA, ATP, auxiliary proteins and suitable buffer and temperature conditions, joint molecules will form spontaneously. If ATP is used the assembly is reversible and will reach equilibrium, but RecA/ssDNA filaments can be stabilized, even in the presence of SSB, by the auxiliary proteins RecO and RecR. Alternatively the T4 uvsX protein may be stabilized in the presence of uvsY protein. In the case of thermostable proteins the temperature of incubation can be higher. If a renewable supply of ATP is required a standard ATP regeneration system can be included in the reaction.

DNA polymerases can use the free 3'-hydroxyl of the invading strand to catalyze DNA synthesis by incorporation of new nucleotides. A number of polymerases can use the 3'-hydroxyl of the invading strand to catalyze synthesis and simultaneously displace the other strand as synthesis occurs. For example E. coli polymerase II or III can be used to extend invaded D-loops (Morel et al., 1997). In addition, E. coli polymerase V normally used in SOS-lesion-targeted mutations in E. coli can be used (Pham et al., 2001). All of these polymerases can be rendered highly processive through their interactions and co-operation with the .β.-dimer clamp, as well as single stranded DNA binding protein (SSB) and other components. Other polymerases from prokaryotes, viruses, and eukaryotes can also be used to extend the invading strand.

In another embodiment of the invention, the primer may be partially double stranded, partially single stranded and with at least one single stranded 3' overhang. In this embodiment, the primer may comprise a invading strand and a non-invading strand as shown in FIG. 8A. In this case, after the invading strand is hybridized to the target DNA and elongated, it serves as a target nucleic acid for a second primer as shown in FIG. 8B. The elongation of the second primer would displace the noninvading strand as shown in FIG. 8C. In this embodiment, as the target nucleic acid is amplified, the non-invading strand of primer 1 is displaced. If both primer one and primer two are partly double stranded primers, then the non-invading strands of both primer one and primer two will accumulate in solution as the target nucleic acid is amplified.

In one embodiment of the invention, at least two of the primers in a RPA reaction are partially double stranded and partially single stranded each generated by the hybridization of an invading strand and a non-invading oligonucleotide strand, which possess sequences of sufficiently complementary that they form a double stranded region. Preferably, the two oligonucleotide strands are sufficiently complementary over the relevant region that they can form a double stranded structure in RPA reaction conditions.

In an embodiment of the invention, the primers, including single-stranded and partially double-stranded primers, are labeled with a detectable label. It should be noted that a fluorescence quencher is also considered a detectable label. For example, the fluorescence quencher may be contacted to a fluorescent dye and the amount of quenching is detected. The detectable label should be such that it does not interfere with an elongation reaction. Where the primer is partially double stranded with an invading strand and a non-invading strand, the detectable label should be attached in such a way so it would not interfere with the elongation reaction of the invading strand. The non-invading strand of a partially double stranded primer is not elongated so there are no limitations on the labeling of the non-invading strand with the sole exception being that the label on the non-invading strand should not interfere with the elongation reaction of the invading strand. Labeled primers offer the advantage of a more rapid detection of amplified product. In addition, the detection of unincorporated label, that is, labeled oligonucleotides that have not been extended, will allow the monitoring of the status of the reaction.

Monitoring a RPA reaction may involve, for example, removing a fraction of an RPA reaction, isolating the unincorporated fraction, and detecting the unincorporated primer. Since the size of an unincorporated primer may be less than 50 bp, less than 40 bp, less than 30 bp or less than 25 bp, and the size of the amplified product may be greater than 1 Kb, greater than 2 Kb, greater than 5 Kb, or greater than 10 Kb, there is a great size difference between the incorporated and unincorporated primer. The isolation of the unincorporated primer may be performed rapidly using size exclusion chromatography such as, for example, a spin column. If a primer is labeled, a monitor procedure comprising a spin column and a measurement (e.g., fluorescence or radioactivity) can be performed in less than one minute. Another alternative for separating elongated primers from unelongated primers involve the use of PAGE. For example, the elongated primer may be separated from the unelongated primer by gel electrophoresis in less than 5 minutes. Yet another alternative for separating elongated primers involves the use of immobilized oligonucleotides. For example oligonucleotides homologous to sequences found uniquely within the amplified DNA sequence can be used to capture nucleic acids produced by primer elongation specifically. These capturing oligonucleotides can be immobilized on a chip, or other substrate. Capture of the elongated oligonucleotides by the capturing oligonucleotides can be performed by RecA protein mediated methods, or by traditional solution hybridizations if necessary.

In another embodiment of the invention, a double stranded primer may be labeled such that the separation of the two strands of the primer may be detected. As discussed above, after multiple rounds of elongation, the invading strand and the noninvading strands of a partially double stranded primer is separated. After this separation, the non-invading strand does not participate in the RPA reaction. This characteristic may be used to detect and monitor a RPA reaction in a number of ways.

In this application, the detectable label may be a fluorescent label or an enzyme and the label quencher (also referred to as the label inhibitor) may be a fluorescence quencher or an enzyme inhibitor. In these cases, the label is detected by fluorescence or enzyme inhibition. The delectability of the label would be the fluorescence if a fluorescent label is used or enzyme activity if an enzyme is used.

In the first method, the invading strand may be labeled with a label and the non-invading strand may be labeled with a detectable label quencher. The label, in the proximity of the label quencher (label inhibitor) on the partially double stranded primer would not be highly detectable. After RPA, the invading strand would be separated from the noninvading strand and thus, the label and the label quencher would be separated. The separation would cause the label to be more detectable. Thus, measuring the increases in the amount of detectable label may monitor RPA reactions.

The second method is similar to the first method except that the invading strand is modified with a label quencher while the noninvading strand is modified with a label. Then RPA is allowed to proceed with the result (same as method 1) of the label being separated from the label quencher. Thus, the overall delectability of the label would increase.

The third method involves labeling the noninvading strand of one double stranded primer with a label. In addition, the noninvading strand of a second double stranded primer is labeled with a label quencher. The two non-invading stands are designed to be complementary to each other. In this configuration, the RPA reaction is initially fluorescent. As the RPA reaction progresses, the two noninvading strands are displaced into solution and they hybridize to each other because they are designed to be complementary. As they hybridize, the label and the label quencher are brought into proximity to each other and the fluorescence of the reaction is decreased. The progress of the RPA reaction may be measured by monitoring the decrease in label detectability.

In a fourth method, the noninvading strands of a first and second double stranded primers are labeled with a first label and a second label. The two noninvading strands are also designed to be complementary to each other. As in the third method, after RPA, the two noninvading strands are hybridized to each other and the proximity of the two labels will be a reflection of the progress of the RPA reaction. The proximity of the two labels may be determined, for example, by direct observation or by isolation of the non-invading strands. As discussed above, isolation of primers and other small nucleic acids can be accomplished by size exclusion columns (including spin columns) or by gel electrophoresis.

In another embodiment of the invention, the non-invading strand of one or both of the primers is homologous to a second region of nucleic acid such that the primer can hybridize to and primer DNA synthesis at the second region of nucleic acid. Using this method, a second RPA reaction using the noninvading stand from the primer of a first RPA may be started. The product of the second RPA may be monitored to determine the progress of the first RPA.

In yet another embodiment of the invention, the non-invading strand is detected by a biosensor specific for the sequence of the non-invading strand. For example, the biosensor may be a surface with a nucleic acid sequence complementary to the non-invading strand. The biosensor may monitor a characteristic that results from the binding of the non-invading strand. The characteristic may be a detectable label.

Suitable detectable labels for any of the methods of the invention include enzymes, enzyme substrates, coenzymes, enzyme inhibitors, fluorescent markers, chromophores, luminescent markers, radioisotopes (including radionucleotides), and one member of a binding pair. More specific examples include fluorescein, phycobiliprotein, tetraethyl rhodamine, and β-gal. Bind pairs may include biotin/avidin, biotin/strepavidin, antigen/antibody, ligand/receptor, and analogs and mutants of the binding pairs.

The recombinase agent of the invention may be RecA, uvsX, RadA, RadB, Rad 51 or a functional analog or homologues of these proteins. If desired, the recombinase may be a temperature-sensitive (referred to herein as "ts") recombinase agent. If a ts recombinase is used, the RPA reaction may be started at one temperature (the permissive temperature) and terminated at another temperature (the non permissive temperature). Combinations of permissive temperatures may be, for example 25° C./30° C., 30° C./37° C., 37° C./42° C. and the like. In a preferred embodiment, the ts protein is reversible. A reversible ts protein's activity is restored when it is shifted from the nonpermissive temperature to the permissive temperature.

In a preferred embodiment, the RPA is performed in the presences of ATP, an ATP analog, or another nucleoside triphosphate. The ATP analog may be, for example, ATPγS, dATP, ddATP, or another nucleoside triphosphate analog such as UTP.

Other useful reagents that may be added to an RPA reaction include nucleotide triphosphates (i.e., dNTPs such as dATP, dTTP, dCTP, dGTP and derivatives and analogs thereof) and a DNA polymerase. Other useful reagents useful for leading/lagging RPA include NTPs (ATP, GTP, CTP, UTP and derivatives and analogs thereof). One advantage of the RPA reaction is that there is no limit on the type of polymerase used. For example, both eukaryotic and prokaryotic polymerases can be used. Prokaryotic polymerase include, at least, *E. coli* pol I, *E. coli* pol II, *E. coli* pol III, *E. coli* pol IV and *E. coli* poly. Eukaryotic polymerases include, for example, multiprotein polymerase complexes selected from the group consisting of pol-α, pol-β, pol-δ, and pol-ε.

In another embodiment of the invention, the RPA process is performed in the presence of an accessory component to improve polymerase processivity or fidelity. Both eukaryotic and prokaryotic accessory components may be used. Preferably, the accessory component is an accessory protein is from *E. coli*. Useful accessory proteins include single-strand binding protein, helicase, topoisomerase, and resolvase. Other useful accessory proteins include a sliding clamp selected from the group consisting of an *E. coli* β-dimer sliding clamp, a eukaryotic PCNA sliding clamp and a T4 sliding clamp gp45. Other accessory components include a DNA Polymerase III holoenzyme complex consisting of β-Clamp, DnaX Clamp Loader, and the Polymerase Core Complex. Still other accessory components include RuvA, RuvB, RuvC, and RecG. The properties endowed by the use of additional components will likely enable the amplification of large DNAs not previously successfully targeted by current methods such as PCR.

In another embodiment, the RPA is performed in the presence of agents used to stabilize recombinase/ssDNA nucleoprotein filaments. For example, the agent may be RecR, RecO, RecF, or a combination of these proteins, or T4 uvsY protein if T4 components are used. Molecular crowding agents may also be employed to modulate biochemical interactions in a favourable manner. Other useful agents include PriA, PriB, DnaT, DnaB, DnaC, and DnaG.

One benefit of the present invention is that the RPA reaction may be performed at reduced temperatures compared to a PCR reaction. For example, the RPA process may be performed between 20° C. and 50° C. Preferably, the RPA process is performed at less than 45° C. More preferably, the RPA process may be performed at less than 40° C. Even more preferably, the RPA process may be performed at less than 35° C. Most preferably, the RPA process may be performed at less than 30° C. One of the reasons that the RPA process can be performed at these reduced temperatures is because RPA may be performed without temperature induced melting of the template nucleic acid. Further, unlike PCR, absolute temperature control is not required and the temperature can fluctuate without adversely affecting RPA. For example, the amount of fluctuation may be anywhere within the temperatures specified above. The temperature necessary for melting of double stranded DNA also contribute to premature enzyme inactivation, a disadvantage absent in the methods of this invention.

RPA may be performed to test for the presences or absences of a genotype. The genotype tested may be associated with a disease or a predisposition to a disease. Alternatively, the genotype may be associated with a normal phenotype or a phenotype that confers special resistance to a disease. The genotype as disclosed above may be any standard genetic variant such as a point mutation, a deletion, an insertion, an inversion, a frameshift mutation, a crossover event, or the presence or absences of multiple copies of a genetic sequence (e.g., the presences of minichromosomes).

One method of detecting a genotype is to detect the distance between a primer pair in an RPA reaction. The distance between a primer pair is reflected by the size of the amplified sequence. In that method, the two primers are selected such that it spans a target region such as, for example, a gene. Then RPA is performed using the primer pair and the RPA product is analyzed. The analysis may involve determining the size or sequence of the amplified product. Methods of determining the size of a DNA sequence, including at least techniques such as agarose gels, PAGE gels, mass spectroscopy, pulsed field gels, gene chips, sucrose sedimentation and the like are known. There are many DNA sequencing methods and their variants, such as the Sanger sequencing using dideoxy termination and denaturing gel electrophoresis (Sanger, F., Nichlen, S. & Coulson, A. R. Proc. Natl. Acad. Sci. U.S.A. 75, 5463-5467 (1977)), Maxam-Gilber sequencing using chemical cleavage and denaturing gel electrophoresis (Maxam, A. M. & Gilbert, W. Proc Natl Acad Sci USA 74, 560-564 (1977)), pyrosequencing detection pyrophosphate (PPi) released during the DNA polymerase reaction (Ronaghi, M., Uhlen, M. & Nyren, P. Science 281, 363, 365 (1998)), and sequencing by hybridization (SBH) using oligonucleotides (Lysov, I., Florent'ev, V. L., Khorlin, A. A., Khrapko, K. R. & Shik, V. V. Dokl Akad Nauk SSSR 303, 1508-1511 (1988); Bains W. & Smith G. C. J. Theor. Biol 135, 303-307 (1988); Dmanac, R., Labat, I., Brukner, I. & Crkvenjakov, R. Genomics 4, 114-128 (1989); Khrapko, K. R., Lysov, Y., Khorlyn, A. A., Shick, V. V., Florentiev, V. L. & Mirzabekov, A. D. FEBS Lett 256. 118-122 (1989); Pevzner P. A. J Biomol Struct Dyn 7, 63-73 (1989); Southern, E. M., Maskos, U. & Elder, J. K. Genomics 13, 1008-1017 (1992)).

One method of detecting a genotype is to use primers that are specific for a particular genotype. For example, a primer may be designed to efficiently amplified one genotype but inefficiently or not amplify another genotype at all. In an embodiment, the primer may comprise a 3' sequence that is complementary to one genotype (e.g., a genetic disease genotype) but not to another genotype (e.g., a normal genotype).

The genotype to be determined may be indicative of a disease such as, for example, the presence of an activated oncogene; the presence of the gene for Huntington's disease or the absence of an anti-oncogene.

The 3' bases of the primers are especially important in determining the specificity and efficiency of an RPA reaction. A primer may be designed so that the 3' base is complementary to one genotype and not complementary to another genotype. This will allow efficient RPA of one genotype and an inefficient RPA (if any) of the second genotype. It is noted that the method is effective if only one primer of the primer pair can differentiate between different phenotypes (by having different efficiencies of amplification). In a preferred embodiment, both primers in an RPA reaction can differentiate between different genotypes. In this above example, the primers are complementary to one genotype and are not complementary to a second genotype by one base at its 3' end. In a preferred embodiment, the primer is not complementary to the second genotype by at least one base at its 3' end. Preferably, the primer is not complementary to the second genotype by at least 2, 3, 4, 5, 6, 7, 8, 9, or 10 bases at its 3' end. Most preferably, the primer is completely non-complementary or cannot hybridize to the second genotype while it can hybridize to the first genotype.

In some of the methods discussed, the presence or absence of an amplified product provides the indication of the presence or absence of a genotype. In these cases, the RPA reaction may be monitored by the methods discussed throughout the specification.

In a preferred embodiment, an RPA reaction for genotyping will amplify a sequence regardless of the genotype of the patient. However, the genotype of a patient will alter a characteristic of the amplified sequence. For example, the amplified sequence may be a different size, or sequence for one genotype than for another genotype. In that way, the RPA reaction will contain an internal control to indicate that the amplification reaction was performed successfully. Naturally, a method of RPA, which includes one or more additional pairs of primers as controls for the performance of the RPA reaction, is also envisioned.

In another embodiment, an RPA reaction may be used to determine the presence or absences of a nucleic acid molecule. The nucleic acid molecule may be from any organism. For example, the microbial composition of a sample may be determined by using a battery of RPA reactions directed to the nucleic acid of different microbes. RPA is especially useful for the detection of microbes. In one embodiment, the pathogens are selected from viruses, bacteria, parasites, and fungi. In further embodiments, the pathogens are viruses selected from influenza, rubella, varicella-zoster, hepatitis A, hepatitis B, other hepatitis viruses, herpes simplex, polio, smallpox, human immunodeficiency virus, vaccinia, rabies, Epstein Barr, retroviruses, and rhinoviruses. In another embodiment, the pathogens are bacteria selected from *Escherichia coli*, *Mycobacterium tuberculosis*, *Salmonella*, *Chlamydia* and *Streptococcus*. In yet a further embodiment, the pathogens are parasites selected from *Plasmodium*, *Trypanosoma*, *Toxoplasma gondii*, and *Onchocerca*. However, it is not intended that the present invention be limited to the specific genera and/or species listed above.

Here we present data that help to define reaction conditions that permit efficient amplification of DNA by RPA.

Single-Stranded DNA Binding Protein

Single-stranded DNA binding proteins are required for RPA reactions. These proteins bind to single-stranded DNA, melt secondary structure, facilitate outgoing strand displacement, and suppress branch migration. In RPA their activity is required during several distinct phases. We have investigated the activities of two single-stranded DNA binding proteins, *E. coli* SSB and bacteriophages T4 gp32. The T4 gp32 has proven to be most useful in our hands. Furthermore we have generated a number of distinct forms of this protein by including hexahistidine (His) peptide tags at the N or C termini, as well as investigating several previously described point mutations. Activities of gp32 variants are depicted schematically in FIG. 21.

Variant Forms of gp32

Figure 12:
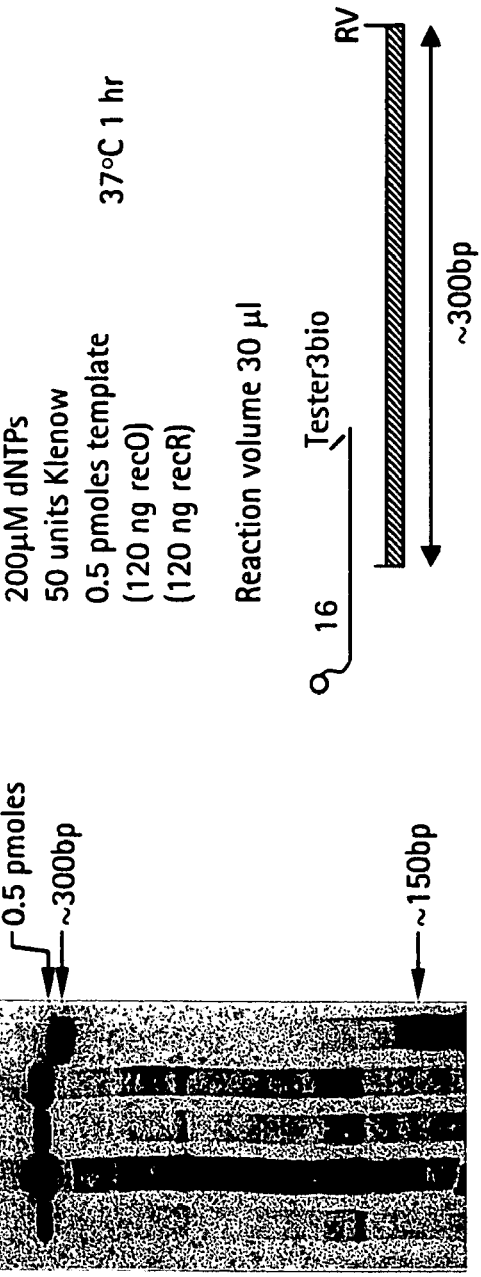
FIG. 12 depicts single stranded binding proteins facilitate recombinase invasion and primer extension. Both E. coli SSB and T4 gp32 with an N-terminal His tag (gp32(N)) stimulate recA-mediated invasion/elongation on a linear DNA template.
Figure 21:
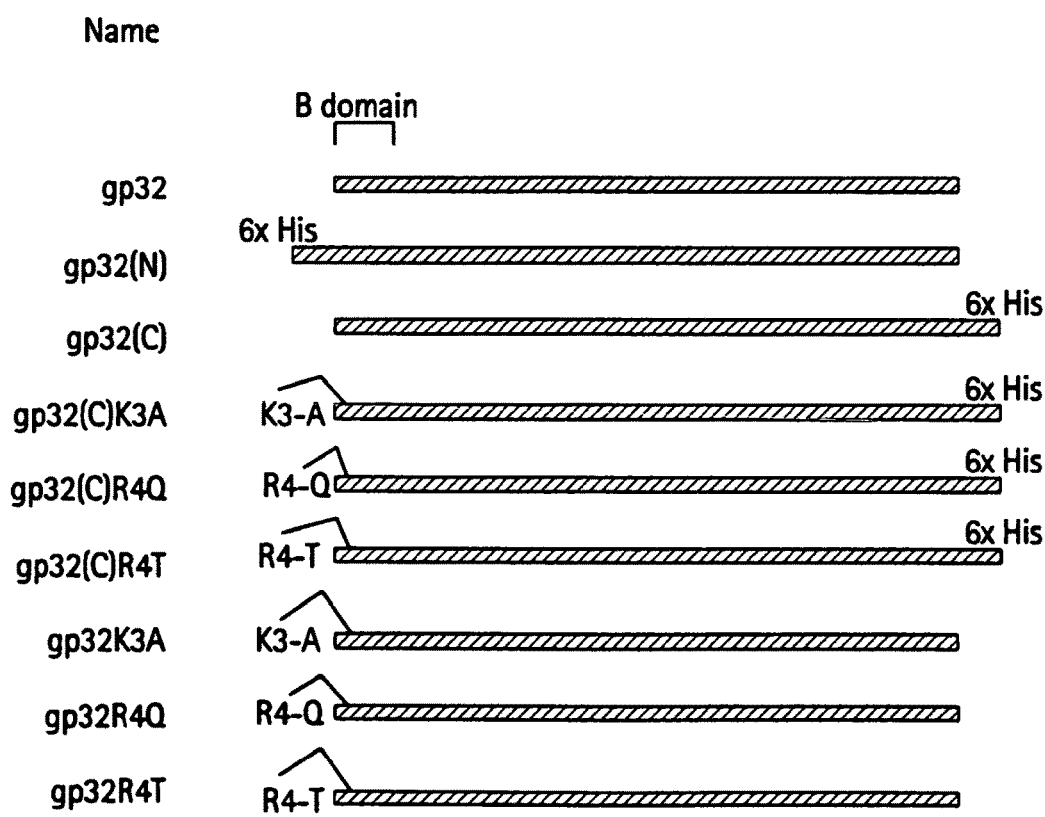
FIG. 21 depicts modified gp32 proteins. Shown is a schematic representation of the bacteriophage T4 gp32 proteins used in this study and the position of various modification and mutations. Figure discloses "6× His" as SEQ ID NO: 81.
Figure 22:
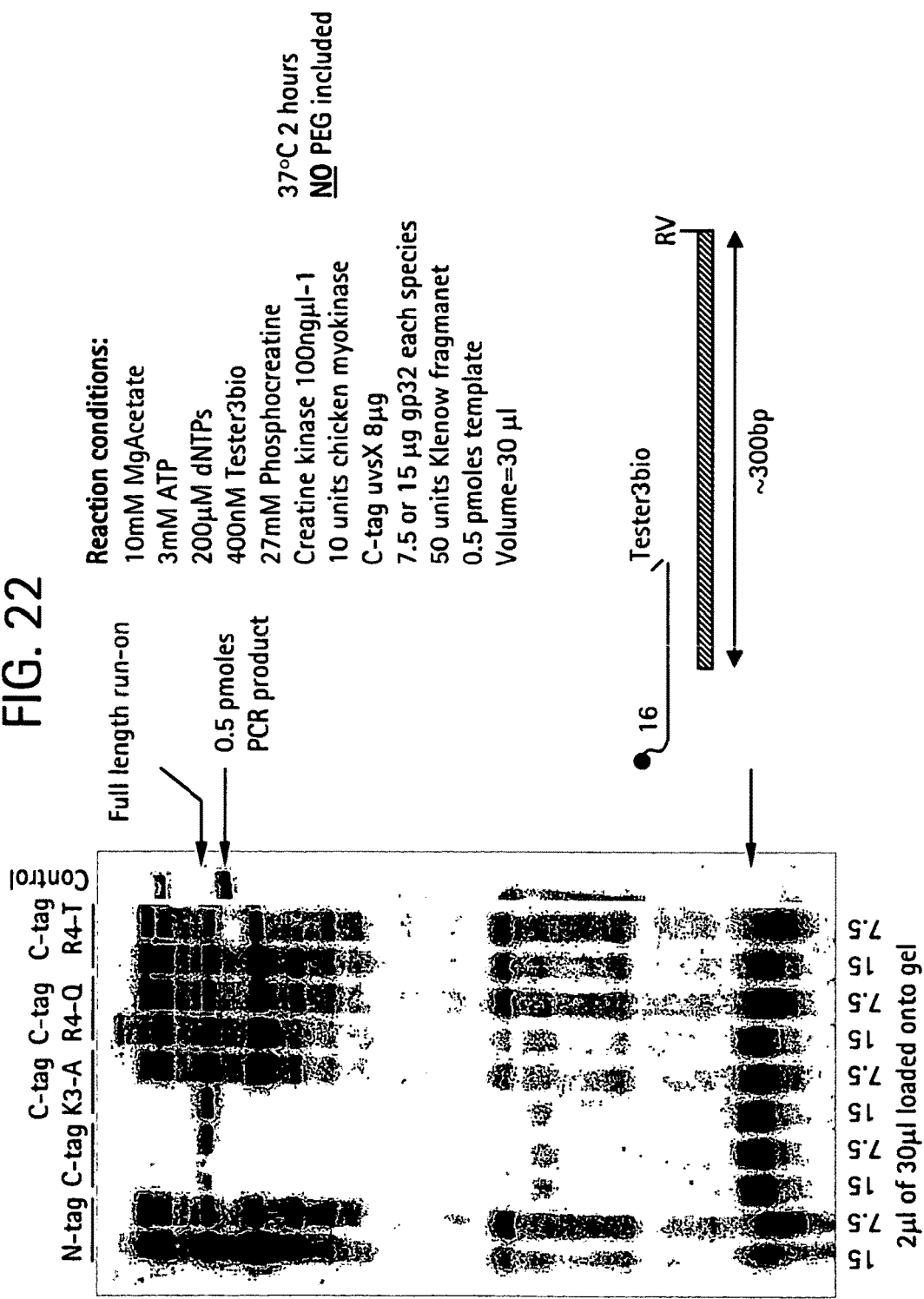
FIG. 22 depicts activity of gp32 protein. Modified gp32 proteins show a variety of activities in linear invasion/run-on assays.

T4 gp32 protein possesses several features that are of potential utility to RPA reactions. Foremost gp32 has a relatively small DNA binding site (8-10 nucleotides), displays similar binding properties under a wide range of salt concentrations, and displays high (unlimited) cooperativity between monomers (Scheerhagen et al., J Biomol Struct Dyn. 1986 April; 3(5):887-98; Kuil et al., Biophys Chem. 1988 December; 32(2-3):211-27). In contrast, E. coli SSB protein has several distinct DNA binding modes that vary with salt concentration all of which possess relatively large DNA binding sites (32, 56 or 65 nucleotides)(Ferrari et al., J Mol Biol. 1994 Feb. 11; 236(1):106-23) and there is complex cooperativity behaviour (Lohman and Ferrari, Annu Rev Biochem. 1994; 63:527-70). Because the initial size of the outgoing strand is small when synthetic oligonucleotides are employed, we reasoned that the properties of the gp32 protein would be optimal for RPA. We expressed and purified gp32 possessing an N-terminal His tag (gp32(N)). In initial experiments we found gp32(N) to function at least as well as the E. coli SSB protein, even when combined in a heterologous system with the E. coli recA recombinase (FIG. 12). This was surprising result as gp32 is reported to display extremely high cooperativity between monomeric subunits and it seemed unlikely that recA would be able to compete effectively for oligonucleotide binding in its presence. When we compared the behaviour of gp32(N) to untagged gp32, however, we discovered that the two proteins did not behave equivalently. As the N-terminal His tag is directly adjacent to the 'B' domain of the gp32 protein, which is required for cooperativity between monomers, we reasoned that gp32(N) must have attenuated cooperativity. We therefore generated a gp32 protein possessing a C-terminal His tag (gp32(C)), as well as point mutant forms of gp32(C) in accordance with previously published mutants having a lysine to alanine change at position 3 (K3 to A), or an arginine either glutamine (R4 to Q) or threonine at position 4 (R4 to T) (FIG. 21). These three point mutant proteins exhibit progressively less cooperativity (FIG. 22) (Villemain, et al. J Biol Chem. 2000 Oct. 6; 275(40):31496-504). We tested the capacity of these proteins at two different concentrations to support invasion/extension reactions on a linearized template in combination with the bacteriophage T4 uvsX protein and the Klenow fragment of E. coli DNA polymerase I (FIG. 22). Firstly we note that gp32(C) yields much less product than other gp32 variants at either concentration (FIG. 22 compare with gp32(N)) and that the products are almost exclusively full-length, in contrast to gp32(N). When we compare these results to those obtained with the point mutant allelic series we note that the gp32(N) protein most closely resembles the profile obtained with gp32(C)R4 to T, which has been reported to be significantly attenuated in cooperativity. This suggests that the N terminal His tag of gp32(N) interferes with the function of the B domain in a manner similar to the point mutations.

There are several other relevant observations. Firstly, the proteins believed to demonstrate the highest cooperativity, i.e. gp32(C)>gp32(C)K3A seem to produce less product. Secondly, for gp32(C) and gp32(C)K3A, more amplified product is generated when less single-stranded binding protein is used, in contrast to gp32(N) and gp32(C)R4T which generate more product in run-on assays when more proteins is used. Taken together these observations suggest an explanation. If the gp32 species is progressively more cooperative then it will form progressively more stable filaments on the oligonucleotides and make it progressively more difficult for recombinase to load. Consequently when the most cooperative gp32 species are employed there is a significant limitation on the availability of recombinase-loaded filaments. If the concentration of gp32 is raised, recombinase loading is further suppressed by gp32 single-stranded DNA binding activity. Consistent with this, as the cooperativity of the gp32 is progressively decreased the amount of amplified product increases. This is consistent with a substantial increase in recombinase-coated filament formation. As relatively un-cooperative gp32 monomers are less likely to coat oligonucleotides and permit the recombinase, uvsX, to seed instead. We note that in the case of gp32(N) and gp32(C)R4T, more product is generated with increased gp32(N) or gp32(C)R4T in DNA run-on assays. This contrasts results using the more cooperative gp32 variants. One possibility is that during and following the strand exchange reaction gp32 is required to stabilise the recombination and synthesis intermediates. This may happen because gp32 cooperativity is so attenuated that it may no longer participate in those aspects of the reaction, or because the recombinase out-titrates gp32 and halts the reaction. The contrasting results of amplification versus run-on assays suggest that the optimal amount of cooperativity may be less than that possessed by the most cooperative gp32 variants. Thus for RPA mutant gp32 variants, with attenuated cooperativity, may be the most appropriate as these will permit higher levels of recombinase loading. Attenuation of gp32 cooperativity must, however, be balanced against noise generated by mispriming events as may be encountered in environments with less gp32 activity.

Finally, there is a substantial difference in the quantity of product generated in RPA using 7.5 µg versus 15 µg of gp32(C)K3A. The 7.5 µg level more closely resembles results with more weakly cooperative mutants. Most likely in some cases during the course of the reaction, which was held at 37° C. for 2 hours, the amount of single-stranded run-on product increases to the point that gp32 no longer effectively saturates single-stranded DNA in the reaction. In such a situation two things would occur. First there would be a rapid increase in the number of homology-searching filaments leading to a significant rate increase in invasion. Then the lack of gp32 to stabilise outgoing strands would lead to many partial extensions by Klenow not being stabilised, and possibly a greater rate of bubble migration separating the new strand from the template. Hence many more synthesised strands would not achieve full length.

A Model of Gp32 Function in Multiple Invasion/Extension Reactions

We had earlier noted that in a heterologous system involving recA and gp32(N), polyethylene glycol was required to permit more than one cycle of invasion and extension from a given template. Here we describe a model to rationalize these observations and explain why targeting DNA ends multiple times requires specific types of single-stranded DNA binding protein. It is clear gp32 activity is required to stabilise the outgoing strand during the strand exchange process. If this does not occur then as the recombinase disassembles the outgoing strand re-hybridises with its complementary strand and displaces the invading oligonucleotide. Following strand exchange the outgoing strand can exist in one of two states, which likely place different demands on the single-stranded DNA binding protein. These two states arise as a consequence of the relationship between the single-stranded searching DNA and the duplex target DNA. If the recombination event can extend to an end of a linear duplex DNA, and it is possible for the outgoing strand to be completely removed from its complement at one end, then the outgoing strand is un-constrained at one end. Under this un-constrained condition the new duplex involving the incoming DNA strand and its complement is able to rewind to form B form DNA. This is necessary because during the pairing reaction the target DNAs are under wound by the activity of the invading recombinase filament. Un-constrained outgoing strands can readily bind single-stranded DNA binding proteins, which will prevent branch migration from occurring and allowing the invading strand to be removed.

Alternatively if the recombination event does not extend to the end of the target duplex, as would occur if an embedded sequence were targeted, then the outgoing strand is topologically constrained because it is physically joined to the complementary strand upstream and downstream of the recombining region. Such intermediates are highly unstable because the newly formed duplex cannot rewind without making the outgoing strand also wind around it. And since the outgoing strand is constrained at both ends this is energetically unstable, and the new hybrid is placed under considerable strain. Consequently a far higher demand is placed on the activity of single-stranded DNA binding proteins in this context because there is substantial drive to eject the incoming strand and rewind the original duplex (FIG. 6).

Figure 29:
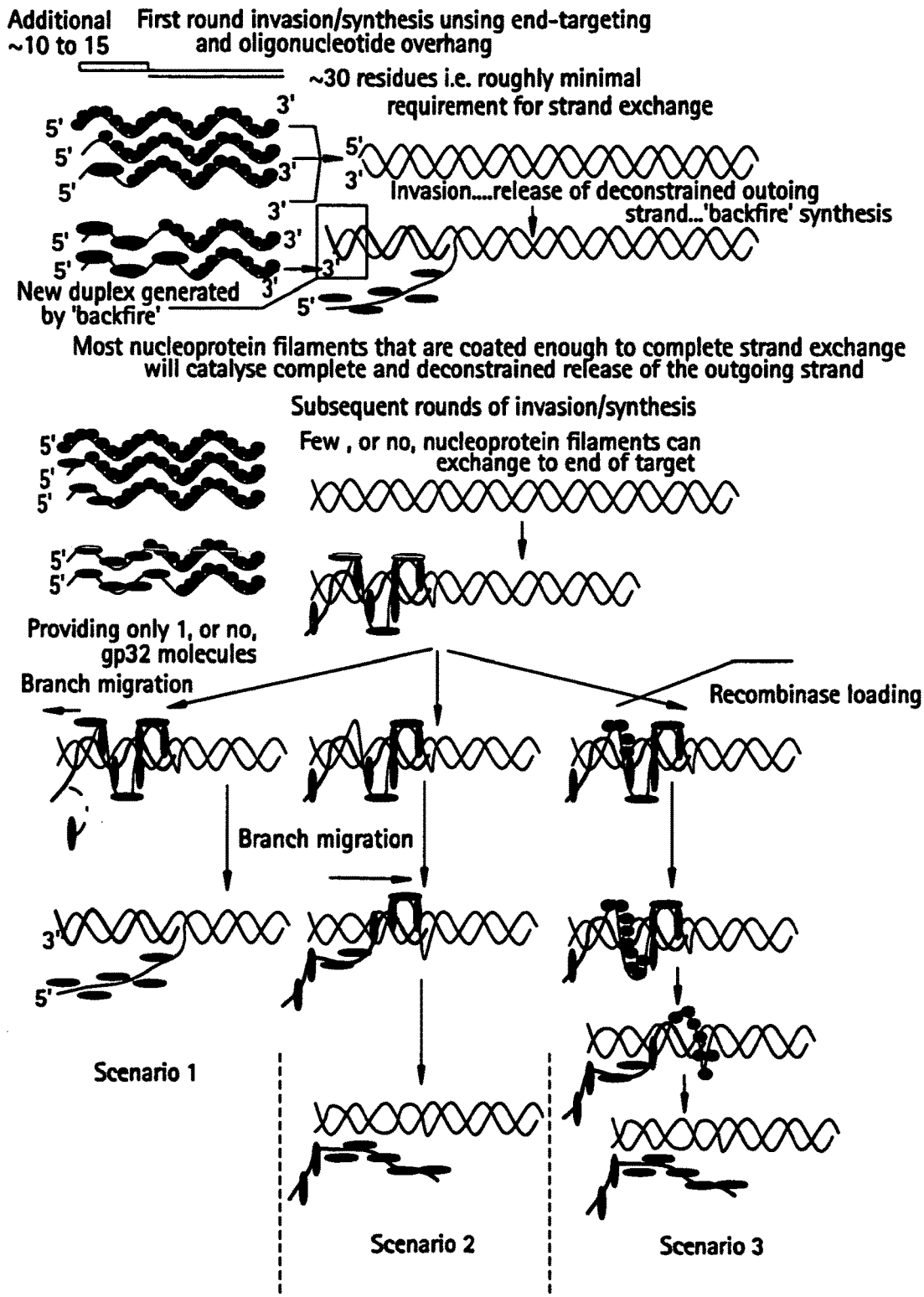
FIG. 29 depicts DNA end directed invasion. Shown is a schematic depicting possible outcomes of end-directed invasion events.

In our efforts to establish effective conditions for repeated strand invasion and extension of linear DNA targets we have noted that only oligonucleotides targeted to the ends of linear sequences are readily extended to full template length, at least when using a distributive polymerase such as the Klenow fragment of E. coli DNA polymerase I. We have found that under certain conditions, for example when using recA with gp32(N) or E. coli SSB, only one round of invasion and extension can readily occur on each target template. These observations may be understood by considering the outcome of invasion events occurring under several different circumstances leading to either fully released outgoing strands (plectonemic joints) or topologically constrained intermediates (paranemic joints). Finally, we have identified certain other conditions that are permissive for multiple rounds of invasion and extension from a single template, a situation ideally suited to the RPA reaction. We propose a model based on our own data to consolidate these observations, and forms a framework around which optimisation of the RPA reaction can be designed. This model takes into account the behaviour of gp32 protein under different reaction environments and justifies gp32 behaviours with the effects of other reaction components (FIG. 29).

The model schematically describes the nature and outcome of recombination events between the end of a target duplex and an invading oligonucleotide that initially possesses a 5' overhang relative to the target. This situation typifies the experimental circumstance we have studied. Despite this starting situation all but the initial cycle involves the invading oligonucleotides having their 5' extreme flush to the 5' extreme of the target duplex DNA. This is the case because the target DNA complementary strand possesses a 3'-end that can be extended during the first round to copy the overhang region of the invading primer, which we term backfire synthesis. Experiments performed with gp32(N) protein (in the absence of PEG), suggest that once the target is flush at the 5'-end to the oligonucleotide i.e. after the first round, then subsequent invasion/extension cycles are very inefficient or do not occur at all. Early experiments showed only a roughly equimolar quantity of run-on product to start template. How does this occur?

We believe that this block to re-invasion/extension arises because invading oligonucleotides are rarely fully coated by recombinase. Thus complete exchange to the 5' flush end of a target will also occur very rarely and corresponding outgoing strands will remain in a constrained state (FIG. 13). The exchange is initially incomplete and the intermediate is unstable due to an inability to allow the new duplex to relax into a B-DNA helix in the presence of the topologically constrained outgoing strand. Such unstable intermediates will have a tendency to rewind the original duplex and eject the invading strand as the recombinase disassembles.

We found, however, that if a crowding agent such as polyethylene glycol is included in the presence of gp32(N), subsequent invasion/extension occurs. One possibility is that under these conditions unstable intermediates are temporarily stabilised by gp32(N), such that elongation can occur. It is possible that polyethylene glycol acts to partly rescue the poor cooperativity of the compromised gp32(N) allowing it to stabilise these otherwise unstable intermediates. This conclusion is supported both by our data showing that N-terminally his-tagged gp32 is cooperatively attenuated, and the known capacity of crowding agents to enhance the effectiveness of interactions between molecules, thus partly making up for the poorer interaction between monomers. We initially believed that this experiment might be best explained by suggesting that recA filaments were more abundant in the presence of PEG, as previously reported elsewhere (Layery P E, Kowalczykowski S C. J Biol Chem. 1992 May 5; 267(13):9307-14), however we feel that this does not adequately account for the observed switch from a dead-end only one round of invasion to productive multiple rounds of invasion/extension.

Figure 15:
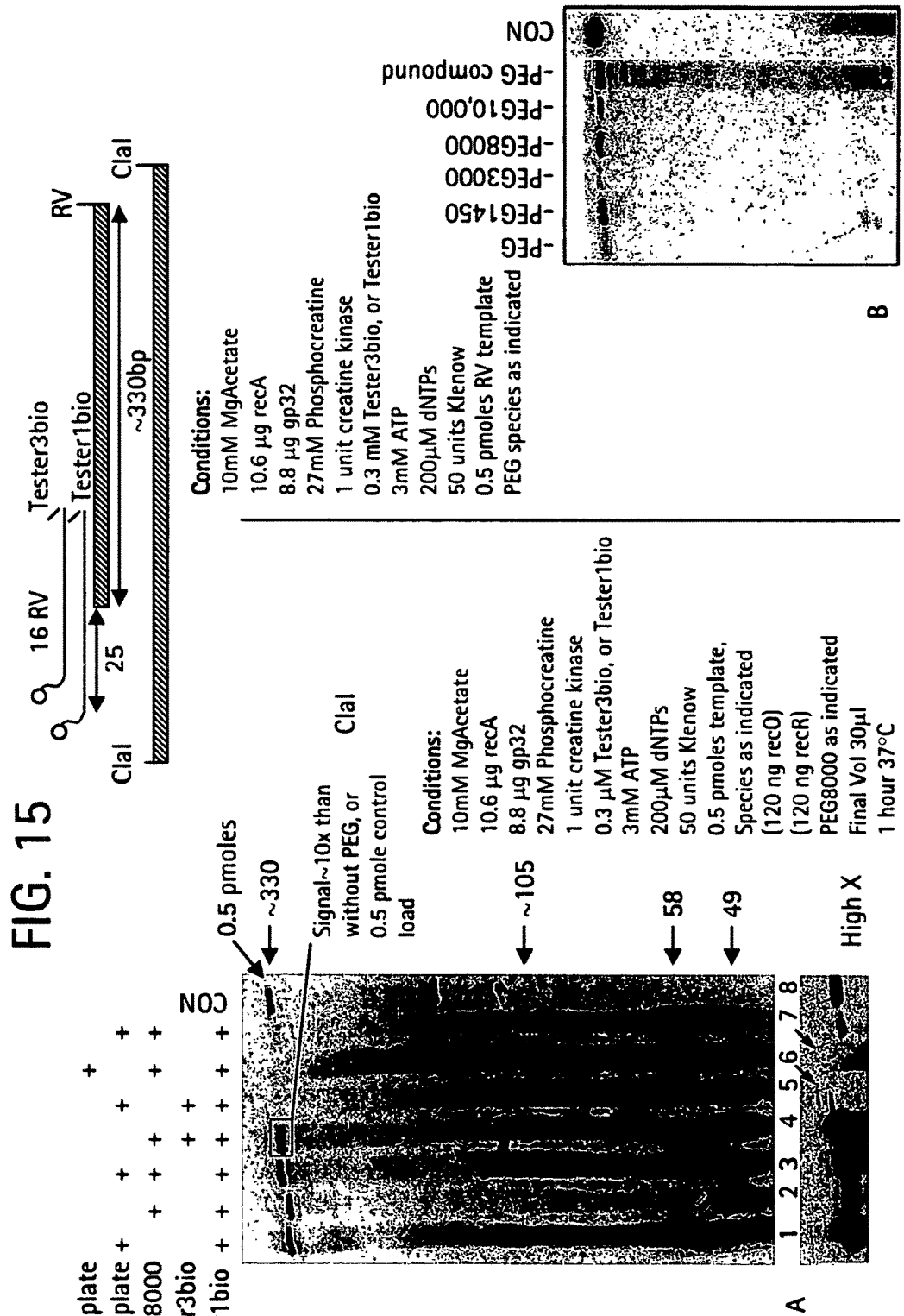
FIG. 15 depicts the effect of crowding agents. Crowding agents can alter the reaction behaviour. In the presence of polyethylene glycols, gp32(N) and recA recombinase, multiple invasion events can be stimulated on single templates without the requirement for 5' overhang in the targeting oligonucleotide.

The difference between PEG stimulation of full-length multiple run-ons at end-directed targets versus the far poorer activity at truly embedded targets (FIG. 15), suggests that the temporary stabilisation of an intermediate, as suggested above, is insufficient alone to generate substantial elongation. If this were the case for run-on assays at embedded targets it should work as well in reinvasion at end-directed targets, but this is not the case (FIG. 15). Alternatively the difference between efficiencies may be explained by supposing that gp32 temporarily stabilises an intermediate in which the 5' extent of the incoming oligonucleotide is not paired but free, and possibly even coated with gp32 dependent on the length. Provided that this unexchanged segment is not coated with gp32, or that the gp32 can readily dissociate, as would be the case without cooperativity, then the 5'-most portion of the oligonucleotide could become paired via rapid branch migration (FIG. 29, scenario 1). In fact there is a difference between truly embedded sequences and re-invasion at DNA ends (FIG. 15). For embedded targets, secondary branch migration leading to unconstrained release of the outgoing strand can never occur because the ends are too distant.

We would therefore conclude that the small DNA binding size, and high cooperativity between subunits permits gp32 proteins permits multiple invasion and extension reactions by stabilising the constrained paranemic joint structures for a sufficient time. There are various possible outcomes (FIG. 29). Either the last small section of oligonucleotide at the 5' end that was not initially exchanged becomes hybridised through a branch migration event, or disassembly of gp32 on the outgoing strand permits the invading/extending oligonucleotide to be lost through branch migration. Alternatively, loading of recombinase onto the outgoing strand and re-invasion ejects the incoming strand (bubble migration). If hybridisation via branch migration occurs then an unconstrained structure arises that can be readily stabilised and extended. If either gp32 disassembly or bubble migration occur then there is a substantial risk that the new extending strand will be lost before it is fully extended. If a single stranded DNA binding protein with a large binding site, like E. coli SSB, or one with poor cooperativity, like. gp32(N), is used in the absence of PEG, then no temporary stabilisation occurs and the invading oligonucleotide is ejected without being extended.

Consequently based on this model, and the earlier conclusions about the frequency of recombinase-loaded filaments in the presence of various g32 forms, we conclude that a balance between the activities of recombinases and gp32 molecules must be struck that best meets the various requirements of the amplification reactions. We can summarise the needs and effects of single-stranded DNA binding proteins in different phases of the RPA reaction as follows.

Phase 1

Single-stranded DNA binding proteins help to prepare single-stranded DNAs for recombinase loading by melting secondary structure so that recombinase loading can occur consistently. Thus the melting activity of single-stranded DNA binding proteins is desirable and also plays a part in silencing non-specific annealing of primers. Despite this, however, excessive levels of protein and excessive cooperativity can significantly reduce number of recombinase-loaded filaments available for invasion.

Phase 2

Single-stranded DNA binding proteins collect the outgoing strand and prevent spontaneous ejection of the incoming oligonucleotide as the recombinase disassembles. The instability of paranemic joints means that invasions occurring on embedded sequences, including the case that oligonucleotide ends are flush to the duplex ends (as would occur during most cycles of an amplification), means that significant cooperative activity may be required for many situations. In general this phase of the reaction will benefit from a surplus of highly cooperative single-stranded DNA binding proteins.

Phase 3

Single-stranded DNA binding proteins bind to the displaced strand that forms during DNA synthesis. As in phase 2 this displaced strand may be unconstrained, or topologically constrained, and these two circumstances place different demands on the single-stranded DNA binding protein.

Phase 4.

In certain configuration of the RPA reaction the displaced single-stranded outgoing strand must hybridise to a partner oligonucleotide to permit subsequent generation of a new duplex. Many single-stranded DNA binding proteins prevent complementary strands from annealing, however T4 gp32 protein aids re-annealing of complementary DNA. Therefore bacteriophage T4 gp32 protein is an ideal protein for this phase.

Oligonucleotide Length:

There is little published evidence to support how effectively recA, or other recombinases, might be used with relatively the short synthetic oligonucleotide primers used for RPA. It is also unclear whether a stable reaction environment can be generated in which such short DNA oligonucleotides remain actively loaded with recombinase. Most studies performed with recA utilise comparatively large substrates such as single-stranded and double-stranded forms of the bacteriophage M13 genome (many thousands of residues) as donor and acceptor DNAs. Experimental assays for recombinase activity often consist of the formation of intermediate, or completed, recombination events measured by electrophoretic migration or electron microscopy (Harris L D, Griffith J. J Biol Chem. 1987 Jul. 5; 262(19):9285-92). A few experiments have been described using short oligonucleotides. Sequences as short as 15 nucleotides have been shown to assemble functional homology-searching complexes with recA in the presence of the non-hydrolysable cofactor analogue ATP-γ-S, but investigations combining short oligonucleotides and ATP are ambiguous (Hsieh P, Camerini-Otero C S, Camerini-Otero R D. Proc Natl Acad Sci USA. 1992 Jul. 15; 89(14):6492-6). The homology-searching function of recombinases is not necessarily sufficient to complete strand exchange and to release from the invasion complex to allow access by other DNA metabolising proteins such as polymerases. Indeed, studies have shown that recA shows transitions between low ATP hydrolysis rate (a useful indicator of combined DNA binding activity and functional recombinase activity) and high hydrolysis rate at oligonucleotide lengths substantially longer than the 15 nucleotides required for searching. Furthermore the type of nucleotide cofactor seems to influence on the length at which such hydrolysis transitions occur (Katz F S, Bryant F R. Biochemistry. 2001 Sep. 18; 40(37):11082-9). The bacteriophage T4 recombinase uvsX has also been shown to exhibit variable properties on short oligonucleotides, and shows some sensitivity to the base composition (Formosa T, Alberts B M. J Biol Chem. 1986 May 5; 261(13):6107-18). Despite this, both uvsX and recA are capable of performing recombination events with single-stranded substrates of roughly 30 base pairs or more in the presence of hydrolysable nucleotides like ATP, suggesting that the use of such short synthetic targeting oligonucleotides is reasonable (Salinas F, Jiang H, Kodadek T. J Biol Chem. 1995 Mar. 10; 270(10):5181-6; Formosa T, Alberts B M. J Biol Chem. 1986 May 5; 261(13):6107-18).

Figure 9:
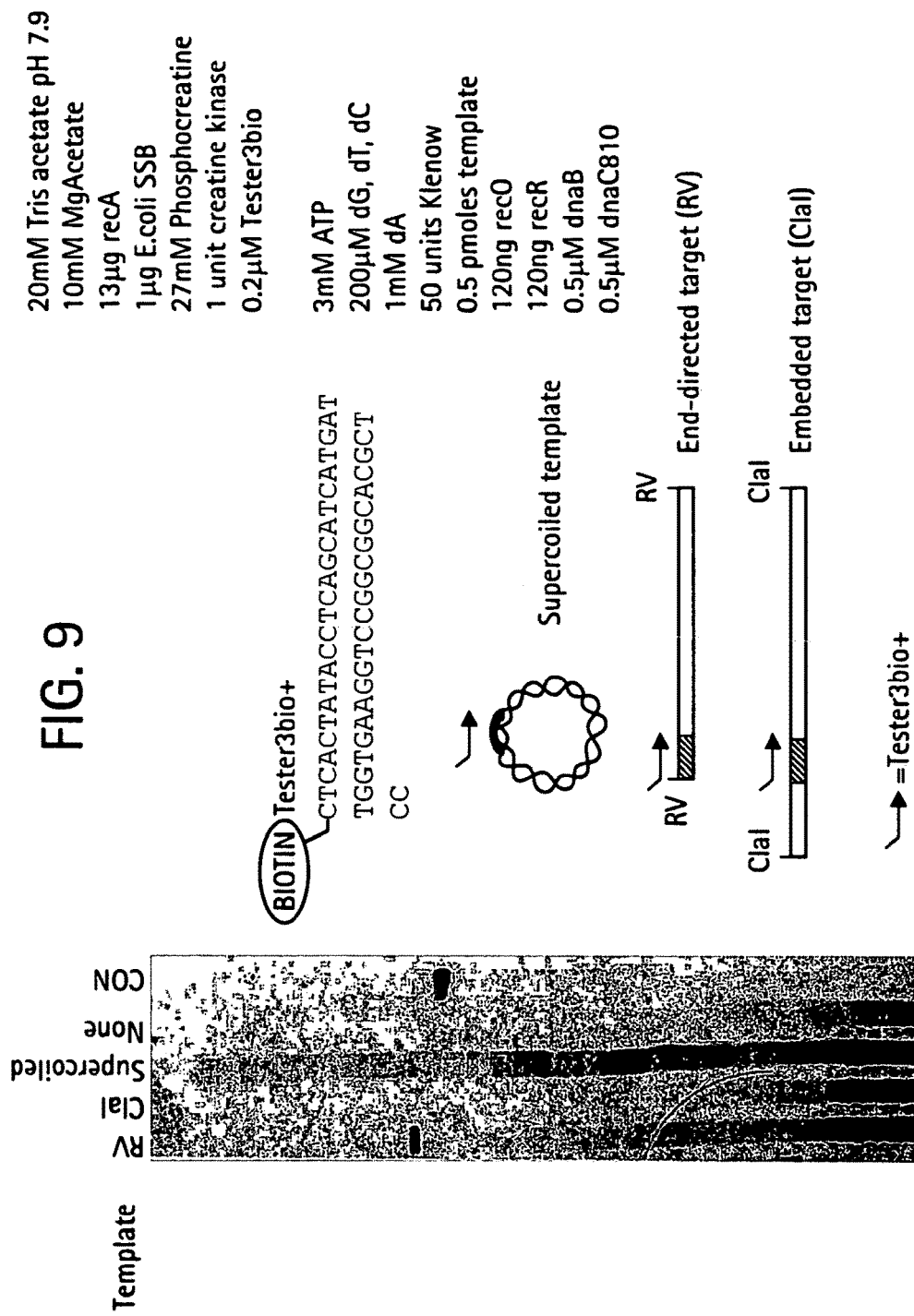
FIG. 9 depicts investigation into the nature of double-stranded DNA targets and targeting oligonucleotides. Experiments using either supercoiled templates or linearized DNAs suggest that recA catalyses the formation of intermediates capable of supporting polymerase elongation most readily on supercoiled DNA or at the ends of linearized DNA. Tester3bio oligonucleotide (SEQ ID NO: 90) is shown.

An oligonucleotide bearing 33 residues of homology with the end of a linearized DNA target can form a pairing intermediate capable of elongation by the Klenow fragment of E. coli (FIG. 9). This experiment and others demonstrate that homology lengths as short as 33 nucleotides are sufficient to direct recombinase/ssDNA filaments to appropriate targets in the presence of ATP and to permit complete strand exchange. Similar results are found when using the bacteriophage T4 uvsX protein.

In addition to a requirement for a minimal oligonucleotide length there may be a progressive loss of invasion/extension efficiency if the oligonucleotide is extended significantly beyond the minimal length required for recombination, at least when distributive polymerases are used. One possibility lies in the nature of recombinase/ssDNA filaments. Filaments coated with recombinases have varying 5' limits to their coating, as recombinases seed randomly and then extend the filament in a 5'-3' direction, there will be a distribution of 5' extents of coating. If less than roughly 25-30 nucleotides are coated then little recombination can occur because there is insufficient nucleoprotein filament for strand exchange. If more than this is coated it is potentially beneficial from the point of view of recombination, but if greater than 10-20 residues is added beyond the minimal length required for exchange there is a possibility that progressively more active filaments will posses recombinase of a sufficient length of DNA to permit exchange, but retain sufficient 5' uncoated DNA for gp32 to bind, which through cooperative binding of the 5' extreme could inhibit the branch migration phase and prevent the outgoing strand from being un-constrained. Consistent with this notion, we note that stimulation of multiple invasion events was less apparent with the oligonucleotide the longer oligonucleotide primer Tester1 bio compared to Tester3 bio (FIG. 15). The only difference between these oligonucleotides is that the first has 25 additional overhanging nucleotides beyond the initial 33 residues of homology, while the second has only 15 additional residues. Regardless of the explanation this experimental observation argues that an optimal maximal length may exist.

There are other reasons to suspect shorter oligonucleotides will be best for efficient RPA. At the relatively low temperatures used in RPA reactions there is a substantial increase in stable secondary structures of oligonucleotides as well as a greater probability of inappropriate hybridisation between primer pairs. Despite an overall excess of single-stranded DNA binding proteins, the dynamic nature of the reaction suggested by the instability of nucleoprotein filaments formed with recombinases in the presence of ATP means that there is likely to be a constant cycling of proteins on and off oligonucleotides, and a steady-state concentration of uncoated, unprotected, oligonucleotides. Consequently the use of short oligonucleotides should reduce the likelihood of undesirable intra- and intermolecular interactions.

Our data indicate that optimal length of oligonucleotide lay between 30 nucleotides and 50 nucleotides, and that progressively larger oligonucleotides can decrease the rate of invasion/extension. It may, however, be desirable to extend the length of the oligonucleotide to accommodate a duplex region in the 3' or 5' region of the searching oligonucleotide. Thus, in one aspect of the invention, the preferred primer length is between about 30 to about 50 bases. Examples of primers sizes that would fit at least one of these criteria includes primers of between 30 to 45 bases, between 30 to 40 bases, between 30 to 35 bases, between 35 to 40 bases, between 40 to 45 bases, and between 45 to 50 bases. While the above-referenced primer sizes are preferred, a recombinase and/or single-stranded binding protein with an optimum primer length of less than 30 bases is also possible and envisioned.

Oligonucleotide Composition, Sequence and Single-Stranded/Duplex Character:

1 Composition and Sequence:

Software to design oligonucleotides for use in vitro DNA synthesis reactions is well established, particularly for use in PCR. The considerations for the RPA method are similar and include the optimisation of the melting temperature of the oligonucleotide, avoidance of hairpin formation within an oligonucleotide and selection against complementarity with other oligonucleotides present in a given reaction. As RPA is performed at relatively low temperatures such considerations are potentially more important. We have observed the accumulation of extended primer products in RPA reactions, which are apparently template-independent and dependent on the combination of primers used. The sizes of the aberrant products generated suggest they are primer dimers, or the consequence of self-priming of a single oligonucleotide. These undesirable primer artifacts are well known for other methods such as PCR. It is therefore important to design oligonucleotide primer pairs to avoid undesirable side reactions. We have observed that oligonucleotides capable of forming hairpins can erroneously self-prime in an RPA reaction.

Besides optimising oligonucleotide sequence design there are additional approaches to reduce or eliminate primer dimer formation. We have observed that reaction noise can be significantly reduced by utilising polymerases lacking 3'-5' exonuclease activity. This suggests mispriming may result from oligonucleotides that have been shortened by the 3'-5' exonuclease activity of polymerases. Consequently 3'-5' exonuclease editing activity, pyrophosphorylysis, or any other similar editing activity can be a source of noise. In addition to using polymerases lacking exonuclease activity and the removal of pyrophosphate with pyrophosphatase, use of synthetic oligonucleotides with a non-hydrolysable backbone at the ultimate and/or penultimate link may be beneficial to reduce reaction noise. Alternative backbones could be selected from the considerable range of chemistries available such as phosphorothioate, morpholino, locked nucleic acid, or peptide nucleic acid.

2) Single-Stranded/Duplex Character:

Deterring aberrant extension of oligonucleotide 3' ends may also be achieved by designing, and including, short competitor oligonucleotides that can efficiently compete for the formation of hybrids with the 3' region of the targeting oligonucleotides. Such an approach could be configured in various ways.

1) A short independent oligonucleotide comprising a perfect complement to the most 3' residues of the targeting oligonucleotide could be employed. This oligonucleotide would be sufficiently long that at the reaction temperature it would be likely to form a hybrid with the targeting oligonucleotide moderately efficiently. This might be between 6 and 15 residues in length. The short oligonucleotide will be non-extendable by having a blocking group at its 3' terminus, such as a dideoxy sugar, or other 3' blocking group. This oligonucleotide also may require a non-phosphate linkage at the ultimate and/or penultimate backbone link to deter removal of bases in the 3'-5' direction by editing activities. Although a large proportion of non protein-coated targeting oligonucleotides may form duplexes with this short oligonucleotide this should not significantly decrease the rate and efficiency of the RPA reaction. Firstly, because at the low RPA reaction temperature there is likely to be an equilibrium between hybridised and unhybridized oligonucleotides there will always be a pool of free melted targeting oligonucleotides available. As the oligonucleotide is a better competitor than other random sequences in the reaction, it will be favoured against other transient interactions. Secondly, single-stranded DNA binding proteins such as recA, uvsX, gp32, and E. coli SSB, tend to melt duplex DNA and thus even if hybrids are relatively stable at the reaction temperature when no proteins are bound, when they bind to the single-stranded part of the oligonucleotide and extend cooperatively to the region of duplex they are likely to enhance its melting, thus the duplex state will tend only to exist on naked oligonucleotides. Finally, recombinases have the capacity to extend strand exchange initiated between a single-stranded DNA region and duplex target into regions in which both DNAs are duplex. This appears to be an ATP-dependant branch migration activity. Taken together these considerations suggest that the short duplex region should not significantly reduce the rate of the RPA reaction, but instead act to suppress the formation of primer dimer or other artifacts generated from non protein-coated oligonucleotides by being a better competitor for binding to the 3' region of the targeting primer than other oligonucleotide sequences available in the reaction. If exonuclease deficient polymerases are used, it may be optimal to design this oligonucleotide to have its 5' most base pairing to the penultimate, rather than ultimate, 3' nucleotide as many polymerases tend to add an additional base to a perfectly blunt end.

Figure 35:
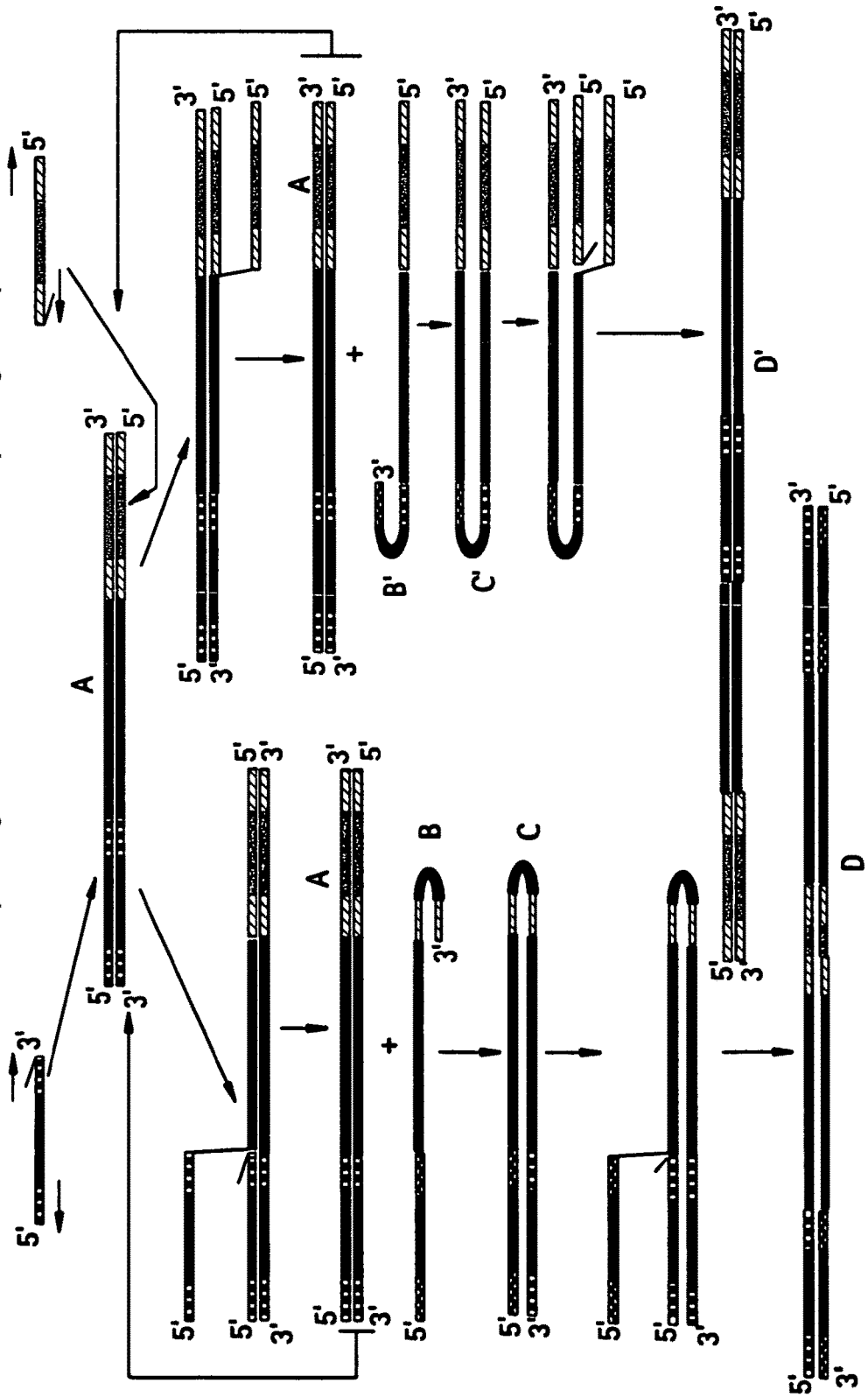
FIG. 35 depicts the use of hairpin oligonucleotides to stimulate self-priming of displaced strands. Shown is a schematic diagram of an amplification using self-complementary hairpin oligonucleotides deliberately to stimulate self-priming of displaced strands.

2) In a second approach, the targeting oligonucleotide possesses a 5' overhang not present in the initial target DNA, and this overhang is the precise reverse complement to the sequence to the 3' end of the same targeting oligonucleotide, perhaps with the most 3' base only unpaired (FIG. 35 part D). The length of this complementary oligonucleotide should be relatively short, but long enough to be a far better competitor than other oligonucleotide sequences present in the reaction. For example between 6 and 10 nucleotides might be optimal. As described for the first approach this arrangement is likely to lead to any uncoated oligonucleotides forming hairpin structures to themselves far more efficiently than to any other sequences. As the design will place the 3' base, or penultimate 3' base, of the oligonucleotide in a perfect base-pairing environment, but at the 5' end of the targeting oligonucleotide, it cannot be extended, apart from the addition of the single residue often catalysed by many polymerases if the end is blunt. In this context it may be fine to leave the editing activity of polymerases intact. Such hairpin forming oligonucleotides may suppress erroneous activity of naked oligonucleotides without deterring the activity of protein-loaded filaments.

There are however some important considerations to taking this approach. Firstly, if the recombinase loading is initiated directly on the partly duplex naked oligonucleotide without initial melting of the duplex section, recombinase may not extend as close to the 5' end of the targeting oligonucleotide as might be optimal. Secondly, as the amplification reaction continues beyond the first round there will be active displacement of products generated from previous rounds of synthesis and if a complete displacement occurs then the very 3' end of a displaced strand, which is complementary to immediately adjacent sequences, may be able to hairpin and rapidly self-primer. Such a rapid self-priming event would result in DNA synthesis and formation of a novel double-stranded DNA with both strands joined by a hairpin at one end. This could be a substrate for further rounds of invasion/synthesis and result in formation of dimer-like products, and possibly more complex products (see FIG. 35). We anticipate that this situation may be perfectly acceptable for diagnostic tests. As the amplified sequences are all dependant upon the presence of bona fide target DNA, and will contain the unique inter-oligonucleotide sequences, and because the self-priming event may be engineered to function efficiently, then this may prove an ideal format for diagnostic assays. We have already experienced the generation of greater than unit length amplified DNA fragment apparently generated from specific targets and suspect that this mechanism may operate in the absence of specific oligonucleotide design. A similar activity has been described although in this case the activity was initiated in a totally different manner using a single very large single-stranded DNA (Morrical S W, Wong M L, Alberts B M. J Biol Chem. 1991 Jul. 25; 266(21):140331-8).

3) In a final approach separate short oligonucleotides with blocked 3'-ends would be employed as described in approach 1. In this case however a linkage is engineered between the 5' end of the targeting oligonucleotide and the 5' or 3' end of the short competitor oligonucleotide (FIG. 35 parts B and C). This approach is similar to approach 1, except that by tethering the competitor oligonucleotide in the close vicinity of the targeting oligonucleotide one ensures efficient competition of this oligonucleotide with any other sequences in the reaction.

Polymerase Choice:

There are many DNA polymerases that might be used for RPA. There are, however, a number of criteria that should be considered when designing the optimal RPA format for a given application. We have identified a number of different polymerases with activity in RPA reactions, and deduced which properties confer specific advantages for different circumstances. One exciting conclusion is that polymerases from heterologous systems can be used effectively. We discuss below the polymerase activities most relevant to RPA.

Polymerase Processivity

Polymerase processivity is measured as the typical number of incorporation events catalysed on each individual interaction with a DNA template. Many of the polymerase enzymes used in molecular biology applications are not highly processive, often because they are functional analogues of the of *E. coli* DNA polymerase I whose primary role is DNA repair and Okazaki fragment processing. Processivity is a more critical consideration for RPA than for PCR. Because RPA uses a double-stranded template, distributive polymerases will produce partially copied strands possessing a joint, which could be ejected by branch migration. In addition, we have evidence to suggest that bubble migration may occur in a variety of RPA configurations. In bubble migration parent strands of the template DNA re-hybridises shortly behind the replication complex leading to ejection of the newly synthesised strand, which is freed as a single-stranded DNA instead of the outgoing strand of the original recombination event. This re-hybridisation has been previously described in the T4 recombination/DNA synthesis system and thought to involve coating of the outgoing strand with the uvsX recombinase and subsequent re-invasion. Alternatively, in the presence of uncooperative single-stranded DNA binding protein, monomers may be lost progressively from one end of the outgoing strand and may lead to progressive branch migration running in a 5'-3' direction, chasing the replication complex.

Thus if the polymerase dissociates prematurely from the template, bubble migration or branch migration may result in the newly synthesised strand being separated from the template as an incomplete single strand. This could be catastrophic for RPA reactions, because if such truncated products are too short to form productive hybrids with similar products generated from the opposing side, these undesired short products will accumulate linearly. The T4 single-stranded DNA binding protein gp32 can alleviate undesirable branch migration. However RPA urges, where possible, the use of relatively processive polymerases, or polymerase complexes, to efficiently amplify larger DNA fragments. Several now commonly used simple polymerases such as Phi-29 DNA polymerase, Bst DNA polymerase and T7 DNA polymerase in complex with thioredoxin are known to be processive. However not all of the known classes of relatively processive polymerases may possess the combined additional properties suitable for RPA; Phi-29 polymerase has not proven able to support geometric RPA amplifications to date, possibly due to an inability to efficiently load onto the recombination intermediates. T7 DNA polymerase lacks sufficient strand displacing activity to be effective. In contrast we surmised that related Pol I enzymes from the Bacilli, such as *Bacillus subtilis* PolI (Bsu), would likely demonstrate optimal characteristics by virtue of sharing with Bst polymerase relative processivity and exonuclease minus status, but retaining optimal solubility and activity profiles at temperatures in the 30-37° C. range. Additionally, multi-subunit replication complexes incorporating sliding clamps could be used such as that from bacteriophage T4, *E. coli*, and others, however assembling all of these components in effective in vitro reactions that maintain the excellent signal:noise and kinetic properties of current RPA reactions remains challenging. We purified the Polymerase I from *B. subtilis* which is related to Bst polymerase. This polymerase is readily overproduced and purified from *E. coli* with an N-terminal hexhistidine tag, and appears to possess ideal biochemical attributes for RPA.

Finally, there are some situations where a distributive polymerase may be more appropriate for RPA. Because in many configurations DNA synthesis is initiated from opposing ends and replication complexes move toward one another, there is the possibility of a collision between complexes resulting in a stalemate in which neither progresses further. This requires either that one polymerase temporarily dissociates from the template, or that the polymerases used are able to pass one another effectively without dissociation. In consequence of the varying requirements for an ideal polymerase for RPA we suggest that experimental evidence will be the best guide, and to date this implies that Pol I class enzymes from eubacteria, in particular from Bacilli, currently show the best properties.

3'-5' Exonuclease Activity Present Associated with the DNA Polymerase:

Many DNA polymerases possess 3'-5' exonuclease activity, and some also possess 5'-3' exonuclease activity, which is probably undesirable in RPA as it results in digestion of one DNA strand progressively as the polymerase moves forward, rather than displacement. The 3'-5' exonuclease has potential advantages as well as its, obvious disadvantages. On the one hand 3'-5' exonuclease activity increases the fidelity of the replication reaction, and can also prevent stalling of polymerases at points of misincorporation. High fidelity amplification is desirable for many DNA applications. The 3'-5' exonuclease activity may also be appropriate for amplification of larger DNA fragments where stalling due to misincorporation could inhibit effective amplification.

Despite these clear advantages of 3'-5' exonuclease activity there are some disadvantages. We have observed that the free oligonucleotides can be subject to end-dependant degradation when polymerases possessing 3'-5' exonuclease are employed. This can be suppressed to a large extent by using saturating amounts of relatively cooperative gp32 protein with some polymerases such as the Klenow fragment, but with enzymes possessing aggressive exonucleases such as T4 DNA polymerase or Phi-29 DNA polymerase, gp32 appears to be insufficient and the oligonucleotides appear to be completely degraded. These data argue that it is advantageous to at least limit to some extent the efficacy of an exonuclease activity in the reaction.

We have found that 3'-5' exonuclease activity of some polymerases may contribute substantially to noise in the reaction. At the relatively low temperatures used in RPA reactions there is a significant tendency for uncoated single-stranded DNA molecules to form inappropriate hybrids, at low complementarity, with other DNAs in the reaction. Such hybrids will prime DNA polymerases elongation. For extension to occur the last base or two must be paired correctly with its complement. While poorly complementing segments within or between oligonucleotides can form weak hybrids at low temperatures these will rarely be combined with a good hybrid match at the very 3' end. Regardless, in the presence of a 3'-5' exonuclease activity the unpaired 3' most bases will be excised until a correctly paired 3' end is formed, as happens normally when an incorrect base is inserted by the polymerase. Our data suggest that partly extended strands that have been displaced by branch migration or bubble migration can fold back onto themselves leaving an unpaired 3' end, which is trimmed thus promoting inappropriate polymerase elongation. There are therefore good reasons to limit or remove exonuclease activities from polymerases used in RPA. There are other methods to inhibit oligonucleotide degradation that may also be used.

Access to 3' Ends

The recombination intermediate formed after invasion must be accessible to the DNA polymerase. The structure near the 3'-end of the targeting oligonucleotide, is not equivalent to the 3'-end of an oligonucleotide hybridised to otherwise single-stranded DNA, which is the situation in PCR. Instead, the outgoing strand, which is hybridised to the template strand immediately, or shortly, downstream of the 3'-end of the invading oligonucleotide may block polymerase loading. Moreover, whether of the outgoing strand is constrained or unconstrained may affect the capacity of certain polymerases to load successfully. Whether a particular polymerase can function effectively in these situations must be addressed experimentally. We find that the Klenow fragment of *E. coli* DNA polymerase I, as well as the Bst DNA polymerase purified from *Bacillus stearothermophilus*, can load onto and extend such recombination intermediates. Helicases such as the T4 dda helicase and T4 gp41 helicase may also function to process recombination intermediates and separate the template and outgoing strands downstream of the exchange event permitting other polymerases to be used, but these helicases may also interfere with other aspects of RPA (see below). Finally, it may be beneficial to use mixtures of polymerases, acting synergistically in the RPA reaction, for example one polymerase efficient at accessing the 3' ends of recombination intermediates, and the other possessing processive, strand-displacing synthetic activity.

Cooperative Component Interactions

We have demonstrated that enzymatic components from heterologous systems can be combined together effectively in various RPA formats. For example, both the Klenow fragment of *E. coli* DNA polymerase I, the Bst DNA polymerase of *Bacillus stearothermophilus*, and the large fragment of *Bacillus subtilis* polymerase I, can extend recombination products generated with the uvsX recombinase of bacteriophage T4 in the presence of the bacteriophage T4 gp32 protein. This suggests that the class of polymerases similar to *E. coli* Pol I are generally effective in RPA reactions, and this may reflect their distinctive properties as strand displacing enzymes, combined with access to recombination intermediates needed for their repair activities. Furthermore, that elongation of recombination intermediates can easily be mediated by polymerases from widely different structure groups is uncertain. Despite early indications from end-directed recombination intermediates stabilized by backfire synthesis, we have been unable to drive RPA reactions using Phi-29 polymerase, and this may reflect that this enzyme cannot readily load onto recombination intermediates. There may be additional synergistic effects when proteins from the same organism are employed together. For example there are known to be physical interactions between the bacteriophage T4 components such as uvsY and uvsX, as well as gp32. This might be extended to other components, foe example the T4 polymerase functionally interacts with the gp41 helicase, and physically with gp32 (Formosa and Alberts PNAS 80, 2442-2446, 1983). However despite the seeming attractiveness of using components from the same organism to enhance RPA efficiency, we have found that one helicase employed for processive DNA synthesis by T4 polymerase may not combine easily with the effective RPA environment as established here. Early experiments suggested that inclusion of T4 dda helicase may disrupt the coating of oligonucleotides in the RPA environment and lead to excessive primer noise preventing sensitive RPA reactions. This is consistent with an earlier published report [insert reference JBC. 1991 May 25; 266 (15):9712-8 Inhibition of protein-mediated homologous pairing byb a DNA helicase. Kodadek T.

Resolution of Replication Complex Collisions

In some formats of RPA, such as when a large DNA product is desired, a processive polymerase would be the optimal choice. Under these conditions, however, there is significant likelihood that replication complexes will converge with one another on the same template. There is a danger that replication complexes will become locked head-to head so that neither can pass. Most useful in this situation are polymerases that are both processive and able to resolve collisions as has been demonstrated for Phi29 DNA polymerase (Elias-Arnanz M, Salas M. EMBO J. 1997 Sep. 15; 16(18):5775-83). Alternatively a fine but critical balance of an ideal level of processivity to permit useful replicative runs combined with a distributive capacity to dissociate fairly frequently may solve this issue.

Recombinases

We have assayed both $E.$ $coli$ recA protein, and bacteriophage T4 uvsX protein in RPA experiments. Both these proteins share some limited protein sequence homology and are believed to have evolved from a common progenitor. Crystallographic and electron microscope studies of nucleoprotein filaments of these proteins, which show a conserved filament structure, in terms of the pitch of the helices formed in both ATP and ADP bound states, suggest a remarkable similarity in their mechanism of action. Furthermore, all prokaryotes possess proteins highly homologous to recA, which suggests that the principle activities of recombinases have been conserved throughout evolution. Hence, what is learned from one recombinase may be applied to, or substituted by, another.

In addition to their similarities, however, there are differences between recA and uvsX relevant to RPA and as additional components of recombination/replication machinery are used in RPA reactions organism-specific protein-protein interactions may have a significant effect on reaction efficiency. The nucleotide hydrolysis rate of uvsX is 10-20 times higher than that of recA, suggesting that it might perform recombination reactions at an accelerated rate (Formosa T, Alberts B M. J Biol Chem. 1986 May 5; 261(13): 6107-18.). An increased hydrolysis rate could be beneficial for RPA reactions in several ways.

1) More dynamic turnover of uvsX on oligonucleotides could increase the overall regeneration of nucleoprotein filaments leading to near complete recombinase coverage to the most 5' end of invading oligonucleotides.

2) More rapid completion and disassembly of recombinase from successful recombination events will permit more efficient polymerase access 3) A more active recombinase will produce a more flexible nucleoprotein filament.

Another major difference between uvsX and recA is that uvsX hydrolyses ATP to ADP plus phosphate, and to AMP plus pyrophosphate whereas recA and other recombinases do not (Formosa T, Alberts B M. J Biol Chem. 1986 May 5; 261(13):6107-18.). The biological significance of this difference is not known but the activity might affect RPA efficiency. For instance, the pitch of nucleoprotein filaments formed with ATP and ADP is different and the hydrolysis of ATP to ADP is associated with overall filament flexibility. It may be that AMP-bound uvsX can adopt a different pitch and possess a distinct flexibility.

Figure 23:
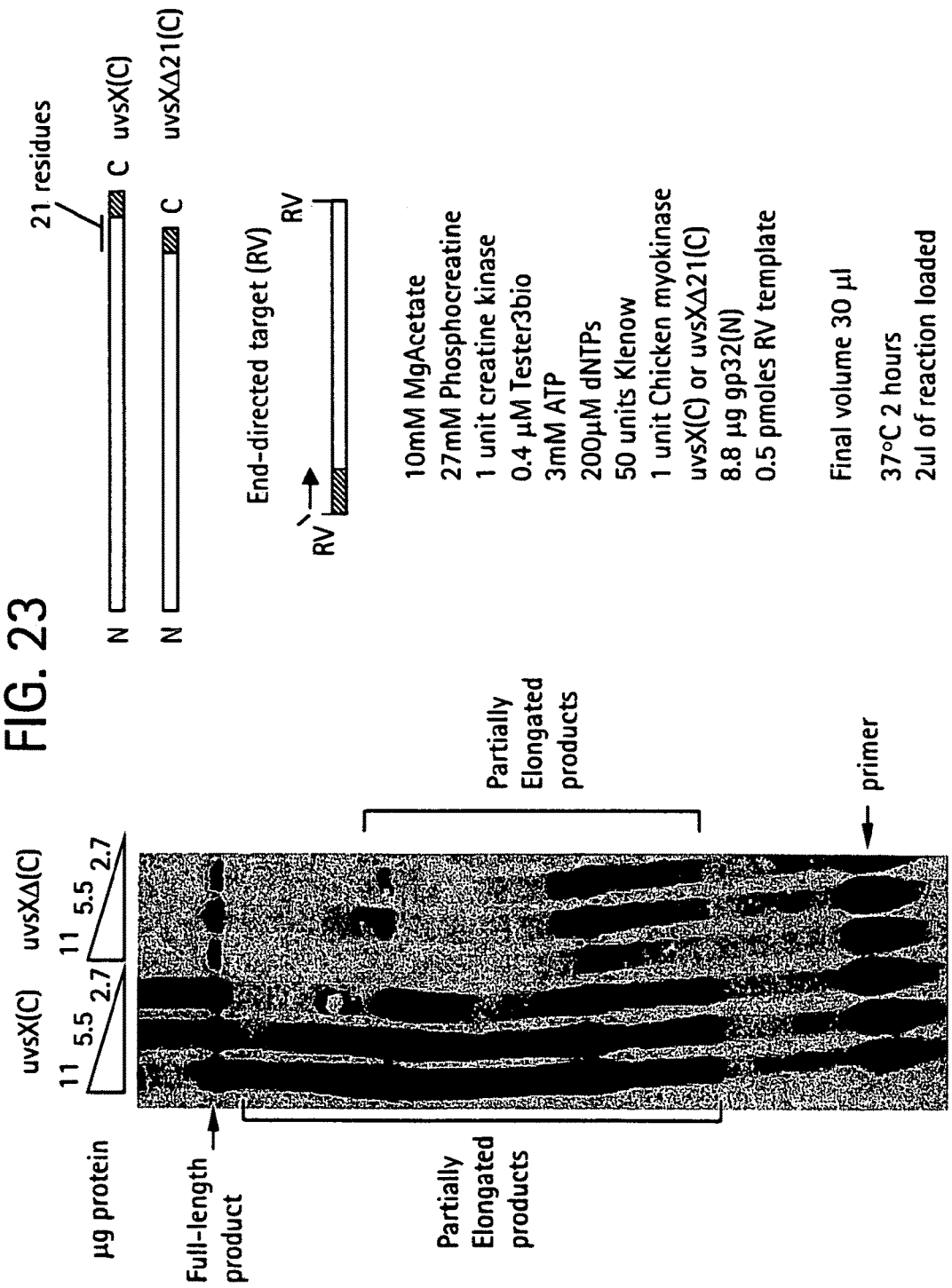
FIG. 23 depicts invasion and extension using uvsX. Modified uvsX protein with a C terminal His tag (uvsX(C)), or an additional deletion of the C-terminal acidic peptide, stimulates invasion/extension in a linear template run-on assay.

The bacteriophage T4 recombinase uvsX stimulates a mode of DNA displacement following synthesis known as bubble migration. In bubble migration uvsX assembles onto the outgoing strand and mediates a re-invasion of the outgoing strand thus displacing the newly synthesised strand. This mode may have biological significance because by displacing the newly synthesised strand, the length of region with topological constraint is limited. This process has not been described for recA, although it may occur. Nevertheless several aspects of bubble migration suggest real differences between uvsX and recA. For example, the bubble migration model suggests that it is possible that uvsX bound DNA extends to the end of the invading or partially extended DNA, but that this structure is still accessible by polymerases for elongation (Formosa T, Alberts B M. Cell. 1986 Dec. 5; 47(5):793-806). This has certainly not been observed for recA, and if anything there is evidence that may be to the contrary (Xu L, Marians K J. J Biol Chem. 2002 Apr. 19; 277(16):14321-8). It is unclear how similar uvsX and recA filaments are in their respective abilities to promote polymerase loading at 3' ends with or without recombinase dissociation. We have found differences between uvsX(C) and recA(C) consistent with the notion that their differences have can affect RPA efficiency. Contrary to our findings with recA, uvsX can mediate multiple invasions to an end structure target even when N-terminally tagged gp32 is used in the absence of polyethylene glycol (FIG. 23). Thus uvsX may be more optimal for use in RPA.

The bacteriophage T4 uvsX recombinase has a well-characterised interaction with its partner loading protein uvsY. Despite reports suggesting that $E.$ $coli$ recO and recR may be functional analogues of uvsY we have not observed significant improvement for RPA reactions. This may be due to problems with our protein preparations, or due to the use of the heterologous gp32 rather than $E.$ $coli$ SSB.

Finally uvsX is likely to behave better with gp32, which we find to be an optimal single-stranded DNA binding protein, because they have evolved to function in concert and may have relevant interactions. Indeed uvsX and other components of the bacteriophage T4 recombination dependant replication machinery, such as the dda helicase, have known protein-protein interactions that may useful for establishing an optimal RPA reaction (Hacker K J, Alberts B M. J Biol Chem. 1992 Oct. 15; 267(29):20674-81).

Despite the apparent advantages of uvsX for RPA, there are features of $E.$ $coli$ recA that may be useful. It has been reported that recA nucleoprotein filaments are more stable, which could be of utility in some circumstances. The lower ATP hydrolysis rate places less strain on establishing a durable ATP regeneration system, and the lack of generation of AMP and pyrophosphate obviates the need to regenerate and mop-up these side-products. It may also be the case that other recA homologues possess activities that are optimal or RPA.

Establishment of a Dynamic Recombination System:

To make RPA robust, it is critical to configure the reaction to provide a sufficient number of active, coated, homology-searching recombinase/DNA filaments. In addition, following completion of homology-searching, filaments must efficiently disassemble, or be otherwise processed, to permit loading DNA polymerase and other components. It is also essential that a sufficient quantity of single-stranded DNA binding protein be present both to facilitate oligonucleotide melting and to collect displaced outgoing strands. And finally, robust RPA requires will require processive strand-displacing DNA synthesis. Underlying these requirements is a competition between two the recombinase and the single-stranded DNA binding protein.

It is widely known that of recombinase-loaded DNA filaments are unstable in the presence of single-stranded DNA binding proteins. Coupled to the finding that nucleotide cofactor hydrolysis is not strictly required for homology searching, led to the use of non-hydrolysable nucleotide analogues of nucleotides such as ATP-γ-S, to load recA onto filaments and produce stable homology-searching complexes. A recA-mediated amplification method using ATP-γ-S has been described (Zarling, et al.), however, has not been widely used. We previously identified a flaw in the method, which we can now observe in our experimental results. The Zarling, et al. method probably fails because recombinase-loaded filaments needs to be dynamic and capable of disassembly as well as other ATP-hydrolysis dependant events to complete strand exchange and permit loading of DNA polymerase other components to the 3' end of the invading oligonucleotide. The use of ATP-γ-S, as well as other modifications such as removing acidic sequences from the C terminus of recombinases, leads to a constant general high affinity for DNA that likely prevents strand exchange and dissociation from the invasion complex. Thus ATP-γ-S-loaded recA filaments become effectively locked onto the target site in the recombination event for an abnormally long time. Consequently non-hydrolysable nucleotide analogues are not generally permissive for recombinase-mediated replication and amplification. Instead, ATP, or other hydrolysable nucleotides capable of supporting recombinase loading, must be employed. In ATP the recombinases are constantly associating with and dissociating from oligonucleotide and are in competition with single-stranded DNA binding proteins. We have addressed the problem this competition poses in two general ways; first by including a recombinase loading protein specific for uvsX, the uvsY protein, and secondly by modulating the cooperative behaviour of gp32, and the recombinases uvsX and recA, by mutation and/or inclusion of crowding agents. It is possible however that limited quantities of non-hydrolysable analogues such as ATP-γ-S, or of non-phosphorylatable analogues such as ADP-β-S, may be included to modulate the global loading/unloading activity of the recombinase.

Additional Reaction Components

A number of specific reaction components have a significant influence on RPA reaction efficacy.

Polyethylene Glycol

Figure 28:
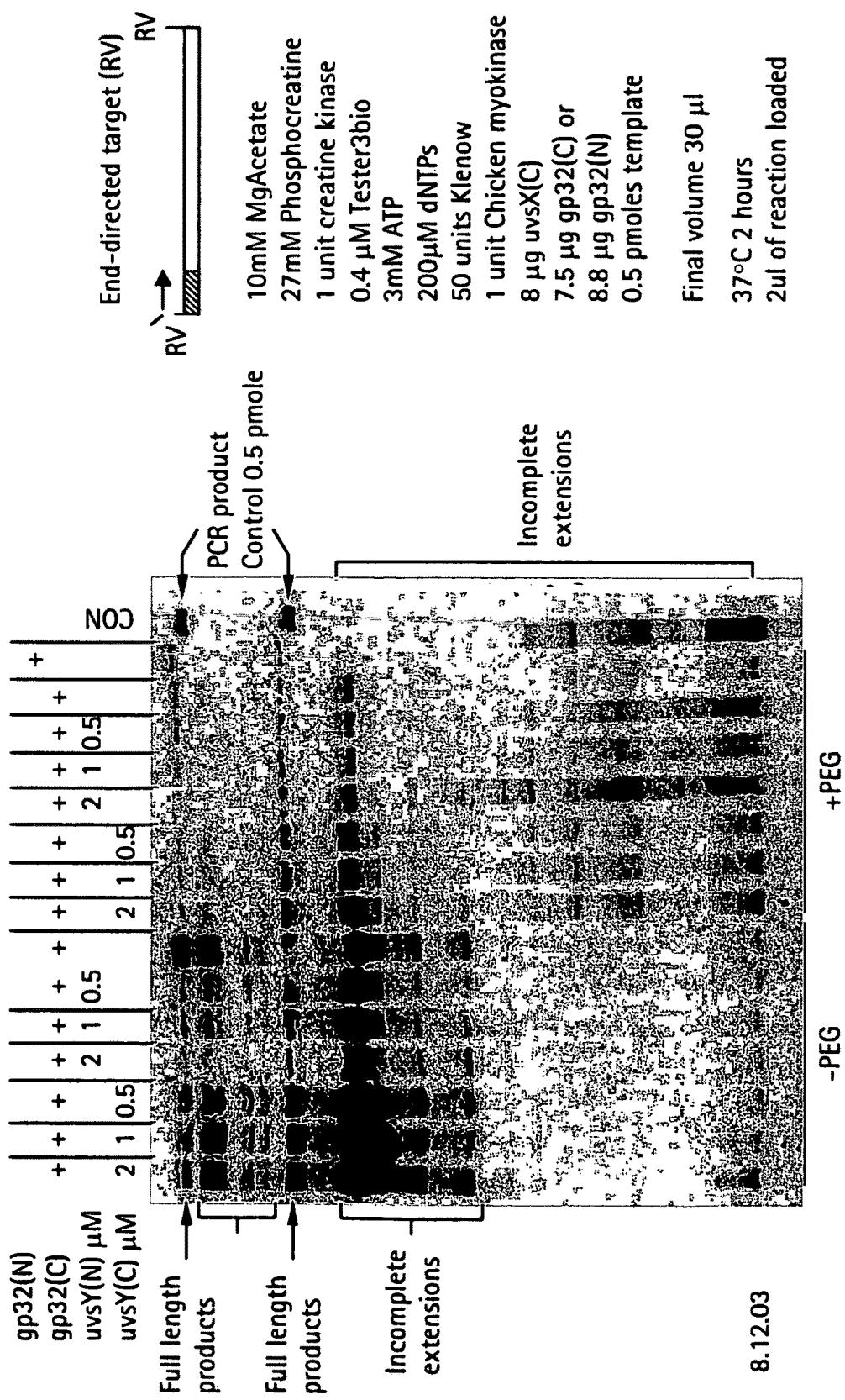
FIG. 28 depicts effects of PEG. PEG can reduce the average length of linear invasion/run-on products in an uvsX-mediated linear run-on experiment in the presence of gp32(C).

Polyethylene glycols (PEGs) have a profound effect on recombination/DNA synthesis. Firstly, we find that PEGs influence the number of multiple invasion/extension cycles that occur, for example when recA is combined with gp32 (N). We have also found that PEGs stimulate amplification reactions configured in several different ways (FIG. 15, Example 3). We also know that in some configurations PEGs alter the length distribution of products formed (FIG. 28). In summary polyethylene glycols, and presumably other similar crowding agents may affect the cooperativity of gp32 and recombinases, affect polymerase processivity and affect the hybridisation rate and behaviour of oligonucleotides in solution. They may imbue cell-like environments by phase partitioning the reactants, and/or causing the development of fractal-like kinetics. Furthermore the chain length of the polyethylene glycol appears to be critical. We find, that of those tested, PEGs of average molecular weight 1450 and 15-20,000 ('PEG compound') produce the best results. The PEGs in aiding gp32 function, particularly gp32 variants with attenuated cooperativity, has been detailed above. PEG is also likely to increase the stability of recombinase-loaded filaments and the increased persistence may increase RPA efficacy. Most importantly we have been completely unable to establish amplification conditions capable of amplifying from trace amounts of sample to detectable levels without employing polyethylene glycols (poorly with PEG 1450, very efficiently with PEG compound). Presumably other agents may also stimulate RPA reactions, however this effect was not evident in preliminary experiments with polyvinyl alcohol. Thus specific features of polyethylene glycols, and more particularly specific variants of PEGs, may be essential.

In what manner PEG compound (carbowax 20M) achieves such a significant stimulatory effect is mysterious. Kinetic models of the manner in which volume exclusion may affect reaction rates would place significant emphasis on the molecular weights of the substrates and enzymes under study in comparison to the crowding component. However the next-most effective agent that we tested, PEG 1450, was also the smallest and stimulation by polyethylene glycols intermediate between PEG1450 and PEG compound were less effective. Consequently we suspect that properties additional to simply average chain length are critical to the effects of these agents. For example specific phase transitions may occur at variant temperatures for different PEGs. It is also known that the alcohol groups of PEGs can lead to additional interactions, such as with proteins, or influencing the ionic environment. We note (data not shown) that the addition of 5% PEG compound (while developing a pH below 7.0 during storage at room temperature) to Tris-buffered solutions used in RPA causes a sharp rise in pH.

As a consequence there is currently no formulaic manner to determine which volume-excluding agents will have the current properties to stimulate high-level dynamic recombination environments, and RPA in particular, except through experimental validation.

ATP Regeneration System Components

An ATP regeneration system is crucial to permit persistent recombination reactions as recombinases have an extremely high rate of ATP hydrolysis when bound to nucleic acids. In particular, the uvsX protein has a hydrolysis rate 10-20 times higher than recA and can consume 200 molecules of ATP per minute per monomer. A number of systems are available and we have routinely used the creatine kinase/phosphocreatine system. When uvsX is employed the AMP that is produced must be converted into ATP. We have used chicken myokinase, which converts a molecule of AMP and one of ATP to two molecules of ADP. ADP is then converted to ATP using the creatine kinase/phosphocreatine system. Poor regeneration of ATP will reduce the reaction rate and likely stop the reaction before detectable levels of product have accumulated.

Pyrophosphatase

Pyrophosphate (PPi) accumulates during DNA synthesis and when uvsX is employed, as it hydryolyses ATP to AMP+PPi. PPi accumulation in the reaction can have several detrimental consequences. Significant pyrophosphate accumulation will permit an unacceptable rate of pyrophosphorylsis, whereby the synthetic reaction of a polymerase is driven into reverse and removes the 3'-most nucleotides from duplex templates. This could lead to unacceptable levels of primer noise, or enhanced levels of undesired self-priming of outgoing strands, because editing activities of the polymerase tend to trim 3'-ends back until a suitable duplex region is revealed to permit rapid elongation. Additionally pyrophosphatase accumulation will lead to inhibition of the recombinase, and to a slowing of the polymerase synthetic reaction.

Improved Signal:Noise by Design of RPA Reactions

RPA displays high of sensitivity and specificity. However samples containing no target at all often generate products derived only from the primers. Such phenomena are not uncommon in other methods. For example the PCR method will ultimately generate non-specific products such as so-called 'primer dimers'. RPA is somewhat prone to such primer-related artifacts because there is no cycle control allowing small amplicons to achieve many doublings within the period of the incubation. Electrophoresis of reaction products permits easy separation of signal and noise, however in simple non-laboratory diagnostic products other approaches must be taken. Here we disclose approaches to make such non-gel diagnostic tests function with adequate signal to noise, and to easily carry out detection. We also disclose the composition of a reaction lyophilizate that can be stored for many days at ambient temperatures, a prerequisite for easy non-laboratory use.

Signal to Noise Ratios in the RPA System

DNA amplification systems generally contend with the fact that amplification of DNA may occur which does not initiate from the bona fide target. This 'noise', particularly apparent under low target conditions, may impose restrictions on the permitted sensitivity, and methods to assess amplification. While initial configurations of RPA offer exquisite sensitivity we believe novel properties of the recombinase-based system lend themselves to previously untapped approaches to improve specificity, and to developing novel product detection schema.

RPA amplification reactions, like PCR, are generally established by combining two oligonucleotides, which flank the desired target DNA. Doubling events occur and, as in PCR, exponential DNA amplification ensues, permitting as much as $10^{12}$-fold amplification for fragments of ~150-400 bp.

Figure 41:
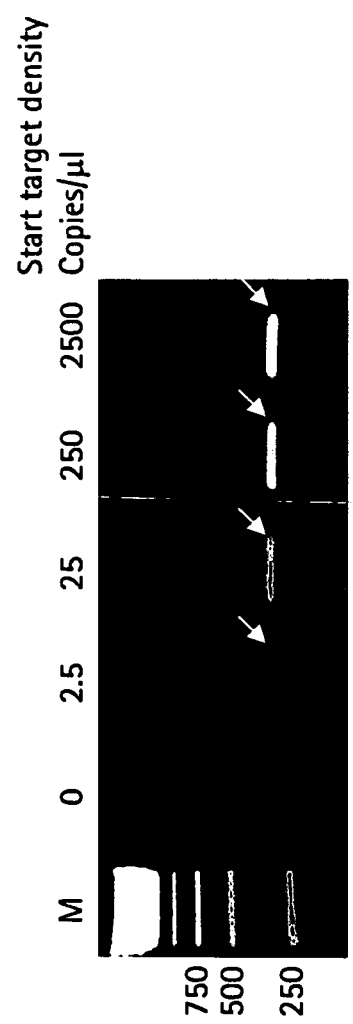
FIG. 41 Primer noise at low target copy number. The consequences of reducing the starting copy density of a target in a typical RPA reaction are shown.

When primers of 30-35 residues and acceptable to standard design algorithms are tested, a significant proportion amplify target with high sensitivity and specificity (FIG. 41). For example, such 'good' primers can successfully amplify targets from starting target concentrations of 2-3 copies per microliter to generate significant levels of the correct amplicon. However below this copy density even good primers tend to generate noise (smear, laddering, and/or well staining), as assayed by gel electrophoresis of all reaction products (see FIG. 41), these products apparently of purely primer origin (although contaminating *E. coli* DNA is likely present and could in theory be specifying highly inefficient spurious amplicons).

In some cases target DNA may not be particularly rare, for example if one wishes to determine a limited SNP profile of a human individual and a modest blood sample can easily be obtained. On the other hand, some tests for pathogens may need to detect just a few copies to be of great practical utility, and in particular distinguish this situation clearly from complete absence of target.

Our efforts to determine the level and nature of noise generated in very low, or no, copy number experiments, as well as other experiments investigating primer length and composition, has revealed a number of key observations, which we believe will aid the development of ideal highly sensitive portable diagnostic systems using RPA.

Figure 45:
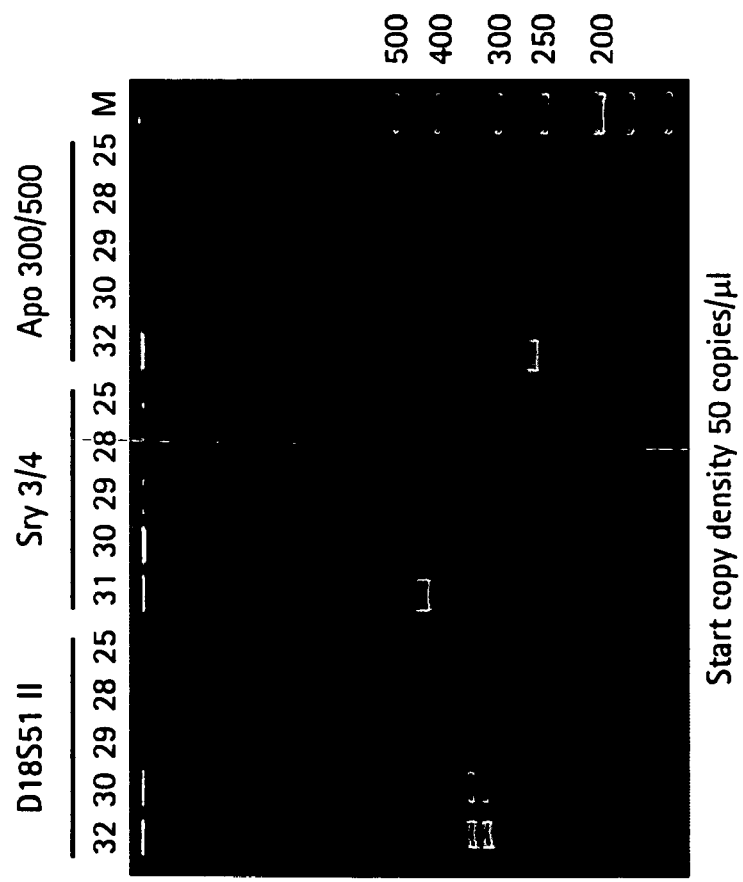
FIG. 45 Consequences of reducing primer length—short primers give less product, but can still retain activity at less than 30 residues.

Firstly we have found that oligonucleotides of less than approximately 30 residues are less effective at RPA, and notably become less 'noisy', generating no visible noise at all when reduced to 25-26 (see FIGS. 45 and 52). Nevertheless shorter oligonucleotides are still capable of, at least, hybridization based elongation (see FIG. 52), and their activity' in (recombinase-mediated) RPA events is probably not zero, instead decreasing progressively with shortening (FIG. 45). This permits some degree of activity/noise tuning.

Figure 42:
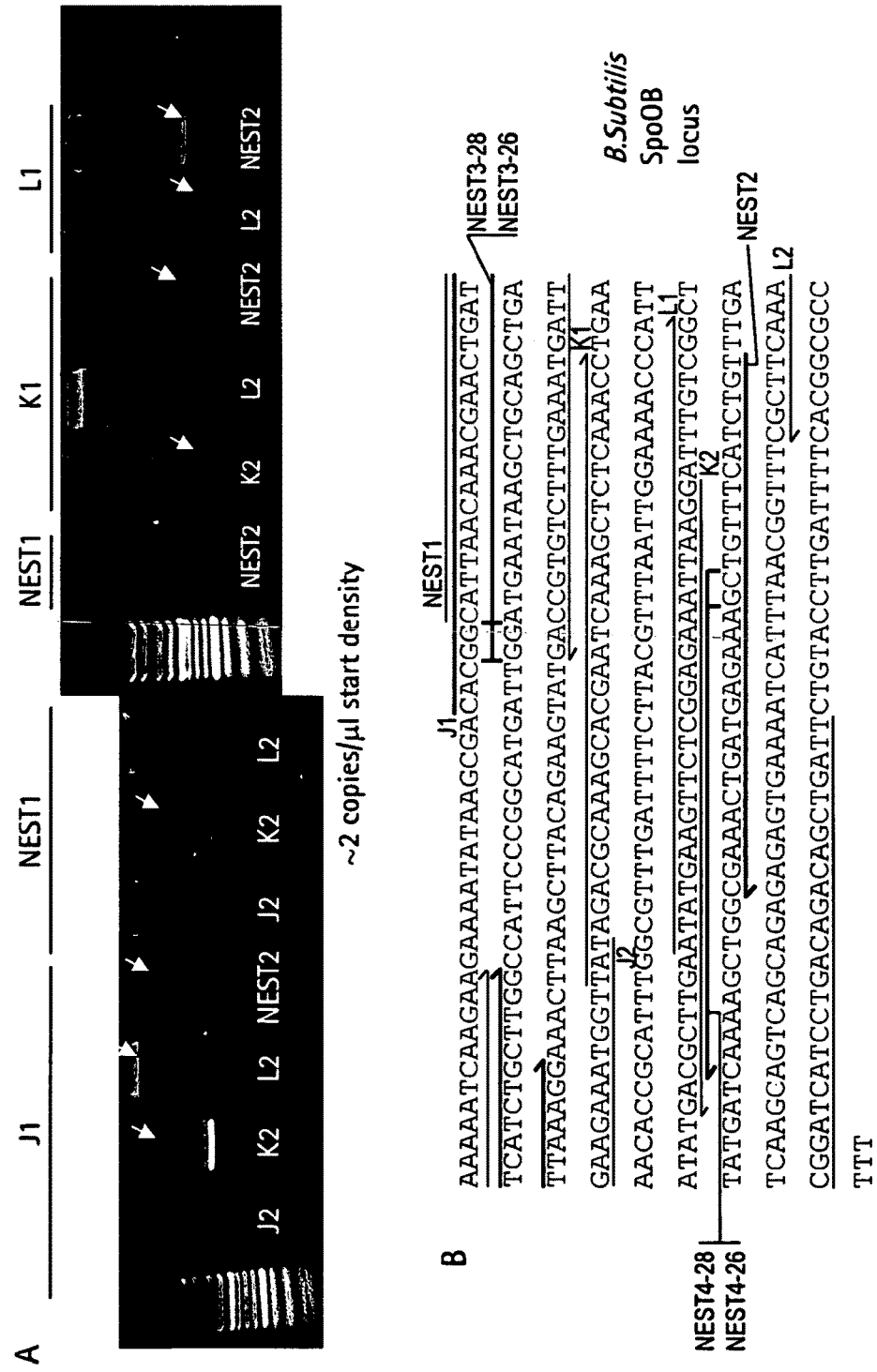
FIG. 42 Selection of optimal primers by combining a selection of candidate forward and reverse primers and testing the outcome at very low start copy densities. Figure discloses SEQ ID NO: 92.
Figure 47:
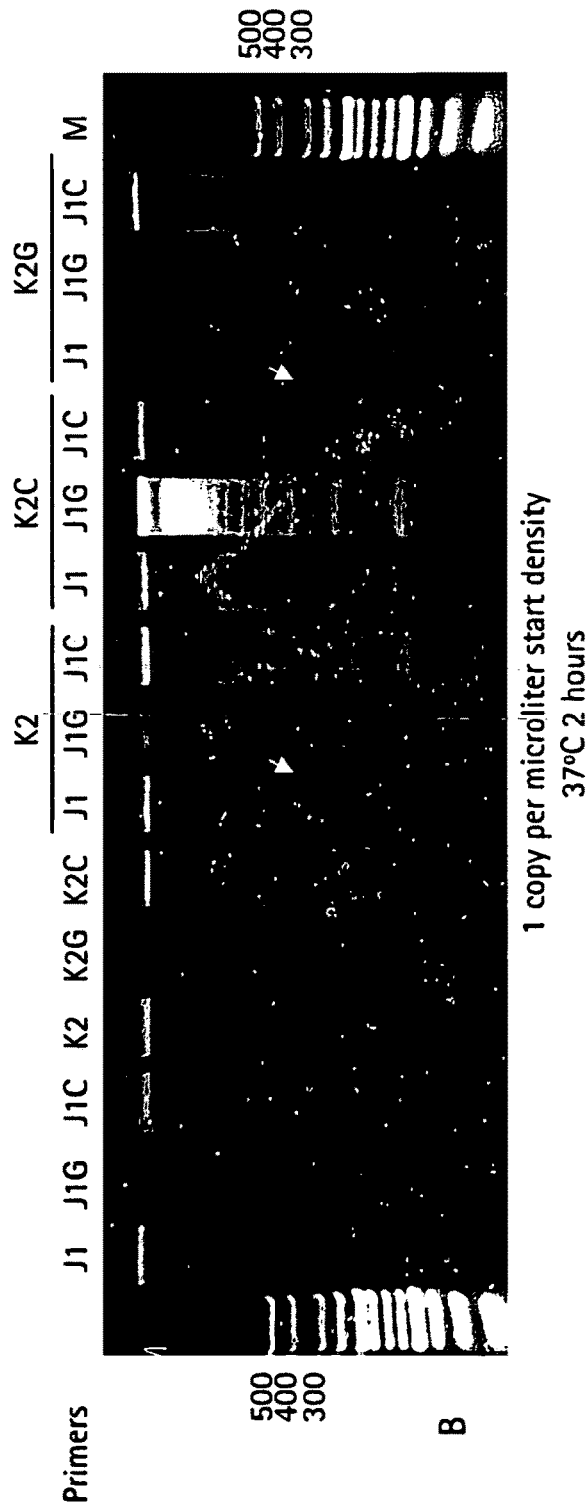
FIG. 47 Adding homopolymeric stretches to the 5' ends of primers (SEQ ID NOS 66, 99-100, 69 and 101-102, respectively, in order of appearance) may alter nucleoprotein activity.

Secondly, we note that primers which are identical except for additional small number of residues at the 5' extent show significant variability in noisiness (even when all are >30 residues), implying that the exact nature of the 5'-most base(s) plays a significant role in the mechanism and likelihood of noise (see FIGS. 42,45 and 47).

Thirdly, primers possessing a locked nucleic acid (LNA) sugar at the 3'-most end reduce/eliminate noise as determined by gel electrophoresis. They also reduce the quantity of product slightly if only one is employed, and significantly if both are used at standard' polymerase concentrations, but remain fully active if polymerase concentration is increased, and under the elevated polymerase concentrations noise still appears suppressed.

Finally low-target concentration noise appears to derive mostly/solely from primers, not sample DNA, and we thus refer to this noise as 'primer gymnastics'. This is clear from experiments in which sample DNA is decreased to zero. Consequently it is possible to focus attention on the limited mechanisms by which primers may interact with and between themselves to find solutions to this problem. How noise may arise is discussed in detail in the following section. An important conclusion of this analysis is that lowering nucleoprotein filament recombination/priming activity may impinge more severely on primer noise generation than bona fide amplicon generation.

Analysis of how Primer Noise May Originate

Unlike PCR, or other methods involving conventional hybridization, RPA's reliance on the formation of extended nucleoprotein filaments undergoing ATP hydrolysis as active homology-searching complexes likely impinges on the parameters determining oligonucleotide activity in ways previously unencountered for in vitro amplification reactions. We suggest that the rapid drop in oligonucleotide activity below 30 residues described above reflects recombination rate slowing, and that most likely this parallels observations made elsewhere on the length-dependance of ATP hydrolysis for the *E. coli* recA recombinase (Bianco P R and Weinstock G M). In particular the length and composition of short sequences was shown to influence ATP hydrolysis. Roughly 30 residues or more are required for maximal ATP hydrolysis (moles ATP per mole DNA-bound recA) when recA is bound to synthetic oligonucleotides, shorter sequences displaying marked drops in hydrolysis rate until it was absent by about 15 residues. We connect the observation of low amplification behaviour with previous data on ATP hydrolysis because there is a clear rationale to think that nucleoprotein recombination activity will be influenced by ATP hydrolysis rate. In a sense the slowest oligonucleotides we have observed are those bound with unhydrolyzable ATP-γ-S in which the rate of completed exchange (formation of resolved plectonemic joints) is near zero (Riddles P W and Lehman I R) We have also proven that ATP-γ-S effectively poisons RPA reactions (Piepenburg et al.). We suggest that high rates of ATP hydrolysis in a nucleoprotein filament underpins the activity of 'fast' primers, and low rates slow primers, who differ principally by the average number of complete recombination events completed in a unit time. Interpreted simply, ATP-hydrolysis is required for dynamic activity of filaments. Oligonucleotides of less than 30 residues become more stable and undynamic, eventually resembling the locked state generated when ATP-γ-S is employed, and are unable to complete exchange slow oligonucleotides may locate sequences as readily but be unable to disassemble readily to permit completion and polymerase access).

Figure 43:
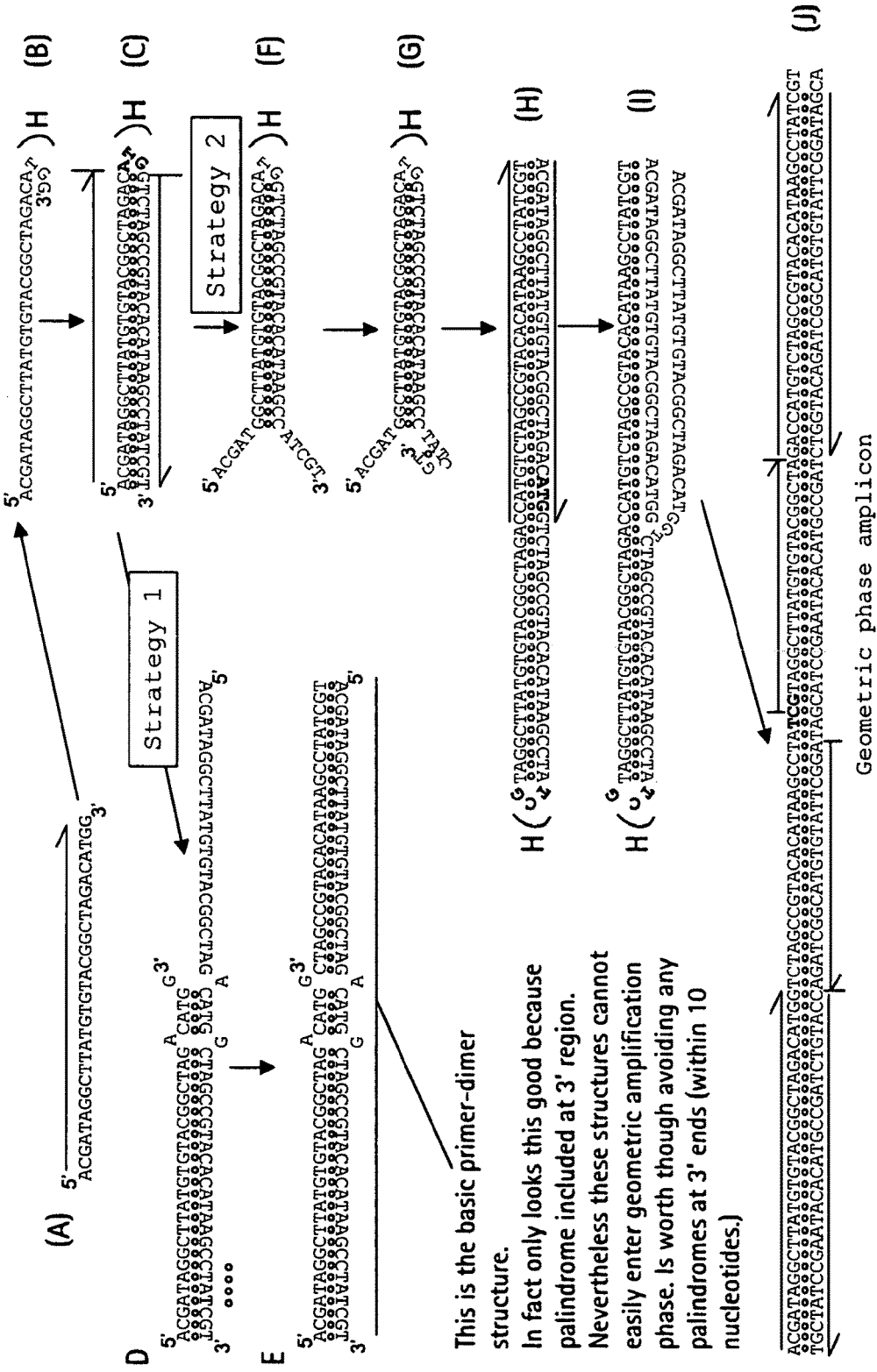
FIG. 43 Theoretical consideration of how primer noise initiates.

A Possible Difference in Dependence on Nucleoprotein Filament Activity for Boa Fide Product and Noise To understand why there might be any advantage to selecting less active 'slower' oligonucleotides we need to explore how primer 'gymnastic' noise might arise. Why might shortened oligonucleotide reduce noise faster than the specific signal? Unlike the geometric phase of amplification seen for both bona fide targets and noise products, the early formation phase of noisy targets from starting primers is probably more complex, and is presumably rather slow. In FIG. 43 we have detailed 2 general mechanisms by which individual primers can become converted to structures with the capacity for geometric amplification. Both strategies diagrammed illustrate the formation of amplicons from a single primer species. In both cases the first step involves self-priming of the oligonucleotide by formation of a short hairpin at the 3'-end. In strategy 1 the resulting hairpin will not easily amplify in geometric phase because of significant mismatches. Instead to become geometric phase amplicons they would need to proceed through a step more akin to that described in strategy 2. In this case the first self-priming event is followed by a second involving the reverse complement to the 5' end of the original oligonucleotide. There are several simple remarks from such modeling. First is that 2 types of event have to occur; there must be elongation from the 3'-end of an oligonucleotide, and then a second similar 3' hairpin and extension which involves the reverse complement to the 5'-end of the original oligo. Note that the very rare and unstable nature of the first events preceding geometric phase are going to be most strongly inhibited if most oligos are coated with either an SSB or recombinase, which have DNA melting activities when bound to ssDNAs. Conversely dynamic recombinase filaments which disassemble spontaneously create time windows in which all, or parts, of an oligonucleotide are uncoated. This very rate limiting step will therefore likely be sensitive to primer ATP hydrolysis rate, dynamicity, and by extrapolation oligonucleotide length. Consequently shortening oligonucleotides may be particularly effective and stemming noise, sufficiently so to justify slowing bona fide target amplification rate in order to achieve it.

These final geometric phase amplicons are inverted repeats. This means that an invasion/elongation originating from one side will displace a strand that immediately folds back on itself to form a long hairpin. This molecule must be targeted by recombinase action in order to be converted back to one similar to the parent, while bona fide targets can employ solution hybridization additionally. This imposes additional necessity for the primer artifacts on recombinase-based invasion to achieve geometric amplification, and consequently they will probably be suppressed more rapidly by lower recombination rate. Further the presence of internal repeats means that even larger and more diverse versions of these amplicons are likely to arise quickly, and this is consistent with the common phenotype of a smear, or ladder, running most of the way up a gel.

A third remark is that the time taken to double a given species of DNA during exponential amplification will be a compound of recombination rate and time taken to synthesise down the template by polymerase. As primer noise products (at least initially) are very small, the time taken for DNA synthesis is very low and so the principle rate limitation may be the recombination rate. Thus decreasing nucleoprotein recombination rate will, while slowing amplification in general, impinge more heavily on short amplicons than long ones, thus generally benefiting bona fide amplicons.

We draw on the above observations to devise ways to combine primers of different length, composition and concentration, to give highly sensitive and specific reactions.

Primary Oligonucleotide Design:

The four observations described above lend themselves to some straightforward oligo design principals.

Oligonucleotide Length

Optimal primer length may be around 30 residues and in some cases a few residues shorter will yield an excellent signal-to-noise ratio. As the average primer length is decreased, the noise generation decreases and seems absent altogether when 26-28 mers are employed (FIG. 45). Although the amplification of the target also decreases, we suspect that noise decreases more quickly than signal. In the previous analysis of how noise may arise, we conclude there are several reasons why primer noise might be more affected by decreased recombination rate than correct amplicons.

5'-Most Sequence Optimization

By comparing the activity of oligonucleotides possessing identical sequences except for the extent of the 5'-most residues we have noted that significant variation in oligonucleotide noisiness is observed (see FIGS. 42, 45, 47). One possibility is that this purely reflects the effects of length variation on nucleoprotein activity as described above. This may not be, however, the only reason if primers being compared are all 30 residues or longer. For example in FIG. 42, the oligonucleotides NEST-1 and J1 are identical except that J1 contains several extra 5' residues. Instead of being noisier, this oligonucleotide is less noisy, while amplifying very well. Based on this and other cases, we propose two other likely mechanisms. First, that an oligonucleotide to become exponentially amplifiable may require a priming event by the reverse complement of the 5'-most sequences, this event critically depends on the exact sequence of bases at the 5'-end. This means that varying the 5'-most bases may lead to significant variation in noise generation. Second, that the base composition of even 5' sequences, even when the oligonucleotide is great than 30 bases, may affect the recombination activity of primers. Evidence to support this comes from an experiment in which 5'tags consisting of homopolymeric stretches were added to primers, and the consequences observed. FIG. 47 shows an experiment in which a run of C residues, or G residues, were appended to the oligonucleotides J1 and K2, and subsequently amplification reaction were established containing all possible modified and unmodified oligonucleotides alone, or in the possible combinations. Surprisingly these oligonucleotides, already determined to be very sensitive and specific, were not improved by adding these particular homopolymeric stretches. Instead it was observed that if a run of Cytosines was added to the 5' end this lead to increased production of non-specific products when incubated alone, while a stretch of Guanosines had the reverse effect, making the oligonucleotides very quiet when left alone. Also, apart from the combination of the original parent unmodified oligonucleotides, the only pair to apparently successfully generate a correct product was the combination of the 2 Cytosine-tailed oligonucleotides (i.e the most noisy oligonucleotides). One explanation that can justify these observations is that a stretch of Cytosines at the 5' end makes the consequent nucleoprotein filament more active, while Guanosines make it less so. In summary oligonucleotide composition, like length, may affect rate behavior, and additional and unrelated sequences at the 5' end can have a significant influence in this respect. Optimal primers may be found by a rational approach to 5' sequence design. Several different 5'-most bases might be tried, and the best selected for employment. Additionally it is likely that tags can be placed at the 5' end whose sequence is unrelated to the target, but confer resistance to snapback hairpin priming from the reverse complement. Determination of optimal sequences that work on many oligonucleotides may be possible. Measurement of ATP hydrolysis rate of oligonucleotides in the presence of reaction components may also prove of utility in designing optimal primer pairs, and permit one to create primer mixes which all share identical amplification rate behavior. Like length, these observations and improvements would not be obvious in other systems because they depend on specific features of a recombinase-driven amplification system and the biochemistry that underlies it.

Locked Nucleic Acid, Ribose, or Other Sugar Modifications

Locked nucleic acids (LNAs) are nucleotides where a linkage has been engineered between the 2' and 4' Carbons of the sugar ring of ribose. Oligonucleotides containing such sugars, most notably at the very 3' position, have been successfully used in PCR assays, and shown to significantly improve the discrimination of correct 3' base pairing (see Vester B. and Wengel J.). We anticipated that LNA residues might be tolerated by the RPA system providing that they were not present at too many position within the oligonucleotides. As they are known to increase specificity in PCR amplifications they might well improve signal-noise in the RPA system.

Earlier experiments employing phosphorothiorate linkages at the most 3' positions proved unable to function properly in RPA, and were notably more noisy (data not shown). We interpreted this as a reflection that both uvsX and gp32, which interact with the sugar-phosphate backbone, would not bind these backbones leading to seriously anomalous reaction behavior. However gp32 binding is less dependant on the sugar as evidenced by its ability to bind to RNA as well as DNA (albeit with altered less cooperativity) (Kowalczykowski S C, et al.). Thus we anticipated that LNA sugars, which retain a normal phosphate group might remain functional with gp32.

We have performed experiments in which oligonucleotides possessing a locked nucleic acid sugar at the most 3' position have been used in amplification reactions. Comparison has been made between reactions with identical oligonucleotides with and without the sugar modification, and reactions involving one modified and one unmodified oligonucleotide. Based on experiment it appears RPA can amplify DNA when one or both oligonucleotides possess a locked nucleic acid residue at the 3' position. Notably the presence of a LNA nucleotide at the 3' end significantly reduced product accumulation under standard' polymerase concentration, and apparently eliminated associated noise. Very low noise, and reduced product, may arise because of lower successful recombination frequency, reduced polymerase takeoff, or a combination. Whatever the reason it is reasonable based on the findings that using locked nucleic acids in one or both primers will significantly reduce or eliminate noise, while retaining an acceptable amplification rate for bona fide product. We found that product levels can be returned to high levels if the polymerase concentration is increased several-fold (from about 30-40 ng/µl to 150 ng/µl), but that noise levels do not rise at an equivalent rate.

Similarly other sugar-modified residues may display improved signal to noise behaviour when present at some frequency in oligonucleotides. For example ribose, 2'-O-methyl modifications, acyclic sugars, or otherwise may prove of utility.

Approaches that Improve Signal to Noise by Combining Nucleoprotein Filaments with Differential Activities The ability to control the rate of recombination and/or elongation from primers on the basis of their length, base composition and distribution, and use of modified sugars (or possibly other backbone modifications) suggests mechanisms to design amplification reactions with optimal signal to noise properties. There are two general ways in which we envision oligonucleotide combination strategies to be employed to benefit. First are strategies in which single tube nesting occurs, and second are the employment of a non-noisy oligonucleotide paired with a more conventional oligonucleotide in such a way that bona fide amplicons are readily formed, but noisy amplicons involve only single oligonucleotides.

Single Tube Nesting

Nesting is the process by which improved sensitivity and signal to noise has been enabled by carrying out a first amplification with an outer pair of primers, and then perform a second amplification with an inner pair of primers. In its most familiar context this approach has been employed in conjunction with the PCR method. In principal the first round amplifies the target more efficiently than random DNA, such that after the first amplification even if it was insufficiently clean to give a clear amplicon against background, it still is so relatively enriched that a second amplification with primers internal to for the first will readily give a very clear and clean result. In practice this normally relies on performing one amplification, then removing a small portion to a new tube, and performing a second amplification with internal 'nested' primers.

While the concept of nesting is visited elsewhere our results suggest an attractive alternative nesting approach in which all the participating primers are combined in a single reaction. The rationale being that the inner and outer oligonucleotide pair are differentially active in recombination and/or elongation rate, and be present at different concentration. For example the outer pair would be configured to have a fast recombination/elongation rate, and the inner pair a slower recombination/elongation rate. Also the outer pair would be present at lower concentration (but still sufficiently high concentration for acceptable activity) and the inner pair would be present at high concentration. What would then happen? In isolation the inner pair would amplify cleanly but rather slowly so that they might not achieve an acceptable degree of amplification within a desirable timeframe. In contrast, in isolation the outer pair would amplify quickly, albeit with some primer noise, but would stop at a rather low concentration due to exhaustion. In combination however these two behaviours would potentially complement nicely. In practice outer primer pairs would generally be fast, over 30 residues in length, unmodified at the 3'-end, and possibly containing additional 5' residues that promote 'fastness'. Inner primers would be slower, as potentially conferred by making them short, modifying the 3' end with LNA or otherwise, adding slowness sequences at the 5' end, and so on.

Non-Noisy/Noisy Nucleoprotein Pairs

Experimental data that we have obtained suggests that much of the primer-derived smears or ladders contain sequences from one primer species only (see FIG. 46). If true this fact alone suggests a simple approach to distinguishing signal from noise merely by determining whether or not the two primers used in the reaction become physically associated in products. Here we suggest that this can be further improved by combining very quiet oligonucleotides with faster (noisier) oligonucleotides. Quiet oligonucleotides, for example short oligonucleotide, may still function efficiently if present with noisier ones providing that they can function in hybridization reactions (see FIG. 52). However if they only engage in amplification via normal hybridization whose kinetics are very different to recombinase-promoted noise amplification they may remain uninvolved in the noise that the faster oligonucleotide engages in alone.

Third Primer and Detection Protocols

The possibility that primers might principally indulge in gymnastics alone, as mentioned above, suggests simple approaches to determining whether or not amplification has occurred efficiently. One simple non-gel detection format would employ one oligonucleotide labeled with a dye or enzyme, or other easily detectable group, and the other labeled with an immobilizable group e.g. biotin (see FIG. 50 Part 1). Thus before, during, or after the main reaction phase the immobilizable oligonucleotide would be immobilized to a surface, and at reaction end this surface would be washed with an appropriate buffer. If the other labeled primer co-associates with the immobilizable primer, which can be easily determined, then amplification of the product has occurred.

Figure 50:
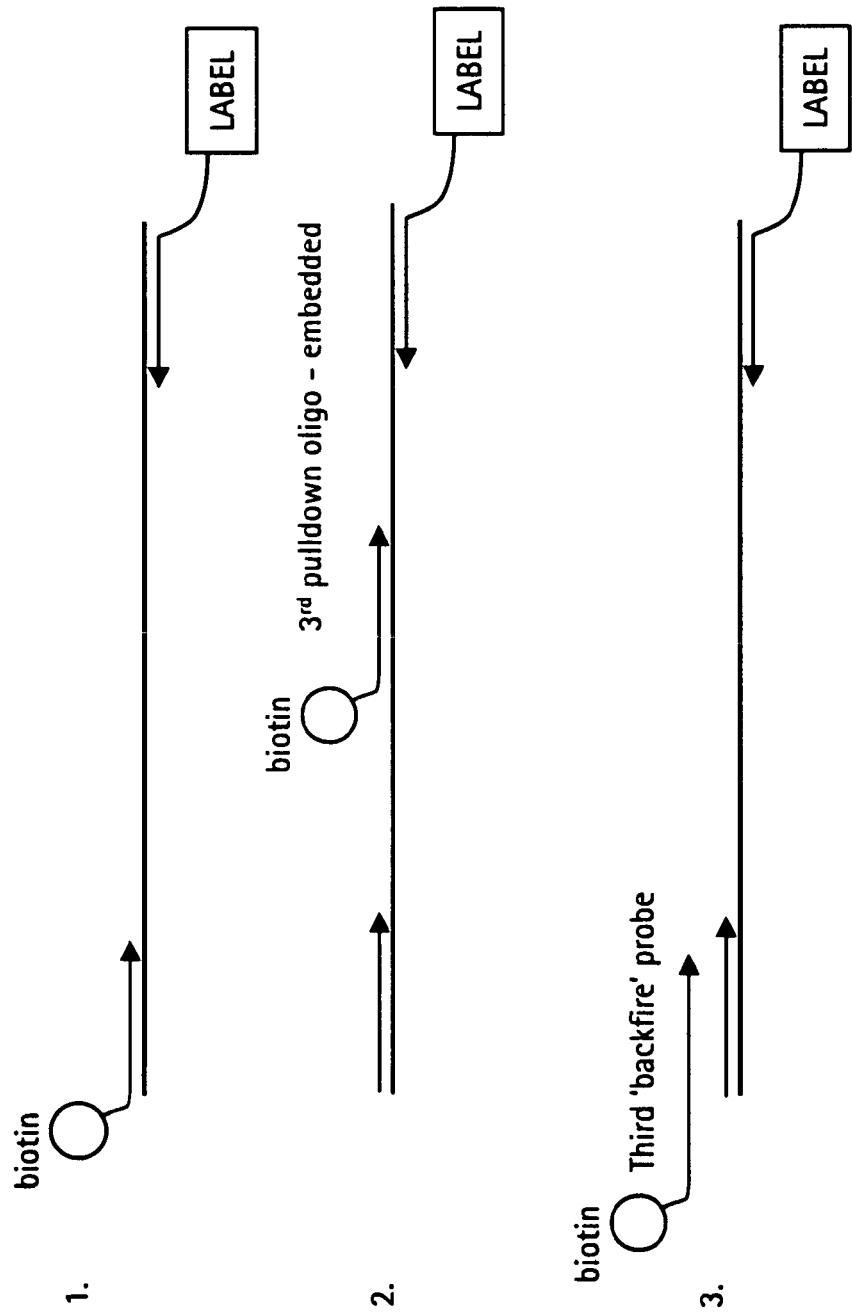
FIG. 50 Detection formats incorporating a 'third' primer for product enrichment

Beyond this we imagine additional ways in which additional levels of stringency on bona fide product amplification might be generated. A simple additional approach involves a 'third' primer which functions to capture onto a surface liquid phase amplicons. This primer would be deterred from generating noise itself either by being engineered as quiet (e.g. a short oligo as described above), or by being added to the system only at a late phase of the reaction. This third primer might target novel internal sequences, but also could immobilize the targets via 'backfire' synthesis described elsewhere to avoid disruptive branch migration (FIG. 50, Parts 2 and 3).

Lyophilization of the RPA Reaction

In order to configure non-laboratory, or near-patient, diagnostic and forensic tests it will be necessary to provide ambient-stable reagents. One obvious way to achieve this is by lyophilizing the reactions, omitting only the sample DNA, and possibly any other component which is stable separately and can be added with the sample such as buffer used to dissolve the sample nucleic acid.

Figure 53:
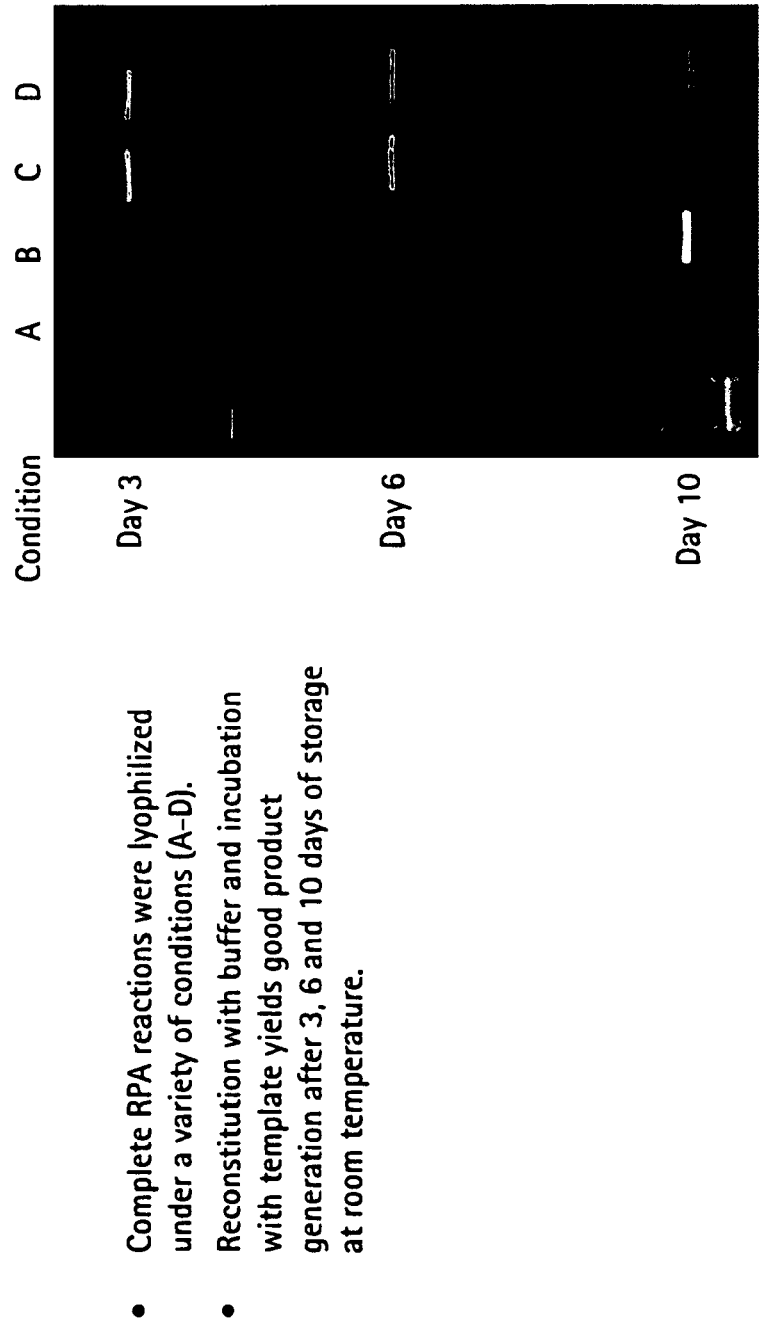
FIG. 53 Trehalose stabilizes lyophilizates to permit all components except buffered sample to remain active for at least 10 days at room temperature.

While lyophilization is a well-established process there is no guarantee that all components of a reaction system will successfully by co-lyophilized and reconstituted under the same conditions. We have attempted to lyophilize RPA reactions with and without various of the final reaction components. FIG. 53 shows that we have successfully managed to lyophilize RPA reactions containing everything except the sample DNA and some buffer component (which can be stored stably at ambient temperatures and used to reconstitute sample DNA). The disaccharide sugar trehalose proves in these experiments to be required to stabilize the lyophilizate, permitting room temperature storage for at least 10 days.

Real-Time Kinetic Analysis of RPA Reactions

The ability to perform kinetic analysis of DNA amplification reactions provides enormous utility compared with purely end-point analysis of similar reactions. For one thing this allows the determination of the number of DNA, or RNA, copies present in a sample and has many uses in research, clinical, and environmental testing applications. In addition to straightforward quantification applications, dynamic reaction product detection offer excellent solutions to other problems, such as permitting the discrimination of single nucleotide polymorphic alleles by virtue of altered accumulation kinetics, and a mechanism to assess presence versus absence of targets in a non gel-based format.

RPA offers an excellent alternative to PCR to amplify specific DNA targets, but by obviating thermal cycling, RPA requires less expensive instrumentation and is easier to implement in non-laboratory settings.

Currently real-time analysis of DNA accumulation is most widely employed in combination with the PCR. PCR shows exponential amplification of DNA up to several cycles after reaching a product detection threshold and can be implemented using relatively inexpensive optics when various fluorescence-based sensors are used. Consequently assessing the cycle number a given sample crosses the detectability threshold, in combination with equivalent results from control samples, permits assignment of the number of copies present in anonymous samples. A number of sensor approaches have been described, and many are currently employed. Fluorescent minor groove binding dyes can be employed which develop strong fluorescence once bound to DNA. Examples of such dyes include SYBR gold and SYBR green (Wittwer et al. [1]). Additional other approaches have been successfully implemented, and these gain from adding target specificity to the sensing permitting greater sensitivity and specificity, particularly at low target levels in the initial sample. One simple format comprises two oligonucleotide primers recognising adjacent internal sequences of the amplicon, each labelled with a fluorophore. If the target is present the two fluorophores become closely situated and fluorescence resonance energy transfer (FRET) occurs, which can be detected with suitable excitation and emission filters (Wittwer et al. 1997 [2]). Other preferred systems employ probes combining the presence of both a fluorophore and a quencher. For some methods hybridisation to the target amplicon causes separation of hairpin-associated fluorophore and quencher and hence an increase in fluorescence. In another method hybridisation of the probe is assessed via the action of an oncoming polymerase possessing a 5'-3' exonuclease which attacks the probe and leads to permanent separation of the fluorophore and quencher (so called 'Taqman' probes) [Heid C A, Stevens J, Livak K J, Williams P M., Real time quantitative PCR. Genome Res. (1996) 6:986-94]. Implementation of these approaches and others is widely documented.

During PCR reactions several distinct and temporally independent phases can be identified. All DNA is single-stranded at the high temperature (e.g. 94° C.) used to melt all DNA strands. Subsequently amplification primers may be annealed at a second low temperature, such as 50-65° C. Finally elongation of primers to generate principally double-stranded products is performed at, typically, 70-75° C. Due to the controlled cyclic nature of PCR it is desired and necessary to assess the accumulated level of DNA at specific distinct points in the cycle. This may occur at the end of the synthesis stage. Alternatively it may be desirable to measure fluorescence at some other point, and at another (fourth) temperature depending on the approach employed.

Unlike PCR, RPA reactions are principally configured to operate at a single temperature. Current configurations of RPA are unphased and therefore a complete variety of reaction 'stages' will be simultaneously present in a sample (phasing may be attained in theory by approaches, for example, such as controlled uncaging of ATP). As a consequence of this lack of phasing at any given moment there is likely to be a mixture of double-stranded DNA, single-stranded DNA (such as displaced strands, as well as oligonucleotides), and intermediates of heterogeneous nature (such as triplex intermediates and/or homology-searching complexes). Despite the heterogeneity of the reaction mixture it will generally be the case that the steady state levels of double-stranded DNA, and possibly single-stranded DNA, will increase during the reaction as product accumulates. On this basis it seemed reasonable that straightforward approaches to measuring product accumulation might be readily employed.

Here we describe quantities of SYBR green and SYBR gold dyes that are compatible with RPA and permit real-time detection of accumulating reaction products. It is also the case that sequence-specific monitoring protocols will be compatible with RPA. Such approaches would include the employment of two fluorescently labelled oligonucleotides, which on hybridisation undergo fluorescence resonance energy transfer, or the use of dual-labeled probes such as those that are quenched until hybridisation results in alterations in FRET, or they are separated by associated nuclease activity. We provide evidence that the Taqman' approach which relies on the so-called 5'-3' exonuclease activity of certain polymerases cannot be used in RPA reactions, as these nucleases are actually structure-specific FLAP endonucleases which inhibit RPA reactions. Furthermore certain approaches, such as molecular beacons, in which natural hairpin-forming properties of the probe are essential, may be less successful in RPA due to likelihood of the probe to be in a melted state in the present of single-stranded DNA binding proteins and recombinases.

Figure 54:
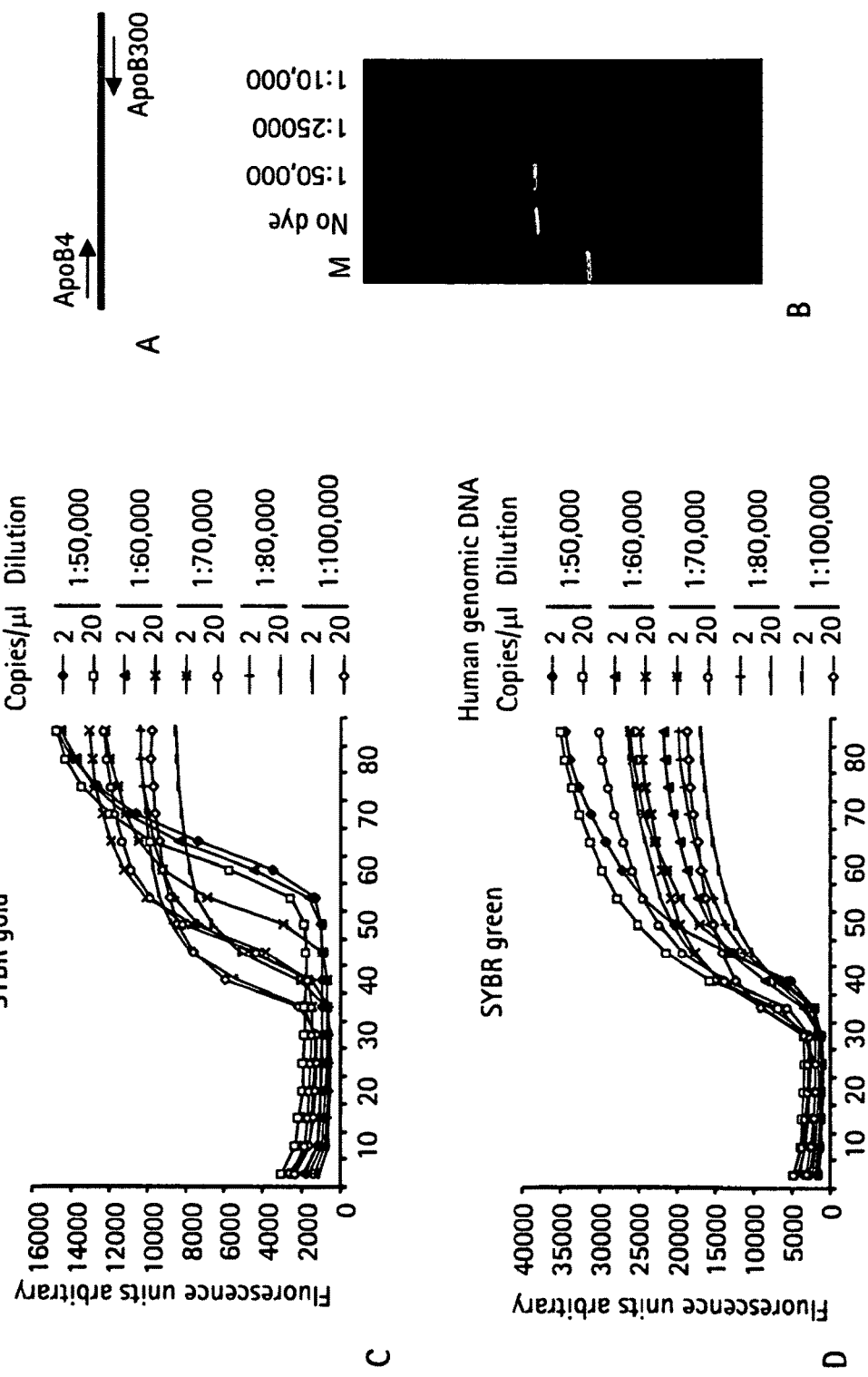
FIG. 54 Minor groove binding dyes SYBR green and SYBR gold can be included in RPA reactions and will sense the accumulation of DNA reaction products.

FIG. 54 shows the results of experiments to determine whether SYBR gold and SYBR green stains are compatible with RPA. An initial experiment with SYBR gold in which various dilutions of the SYBR gold dye were made form the supplied stock (described as a 10,000.times. stock from molecular probes in DMSO) was performed using primers to amplify a fragment of the human apoliporotein B locus (FIG. 1 A,B). The reaction is clearly inhibited if the final concentration was 1.times. (1:10,000 from stock) or 0.4.times. (1:25,000 from stock), but was not significantly observed at 0.2.times. (1:50,000 from stock). This concentration of 0.2.times. was then employed as the highest concentration in a dilution series in 50 microliter reactions established with the same two human-specific primers, at two (low) target concentrations of total human genomic DNA (2 or 20 copies per microliters starting copy density) (FIG. 54 C). A master mix was assembled on ice and aliquoted into wells in a 96-well microplate cooled to ice temperature. Once mixed the plate we transferred to a fluorescence microplate reader with a stage set to 37° C. The reader was set to collect fluorescence readings at excitation 485 nm, emission at 528 nm, at 1 minute intervals over a period of 1 hour. In the same run SYBR green dye was diluted to the same degree (D) and concurrently assayed in similar samples. This experiment revealed several key facts relevant for configuring real-time RPA reactions with SYBR gold or SYBR green. First, direct comparison of detection times within the SYBR gold experiment shows that apparently even 1:50,000 fold dilutions slow the reaction relative to higher dilutions. Indeed 1:100,000 or 1:80,000 gave significantly faster reaction kinetics, and thus would appear to be a better quantity of SYBR gold to use than the 1:50,000, which appeared acceptable by earlier end-point analysis. However, the relative maximal fluorescence signals obtained with the higher dilutions were significantly less than with the lower, suggesting that the dye were becoming limiting. Also, even at the highest dilution of SYBR gold fluorescence increases over background was detected later than the samples in the SYBR green experiment, and the overall fluorescence signals for all SYBR gold concentrations were much less than for SYBR green. In contrast the SYBR green samples were in all cases detected earlier than the SYBR gold experiments. In conclusion we suggest that while both dyes can be implemented in real-time RPA, SYBR green appears the more robust for standard analyses. It appears to work well at final dilutions of between 1:50,000 and 1:100,000, but the more concentrated samples (1:50,000) gave higher overall fluorescence and longer detectable exponential phase suggesting that 1:50,000 dilution was the best in these experiments. We have also assayed with higher SYBR green concentrations successfully, but there is some indication that inhibition may eventually occur. We suggest that between 1:50,000 and 1:25,000 is the optimal SYBR green concentration for dynamic real-time RPA assays.

Figure 55:
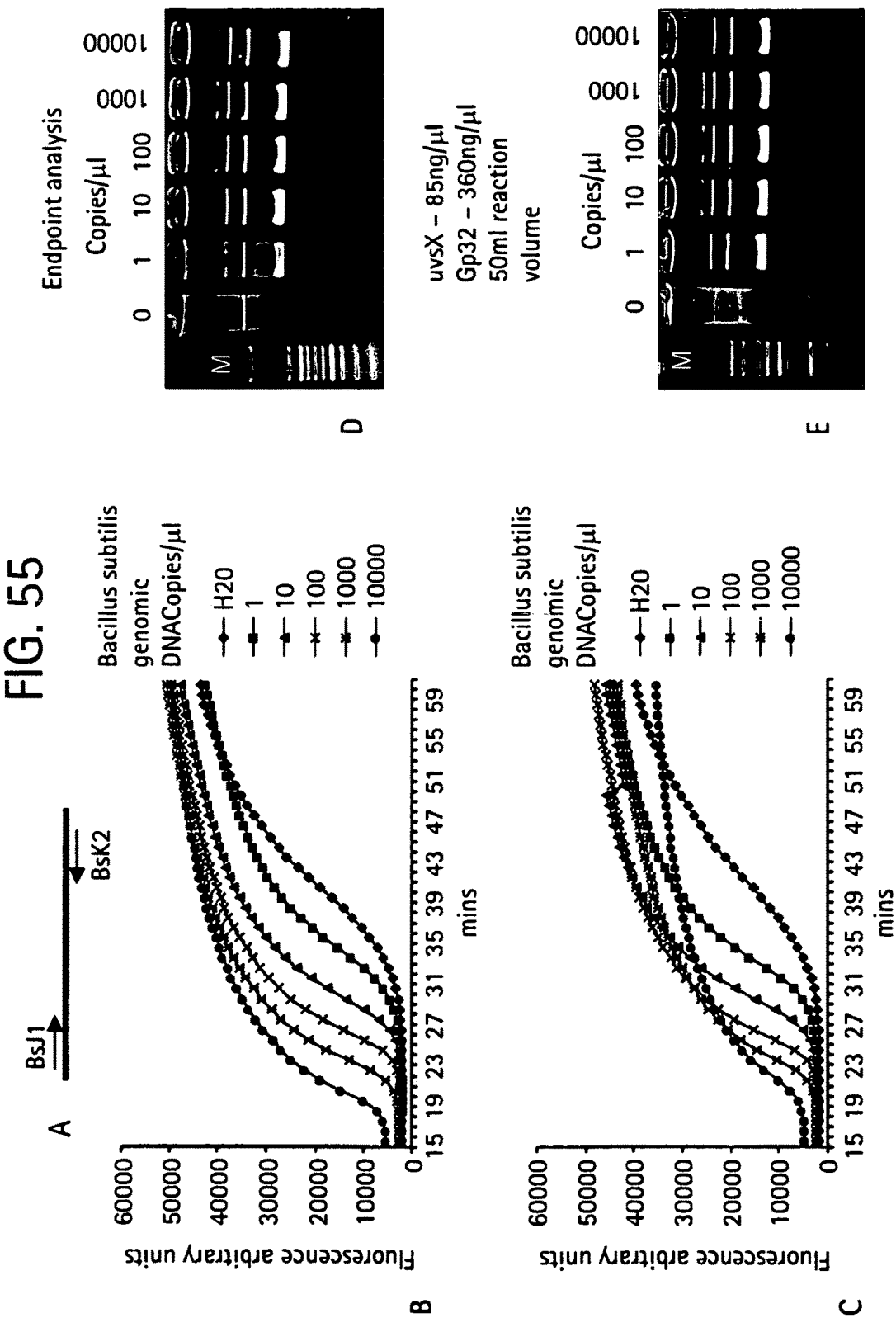
FIG. 55 Using SYBR green dye for quantitative assessment of *Bacillus subtilis* genomic DNA copy number can be made over four order of magnitude.
Figure 56:
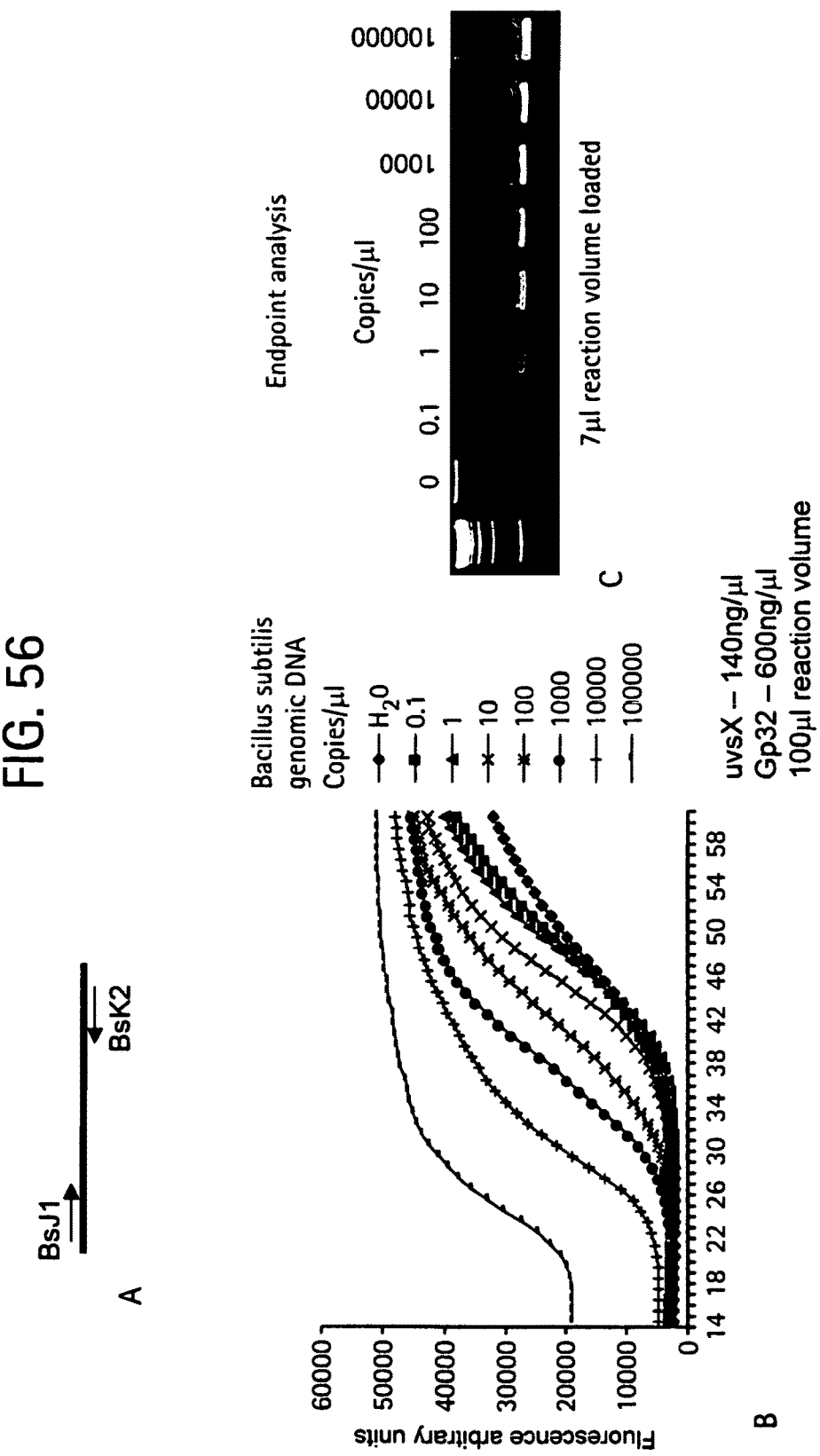
FIG. 56 Using SYBR green dye quantitative assessment of *Bacillus subtilis* genomic DNA copy number can be made over at least five orders of magnitude.

FIG. 55 shows an example of two experiments to determine the capacity of the system to distinguish between different numbers of copies of a DNA target (present in *B. subtilis* genomic DNA). Starting number of template molecules of 500,000, 50,000, 5,000, 500, 50 or zero copies of *B. subtilis* DNA were present in the various samples and amplification was performed with *B. subtilis* SpoOB locus-specific primers BsJ1 and BsK2. In many independent experiments the system successfully generated profiles similar to the representative experiment shown in FIG. 56. Note that the spacing between the exponential phase curves is similar between 10-fold copy number dilutions as required for a quantitative system. We conclude that RPA is quantitative over at least 4 orders of magnitude of starting template number, but quantitative results over a larger range may be possible. Note that in (FIG. 55C), the second *B. subtilis* titration experiment, the highest target concentration trailed off unexpectedly early. Later experiments indicate that this may arise sporadically as a consequence of the relatively low levels of gp32 and uvsX employed in these experiments compared to later experiments with roughly double the levels (FIG. 56).

Figure 57:
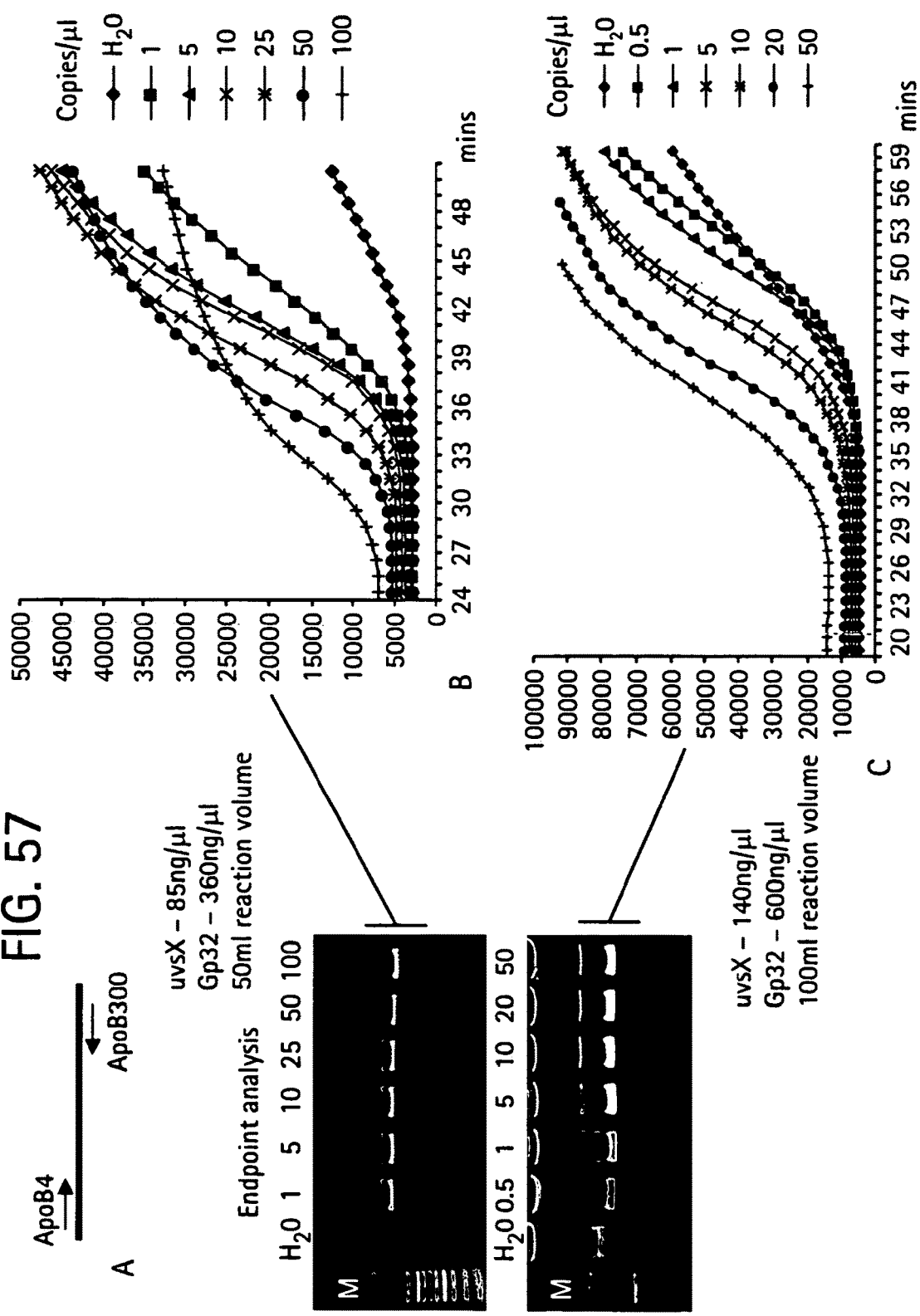
FIG. 57 Quantitative real-time RPA responds excellently to titration of human genomic DNA.

We also investigated similarly the ability of the SYBR green RPA system to monitor a range of starting template copies of human DNA by amplifying with a number of dilutions of human DNA. FIG. 57 shows the results of such analyses. As expected the data fit the expected profile indicating that RPA behaves in a quantitative manner and can easily be assayed with SYBR green. A similar trailing effect was observed for the highest target samples, but was corrected in later experiments in which higher amounts of gp32 and uvsX were employed (see FIG. 57 C versus B, and the concomitant increase in overall end-point product levels).

We show that using fluorescent dyes it is possible to monitor the kinetics of RPA reactions, and that this in turn can be used to indicate the quantity of specific targets in a sample. The simplest interpretation is that double-stranded DNA accumulates in an exponential fashion in RPA reactions until a mass point above the detection limits of SYBR green fluorescence. It is possible, however, that the fluorescence profile of SYBR green RPA reactions reflects additional activities. For example RPA products may under some circumstances engage in recombination reactions with other products leading to complex intermediates whose SYBR green binding behaviour is not well understood. Also the kinetic profile of product accumulation may alter as a consequence of reaction ageing phenomena only partly related to the starting copy number. This may underlie the spurious early fluorescence trailing observed for the highest copy number samples in some of these early experiments, although later experiments with increased uvsX and gp32 levels avoided this phenomenon.

We observed in a number of cases that the water control appeared to begin rising in a similar timeframe to the lowest concentration of sample (typically 1 copy per microliter start density, or less), however the kinetics of the water control product accumulation seemed distinct from the target-containing samples, having a shallower exponential phase indicative of slower doubling times. This observation is probably due to structural properties the amplicons possess (e.g. internal repeats) that reduce the rate of synthesis in the RPA system. We commented earlier on the possibility that primer-derived amplicons would tend to contain inverted repeat structures that would often require 2 rounds of invasion/synthesis per duplex doubling, rather than the single one that could suffice for bona fide target amplicons. Regardless of the origin of this phenomenon we speculate that with sophisticated data analysis software and suitable experimental internal controls, this noise might be identified and distinguished from the kinetic behaviour of true target amplification. Furthermore we observed some distinct variation in the time taken to reach detection, and the slopes of the curves, between distinct amplicons. This would be expected as variation in the activity of different primers, and the variant lengths and sequence composition of different amplicons, suggests that average doubling times would vary between amplicons. The slopes of the fluorescence profiles by this criteria alone are likely to vary between different types of amplicons, and this may be usefully employed in analysis.

The experiments performed here suggest that kinetic RPA reactions can be used to decrease the time taken to assess the presence of target DNA in samples compared to later gel electrophoresis. The experimental set-up we have used here is far from ideal as the 96-well plates used are made of thick plastic, and the heated plate on the fluorometer is not in direct contact with the sample wells. We estimate that it takes up to 5 minutes for a 50 µl volume reaction to attain temperature under these conditions, and perhaps 8 minutes for a 100 µl volume. In an optimised device these long lag times would not exist. Consequently we estimate that for a clinically relevant quantity of human DNA (say 1000-3000 copies, ~3ng-9ng) amplification could be assessed readily in roughly 30 minutes with the appropriate equipment using typical conditions shown here. Despite the limitations of these experiments using 96-well plates and a conventional fluorometer, these pilot experiments are highly encouraging and indicate that kinetic monitoring of RPA reactions offers a tractable approach to quantification, and that this is quantification may be practically implemented to assess DNA levels over at least 5 orders of magnitude.

RPA Reaction Control Mediated by ATP Concentration

RPA is a versatile method, but it can be improved by incorporation of features to control precisely when in the reaction recombinases are active. Such control can be gained through the periodic release of ATP by photolysis of caged-ATP. Alternatively, the reaction concentration ATP or other nucleoside triphosphates, can be cyclically regulated by repeated manual addition or the use of a biochemical oscillator.

Caged ATP cannot supporting either the DNA binding and recombinase function of *E. coli* recA protein [Butler B C, Hanchett R H, Rafailov H, MacDonald G (2002) Investigating Structural Changes Induced By Nucleotide Binding to RecA Using Difference FTIR. Biophys J 82(4): 2198-2210]. Following photolysis, however, released ATP enables recombinase function. All prokaryotic recombinases so far studied are direct homologues of the recA protein with primary sequence homology, and structural homology. Moreover, all recA homologues studied, including the eukaryotic homologues, require binding to ATP to enable recombinase function. We expect that similar phenomena with therefore be mediated with T4 uvsX and other recombinases accordingly.

The role of nucleotides in regulating recombinase action is relatively well documented. In the case of prokaryotic recombinases, e.g. *E. coli* recA and T4 phage uvsX, the recombinases hydrolyse ATP to ADP (and AMP in the case of uvsX). Hydrolysis is occurring with high activity as long as the recombinases are bound to DNA. The ADP-bound state has lower affinity for DNA and is generally associated with filament disassembly from DNA (and altered nucleoprotein filament pitch). Under typical in vitro conditions ATP is maintained at a relatively high concentration in excess to ADP, to ensure that rapid of exchange of ADP for ATP in nucleoprotein filaments deters premature disassembly. Consequently, the recombinases in a reaction respond to the ATP:ADP ratio and to some approximation net disassembly of the nucleoprotein filament occurs when the ADP concentration exceeds the ATP concentration.

RPA reactions rely on the action of recombinases to load onto synthetic single-stranded oligonucleotides and carry out homology-searching activity. As described the activity of the recombinases is dependant on the presence of nucleotide triphosphates, most obviously ATP. When recombinases are DNA bound they hydrolyse the nucleotide triphosphate at a high rate, for example the T4 uvsX protein is known to hydrolyse 200 molecules of ATP per protein molecule per minute at 37° C. on single-stranded DNA (although rates on shorter oligonucleotides may be more variable). Consequently there is a need for a large supply of ATP to maintain an active recombination reaction in which a large proportion of oligonucleotides are associated with recombinase filaments, particularly when the oligonucleotides are present at near micromolar concentrations.

Consider the flux of reaction nucleotide levels that might occur during a typical RPA reaction. If a pair of oligonucleotides is employed in a reaction at a concentration of 1 µM each, the oligonucleotides being 35 residues in length, then at 10% saturation of the oligonucleotide with recombinase, there is roughly a bound-recombinase concentration of 2.8 µM (a value of 10% saturation in 3-5% PEG compound is roughly consistent with the results of experiments in our hands, but could be slightly higher or lower). This would convert a 0.56 mM solution of ATP to the equivalent amount of ADP every minute based on the published hydrolysis rate. Consequently if a 3 mM solution of ATP was used to initiate the reaction, and no ATP regeneration system were present, then after only 3 minutes the ADP concentration would rise to levels equal to the ATP and the recombinase would become inactive.

We have routinely used a total oligonucleotide concentration of 0.6 µM, and a uvsX concentration of roughly 3 µM. Should all of this uvsX be bound to oligonucleotides it would consume roughly a 0.6 mM solution of ATP in 3 minutes, given a reaction rate 200 molar quantities per minute on oligonucleotides. Based on our data limited hydrolysis data, however, it is unlikely that complete binding of uvsX molecules to single-stranded DNA is ever achieved under our typical RPA conditions. Although it is formally possible that the per monomer hydrolysis rate is lower for the length of oligonucleotides we employ. These alternatives are suggested by the fact that in some cases we have been able to amplify a target DNA to levels detectable by ethidium bromide staining levels without the presence of a regeneration system. Other experiments suggest that is takes roughly 30 minutes to achieve this level of amplification, and by deduction we calculate that a maximum of only 0.15 mM ATP could possibly have been consumed in each 3 minute period, a quarter of the predicted level).

Analysis of effective concentrations of uvsY in reactions is consistent with the expected stoichiometries. We have routinely used roughly a half to equi-molar concentrations of uvsY compared to uvsX protein, and published data suggests that uvsY protein probably functions as a hexamer. If this is so and one hexamer is required to load, and stabilise, each loaded filament, then whereas there would be a need for roughly 12-14 uvsX molecules per oligonucleotide (30-35 mer) there would need to be 6 uvsY molecules per oligonucleotide, i.e. roughly half the molar concentration. This experimentally determined optimum satisfies nicely the theoretical prediction that half to equi-molar concentrations of uvsY to uvsX are required.

In summary, the conversion of ATP to ADP in a typical uvsX-supported RPA reaction with 0.6 µM oligonucleotides, 3 µM uvsX, and 1-3 µM uvsY is about 50 µM per minute and no more than that. Roughly 16 molecules of ATP are hydrolysed per uvsX molecule per minutes in the reaction. This figure is six-fold less than that predicted if all uvsX molecules were bound to ssDNA and hydrolysing ATP at 200 molecules per uvsX per minute, and presumably reflects either that only a fraction of the uvsX is bound at any one time, that hydrolysis rates are lower on short oligonucleotides, and/or that in reactions with no regeneration the hydrolysis rate falls off significantly as the ADP levels rise. We suggest that while the last factor may become important eventually, during most of the reaction this is not the primary factor.

Having deduced experimentally the consumption rate of ATP in a typical RPA reaction, it now remains to estimate what size pulse of ATP concentration we would need to use to stimulate suitable bursts of recombinase activity. To do this we need some estimate of the $K_m$ for a particular recombinase.

The $K_m$ of ATP hydrolysis by recA is reported to be 20 µM. Consequently relatively little free ATP needs to be released into a recombinase system to promote activity. Assuming this is also true for uvsX, a pulse of ATP that changes the reaction concentration from zero to 50 µM would amply support homology searching until such time that the ADP level accumulates to a 1:1 ratio. Under standard conditions this would be roughly 30 seconds and would eventually produce 25 µm ADP and 25 µM ATP. A 30 second burst of recombinase activity is likely to be longer than what is required for a round of invasions to occur. Additional pulses of ATP can readily generate additional bursts of recombinase activity. For example a further pulse of 50 µM rise would raise the ATP level to 75 µm compared to 25 µM ADP. After 30 seconds the ATP level will equilibrate to 50 µM ATP and 50 µm ADP and the reaction will again halt. A further pulse will raise the ATP to 100 µM and the ADP to 50 µm, and after 30 seconds further 75 µM of each will be equilibrated. Thus 30 second bursts of excess ATP could be released in 50 µM bursts to support burst of recombinase activity. Of course the changing overall absolute concentrations of ADP and ATP are likely to affect the reaction behaviour necessitating adjustments and possibly slightly larger pulses of ATP may need to be release at each round. Nevertheless it is apparent that with a starting concentration of caged-ATP of 3 mM (similar to that used in our earlier experiments) and pulses of 50 µM is possible to support 60 independent pulses. Even if the burst size needs to increase progressively to account for the overall increase in ADP concentration it is fairly likely that 30 cycles can be accommodated. Furthermore the ADP may be removed from the reaction by inclusion of ADP metabolising enzymes in the reaction. These could include hydrolysis of ADP, or alternatively regeneration of ADP to ATP and a constant source of alternative consuming ATP activity such as NADH generation.

Caged ATP is readily commercially available, and recently cheap low power devices that might be used to drive uncaging have become available. Advances in light-emitting diodes (LEDs) have lead to the development of small cheap low power sources to generate light of wavelength 365 nm. We envision integration of such devices into low power heated cells, which are portable and battery-operated. Alternatively brief periods of recombinase activity could be generated simply by repeated addition of small volumes of additional ATP, or by using an oscillator system, such as the phosophofructokinase oscillator.

RPA Reaction Control Mediated by Use of Asymmetric Primers

One-sided RPA reactions can be driven from a single primer target site. In the absence of a facing primer, such reactions will generate single-stranded DNA. We have found that oligonucleotides possessing a 3' locked nucleic acid (LNA) [Di Giusto D A, King G C (2004) Strong positional preference in the interaction of LNA oligonucleotides with DNA polymerase and proofreading exonuclease activities: implications for genotyping assays. Nucl Acids Res 32(3): e32] nucleotide, cannot server as primers for recombinase-mediated elongation by certain polymerases, such as the *Bacillus stearothermophilus* and *Bacillus subtilis* polymerase I, but do serve as primers for other polymerase such as the *E. coli* Klenow fragment consistent with prior data showing that such 3'LNA capped primers can serve as primers in polymerase extension reactions when they hybridise to target single-stranded DNAs. We have also found that not all polymerases seem to be able to initiate from recombination intermediates, perhaps reflecting that for some polymerases longer stretches of single-stranded DNA with bound primers are required. For example we have found that phi-29 polymerase is unable to initiate synthesis from a recombination intermediate. We also have evidence that it can however synthesise from a 3'LNA-capped primer. Finally consistent with published reports, we have found that for a given recombinase, there is a minimal primer length required for recombinase-assisted strand-exchange to occur efficiently. Specifically oligonucleotides shorter than 27-30 base pairs are poor substrates for uvsX. Nevertheless primers as short as 20-27 nucleotides may be perfectly adequate to support hybridisation-mediated priming. Thus by combining a longer and a shorter primer one can bias RPA reactions to use one primer for invasion-driven elongation and the other for hybridisation-driven elongation.

Taken together these facts suggest a variety of configurations in which reactions can be assembled in a way that synthesis initiates from one side, and only when it has passed the second site does opposing synthesis begin. For example, an RPA reaction may be configured such that one primer is a normal oligonucleotide and the opposing primer is a 3'LNA-capped oligonucleotide. In the same reaction a polymerase that cannot use 3'LNA-capped oligonucleotides, but works from invasion structures, is mixed with one that can use 3'LNA-capped oligonucleotides but works only from hybridisation structures. Recombinase-mediated invasion and extension from the normal primer will generate single-stranded DNA molecules, which can then serve as templates for synthesis by the second polymerase when a 3'LNA-capped opposing primer hybridises to its target site. Alternatively a short second primer that functions only in hybridisation would also ensure asymmetric primer use. Other configurations of oligonucleotide length and nature, with different polymerases, may be used to generate the desired effect. Thus the use of asymmetric primers should resolve any interference from replication fork collision; however, it may be necessary also to control recombinase activity to avoid re-invasion of single-stranded DNAs displaced by synthesis from the normal primer.

The combination of asymmetric primers and control of ATP levels may provide conditions sufficient to amplify long (>10 kb) DNAs. One other factor that may affect the efficiency of amplification of long DNAs is interference from other template DNAs, other non-template DNA, and product of the RPA reaction itself such as displaced single-stranded DNAs. In addition to the possibility that recombinase may associate with a displaced single stranded DNA and mediate an invasion reaction onto template DNA, there is also the possibility that single stranded DNAs and other non-template DNAs from the sample may hybridise inappropriately with target template DNAs and interfere with efficient replication. To avoid some of these difficulties, at least for the first few rounds of replication it would be helpful to spatially fix template DNA and prevent association with other long DNAs. One convenient means to achieve this is to assemble RPA reactions in a gel matrix, such as a polyacrylamide gel adjusted with an average pore size that will allow free mobility of small RPA components, such as the enzymes and primers, but not allow free motility of long DNAs. Sample DNAs at low starting concentration will be physically separated, unable to associate with one another, while smaller RPA components will remain relatively free to associate with template molecules. Church and colleagues have described using polyacrylamide gels in this way for PCR and colleagues to produce spatially isolated amplicons, resolvable in two dimensions, known as polymerase colonies, or polonies [Mitra R, Church G (1999) In situ localized amplification and contact replication of many individual DNA molecules. Nucl Acids Res 27(24): e34i-vi.]. Typically, polonies are used to image amplicons from distinct templates and so are generated on microscope slides. For amplification of long DNAs, however, it would not be necessary to resolve individual polonies, thus reactions could be assembled in any appropriate vessel.

The polony assay itself may benefit from using RPA instead of PCR. There are at least two difficulties with the use of PCR. Firstly, because polonies are usually generated on microscope slides, and glass is a poor conductor of heat, the times required for PCRs can be significantly longer than for normal bulk phase PCR. This means that diffusion of amplification product leads to fairly large polony sizes, incompatible with high density, high throughput assays. Secondly, because PCR requires the thermal melting of template DNA, temperatures in excess of 90° C. are required for extended periods. These high temperatures will increase diffusion rates further increasing the average polony size. RPA with its low constant temperature will overcome both of these problems.

Using the RPA Dynamic Recombination Environment to Permit Identification of the Polymorphic Status of a Given Amplicon It is widely demonstrated that the presence or absence of a defined nucleic acid sequence can be determined by forming a hybrid between a sample nucleic acid with a nucleic acid probe of previously determined nature, followed by an appropriate method of detecting such an interaction. For example, microarrays are now widely used in which DNA, RNA or other backbone oligonucleotides are spatially separated and immobilized to a support. The presence or absence of a homologous sequence in a sample is then determined by co-incubating the samples under appropriate buffer and temperature conditions that allows hybrids to form between the immobilized probe and sample nucleic acids. In this case both sample and probe are provided in a completely or partially melted status so that they are able to hybridize. Provided a label is incorporated into the sample then the interaction can be subsequently quantified.

Alternative approaches to forming sequence-specific hybrids have been described in which one of the participating nucleic acids is double-stranded at the outset, and a three-stranded protein-containing hybrid is formed by the action of recombinase enzymes such as $E.\ coli$ recA in the presence of non-hydrolysable nucleotide triphosphate analogs (see U.S. Pat. Nos. 5,460,941, and 5,223,414). Also described are alternative methods that employ recombinases but seek to stabilize protein-free recombination intermediates by forming four-stranded structures (see U.S. Pat. No. 5,273,881). These approaches however differ from those described herein both in method and outcome as described further below.

In many cases the process of hybrid formation is of sufficient fidelity to discriminate between the presence and absence of the target, and further to determine whether it is a perfect match or not. For example, short primers (e.g. 7 to 18 nucleotides in length) can discriminate between perfect and imperfect complements if hybridization conditions are stringently controlled. However, if the nucleic acid is longer and there are only small variations between a perfect hybrid and an imperfect hybrid, for example a few nucleotides over a region of say one hundred or more, then it unlikely that a sufficiently great difference in efficiency of hybridization will exist between such a variant and a perfect match.

This invention concerns determining the polymorphic state of a sample nucleic acid by forming hybrids between the products of an amplification reaction and previously synthesized and immobilized probe nucleic acids present at defined locations, and each individual location containing a pure population of fragments representing one of the known repeat lengths present in the population.

DNA sequences amplified by the recombination polymerase amplification (RPA) method are ideal targets for such a hybrid-formation based assay for the following reasons. Firstly, it is possible to configure the RPA method to generate mostly double-stranded DNA product, or mostly single-stranded DNA product, for example by altering the ratios of amplification primers. Secondly, RPA reactions contain all of the necessary components to permit the association of hybrids between initially duplex DNA and single-stranded DNAs with no requirement to thermally melt the double-stranded DNA. Thus little additional sample handling is required.

Other methods have been described which employ recombinases and the use of non-hydrolysable analogs of ATP, such as ATP-γ-S, to stabilize hybrids of related complementary nucleic acids in a poorly defined 'triplex' intermediate involving the continued presence of the recombinase. Such an approach, however, will not work in this the context described here, because these highly stable structures are not dynamic and present significant resistance of reaction products to access by other agents. As a consequence use of recombinases with non-hydrolysable ATP analogs leads to formation of extremely stable hybrids between DNAs containing a significant degree of mis-match, thus not allowing efficiently discrimination between sequences. In contrast, the approach described here employs a dynamic system utilizing ATP or other hydrolysable analogs in which hybrids are readily destabilized as well as generated. The net result is a large enrichment for interactions of perfect complementary.

Figure 58:
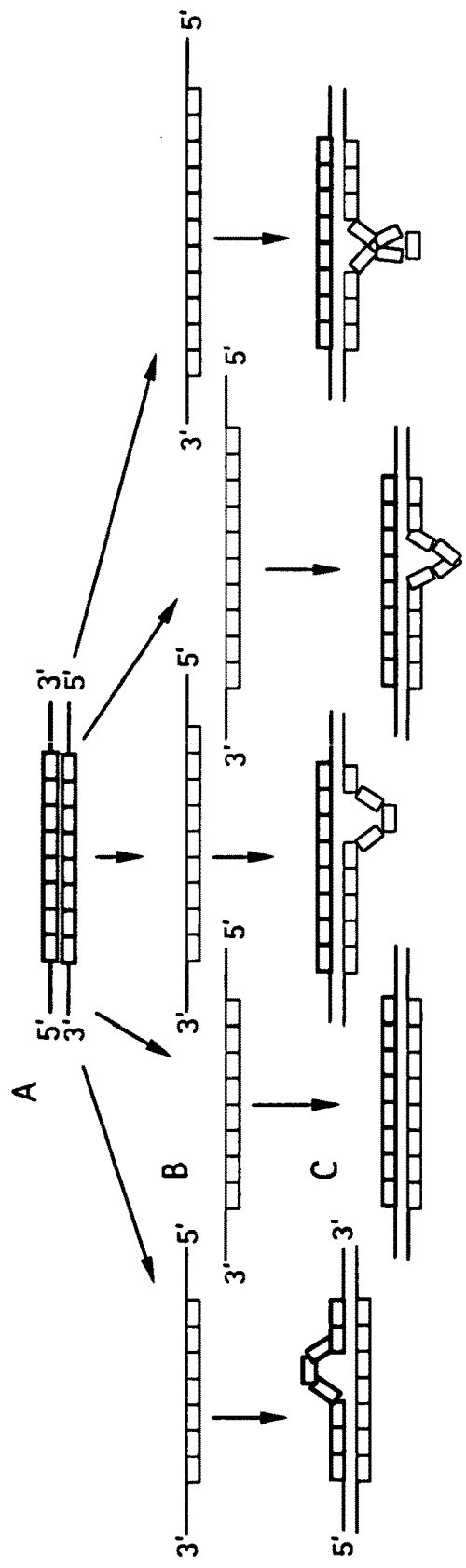
FIG. 58 The presence of single-strand bubbles in imperfect probe:target hybrids leads to enhanced overall duplex disruption in a dynamic recombination environment FIG. 59 Hybridization of amplicons to an array of potential length polymorphism probes in a dynamic recombination environment leads to enrichment of hybrids of perfect or near-perfect match as compared to classical hybridization, or non-dynamic recombination environment.
Figure 59:
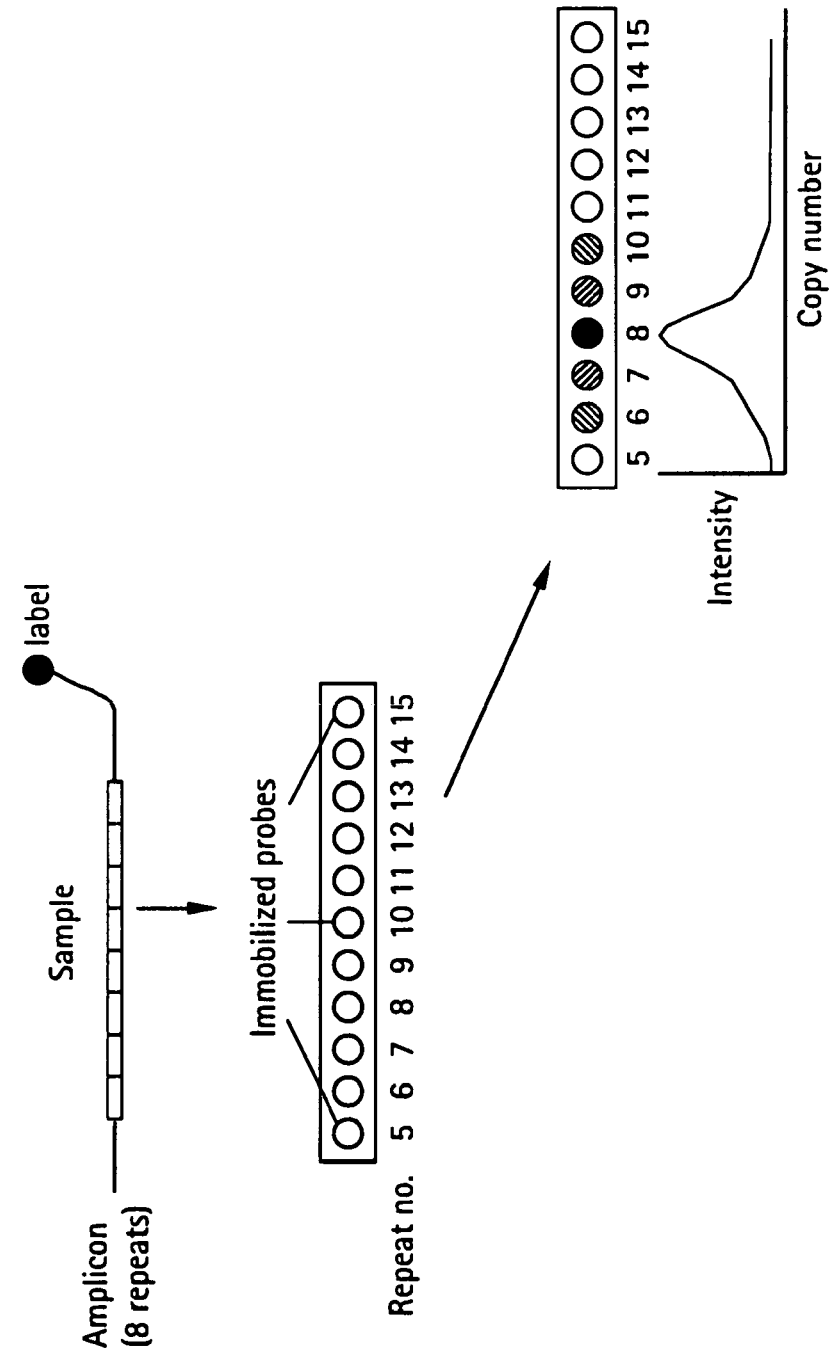

In a preferred embodiment, following the completion of an RPA reaction or concomitant with it, the reaction mixture is contacted to an array of probe molecules such that each amplified polymorphic DNA will in the first instance locate the correct immobilised probe nucleic acid containing exactly the same, or complementary, sequence. Should this initial hybrid-forming reaction not occur with sufficient efficiency or fidelity, as is likely with very similar sequences, then the dynamic nature of the recombinase-driven reaction should resolve mismatches. This is because imperfect hybrids will contain bubbles and non-duplex features, which act to aid the reloading of recombinase onto these hybrids and cause an increased rate of hybrid disruption when compared to perfect matches. New duplex-forming events are permitted to occur and only if perfect hybrids are formed do they become relatively resistant to further reaction. In practice, if all of the possible number of an STR repeat were arrayed in order of repeat number, then at the end there may result a gradient of hybrids formed which peaks at exact matches, is weaker on the direct flanks and absent further way. As the mis-match bubbles increase in size, there is a progressively greater tendency for recombinase to reload onto the single-stranded bubble region. (FIGS. 58 and 59).

Additionally, if the dynamic recombinase system is not sufficiently specific to discern between perfect and imperfect hybrids, additional hybrid-disrupting components can be included in the reaction. Such agents include, but are not limited to, helicases, nucleases, recombinases, polymerases, and other DNA-binding agents. Various helicases and nucleases exist which selectively target specific forms of DNA, or structures, such that they interact with and resolve mismatches or bubbles, but not on perfect hybrids. For example, the PriA helicase of *E. coli* interacts with regions in which single-stranded DNA is exposed adjacent to double-stranded DNA, as would occur in a mismatch in repeat number that could occur with STR hybridizations, and subsequently can act to unwind DNA in a 3' to 5' direction. Such destabilization would permit recombinase to re-load onto these separated strands allowing a new alternative hybrid to form instead. Over time such a mechanism would enrich for hybrids only between the correct target and probe. Similarly, the replication helicase of *E. coli*, DnaB, will load onto single-stranded DNA and unwind duplex DNA, in a 5'-3' direction, opposite of that of PriA. The dda helicase of bacteriophage T4 loads onto single-stranded DNA. The dda helicase is so powerful it can displace other DNA bound proteins in its path. The dda helicase has been shown to disrupt very high affinity streptavidin-biotin interactions (when the biotin is on the 3' end of the oligonucleotide), thus dda helicase could be used to destabilize immobilized probe complexes on a surface (Byrd and Raney, 2004) (Morris and Raney, 1999).

Alternatively the *E. coli* RuvA and RuvB gene products form a helicase that can encircle double-stranded DNA and drive branchpoints along DNA. In this manner a bubble could be 'pushed' to the end of the template causing sufficient destabilization to permit recombinase loading as well as other event. Nucleases that would target imperfections in duplex character would include, for example, S1 nuclease, which can nick double-stranded DNA at a mismatch or bubble. Other such nucleases with structure-specific characteristics exist. Such nicks can serve to initiate strand-displacing polymerase elongation. Alternatively if the nuclease cleaves the probe DNA then it is possible to have a chemical or enzymatic group released from the site of immobilization so that over time a signal generated later remains only at the point at which perfect hybrids formed.

Thus by combining the necessary components it should be possible to create an environment in which perfect hybrids significantly dominate and imperfect sites are depleted, or are rendered undetectable. Key to this approach is the establishment of a dynamic environment in which hybrids can be formed, and disrupted such that the stability of perfect and imperfect hybrids allows sensitive discrimination of reaction products with differing polymorphic features. This environment is ideally provided by the dynamic/stable recombinase system comprising gp32, uvsX, uvsY, PEG compound, and an ATP regenerating system as described.

The presence or absence of a productive hybrid, or the loss of a label from an immobilization site (e.g. see nuclease approach above) can be measured by standard methods. These include incubation of the reaction at the end-point with a substrate for an enzyme immobilized on the DNA target or DNA probe. Other detection approaches are possible and described widely elsewhere.

The Dynamic Persistent Recombinase Environment for Broad Use in Molecular Techniques We set about establishing the perfect environment for dynamic recombinase activity with a mind to permitting massively geometric amplification of nucleic acids at low constant temperature. However the established environment might obviously be employed in combination with other enzymes, or indeed without them, in a variety of contexts to replace classical hybridisation reactions in general. For example molecular cloning procedures might take advantage of the possibility of recombining large tracts of DNA with one another much more effectively than by thermal melting and annealing. Also many other enzymes that might be employed for in vitro molecular processes could benefit from the low temperature environment compatible with most mesophilic enzymes. Such enzymes would include, in addition to polymerases, helix-distortion recognising nucleases (e.g. S1 nuclease), FLAP endonucleases, restriction endonucleases, base modifying or removing enzymes, lyases, helicases, topoisomerases, ligases, reverse transcriptases, RNase H activity, resolvases, RNA polymerases, and any other enzyme that acts on, or interacts with, nucleic acids. They could also involve other enzymes pertinent to the in vitro system in addition to DNA metabolising enzymes, such as alkaline phosphatase or horseradish peroxidase used in detection protocols. The combination of the unique properties of the stable dynamic recombination system with other enzymatic activities enables a potentially very large number of new methods and applications.

In addition to recognising the important impact of combining wholly low-temperature dynamic enzymatic hybridisation systems with other enzyme systems, we have established sequence knowledge for the optimal assembly of highly active recombination using short oligonucleotide primers on the basis of experiments using RPA. We have noted that very active primers were characterised by a particularly rich distribution of pyrimidines. Guanosine residues, in contrast, appeared poorly represented in the most active oligonucleotides that we have analysed, and earlier results suggested that when appended to the 5' end of oligonucleotides they might lower their activity. In this disclosure we report the experimental results of dynamic monitoring of the reaction to study the affects of appending DNA sequences to the 5' ends of oligonucleotides. Appending sequences to the very 5' extent of otherwise identical oligonucleotides has a significant effect on their activity in RPA. We suggest that these observations are best interpreted as reflecting the loading behaviour of the recombinase on single-stranded, and possibly duplex, DNA. They may also have roles in controlling defined phasing of recombinases on ssDNAs.

As a starting point, we had come to note through kinetic studies (non real-time), and general observations, that some primer pairs were capable of mediating more rapid DNA amplification than others. Particularly rapid primers were identified for the human STR marker CSF1PO, which appeared to have an average doubling time of roughly 30 seconds (as estimated as average doublings per unit time from start to detectable product accumulation), and capable of generating detectable levels of product within 15 minutes starting with a few thousand copies of target (see FIG. 67). Other primer pairs typically took, taking 20-35 minutes to achieve similar results. We sought to learn more about the source of this variability (see FIG. 67, and data not shown).

Figure 68:
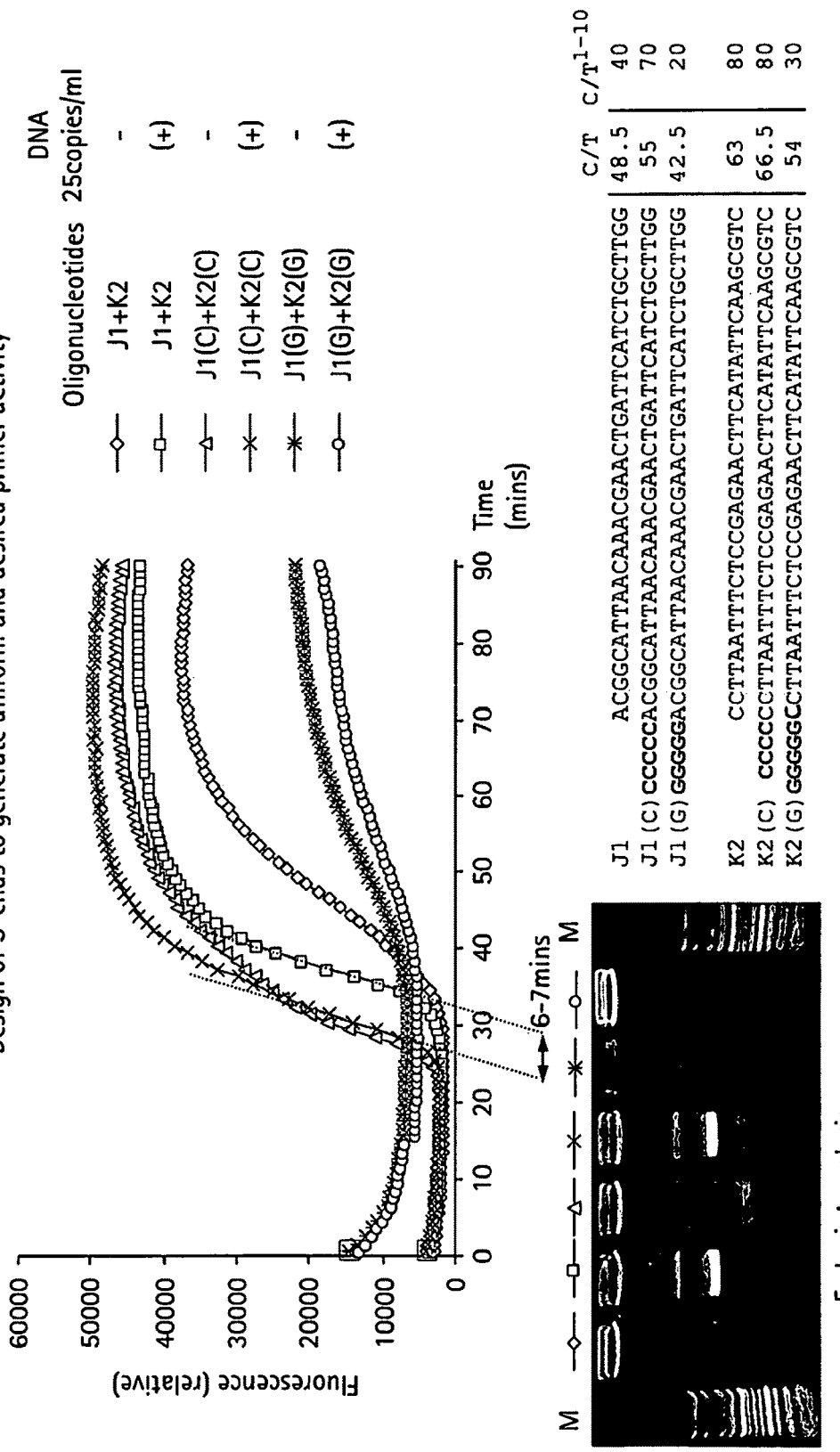
FIG. 68 Utility of real-time RPA analysis in optimising reaction environment; heterologous 5' sequences appended to oligonucleotides influence reaction behaviour. Figure discloses SEQ ID NOS 66, 99-100, 69 and 101-102, respectively, in order of appearance.

Analysis of the DNA sequence of the CSF1PO primers revealed that they were relatively rich in pyrimidines, and also were rather low in guanosine. This observation correlated with a piece of data arising from an earlier experiment in which we had investigated how appending a stretch of cytosine or guanosine residues to the 5' end of oligonucleotides affected their behaviour in RPA. In FIG. 68 a real-time amplification experiment is shown in which primers specific for the *Bacillus subtilis* sporulation locus SpOB, referred to as J1 and K2, were used to amplify a fragment from *B. subtilis* genomic DNA. In the experiment shown in FIG. 67 we had noted that a stretch of guanosines had 'quietened' the overall reaction, while a stretch of appended cytosines had 'noisened' amplification reactions. We repeated this experiment and monitored the reaction in real-time, the findings shown in FIG. 68. The results were consistent with the notion that appended bases affected, at the very least, the rate behaviour and presumably activity of primers. Primers J1 and K2, in which all bases match genomic target, generate a product which is first detectable with SYBR green dye at a little over 30 minutes in this experiment (faster kinetics were observed in later experiments, and variation may have arisen due to non-optimal temperature ramping when using a conventional microplate reader, as occurred in these experiments). A sample with target DNA, and one without, were distinguishable in this experiment by virtue of a small delay in product accumulation, and variant accumulation kinetics. Primers appended with additional cytosine residues, J1(C) and K2(C), were clearly capable of amplifying DNA significantly more quickly. We note however that the accumulation of (primer-derived) artifacts occurs on a timescale similar to that with the target DNA, distinctly less-well separated than in the unappended primers. We deduce that C-tailed primers are simply faster primers (although 'noisier' also in this case). Conversely accumulation kinetics for the primers appended with G residues was very poor, and no clearly identifiable expected end-product was observed on gel electrophoresis even at 90 minutes.

Based on our results, and integrating these findings with published work, lead us to speculate that sequence-composition might affect recombinase-loading onto primers, and that pyrimidines might promote this loading process. Published work is conflicting in this area; in some studies a case has been made for preference of recA binding to recombination processes for G and T residues which are enriched in *E. coli* recombination hotspots (Tracy and Kowalczykowski). Conversely, studies of recA loading dynamics performed using fluorescence anisotropy drew startlingly different conclusions (Bar-Ziv and Libchaber). In this case the barrier to recA nucleation (the slow phase of nucleoprotein filament formation) was highly sensitive to composition, showing a strong favourable bias towards pyrimidines. These latter observations would be more consistent with our observations. Indeed, as RPA tends to employ rather short oligonucleotides, it becomes easy to see how important the recombinase nucleation event is in giving effective amplification behaviour. Not only is rapid nucleation highly desirable to permit acceptable levels of filament loading, but additionally it will be critical that this occurs preferentially towards the very 5' end of the filament. If the 5' end is a poor substrate for nucleation, while an internal sequence is rather good, there is a likelihood that most filaments will be only partially loaded, and as such fail to function properly in RPA. Such partially loaded filaments may be insufficiently loaded to hydrolyse ATP properly, unable to efficiently undergo strand exchange, and be effectively drawn away from an active pool of filaments. Even worse, they may 'poison' the reaction by forming homology-searching complexes with DNA, but, being unable to undergo the normal dynamic behaviour (if they are below necessary length to promote hydrolysis), lock up target DNA in unproductive complexes, as occurs when ATP-γ-S is employed.

Despite our early results being consistent with the notion that pyrimidines are good nucleation sites, and the attractive possibility that this alone accounts for the observed variation, we must point out that neither of the above assays is truly equivalent to the experimental system that we are employing. Filament loading, unloading, hydrolysis behaviour and so on, are all relevant in concert in the amplification situation, and multiple factors could be at play. Also, it likely that recombinase phasing could play a role in determining the activity of primers, and that this established by preferential nucleation at particular locations, a phenomenon reported earlier for recA (Volodin et al.; Volodin and Camerini-Otero). In this case nucleation would occur preferentially at the 5' end, establish a committed phase to the entire filament, and the filament length would need to have a perfect length to place the last protein over the 3' end in the most desirable manned. In addition to the further complexities associated with the amplification situation as described, these earlier studies were all performed with *E. coli* RecA protein, and not T4 UvsX protein, and as these proteins are significantly diverged at the primary sequence level, it may not be possible to extrapolate conclusions from RecA studies to the UvsX protein. Nonetheless, realising the importance of sequence composition, and in particular 5' sequence composition, we have begun to analyse in more depth which sequences are most effective for appending to the very 5' end, i.e. we seek to determine idealised 'landing sites' for the recombinase in this system, and/or those that are associated with other beneficial properties for amplification and in vitro processes in general. Yet further, we anticipate that phasing of recombinases may play a significant role in overall activity, and that this will be influenced by composition and precise length of the oligonucleotide.

Figure 69:
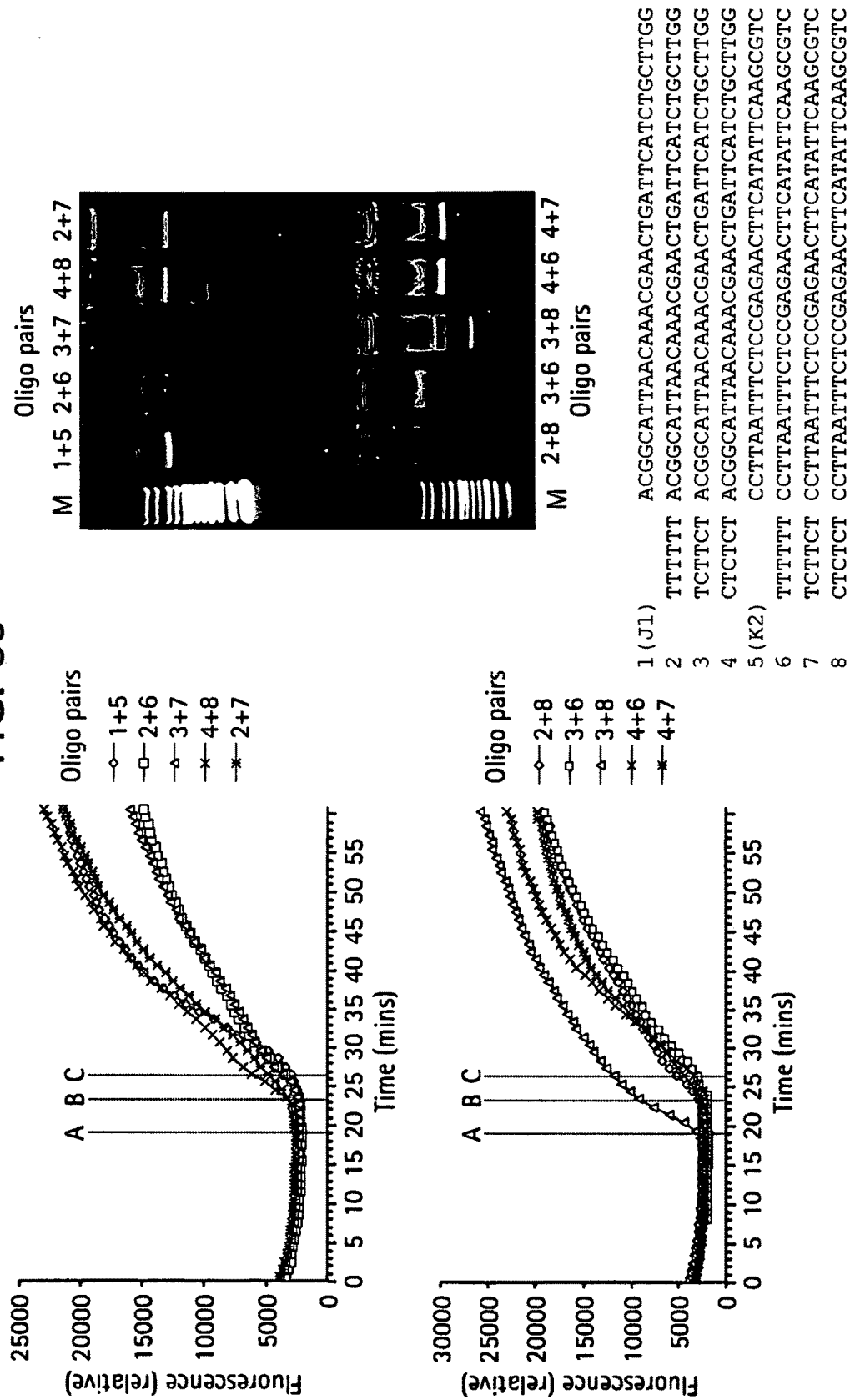
FIG. 69 Utility of real-time RPA analysis in optimising reaction environment; heterologous 5' sequences appended to oligonucleotides influence reaction behaviour—not all pyrimidine-rich 5' sequences drive excellent kinetic behaviour. Figure discloses SEQ ID NOS 66, 103-105, 69 and 106-108, respectively, in order of appearance.

We investigated whether appending a stretch of Thymine residues, or a mixture of cytosine and thymines (pyrimidines) would be as effective as a stretch of cytosine residues in stimulating greater primary activity. The results of this analysis are shown in FIG. 69. Interestingly, appending a run of Thymines to the very 5' end of the oligonucleotides did not, in this experiment, improve the amplification rate behaviour. In fact rather to the contrary combining primers with appended thymines gave very poor amplification behaviour in this experiment. We also tested primers in which the appended sequence was a mixture of cytosine and thymine, as indicated. The behaviour of these primers in various combinations was rather more variable and complex. For example we noted the presence of additional bands consistent, but not proven to be, single-stranded equivalents of the product. Careful analysis shows that in different combinations the migration behaviour of this possible single-stranded band was either of one type, or a second type, and that this correlated with the primer used. In brief, we suspect that in these reactions one, or other, primer was more active leading to development of asymmetry in the reaction and single-stranded DNA accumulation not seen with the parent, unappended, oligonucleotides. It was difficult to rationalize the results, but we can conclude that in this experiment stretches of thymine were not effective, nor were mixed polymers very effective despite a slight tendency to appear more active if more cytosines were present.

In our next experiment we appended yet more residues to the end of oligonucleotides and compared their behaviour in a real-time analysis. Once again there was variability between primers, and in this experiment we included as a control each primer incubated on its own. Interestingly we noted that, at the very low concentrations of target used here (1 copy per microliter start density), noise generated by single primers appeared in a timeframe similar to the accumulation of product DNA observed when primer pairs were used. Furthermore, this is most obvious for the oligonucleotide K2(C), studied previously, and responsible for very rapid amplification when combined with J1 oligonucleotides. This suggests that monitoring oligonucleotides individually for their rate of noise generation is of utility in determining their overall activity. Finally, and puzzlingly, an oligonucleotide just one base pair shorter than K2(C), oligonucleotide 9 in the series in FIG. 70, lacked this strong and rapid amplification behaviour. While the oligonucleotides used in this study were not HPLC purified, we nonetheless assume that most of the oligonucleotides are the full length form (based on gel pictures supplied by the manufacturer). Taken at face value, this surprising observation must be taken to reflect that either the number of C residues, changing from 5 to 6, at the 5' end is a point of significant transition for some structural feature of this oligonucleotide, or it could be taken to reflect the additional influence of some phasing behaviour. In this latter case we would speculate that 5' sequences strongly influence the phasing and deposition of the first UvsX monomer, and that this phasing is maintained all the way down to the 3' end. Presumably whether or not the most 3' UvsX monomer sits perfectly over the end of the oligonucleotide, or there is slightly too many or too few base pairs to permit each UvsX monomer to bind to its maximal number of backbone residues, may well influence the likelihood that recombination proceeds efficiently to completion. It may also influence the background, as if there are a few 'spare' bases popping out of the 3' end this might well promoter enhanced primer noise.

In conclusion, we have shown here how critical the length and sequence composition of oligonucleotides may be to elicit the best performance in RPA, and other recombinase-driven processes. Further, we formally demonstrate that non-target sequences can be appended to the 5' ends of oligonucleotides to effect regulation of their activity in RPA.

In addition to DNA amplification, a recombinase system including hydrolysable ATP analogs, and components to ensure high loading of DNA molecules in this situation, could be employed as a replacement for other described hybridisation approaches.

Contamination Control in RPA Reactions

As RPA is a very sensitive detection method we have encountered problems with carry-over contamination seen with other ultra-sensitive amplification protocols such as PCR. We show here that dUTP can be used to partially or wholly replace dTTP in RPA reactions, thus offering a simple way to distinguish the products of previous RPA reactions from bona fide sample targets. As heat treating RPA reactions at their initiation with a mind to inactivating dUTP deglycosylase (as occurs in PCR protocols with contamination control) is not desirable, we suggest as alternative approach in which deglycosylase inhibitors are mixed with reactions to permit initiation (see FIGS. 61 and 62).

Reverse-Transcription RPA

In circumstances in which detection of the presence of specific RNA molecules is desired it is possible to use RPA to detect them providing that the RNA is first converted to a DNA form using reverse transcriptase activity. Most convenient would be if reverse transcription and RPA could all be performed in a single homogeneous environment. We show that reverse transcription RPA reactions (RT-RPA) can be performed in a single tube environment by including reverse transcriptase in the reaction environment, and with other minor modifications (see FIG. 60).

Straightforward Detection and Assessment of Amplification Reactions Using Lateral Flow Membranes.

Features of RPA make it ideally suited to configuring portable easy-access diagnostic intergrated products. In one set of cases assessment of whether a specific DNA amplification reaction has occurred or not, with only a moderate need for quantitative analysis, can be performed by simple formats to assess whether two labelled primers have become physically associated within an amplicon. We here show that this simple idea is effective, and in particular that the widely-employed technology of lateral-flow strip systems are ideal to perform this role. RPA reactions can be mixed directly with sample running buffer for these systems, and the presence of amplicon determined within several minutes (see FIG. 63).

Compatibility of Crude Preparations of Biological Samples with RPA

We here show that simple lysates of blood can be used directly in RPA reactions. This offers the possibility that the format of diagnostic products containing the RPA system may require only trivial treatment of samples prior to direct addition to RPA reactions (see FIG. 64).

Figure 73:
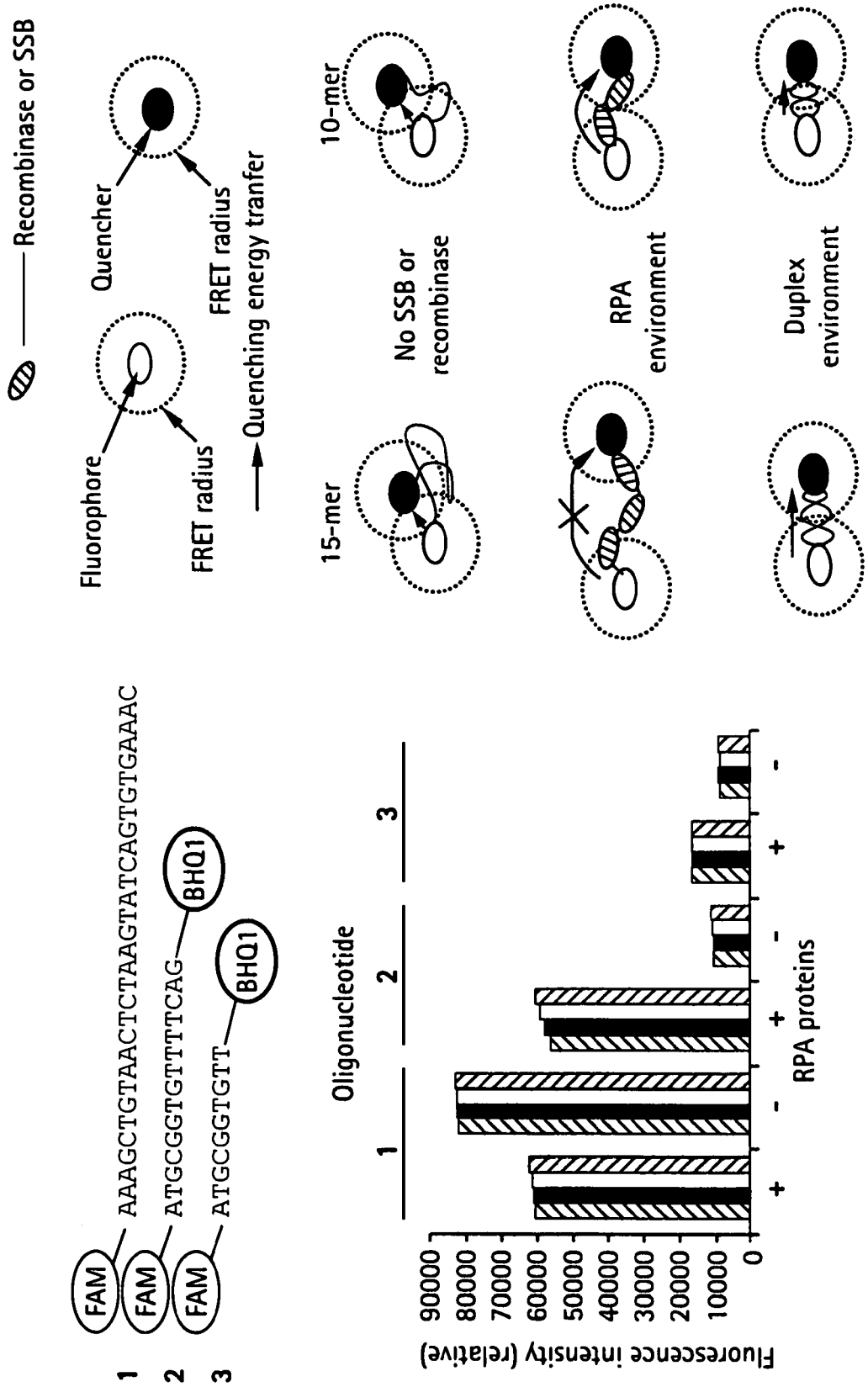
FIG. 73 Fluorescent probes demonstrate significantly different properties in the RPA environment compared to standard environments used in other amplification reactions. Figure discloses SEQ ID NOS 117-119, respectively, in order of appearance.

Behaviour of Fluorescent Probes in the Stable, Persistent, Dynamic Recombination Environment We here show that the presence of the dynamic recombination environment used in RPA alters the behaviour of fluorescent probes relative to equivalent environments in other techniques such as PCR. Most particularly if dual-labeled probes containing fluorophores and quenchers are to be used, the number of bases separating the two groups in the oligonucleotide must be less, presumably because the saturating DNA binding proteins stretch the probes relative to both their state in B-form duplex DNA, as well as the random coil that exists for oligonucleotides in free solution (FIG. 73). Furthermore we have identified key enzymes that may be employed to specifically process duplex hybrids between such probes and their target DNA's. These approaches teach the approach by which real-time 'third' probe strategies musts be configured with RPA, and how that differs to the well-established approaches in PCR such as the Taqman' approach, molecular beacons, and the like. In particular we have determined that the Taqman' approach cannot be employed in RPA presumably because the 5' nuclease associated with *E. coli* Pol I like enzymes has FLAP endonuclease activity which inhibits RPA reactions.

REFERENCES

Adams, D. E., Tsaneva, I. R. and West, S. C. (1994). Dissociation of RecA filaments from duplex DNA by the RuvA and RuvB DNA repair proteins. Proc Natl Acad Sci USA 91, 9901-5.

Alexseyev, A. A., Bakhlanova, I. V., Zaitsev, E. N. and Lanzov, V. A. (1996). Genetic characteristics of new RecA mutants of *Escherichia coli* K-12. J Bacteriol 178, 2018-24.

Bar-Ziv R, Libchaber A. (2001). Effects of DNA sequence and structure on binding of RecA to single-stranded DNA. PNAS USA July 31; 98(16):9068-73

Baumann, P., Benson, F. E., Hajibagheri, N. and West, S. C. (1997). Purification of human Rad51 protein by selective spermidine precipitation. Mutat Res 384, 65-72.

Benkovic, S. J., Valentine, A. M. and Salinas, F. (2001). Replisome-mediated DNA replication. Annu Rev Biochem 70, 181-208.

Bennett, R. L. and Holloman, W. K. (2001). A RecA homologue in *Ustilago maydis* that is distinct and evolutionarily distant from Rad51 actively promotes DNA pairing reactions in the absence of auxiliary factors. Biochemistry 40, 2942-53.

Better, M. and Helinski, D. R. (1983). Isolation and characterization of the RecA gene of *Rhizobium meliloti*. J Bacteriol 155, 311-6.

Bianco, P. R. and Weinstock, G. M. (1996). Interaction of the RecA protein of *Escherichia coli* with single-stranded oligodeoxyribonucleotides. Nucleic Acids Research December 15; 24(24):4933-9

Bork, J. M., Cox, M. M. and Inman, R. B. (2001). The RecOR proteins modulate RecA protein function at 5' ends of single-stranded DNA. EMBO J 20, 7313-22.

Bork, Cox and Inman J Biol Chem. 2001 Dec. 7; 276 (49):45740-3

Butler B C, Hanchett R H, Rafailov H, MacDonald G (2002) Investigating Structural Changes Induced By Nucleotide Binding to RecA Using Difference FTIR. Biophys J 82(4): 2198-2210

Byrd A K, Raney K D (2004). Protein displacement by an assembly of helicase molecules aligned along single-stranded DNA. Nat Struct Mol Biol. June; 11(6):531-8

Cox, M. M., Goodman, M. F., Kreuzer, K. N., Sherratt, D. J., Sandler, S. J. and Marians, K. J. (2000). The importance of repairing stalled replication forks. Nature 404, 37-41.

Cox, M. M., McEntee, K. and Lehman, I. R. (1981). A simple and rapid procedure for the large scale purification of the RecA protein of *Escherichia coli*. J Biol Chem 256, 4676-8.

Cromie, G. A. and Leach, D. R. (2000). Control of crossing over. Mol Cell 6, 815-26.

Dillingham, M. S, and Kowalczykowski, S. C. (2001). A step backward in advancing DNA replication: rescue of stalled replication forks by RecG. Mol Cell 8, 734-6.

Eggler, Lusetti and Cox, J Biol Chem. 2003 May 2; 278(18):16389-96

Eggleston, A. K. and West, S. C. (2000). Cleavage of holiday junctions by the *Escherichia coli* RuvABC complex. J Biol Chem 275, 26467-76.

Elias-Arnanz M, Salas M. EMBO J. 1997 Sep. 15; 16(18):5775-83

Ferrari et al., J Mol Biol. 1994 Feb. 11; 236(1):106-23

Formosa T, Alberts B M. J Biol Chem. 1986 May 5; 261(13):6107-18

Formosa T, Alberts B M. Cell. 1986 Dec. 5; 47(5):793-806. DNA synthesis dependant on genetic recombination: characterization of a reaction catalyzed by purified bacteriophage T4 proteins.

Glover, B. P. and McHenry, C. S. (2001). The DNA polymerase III holoenzyme: an asymmetric dimeric replicative complex with leading and lagging strand polymerases. Cell 105, 925-34.

Goodman, H. J., Parker, J. R., Southern, J. A. and Woods, D. R. (1987). Cloning and expression in *Escherichia coli* of a RecA-like gene from *Bacteroides fragilis*. Gene 58, 265-71.

Hacker K J, Alberts B M. J Biol Chem. 1992 Oct. 15; 267(29):20674-81

Harris L D, Griffith J. J Biol Chem. 1987 Jul. 5; 262(19): 9285-92

Heid C A, Stevens J, Livak K J, Williams P M. Real time quantitative PCR. Genome Res. 1996 October; 6(10):986-94.

Heyer, W. D. and Kolodner, R. D. (1989). Purification and characterization of a protein from *Saccharomyces cerevisiae* that binds tightly to single-stranded DNA and stimulates a cognate strand exchange protein. Biochemistry 28, 2856-62.

Hickson, I. D., Gordon, R. L., Tonikinson, A. E. and Emmerson, P. T. (1981). A temperature sensitive RecA protein of *Escherichia coli*. Mol Gen Genet 184, 68-72.

Hsieh, P., Camerini-Otero, C. S, and Camerini-Otero, R. D. (1992). The synapsis event in the homologous pairing of DNAs: RecA recognizes and pairs less than one helical repeat of DNA. Proc Natl Acad Sci USA 89, 6492-6.

Hsieh P, Camerini-Otero C S, Camerini-Otero R D. Proc Natl Acad Sci USA. 1992 Jul. 15; 89(14):6492-6

Kato, R. and Kuramitsu, S. (1993). RecA protein from an extremely thermophilic bacterium, *Thermus thermophilus* HB8. J Biochem (Tokyo) 114, 926-9.

Katz F S, Bryant F R. Biochemistry. 2001 Sep. 18; 40(37):11082-9 Kelman, Z. and O'Donnell, M. (1995). DNA polymerase III holoenzyme: structure and function of a chromosomal replicating machine. Annu Rev Biochem 64, 171-200.

Komori, K., Miyata, T., DiRuggiero, J., Holley-Shanks, R., Hayashi, I., Cann, I. K., Mayanagi, K., Shinagawa, H. and Ishino, Y. (2000). Both RadA and RadB are involved in homologous recombination in *Pyrococcus furiosus*. J Biol Chem 275, 33782-90.

Kornberg, A. and Baker, T. A. (1992). DNA Replication. New York: W. H. Freeman and Company. Kuil et al., Biophys Chem. 1988 December; 32(2-3):211-27

Kowalczykowski S C, Lonberg N, Newport J W, Paul L S, von Hippel P H., Biophys J. 1980 October; 32(1):403-18.

Kuramitsu, S., Hamaguchi, K., Ogawa, T. and Ogawa, H. (1981). A large-scale preparation and some physicochemical properties of RecA protein. J Biochem (Tokyo) 90, 1033-45.

Kurumizaka, H., Ikawa, S., Ikeya, T., Ogawa, T. and Shibata, T. (1994). A chimeric RecA protein exhibits altered double-stranded DNA binding. J Biol Chem 269, 3068-75.

Layery P E, Kowalczykowski S C. J Biol Chem. 1992 May 5; 267(13):9307-14

Liu, J., Nurse, P. and Marians, K. J. (1996). The ordered assembly of the phiX174-type primosome. III. PriB facilitates complex formation between PriA and DnaT. J Biol Chem 271, 15656-61.

Lohman and Ferrari, Annu Rev Biochem. 1994; 63:527-70

Lovett, C. M., Jr. and Roberts, J. W. (1985). Purification of a RecA protein analogue from *Bacillus subtilis*. J Biol Chem 260, 3305-13.

Maeshima, K., Morimatsu, K. and Horii, T. (1996). Purification and characterization of XRad51.1 protein, *Xenopus* RAD51 homologue: recombinant XRad51.1 promotes strand exchange reaction. Genes Cells 1, 1057-68.

Marians, K. J. (1992). Prokaryotic DNA replication. Annu Rev Biochem 61, 673-719.

Marians, K. J. (1999). PriA: at the crossroads of DNA replication and recombination. Prog Nucleic Acid Res Mol Biol 63, 39-67.

Mazin, A. V. and Kowalczykowski, S. C. (1998). The function of the secondary DNA-binding site of RecA protein during DNA strand exchange. EMBO J 17, 1161-8.

McGlynn, P. and Lloyd, R. G. (1999). RecG helicase activity at three- and four-strand DNA structures. Nucleic Acids Res 27, 3049-56.

McGlynn, P., Mandi, A. A. and Lloyd, R. G. (2000). Characterisation of the catalytically active form of RecG helicase. Nucleic Acids Res 28, 2324-32.

Mitra, R., Church, G. (1999). In situ localized amplification and contact replication of many individual DNA molecules. Nucl Acids Res 27(24): e34i-vi Morel, P., Cherny, D., Ehrlich, S. D. and Cassuto, E. (1997). Recombination-dependent repair of DNA double-strand breaks with purified proteins from *Escherichia coli*. J Biol Chem 272, 17091-6.

Morrical S W, Wong M L, Alberts B M. J Biol Chem. 1991 Jul. 25; 266(21):14031-8. Amplification of snapback DNA synthesis reactions by the uvsX recombinase of bacteriophage T4.

Morrical and Alberts J Biol Chem. 1990 Sep. 5; 265(25): 15096-103. The UvsY protein of bacteriophage T4 modulates recombination-dependant DNA synthesis in vitro.

Morris P D, and Raney K D. (1999). DNA helicases displace streptavidin from biotin-labeled oligonucleotides. Biochemistry April 20; 38(16):5164-71

Ng, J. Y. and Marians, K. J. (1996a). The ordered assembly of the phiX174-type primosome. I. Isolation and identification of intermediate protein-DNA complexes. J Biol Chem 271, 15642-8.

Ng, J. Y. and Marians, K. J. (1996b). The ordered assembly of the phiX174-type primosome. II. Preservation of primosome composition from assembly through replication. J Biol Chem 271, 15649-55.

Paulus, B. F. and Bryant, F. R. (1997). Time-dependent inhibition of RecA protein-catalyzed ATP hydrolysis by ATP-γS: evidence for a rate-determining isomerization of the RecA-ssDNA complex. Biochemistry 36, 7832-8.

Pham, P., Bertram, J. G., O'Donnell, M., Woodgate, R. and Goodman, M. F. (2001). A model for SOS-lesion-targeted mutations in *Escherichia coli*. Nature 409, 366-70.

Pierre, A. and Paoletti, C. (1983). Purification and characterization of RecA protein from *salmonella typhimurium*. J Biol Chem 258, 2870-4.

Rashid, N., Morikawa, M., Kanaya, S., Atomi, H. and Imanaka, T. (2001). RecA/Rad51 homolog from *Thermococcus kodakaraensis* KODI. Methods Enzymol 334, 261-70.

Reddy, Weitzel and Von Hippel, Proc Natl Acad Sci USA. 1993 Apr. 15; 90(8):3211-5

Riddles P W, Lehman I R. J Biol Chem. 1985 Jan. 10; 260(1):170-3

Rosselli, W. and Stasiak, A. (1990). Energetics of RecA-mediated recombination reactions. Without ATP hydrolysis RecA can mediate polar strand exchange but is unable to recycle. J Mol Biol 216, 335-52.

Salinas F, Jiang H, Kodadek T. J Biol Chem. 1995 Mar. 10; 270(10):5181-6. Homology dependence of UvsX protein-catalyzed joint molecule formation.

Scheerhagen et al., J Biomol Struct Dyn. 1986 April; 3(5):887-98

Shan, Q., Bork, J. M., Webb, B. L., Inman, R. B. and Cox, M. M. (1997). RecA protein filaments: end-dependent dissociation from ssDNA and stabilization by RecO and RecR proteins. J Mol Biol 265, 519-40.

Singleton, M. R., Scaife, S, and Wigley, D. B. (2001). Structural analysis of DNA replication fork reversal by RecG. Cell 107, 79-89.

Spies, M., Kil, Y., Masui, R., Kato, R., Kujo, C., Ohshima, T., Kuramitsu, S. and Lanzov, V. (2000). The RadA protein from a hyperthermophilic archaeon *Pyrobaculum islandicum* is a DNA-dependent ATPase that exhibits two disparate catalytic modes, with a transition temperature at 75 degrees C. Eur J Biochem 267, 1125-37.

Steffen, S. E. and Bryant, F. R. (2000). Purification and characterization of the RecA protein from *Streptococcus pneumoniae*. Arch Biochem Biophys 382, 303-9.

Tang, M., Pham, P., Shen, X., Taylor, J. S., O'Donnell, M., Woodgate, R. and Goodman, M. F. (2000). Roles of *E. coli* DNA polymerases IV and V in lesion-targeted and untargeted SOS mutagenesis. Nature 404, 1014-8.

Tissier, A. F., Lopez, M. F. and Signer, E. R. (1995). Purification and characterization of a DNA strand transferase from broccoli. Plant Physiol 108, 379-86.

Tracy R B, Kowalczykowski S C (1996). In vitro selection of preferred DNA pairing sequences by the *Escherichia coli* recA protein. Genes Dev. August 1; 10(15):1890-903.

Vester B, Wengel J., Biochemistry. 2004 Oct. 26; 43(42): 13233-41Villemain, et al. J Biol Chem. 2000 Oct. 6; 275 (40):31496-504

Volodin A A, Camerini-Otero R D (2002). Influence of DNA sequence on the positioning of RecA monomers in RecA-DNA cofilaments. J Biol Chem. January 11; 277(2): 1614-8.

Volodin A A, Smirnova H A, Bocharova T N, Camerini-Otero R D (2003). Phasing of RecA monomers on quasi-random DNA sequence. FEBS Lett. July 10; 546(2-3):203-8

Webb, B. L., Cox, M. M. and Inman, R. B. (1995). An interaction between the *Escherichia coli* RecF and RecR proteins dependent on ATP and double-stranded DNA. J Biol Chem 270, 31397-404.

Webb, B. L., Cox, M. M. and Inman, R. B. (1997). Recombinational DNA repair: the RecF and RecR proteins limit the extension of RecA filaments beyond single-strand DNA gaps. Cell 91, 347-56.

Webb, B. L., Cox, M. M. and Inman, R. B. (1999). ATP hydrolysis and DNA binding by the *Escherichia coli* RecF protein. J Biol Chem 274, 15367-74.

West, S. C., Countryman, J. K. and Howard-Flanders, P. (1983). Purification and properties of the RecA protein of *Proteus mirabilis*. Comparison with *Escherichia coli* RecA protein; specificity of interaction with single strand binding protein. J Biol Chem 258, 4648-54.

Wetmur, J. G., Wong, D. M., Ortiz, B., Tong, J., Reichert, F. and Gelfand, D. H. (1994). Cloning, sequencing, and expression of RecA proteins from three distantly related thermophilic eubacteria. J Biol Chem 269, 25928-35.

Wittwer C T, Hermann M., Moss A A, and Rasmussen R P. Continuous fluorescence monitoring of rapid cycle DNA amplification. Biotechniques. 1997 January; 22(1):130-1, 134-8

Wittwer C. T., Ririe K M, Andrew R V, David D A, Gundry R A, Balis U J. The LightCycler: a microvolume multisample fluorimeter with rapid temperature control. Biotechniques. 1997 January; 22(1):176-81Xu L, Marians K J. J Biol Chem. 2002 Apr. 19; 277(16): 14321-8.

EXAMPLES

As shown herein, we have developed an in vitro DNA amplification system that couples recombinase-driven sequence targeting with strand-displacement synthesis. This permits DNA amplification without global thermal, chemical, or enzymatic template melting. Reactions are sensitive, specific and operate at 37° C. with no pre-treatment of sample DNA. As much as 1012-fold amplification is observed within 1-1$^{1/2}$ hours. Less than 10 copies of a given target DNA can be detected in a complex sample with a simple single-step reaction. This method is an ideal alternative to PCR for a variety of applications and will enable highly portable DNA diagnostic systems.

The examples are presented in order to more fully illustrate the preferred embodiments of the invention. These examples should in no way be construed as limiting the scope of the invention, as encompassed by the appended claims.

Example 1

An Example of a Leading Strand Recombinase-polymerase Amplification (lsRPA)

DNA sequences can be amplified using leading strand synthesis according to the Recombinase-Polymerase amplification (RPA) method depicted in FIG. 1. FIG. 1 shows RecA/primer loading. Prior to the addition of template DNA and/or Polymerase, RecA and SSB will compete for binding to single-stranded oligonucleotide primers. In the presence of a RecR and RecO, RecA is selectively stabilized onto the single-stranded primers forming RecA nucleoprotein filaments in a complex with RecO and RecR. This complex is competent to invade double-stranded DNA to form a D-loop at sites homologous to the oligonucleotide primers. Alternatively, RecA, RecO and RecR can be pre-loaded onto oligonucleotide primers prior to the introduction of SSB to the reaction mixture.

The following details the likely composition of an RPA reaction assembled with *E. coli* recA and *E. coli* recO and recR stabilizing agents:

D-Loop Formation/Resolution Components

| Component | Concentration |
| --- | --- |
| RecA | 20 μM |
| Single-stranded oligonucleotide primers | 0.25 μM |
| ATP | 3 mM |
| RecF | 0.1 μM |
| RecO | 0.13 μM |
| RecR | 0.5 μM |

| Component | Concentration |
| --- | --- |
| Single-stranded Binding protein (SSB) | 1 to 10 μM |
| DNA polymerase V | 5 units |

Polymerase/Helicase/Resolvase Mix

| Component | Concentration |
| --- | --- |
| DNA Polymerase | 5 units |
| RuvA | 0.5 μM |
| RuvB | 0.5 μM |
| RuvC | 0.5 μM |
| RecG | 10 nM |

Reaction Buffer

| Component | Concentration |
| --- | --- |
| MgCl2 2 | 2 to 10 mM |
| TrisHCl pH 7.2 | 50 mM |
| DTT | 0 to 10 mM |
| KCl | 0 to 50 mM |
| Deoxyribonucleotide triphosphates | 0.2 mM |
| Bovine serum albumin (BSA) | 0 to 10 μg per ml |

The reaction is assembled so that the final concentration satisfies the D-Loop Formation/Resolution Components, Polymerase/Helicase/Resolvase Mix, and Reaction Buffer with the DNA polymerase and/or template added last if necessary. For example, a 2.times. concentrated solution of D-Loop Formation/Resolution Components and of the Polymerase/Helicase/Resolvase Mix may be made in 1× reaction buffer. The reaction may be initiated by mixing an equal volume of each of the two components (each in 1× reaction buffer). Optionally, and as stated above, the DNA polymerase or template (target DNA) may be added last. The reaction is incubated for a sufficient time of until the reactants are exhausted. Typical incubation times would range from 1 hour, 2 hours, 3 hours, 5 hours, 10 hours or overnight (about 16 hours). Unlike PCR, which requires small volumes for rapid temperature change, there is no limit to the reaction volume of RPA. Reaction volumes of 25 μl, 50 μl, 100 μl, 1 ml, 10 ml and 100 ml or larger may be performed in one vessel. Incubation temperature may be a typical laboratory temperature such as 25° C., 30° C., or 37° C.

Prior to the addition of template DNA and/or Polymerase, recombinase and SSB will compete for binding to single-stranded oligonucleotide primers. In the presence of a RecR and RecO, RecA is selectively stabilized onto the single-stranded primers forming RecA nucleoprotein filaments in a complex with RecO and RecR. This complex is competent to invade double-stranded DNA to form a D-loop at sites homologous to the oligonucleotide primers. Alternatively, RecA, RecO, and RecR can be pre-loaded onto oligonucleotide primers prior to the introduction of SSB to the reaction mixture (FIG. 1).

The invading strands will be extended by the polymerase in a 5' to 3' direction. As D-loops are formed and synthesis proceeds, displaced single stranded DNA becomes coated with SSB. RecA release from double-stranded DNA can occur via ATP hydrolysis in a 5' to 3' direction or as a result of helicase/resolvase or polymerase activity (FIG. 2A, B). New rounds of invasion/synthesis will continuously occur. The third round of strand-invasion/synthesis will release discrete products released whose ends correspond to the two facing primer sites. These fragments will soon become the dominant reaction product and will accumulate to high levels. As each synthetic complex processes to the end of the template RecA protein is displaced either by polymerase activity or by the activity of helicases, such as RuvAB or resolvases, such as RuvC. Once primers, ATP, deoxynucleoside triphosphates, or any other limiting component is exhausted, the reaction will stop.

The inclusion of temperature-sensitive recombinase mutants will allow the controlled initiation of DNA synthesis. In such a situation, the initiation reaction is performed at 25 to 37° C. permitting the formation of D-loops. Elongation reactions are performed at 42° C., which is non-permissive for RecA mediated double-strand invasion. The number of cycles will determine the amount of reaction product. Extended elongation phases will permit the amplification of extremely long DNAs without interference of re-invasion.

Example 2

Nested RPA

The RPA reaction is performed as described in Example 1. A fraction of one tenth (1/10) and one hundredth (1/100) of the reaction is removed and used in place of the DNA template in a second round of RPA. LsRPA, leading/lagging RPA, and combinations thereof may be used for nested RPA.

Example 3

Simultaneous Leading and Lagging Strand Recombinase-polymerase Amplification

DNA sequences can be amplified using simultaneous leading and lagging strand synthesis according to the Recombinase-Polymerase amplification (RPA) method depicted in FIG. 2. This figure specifically illustrates lsRPA. FIG. 2A shows that RecA/primer nucleoprotein filaments invade double stranded template DNA preferentially associating with homologous target sites. As D-loops are formed and synthesis proceeds, displaced single stranded DNA becomes coated with SSB (FIG. 2A). RecA release from double-stranded DNA can occur via ATP hydrolysis in a 5'-3' direction or as a result of helicase/resolvase or polymerase activity (FIG. 2A). As synthesis continues (FIG. 2B), polymerases encounter SSB bound, displaced single-stranded template. Double-stranded target sites are re-invaded by RecA/primer nucleoprotein filaments. Subsequent rounds of lsRPA proceed from re-invaded sites (FIG. 2B).

The following details likely components of a replisome-mediated amplification utilizing components from *E. coli*. A reaction is assembled with the following composition:

D-Loop Formation/Resolution Components

| Component | Concentration |
|---|---|
| RecA | 20 μM |
| Single-stranded oligonucleotide primers | 0.25 μM |
| ATP | 3 mM |

-continued

| Component | Concentration |
|---|---|
| RecF | 0.1 μM |
| RecO | 0.13 μM |
| RecR | 0.5 μM |
| Single-stranded Binding protein (SSB) | 1 to 10 μM |
| DNA polymerase V | 5 units |

Helicase/Resolvase Mix

| Component | Concentration |
|---|---|
| RuvA | 0.5 μM |
| RuvB | 0.5 μM |
| RuvC | 0.5 μM |
| RecG | 10 nM |

Primosome Complex

| Component | Concentration |
|---|---|
| PriA | 20 nM |
| PriB | 20 nM |
| DnaT | 100 nM |
| DnaB | 100 nM |
| DnaC | 200 nM |
| DnaG | 200 nM |

DNA Polymerase III Holoenzyme Complex

| Component | Concentration |
|---|---|
| β-Clamp | 2 μM |
| DnaX Clamp Loader | 500 nM |
| Polymerase Core Complex | 500 nM |

Lagging Strand Mix

| Component | Concentration |
|---|---|
| DNA polymerase I | 5 units |
| DNA ligase | 2 units |
| Polymerase Core Complex | 500 nM |

Reaction Buffer

| Component | Concentration |
|---|---|
| MgCl$_2$ | 2 to 10 mM |
| TrisHCl pH 7.2 | 10 to 60 mM |
| DTT | 0 to 10 mM |
| KCl | 0 to 50 mM |
| Deoxyribonucleotide triphosphates | 0.2 to 0.4 mM |
| Bovine serum albumin (BSA) | 0 to 10 μg per ml |

The reaction is assembled so that the final concentration of all the reagents is as listed above. Thus, for example, a 5 fold concentrated solution of each of the components (D-loop Formation/Resolution Components, Helicase/Resolvase Mix, Primosome Complex, DNA Polymerase III holoenzyme Complex, Lagging Strand Mix) is made in 1× reaction buffer.

Then, the five solutions are mixed together in equal volumes to initiate the reaction. The reaction is incubated for a sufficient time of until the reactants are exhausted. Typical incubation times would range from 1 hour, 2 hours, 3 hours, 5 hours, 10 hours or overnight (about 16 hours). As stated above, there is no limit to the reaction volume of RPA. Reaction volumes of 25 µl, 50 µl, 100 µl, 1 ml, 10 ml and 100 ml or larger may be performed in one vessel. Incubation temperature may be a typical laboratory temperature such as 25° C., 30° C., or 37° C.

Figure 3A:
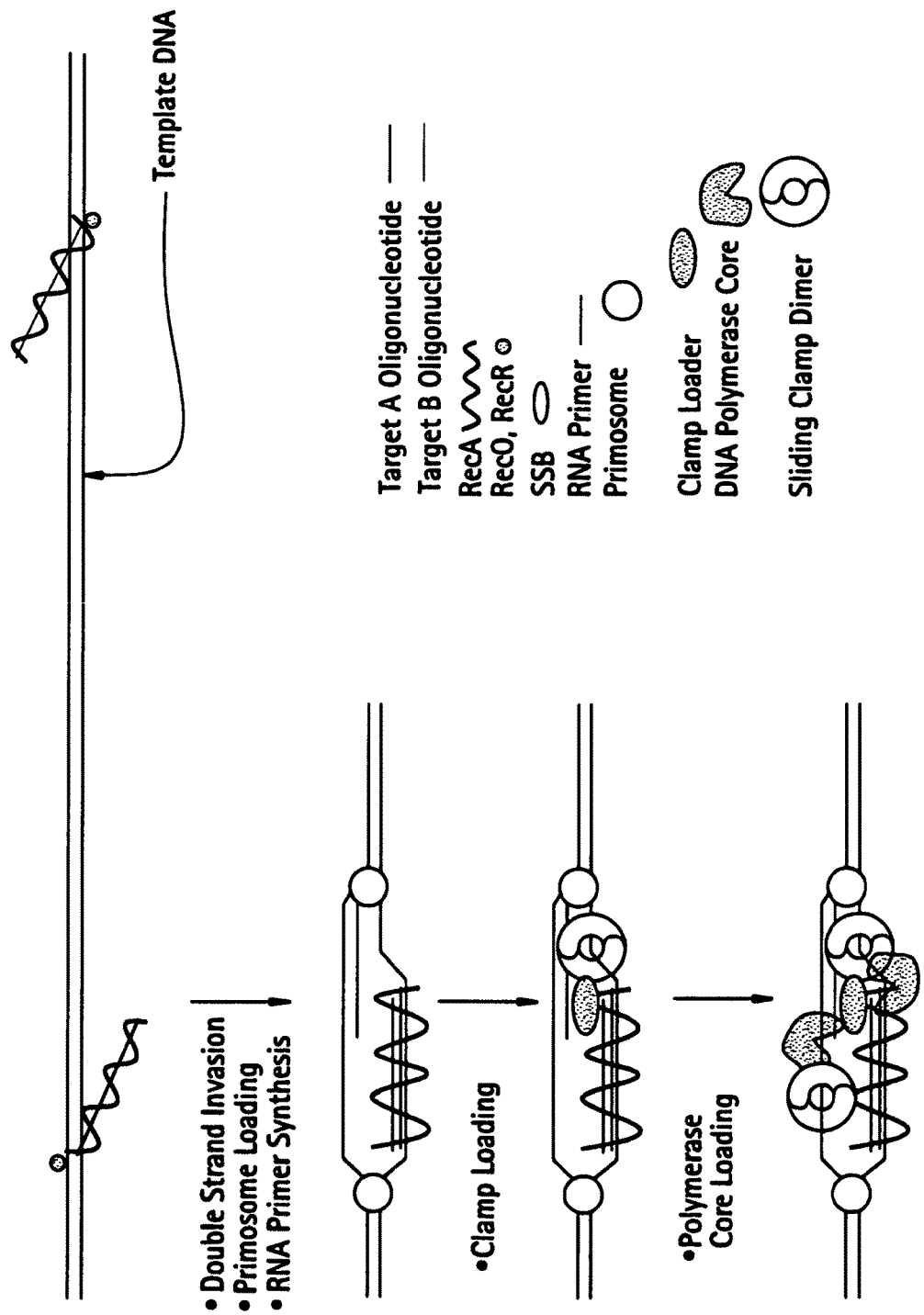

FIG. 3 shows initiation (FIG. 3A), synthesis (FIG. 3B), and polymerase amplification (FIG. 3C-3D). First, the primosome loads onto the D-loop formed by RecA nucleoprotein filament invasion (FIG. 3A). The primosome synthesizes a stretch of RNA primer. Finally, the primosome recruits the clamp loader, which recruits both the sliding clamp dimer and the asymmetric DNA polymerase core (FIG. 3A). Synthesis occurs simultaneously in both the leading and lagging directions. Eventually lagging strand synthesis stops and the lagging strand clamp is unloaded (FIG. 3B). Synthesis of the leading strand continues until a new site of lagging stand synthesis is formed (FIG. 3B). While leading strand synthesis continues, a new site of lagging stand synthesis is formed. Lagging strand synthesis continues back to the previous Okazaki fragment where the lagging strand clamp is unloaded (FIG. 3C). DNA Polymerase I removes the RNA primer, and fills in the gap while DNA ligase connects the two Okazaki fragments forming a continuous lagging strand (FIG. 3D).

Example 4

Establishment of an Amplification Environment Using the Assembly of Heterologous Components *E. coli* recA(C) and T4 gp32(N)

Figure 18:
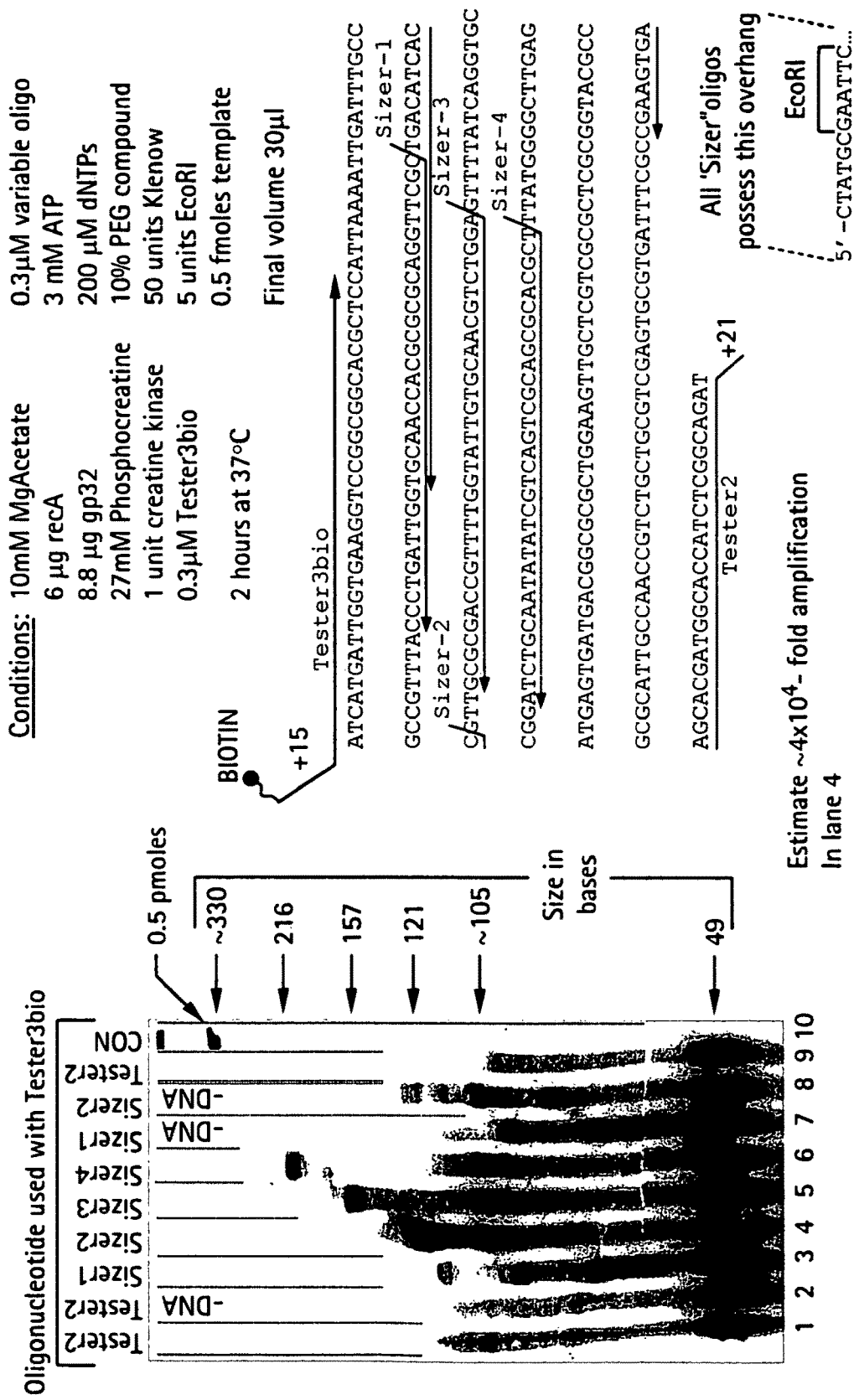
FIG. 18 depicts spacing dependence of RPA primers. There is an optimal interoligonucleotide length for RPA when using the Klenow fragment of E. coli DNA polymerase I. The template (SEQ ID NO: 1) and EcoRI overhang (SEQ ID NO: 91) sequences are shown.

FIG. 18 shows the results of an experiment in which recA(C) has been combined with gp32(N) in the presence of pairs of oligonucleotides, Tester3bio (possessing a 5' biotin label) and Sizer1, Sizer2, Sizer3, Sizer4 or Tester2. These latter unbiotinylated oligonucleotides were positioned progressively further away from the common Tester3bio oligonucleotide. The template was a linear DNA fragment, approximately 300 bp, released from a plasmid. Tester3bio was designed to be complementary to one end of this fragment and included a 5' overhang relative to this sequence.

The reaction buffer included Magnesium acetate at 10 mM, required to support recA binding to DNA, and 3 mM ATP. Also included was an ATP regeneration system, comprising phosphocreatine and creatine kinase, as well as dNTPS at 200 µM, and the Klenow fragment of *E. coli* DNA polymerase I. PEG compound was employed as shown. Double stranded template DNA (0.5 fmoles), derived from a plasmid carrying the *E. coli* ruvB gene, was used as a starting target. The Sizer1, Sizer2, Sizer3, and Sizer4 oligonucleotides did not recognise the other end of the template. Instead, these oligonucleotides were positioned to face Tester3bio with increasing distance between their relative 3' ends.

After an incubation of 2 hours at 37° C., there was a substantial amplification of specific fragments of the correct size when Tester2, 3, and 4 were used. In the best conditions (with Sizer2), we estimated that the amplification product were $10^4$ fold greater than the starting template.

Example 5

The Nature of Amplification Products and the Sensitivity of the Reaction Using a Heterologous Assembly of *E. coli* recA(C) and Bacteriophage T4 gp32(N)

Figure 19:
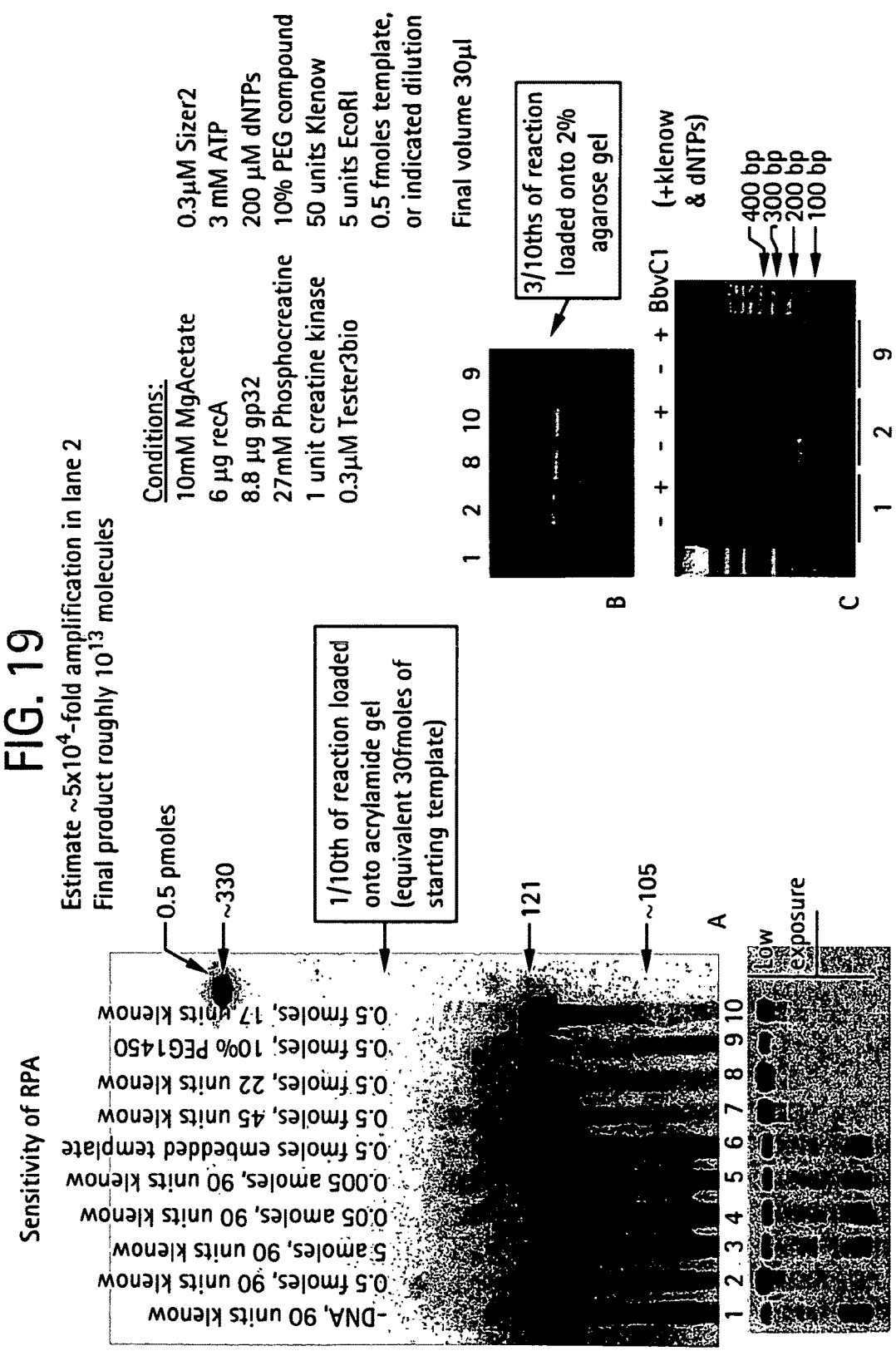
FIG. 19 depicts RPA products that are largely double stranded. RPA reaction can generate double-stranded DNA products as evidenced by agarose gel electrophoresis and restriction enzyme cleavage.

FIG. 19 shows the results of an experiment in which recA(C) has been combined with gp32(N) in the presence of the pair of oligonucleotides, Tester3bio (possessing a 5' biotin label) and Sizer2, under conditions similar to those used in Example 1. PEG compound or PEG 1450 were employed as shown and 0.5 fmoles of template was used as a starting template amount. In this example, progressive dilution of the template was investigated. Alternatively we explored the use of linearised starting template possessing no end that overlaps the primer (by using a ClaI digest of the *E. coli* ruvB gene carrying plasmid), and dilution of the Klenow fragment. Amplification of correctly sized fragments occurred in all lanes and was strongest in the case of 0.5 fmoles-starting template in the presence of PEG compound.

When the products of these optimal reactions were electrophoresed on agarose gels and stained with ethidium bromide, a clean band of double-stranded DNA of the correct size was observed. When this sample was treated with BbvC1 restriction enzyme prior to electrophoresis the expected increase in gel mobility occurs consistent with a single cut as expected. Amplification of a product of the correct size was observed with starting template dilutions of 100-fold, or greater, although the product was less abundant and includes a ladder of shorter products below the main band. A similar pattern was observed when uncut template is employed or when no template is employed. We reasoned that the proteins used in these studies were significantly contaminated with *E. coli* genomic DNA (naturally carrying the ruvB gene) as they were purified in single column purifications without the use of nucleases. Consequently we believe this test system generates false positives when the sensitivity is high enough.

Example 6

Establishment of an Amplification Environment Using an Assembly of gp32(N) and uvsX(C)

Figure 24:
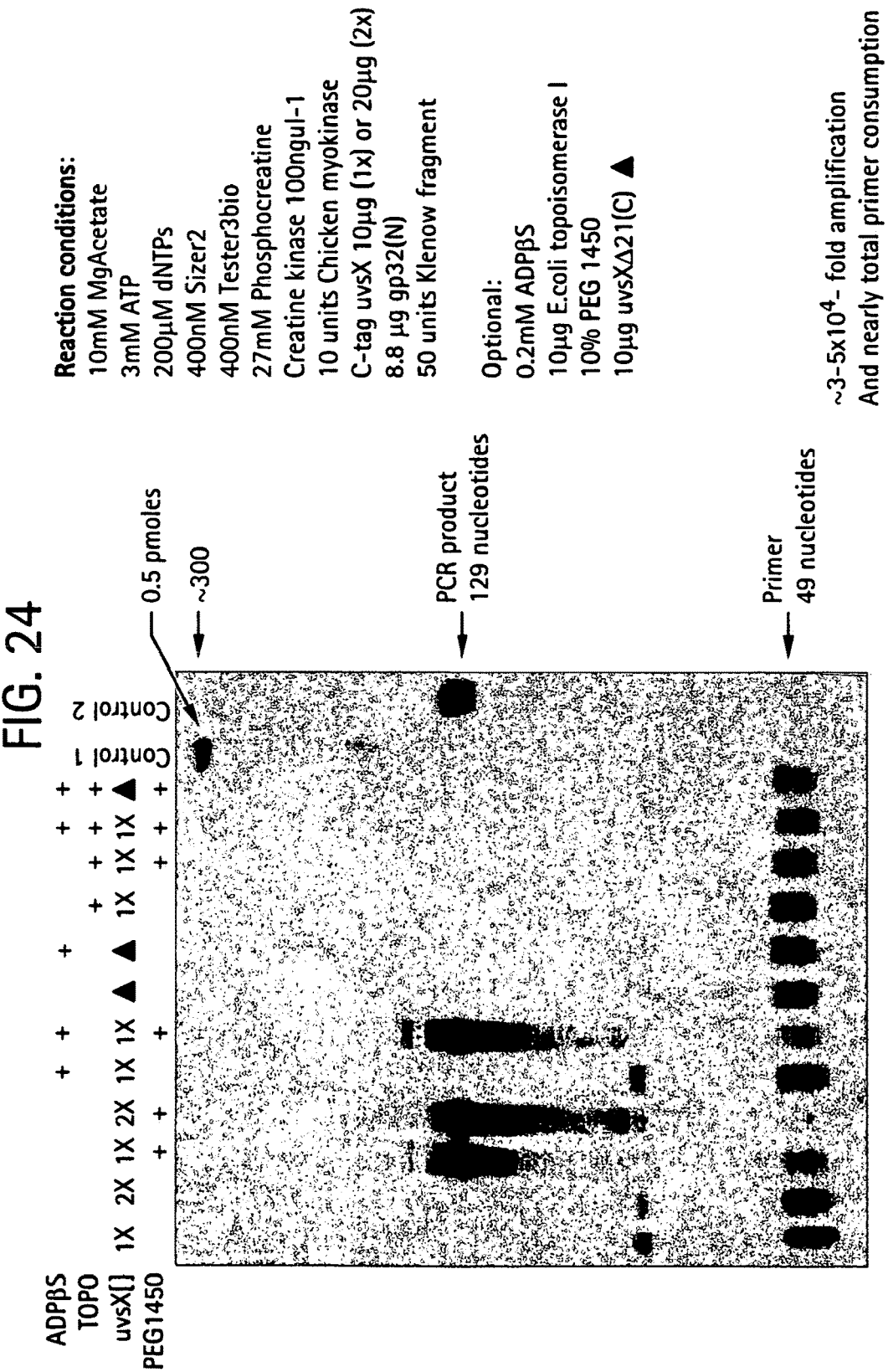
FIG. 24 depicts RPA using uvsX(C). The modified recombinase uvsX(C) can support DNA amplification in the presence of gp32(N), the Klenow fragment of E. coli DNA polymerase I and polyethylene glycol (PEG).

FIG. 24 shows results of an experiment in which uvsX(C) has been combined with gp32(N) in the presence of the oligonucleotides Tester3bio and Sizer2. The template DNA in this experiment was an EcoRV digestion of the *E. coli* ruvB gene carrying plasmid used in Examples 1 and 2. Tester3bio recognised one end of an approximately 300 base pair fragment and included a 5' overhang relative to the end of the target sequence. Sizer2 recognised the other strand of this template. This oligonucleotide was directed toward embedded sequences such that its 3' end was about three and a half helical turns from the end of Tester3bio.

In the presence of PEG1450, we observed the amplification of the expected fragment within the 2 hours of the reaction. In the cases where amplification has occurred, almost the entire of population of oligonucleotides was consumed indicating an amplification of 3-5×10$^4$. The reaction components are indicated on FIG. 24. Included in some samples were additional components. We found that 200 µM ADP-β-S included in this reaction slightly increased the amount of product formed under these conditions. Conversely, under the conditions used here, inclusion of E. coli toposiomerase I was inhibitory to DNA amplification. Under the conditions used, we detected no amplification with uvsX(C)delta protein. However, no PEG1450 was included in these samples and uvsX(C) also failed to amplify under these conditions without PEG1450.

Example 7

Figure 30:
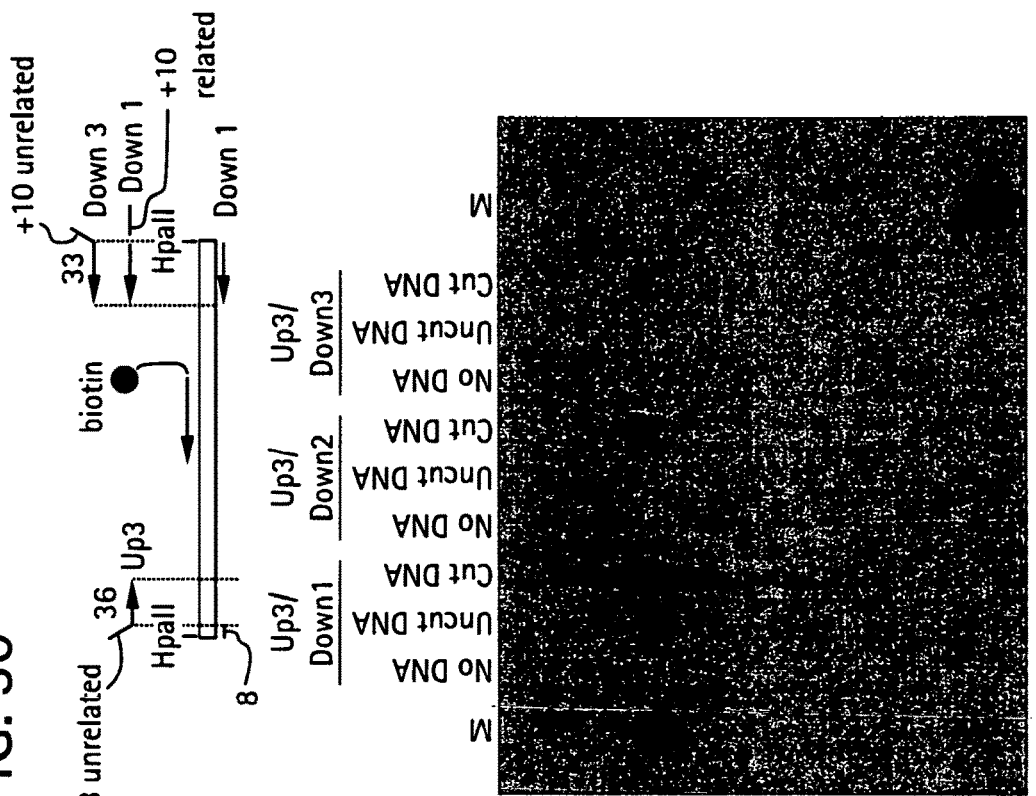
FIG. 30 depicts RPA in a complex sample. The amplification of specific DNA targets from human genomic DNA.

Amplification of a Target from Human Genomic DNA Using T4 Recombination Proteins FIG. 30 shows the results of an experiment in which several pairs of primers were employed to amplify a specific DNA fragment from human genomic DNA. The reaction included bacteriophage T4 gp32(C)K3A, uvsX(C) and uvsY (N) proteins, as well as exonuclease deficient Klenow fragment, and proteins comprising the ATP regeneration system to convert ADP and AMP. To detect the specific DNA fragment, we transferred the electrophoretically separated reaction products to nylon membrane, then hybridised a biotinylated probe, which recognised a unique non-primer internal sequence.

Three primer pairs were employed, and in each case a comparison was made between no input genomic DNA, 10,000 copies of uncut human genomic DNA, and 10,000 copies of HpaII cut genomic DNA (which generates at least one end for the primer pairs). In all cases, specific amplification of the desired DNA sequence occurred, while the efficiency showed variation between primer pairs, and between uncut and cut DNAs. In all cases, prior HpaII digestion of the DNA sample was not absolutely required, but improved the efficiency of amplification. In all cases, input genomic DNA was important. In the best amplification (shown in lane 4), we estimated at least 10$^{11}$ molecules, indicating an amplification of the approximate order 10'.

Example 8

Sensitivity of lsRPA when Targeting a Complex DNA—Human Genomic DNA

Figure 31:
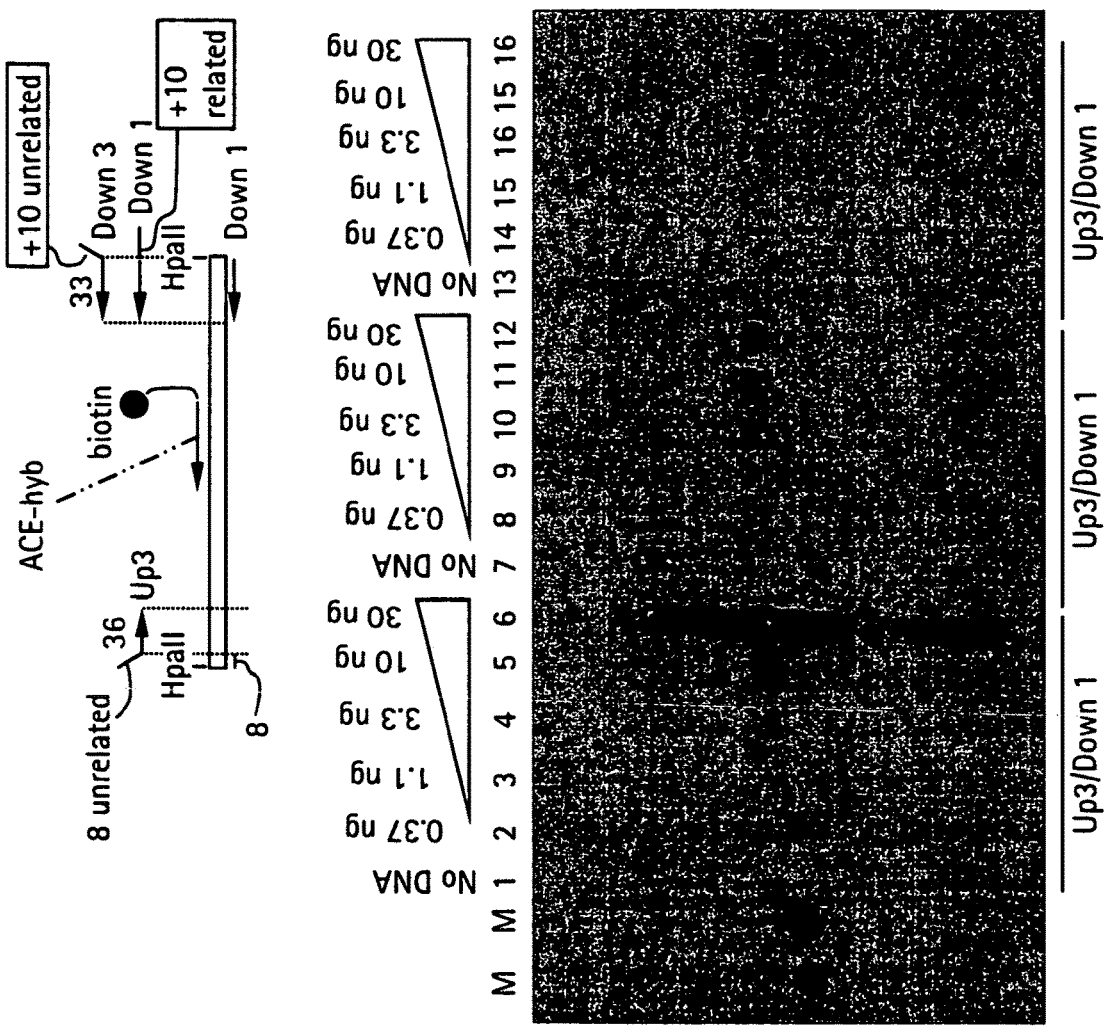
FIG. 31 depicts RPA sensitivity. The sensitivity of amplification of specific DNA targets from human genomic DNA.

FIG. 31 shows the results of an experiment in which several pairs of primer were employed to amplify a specific DNA fragment from human genomic DNA. The reaction included bacteriophage T4 gp32(C)K3A, uvsX(C) and uvsY (N) proteins, as well as an exonuclease deficient Klenow fragment, and comprising the ATP regeneration system to convert ADP and AMP. To detect the specific DNA fragment, we transferred the electrophoretically separated reaction products to nylon membrane. Then we hybridised a biotinylated probe, which recognises a unique non-primer internal sequence.

Three primer pairs were employed and in each case a comparison is made between no starting template and approximately 10, 100, 1000, 3000, and 10,000 copies of the genomic target. In all cases, clear amplification was detected when at least 1000 copies of the genomic target were used (a weak signal is seen with the best primer pair at 100 copies). We concluded that during that lsRPA reactions configured in this way were capable of amplifying DNA from very complex targets with a sensitivity of at least 1000 copies, and potentially higher.

Example 9

Figure 32:
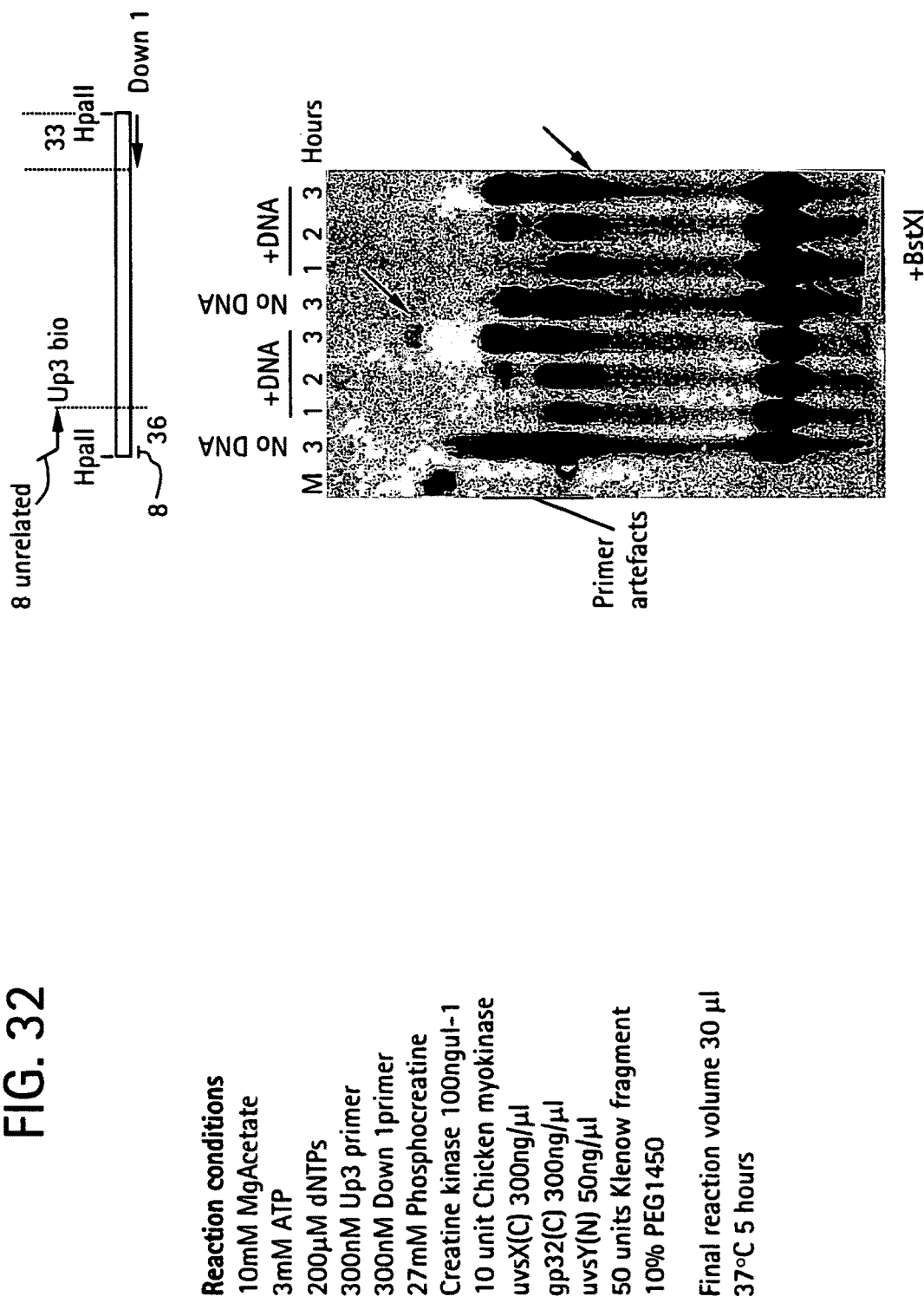
FIG. 32 depicts RPA sensitivity and template independent artifacts. The sensitivity of amplification of specific DNA targets from human genomic DNA, and the existence of competing template-independent primer artifacts.

Competition Between the Accumulation of Bona Fide Product and Primer (Template-independent) Artifacts During Reactions FIG. 32 shows the results of an experiment in which a pair of primers was employed to amplify a specific DNA fragment from human genomic DNA. Employed in the reaction were bacteriophage T4 gp32(C), uvsX(C) and uvsY(N) proteins, as well as an exonuclease deficient Klenow fragment, and proteins comprising the ATP regeneration system to convert ADP and AMP. PEG 1450 was included at 10% w/v. One of the oligonucleotides included a 5'-biotin so that all reaction products could be observed at the end of the amplification. Samples were taken at 1, 2 and 3 hours to observe how the reaction progressed. In one sample, when a minimal amount of uvsY(N) was employed (50 ng/µl), amplification of the correct fragment was observed (see arrow in lane 4). This fragment was cleaved by BstXI to the expected size fragment, indicating it was principally double-stranded. However the fragment was less abundant than apparently template-independent bands that also accumulated during the reaction. The size and template-independent nature of these bands suggested that they were primer artifacts, e.g., primer dimers and/or snapback synthesis products. The absence of amplification of the specific fragment suggested that, at uvsY(N) concentrations greater than 50 ng/µl, the reaction occurred suboptimally. This was borne out by later experiments.

Example 10

Figure 36:
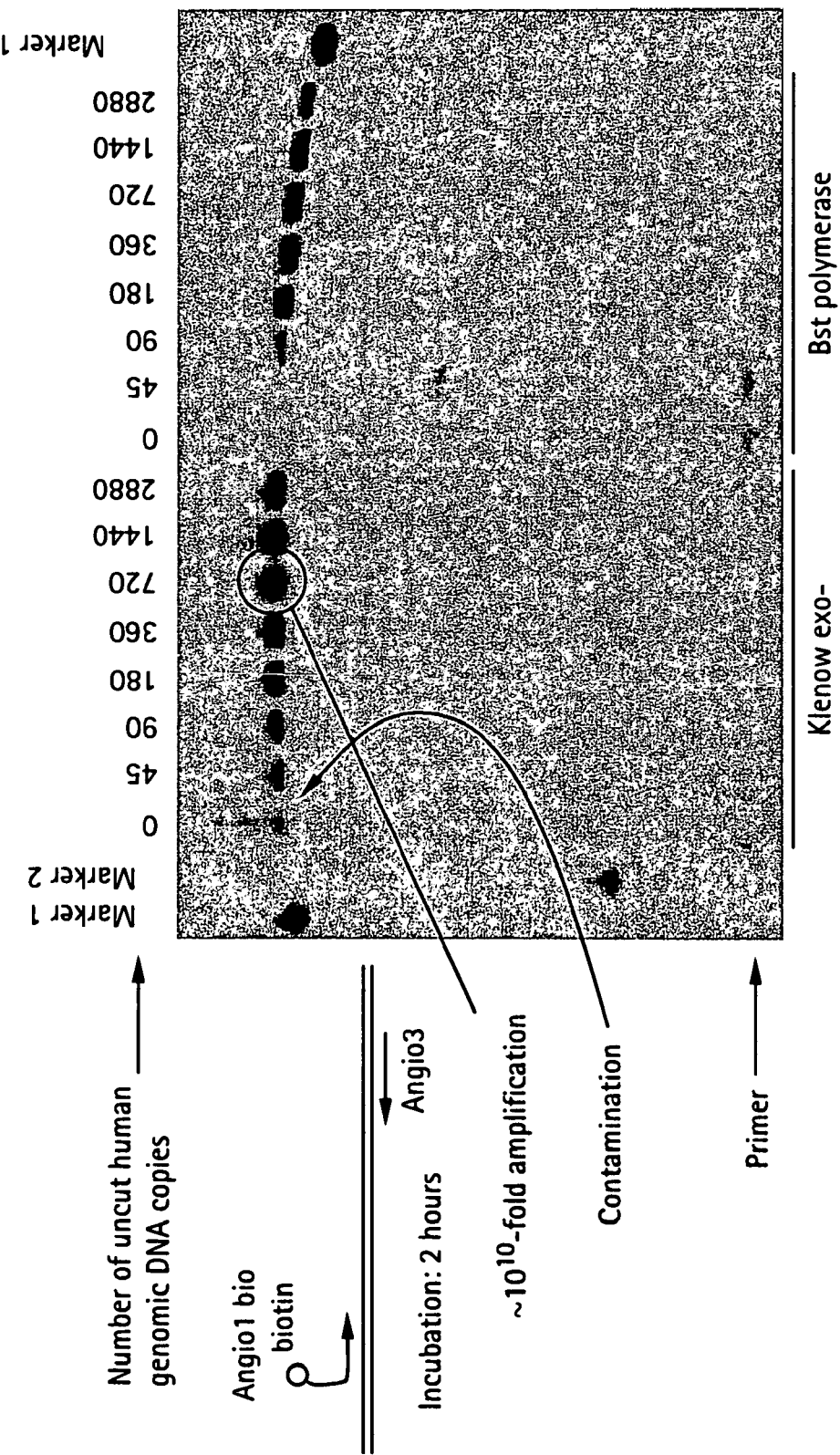
FIG. 36 depicts conditions that enable highly efficient noise-free amplification from complex DNA sources. The sensitivity of amplification of specific DNA targets from human genomic DNA under optimised conditions that reduce or eliminate primer artifacts.

Optimisation of Reaction Composition to Severely Limit or Eliminate Primer Artifacts and Enable Sensitive Noise-Free Amplification from Complex Templates FIG. 36 shows the results of an experiment in which a pair of primers was employed to amplify a specific DNA fragment from human genomic DNA. Employed in the reaction were bacteriophage T4 gp32(C), uvsX(C) and uvsY(N) proteins, as well as an exonuclease deficient Klenow fragment, or Bst polymerase, and proteins comprising the ATP regeneration system to convert ADP and AMP. One of the oligonucleotides included a 5'-biotin so that all reaction products could be observed at the end of the amplification. Amplified fragments were visualized following separation of fragments by size by running a small sample of the reaction on an acrylamide gel. In this experiment, uncut human genomic DNA was titrated from zero copies, 45 copies, and then doublings in target copy number up to 2880. Slightly different conditions were employed in this experiment for each of the two polymerase species with regard to both buffer and temperature. The reaction with the Klenow fragment was performed at 37° C., while that with Bst polymerase was performed at 42° C. The details of the buffer composition are given in the figure description.

Of note, and important to the efficiency of reactions under these optimised conditions, PEG compound was included at 5% final weight to volume in both cases. Both polymerases have effectively amplified the correct fragment, and in some cases, utilised most of the available primers. Under the conditions used for the Klenow fragment, the sensitivity was so great that a weak signal was observed even in the zero copies lane presumably reflecting contamination with a quantity of human DNA representing less than the 45 copies present in the lane immediately adjacent. At the level of sensitivity that is demonstrated here, it was difficult to eliminate trace levels of contamination from the equipment that was used leading to signals in the negative controls. Routine employment of conditions similar to those utilised in the Klenow-mediated amplification proved effective for noise-free amplification of numerous primer pairs in later experiments. This suggested that these conditions were close to one optimum for reactions involving this set of protein components.

Example 11

Experimental Methods for Production of Clones and Proteins

All clones have been constructed by cloning PCR amplified products from *E. coli*, T4 phage, *B. subtilis*, or Phi-29 phage. All stock organisms used for amplification were obtained from a public source at the DSMZ. Cloned DNA's used for protein expression have in general been cloned into pET vectors (e.g., pET-21) with the insertion of a hexahistidine peptide tag at either the N or C terminus during the PCR amplification of the fragment, or into pQE vectors (e.g., pQE31) in the case of Pol I from *B. subtilis* (Bsu polymerase). In this disclosure all proteins containing an N terminal tag are referred to as the protein name followed by (N), e.g. gp32(N), or if containing the tag at the C terminus the name is followed by (C), e.g. gp32(C). Additionally we have constructed several clones to produce otherwise modified proteins. These include a recA(C) with a deletion of the last 17 amino acid residues of the native protein, referred to as recA(C)delta 17. A similar form of the T4 UvsX(C) protein has been generated and is referred to as UvsX(C) delta 21. We have also constructed mutant forms of gp32, which modify either lysine 3 or arginine4.

All proteins were overexpressed in *E. coli* and purified using conventional protocols. Proteins have generally been purified by standard procedures on Nickel resin in 1 M NaCl and phosphate buffer. Proteins were eluted with 250 mM imidazole and dialysed into appropriate buffers. Proteins produced from clones generated in-house include: *E. coli* recA(C), *E. coli* SSB(N), *E. coli* PriA(N), *E. coli* PriB, *E. coli* PriC, *E. coli* DnaB, *E. coli* DnaC, *E. coli* DnaC810, *E. coli* DnaT, *E. coli* RuvA, *E. coli* RuvB, T4 phage UvsX(C), T4 phage UvsX(N), T4 gp32(N), T4 gp32(C), T4 gp32(C) K3A, T4 phage gp32(C)R4Q, T4 phage gp32(C)R4T, T4 phage gp32, T4 phage gp32 K3A, T4 phage gp32R4Q, T4 phage gp32R4T, T4 phage UvsY(N), T4 phage UvsY(C), T4 phage gp43, T4 phage gp43(exo-), *E. coli* Klenow fragment, *E. coli* Klenow exo-. Untagged gp32 proteins were purified by a 2-column procedure involving DEAE sepharose anionic exchange followed by binding to single-stranded DNA cellulose matrix.

DNAs Used in RPA Reactions.

We have employed several different target DNAs in this study, and a number of oligonucleotides. The sequence of the relevant section of the templates, and the sequence of the oligonucleotides is given below.

The *E. coli* RuvB Gene Target

The sequence of the EcoRV fragment of the RuvB gene is given below.

```
                                              (SEQ ID NO: 1)
ATCATGATTGGTGAAGGTCCGGCGGCACGCTCCATTAAAATTGATTTGCC

GCCGTTTACCCTGATTGGTGCAACCACGCGCGCAGGTTCGCTGACATCAC

CGTTGCGCGACCGTTTTGGTATTGTGCAACGTCTGGAGTTTTATCAGGTG

CCGGATCTGCAATATATCGTCAGTCGCAGCGCACGCTTTATGGGGCTTGA

GATGAGTGATGACGGCGCGCTGGAAGTTGCTCGTCGCGCTCGCGGTACGC

CGCGCATTGCCAACCGTCTGCTGCGTCGAGTGCGTGATTTCGCCGAAGTG

AAGCACGATGGCACCATCTCGGCAGAT
```

The sequence of oligonucleotides targeting this template mentioned in this study are given below:

```
Tester2
                                              (SEQ ID NO: 2)
CTAGCGATGGTGCCATCGTACAGAATTCCCTCAGCATCTGCCGA Tester3
                                              (SEQ ID NO: 3)
CTCACTATACCTCAGCATCATGATTGGTGAAGGTCCGGCGGCAC Tester1 bio
                                              (SEQ ID NO: 4)
5'-biotin-GCTAATACGACTGACTATACCTCAGCATCATGATTGGT
GA AGGTCCGGCGGCAC Tester3 bio
                                              (SEQ ID NO: 5)
5'-biotin-CTCACTATACCTCAGCATCATGATTGGTGAAGGTCCGG
CG GCAC Sizer1
                                              (SEQ ID: 6)
CTATGCGAATTCAGCGAACCTGCGCGCGTGGTTGCACCAATCAGGG Sizer2
                                              (SEQ ID NO: 7)
CTATGCGAATTCGGTGATGTCAGCGAACCTGCGCGCGTGGTTGCA Sizer3
                                              (SEQ ID NO: 8)
CTATGCGAATTCTCCAGACGTTGCACAATACCAAAACGGTCGCGC Sizer4
                                              (SEQ ID NO: 9)
CTATGCGAATTCCGTGCGCTGCGACTGACGATATATTGCAGATCC Gen2bio
                                              (SEQ ID NO: 10)
5'-biotin-ATCTGCCGAGATGGTGCC
```

The sequence of part of the human angiotensin converting enzyme targeted in this study is shown below:

```
                                              (SEQ ID NO: 11)
AACCAACTCCGCCCCGGGCCACGGCCTCGCTCTGCTCCAGGTACTTTGTC

AGCTTCATCATCCAGTTCCAGTTCCACGAGGCACTGTGCCAGGCAGCTGG

CCACACGGGCCCCCTGCACAAGTGTGACATCTACCAGTCCAAGGAGGCCG

GGCAGCGC
```

Underlined are HpaII restriction sites that have been targeted with HpaII in the preparation of some DNAs in some experiments.

The sequence of oligonucleotides used to target part of the human ACE gene are shown below:

Up3
(SEQ ID NO: 12)
ATTCGTCAGCCTCGCTCTGCTCCAGGTACTTTGTCAGCTTCATC

Down1
(SEQ ID NO: 13)
GCCTCCTTGGACTGGTAGATGTCACACTTGTGC

Down2
(SEQ ID NO: 14)
GCGCTGCCCGGCCTCCTTGGACTGGTAGATGTCACACTTGTGC

Down3
(SEQ ID NO: 15)
TATGCGAATTGCCTCCTTGGACTGGTAGATGTCACACTTGTGC

Angio1bio
(SEQ ID NO: 16)
5'-biotin-GCCTCCTTGGACTGGTAGATGTCACACTTGTG

Angio3
(SEQ ID NO: 17)
GGCCACGGCCTCGCTCTGCTCCAGGTACTTTGTCAGCTTCATC

Example 12

Experimental Results and Analysis

FIG. 9 shows the results from investigations into the nature of double-stranded DNA targets and targeting oligonucleotides. Experiments using either supercoiled templates or linearised DNAs suggested that recA catalyses the formation of intermediates capable of supporting polymerase elongation most readily on supercoiled DNA, or the ends of linearised DNA. Shown are the results of an experiment in which the biotinylated oligonucleotide, Tester3bio, has been incubated with either supercoiled target DNA, or a target template linearized with EcoRV, or ClaI. This generated an end that overlapped with the oligonucleotide or embedded sequences respectively. The reaction solution included 20 mM Tris-acetate pH 7.9, 10 mM Mg-acetate, 13 µg rec A, 1 µg E. coli SSB, 27 mM phosphocreatine, 1 U creatine kinase, 0.2 µM Tester3bio, 3 mM ATP, 200 µM dG, dC, and dT; 1 mM dA, 50 U Klenow, 0.5 pmoles template, 120 ng recO, 120 ng recR, 0.5 µM dnaB, and 0.5 µM dnaC810. E. coli recO and recR proteins, as well as dnaB and dnaC810 proteins, were included in this experiment although they did not significantly affect the results. After 2 hours of reaction at 37° C., the reaction was precipitated and run on a 6% denaturing gel, transferred to nylon membrane, and incubated with streptavidin-HRP prior to performing ECL to detect reactive material. In each reaction, 0.5 pmoles of template was used. Included on the gel as a control for size and amount was 0.5 pmoles of biotinylated PCR fragment (labeled CON). Other reaction components and conditions are indicated on the figure.

Figure 10:
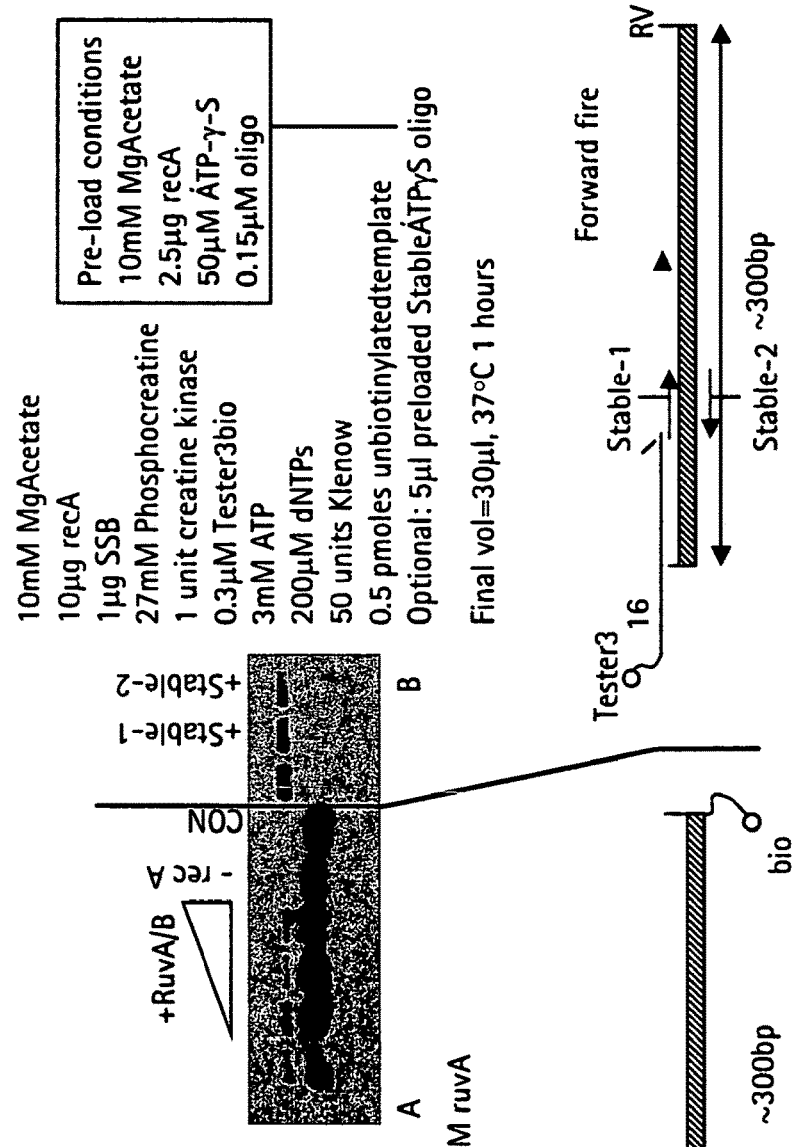
FIG. 10 depicts backfire synthesis. Backfire synthesis occurs when a recA-coated targeting oligonucleotide possessing a 5' overhang invades a duplex DNA end in the presence of a suitable polymerase and dNTPs. This new duplex region is stable to subsequent branch migration and can be utilised as a platform for other activities. Forward fire, that is the elongation from the invading oligonucleotide, can also occur.

FIG. 10 shows backfire synthesis. Backfire synthesis occurs when a recombinase-coated targeting oligonucleotide possessing a 5' overhang invades a duplex DNA end in the presence of a suitable polymerase and dNTPs. This new duplex region is stable to subsequent branch migration and can be utilised as a platform for other applications. Forward fire is the elongation of the invading oligonucleotide, which also occurs in these reactions. Shown are the results of experiments to detect the activity of polymerases on intermediates formed when the oligonucleotide Tester3, possessing a 5' overhang relative to the end of a linearized target DNA, is incubated with various templates.

In part A, the template used is a double-stranded PCR product generated such that the product has a biotin label at the 5' end of the strand complementary to the targeting oligonucleotide. This fragment is otherwise similar to the EcoRV fragment released from a plasmid carrying the E. coli RuvB gene used elsewhere in this study, and which is a target for the Tester3bio oligonucleotide. The reaction solution included 10 mM Mg-acetate, 7.5 µg recA, 1 µg SSB, 27 mM phosphocreatine, 1 U creatine kinase, 0.3 µM Tester3bio, 3 mM ATP, 200 µM dNTPs, 50 U Klenow, 0.5 pmoles biotinylated template. Optionally, we included 0.5 µM ruvA and 0.5 µM ruvB; or 1 µM ruvA and 1 µM ruvB; or 1.5 µM ruvA and 1.5 µM ruvB. The final volume was 30 µl. Incubation was carried out for 1 hour at 37° C. In the presence of recA, the biotinylated strand of the target was extended by 16 bases, as would be expected if a recombination intermediate were accessible by a polymerase to copy the overhang region of the invading oligonucleotide.

In part B, the reaction is configured in a similar manner except that the template is not biotinylated, and the invading oligonucleotide is biotinylated. Several polymerases were investigated in this experiment, and only unmodified Klenow fragment gave a significant production of product. In this experiment, we also investigated including a small oligonucleotide designed to recognise the target directly downstream of the Tester3 targeting site. The reaction solution included 10 mM Mg-acetate, 10 µg recA, 1 µg SSB, 27 mM phosphocreatine, 1 U creatine kinase, 0.3 µM Tester3bio, 3 mM ATP, 200 µM dNTPs, 50 U Klenow, 0.5 pmoles unbiotinylated template. Optionally, we included 5 µl preloaded stable ATPγS oligonucleotide. The final volume was 30 µl. Incubation was carried out for 1 hour at 37° C. We pre-incubated with recA in the presence of ATP-γ-S in an effort to load recombinase stably onto it. Pre-load solution included 10 mM Mg-acetate, 2.5 µg recA, 50 µM ATPγS, and 0.15 µM oligonucleotide. The pre-load solution was added into the Tester3bio invasion/extension mixture. In all cases, the yield of product was decreased by inclusion of this premixed material. Based on our data, we believe that the presence of ATP-γ-S (final concentration ~8 µM) in the reaction was mildly inhibitory. The purpose of this experiment was to address whether the presence of a stable 3-stranded hybrid formed immediately downstream of the Tester3 targeting site would stabilise these invasions to branch migration.

Figure 11:
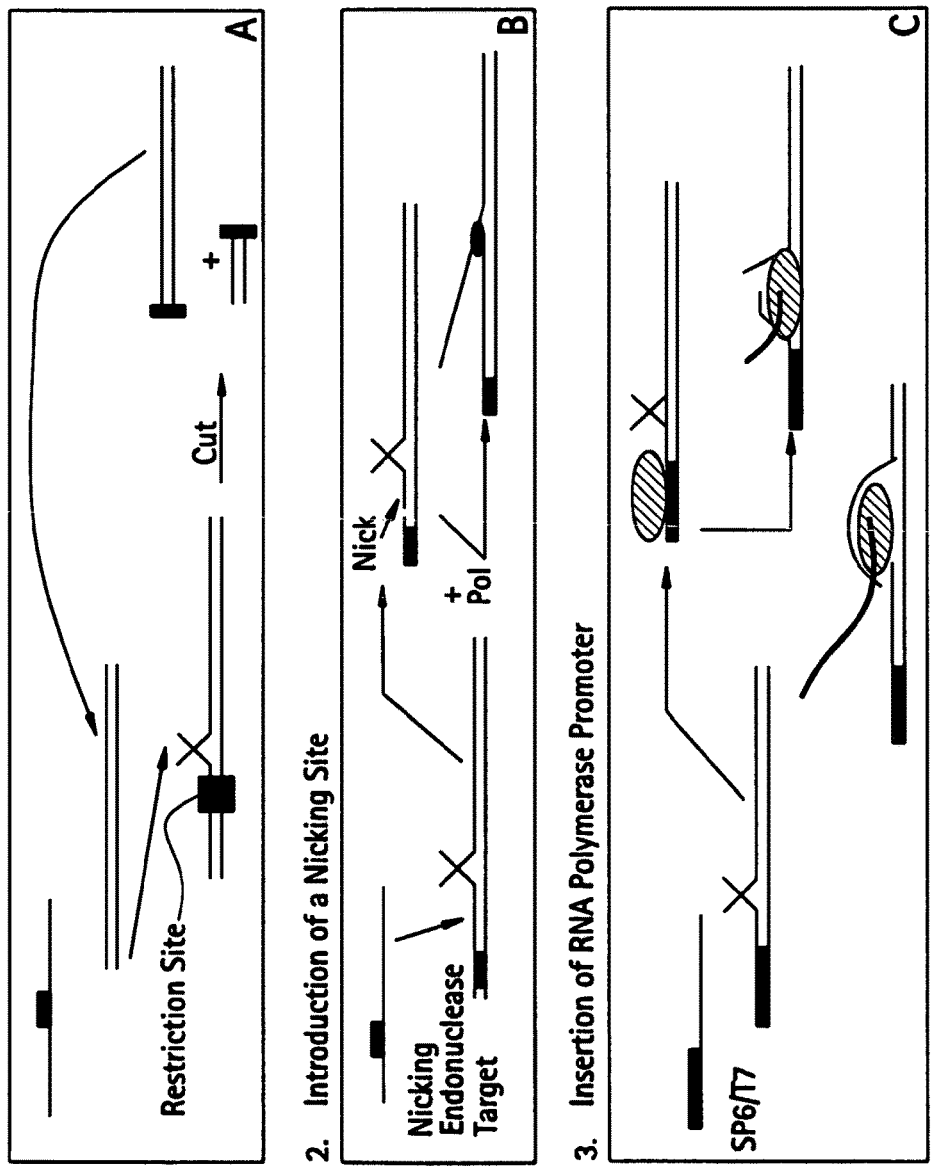
FIG. 11 depicts uses of backfire synthesis. Backfire synthesis can be useful because it generates a branch migration resistant structure that can be used for application other than normal oligonucleotide priming. Some examples are shown here including introduction of a nicking enzyme target site, introduction of an RNA polymerase promoter, and the linear generation of short dsDNA fragments through successive invasion/synthesis/cleavage events.

FIG. 11 shows uses of backfire synthesis. Backfire synthesis can be useful because it generates a branch migration resistant platform that can be employed in applications other than straightforward forward fire. Some examples are shown here, including introduction of a nicking enzyme target site, introduction of an RNA polymerase promoter, and the linear generation of short dsDNA fragments through successive invasion/synthesis/cleavage events. If a restriction enzyme site is included in the additional overhang sequence such that after targeting a suitable linearized fragment, backfire synthesis will generate the duplex target for the restriction enzyme. The enzyme can then cut the sequence releasing a short double-stranded DNA, and a longer double-stranded DNA, which is a target for further invasion events.

In FIG. 11B, the 5' overhang of a targeting oligonucleotide is designed such that should backfire synthesis occur, a target for a nicking endonuclease is generated. In the presence of the nicking endonuclease, for example BbvC1a or b, a suitable polymerase, for example the Klenow fragment, can extend from the nick and displace a DNA strand. Multiple strands may be run-off by successive nicking and elongation from a single template. In FIG. 11C, the 5' overhand that is converted to duplex by backfire synthesis contains the sequence of an RNA polymerase promoter, such as the phage T7 RNA polymerase gene. In the presence of the necessary polymerase and suitable nucleoside triphosphates, transcription can initiate downstream of the promoter to generate an RNA as shown. The presence of a break in the non-template strand is not predicted to prevent successful elongation. RNA products might be used in some form of amplification reaction, or for other purposes.

FIG. 12 shows that single stranded binding proteins facilitate recombinase invasion and primer extension. Both E. coli SSB and bacteriophage T4 gp32 with an N-terminal His tag (gp32(N)) are able to stimulate recA-mediated invasion/elongation on a linear DNA template. The results of an experiment are shown in which 0.5 pmoles of target template (the EcoRV fragment released from a plasmid carrying the E. coli ruvB gene) was incubated with the Tester3bio oligonucleotide that overlaps one end of the template. Either the E. coli SSB protein, or the T4 gp32(N) protein was included to stimulate the reaction. The reaction solution included 10 mM Mg-acetate, 6 µg rec A, 8.8 µg gp32 or 1 µg SSB, 27 mM phosphocreatine, 1 U creatine kinase, 0.3 mM Tester3bio, 3 mM ATP, 200 µM dNTPs, 50 U Klenow, 0.5 pmoles template. Optionally, we included 120 ng recO and 120 ng recR. The final volume was 30 µl. Incubation was carried out for 1 hour at 37° C. Other reaction components and conditions are indicated in the figure. The figure also shows the general relationship of the primer and target DNA. In the reactions where E. coli recO and recR proteins were included, little effect was seen from their addition under these conditions. Invasion and elongation appeared to have proceeded in all cases, and the gp32(N) appeared to have stimulated synthesis even better than E. coli SSB, although it was used at higher concentration in this experiment.

FIG. 13 shows the requirement for a minimal oligonucleotide length or overhang for invasion and elongation during end targeting of linear templates. The results of an experiment are shown in which 0.5 pmoles of target template (the EcoRV fragment released from a plasmid carrying the E. coli ruvB gene) was incubated with the either the Tester3bio oligonucleotide. This oligonucleotide overlaps one end of the template, or the Gen2bio oligonucleotide, which is flush to the other end of the template and is only 18 residues long. The reaction solution included 10 mM Mg-acetate, 27 mM phosphocreatine, 1 U creatine kinase, 0.2 µM Tester3bio or Gen2bio, 10 mM dATP, 3 mM ATP, 200 µM dNTP mixture, 50 U Klenow or Phi29 polymerase, 13 µg recA(C), 1 µg E. coli SSB, and 0.5 pmoles template. The final volume was 30 µl. Incubation was carried out for 2 hours at 37° C., and 2 µl or the reaction was loaded in each lane of the gel. Other reaction components, conditions, and the general relationship of the primers and target DNA are indicated on the figure. Invasion and elongation appeared to have proceeded efficiently in the presence of the Klenow fragment, less efficiently with the Phi29 polymerase, and less well with the Gen2bio primer and the Klenow fragment. We concluded that a minimal primer length and/or an overhand relative to the template was-required to stimulate efficient invasion and elongation.

Figure 14:
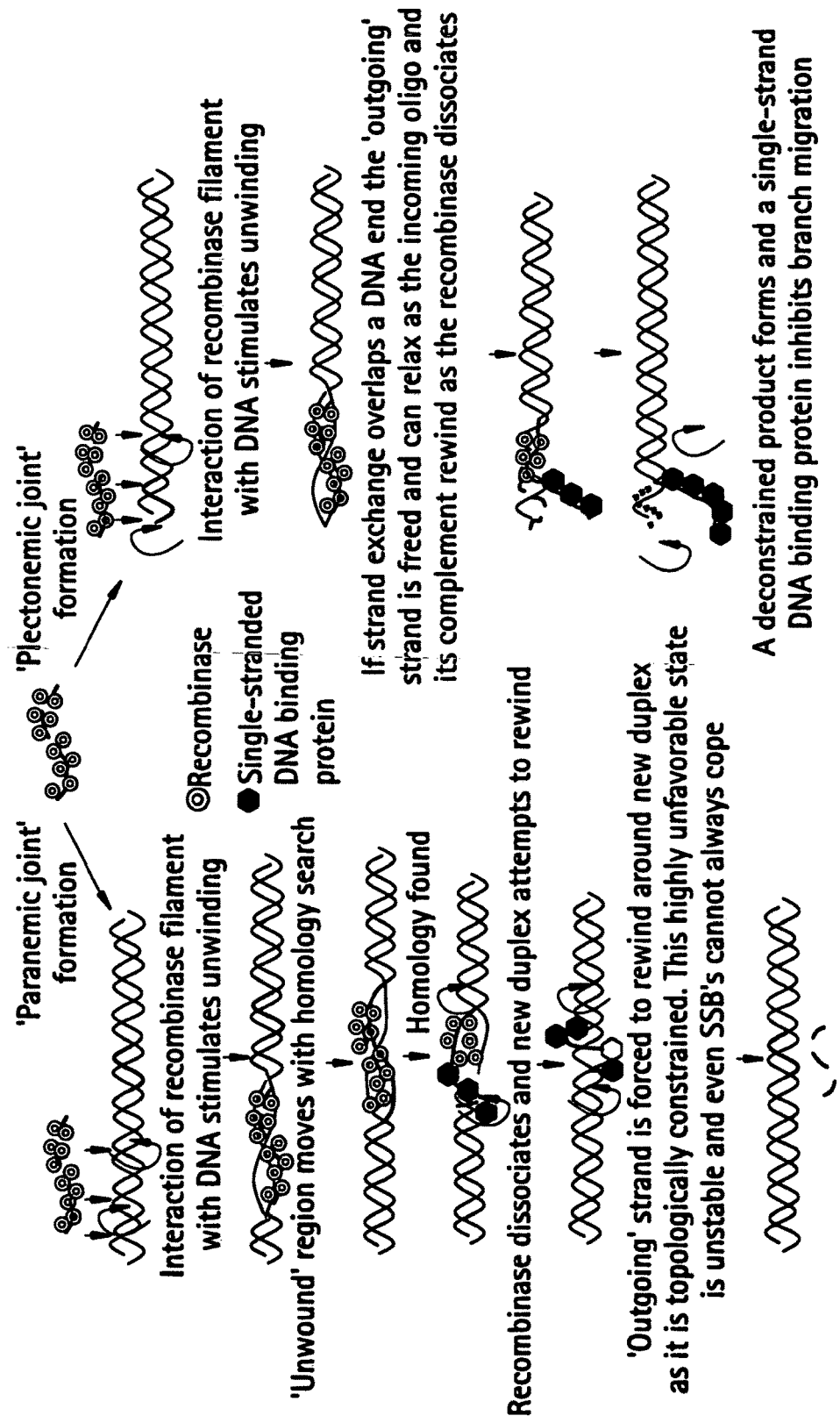
FIG. 14 depicts paranemic and pletonemic joints. Schematic description of the formation of paranemic and plectonemic joints by recombination events involving DNA ends or embedded sequences.

FIG. 14 shows paranemic (A-E) and pletonemic (F-H) joints. For paranemic joints, the interaction of the recombinase filament with DNA stimulates unwinding (FIG. 14A). The unwound region moves with the homology search (FIG. 14B). The homology is found (FIG. 14C). The recombinase dissociates and a new duplex attempts to rewind (FIG. 14D). Because it topologically restrained, the 'outgoing' strand is forced to rewind around the new duplex (FIG. 14E). This state is highly unfavorable and unstable, and cannot always be managed by SSBs (FIG. 14E). For plectonemic joints, the interaction of the recombinase filament with DNA stimulates unwinding (FIG. 14F). If strand exchange overlaps with a DNA end, the 'outgoing' strand is freed and can relax as the incoming oligo and its complement rewind as the recombinase dissociates (FIG. 14G). This forms a deconstrained product, and a single-strand DNA binding protein inhibits branch migration (FIG. 14H).

This figure compares the likely events that occur when a nucleoprotein filament initiates strand exchange with a homologous sequence located at the end of a linearized duplex (right side of figure), or within a duplex which lacks homology on either side (left side of figure). Starting with the left side, once the nucleoprotein filament has located the correct sequence it will pair the searching DNA to its complement, and one strand of the original duplex becomes unpaired. In fact, the exchange complex consists of 3 strands, which are relatively under-wound and stabilised by the recombinase. As the recombinase begins to disassemble in a 5' to 3' direction, the under-wound 3-stranded intermediate becomes unstable. For the new duplex to regain the normal conformation of relaxed DNA, it must rotate. However, in doing so, it must co-rotate the outgoing strand, as it is linked upstream and downstream to its original partner. This results in over-winding the outgoing strand, as it has to make the same number of turns but take a longer path around the new duplex, and is energetically unfavourable. Consequently there is a requirement for single-stranded binding proteins with very stable DNA interactions to permit such structures to exist for any significant time. Alternatively the right side of the diagram indicates that should the exchange include an end of the duplex then exchange can cause the complete release of the outgoing strand at one end and thus permit it to rotate freely unconstrained by the other strands involved in recombination. This leads to a stable situation in which the new duplex is free to rewind after recombinase disassembly, and single-stranded DNA binding proteins need only deter spontaneous branch migration.

FIG. 15 shows the effect of crowding agents. In the presence of polyethylene glycols, gp32(N) and recA recombinase can mediate multiple invasion events on single templates without a requirement for regeneration of the template ends that would permit 5' overhangs in the targeting oligonucleotide. FIG. 15A shows the results of an experiment in which either the Tester1bio, or Tester3bio oligonucleotides (which differ in the length of 5' overhang relative to the template) were incubated with the EcoRV fragment released from a plasmid carrying the E. coli ruvB gene, or the ClaI digest of the plasmid, in the presence or absence of 10% PEG 8000. The reaction solution included 10 mM Mg-acetate, 10.6 µg recA, 8.8 µg gp32, 27 mM phosphocreatine, 1 U creatine kinase, 0.3 mM Tester3bio or Tester1bio, 3 mM ATP, 200 µM dNTP mixture, 50 U Klenow, and 0.5 pmoles template (species indicated in figure). Optionally, we included 120 ng recO and 120 ng recR. PEG8000 was included as shown. The final volume was 30 µl. Incubation was carried out for 1 hour at 37° C.

The diagram shown represents the relationship of the oligonucleotides to the two possible templates. In particular, both oligonucleotides recognised an embedded sequence within the ClaI fragment. In each case, 0.5 pmoles of template was used, other conditions were carried out as indicated. Both primers stimulated invasion/elongation on the EcoRV template. Based on signal intensity, approximately one elongation occurred per target template. However, in the presence of 10% PEG 8000, the intensity of the fully elongated fragment was significantly greater than in its absence and stronger than the 0.5 pmoles of control biotinylated PCR product. The strongest signal was seen with the Tester3bio oligonucleotide. In that case, we estimated at least 10 invasion/run-ons occurred per template.

In FIG. 15B, we compared the stimulation of invasion/elongation in 10% w/v of various commercially available polyethylene glycols. The reaction solution included 10 mM Mg-acetate, 10.6 µg recA, 8.8 µg gp32, 27 mM phosphocreatine, 1 U creatine kinase, 0.3 mM Tester3bio or Tester1bio, 3 mM ATP, 200 µM dNTPs, 50 U Klenow, and 0.5 pmoles RV template. PEG species were included as shown. There was significant variation observed in the degree of stimulation. PEG compound (MW=15,000 to 20,000) appeared to be the most effective, followed by PEG1450.

Figure 16:
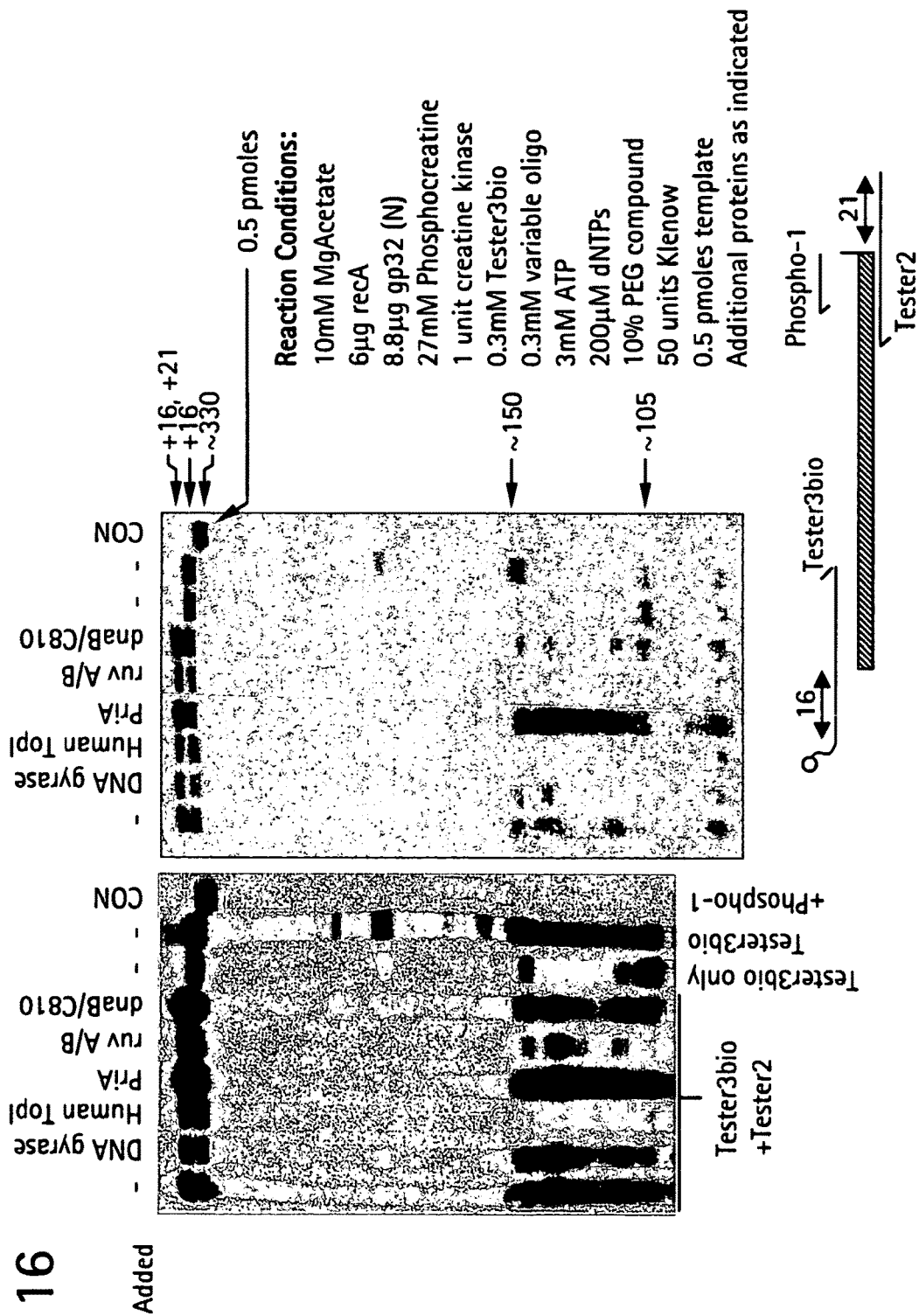
FIG. 16 depicts end targeted amplification using leading strand RPA. Amplification of a target DNA using end-directed oligonucleotides, recA(C) protein, and the Klenow fragment of E. coli DNA polymerase I.

FIG. 16 shows the effect of end targeted amplification using leading strand RPA. Amplification comprising several rounds of invasion and extension was demonstrated, achieving at least a 10 fold amplification from 0.05 pmoles of template. In this experiment, we have employed pairs of oligonucleotide primers to establish an amplification reaction. Shown schematically is the relationship of the oligonucleotides used to the EcoRV fragment from a plasmid carrying the E. coli ruvB gene, which was used as template. The reaction solution included 10 mM Mg-acetate, 6 µg recA, 8.8 µg gp32(N), 27 mM phosphocreatine, 1 U creatine kinase, 0.3 mM Tester3bio, 0.3 mM variable oligonucleotide, 3 mM ATP, 200 µM dNTPs, 10% PEG compound, 50 U Klenow, and 0.5 pmoles template. Additional proteins were used as indicated.

Tester3bio included a 16-nucleotide overhang relative to the starting template, while Tester2 included a 21-nucleotide overhang and was targeted to the other end of the template. Phospho1 was used as an oligonucleotide with a phosphorothiorate backbone. This oligonucleotide was 15 residues long, and was flush to the target end. Phospho-1 was predicted not to interact with recombinase or single-stranded DNA binding protein as it lacked a phosphate backbone. However, it was predicted to function in straightforward solution hybridisation. A control fragment of biotinylated PCR product was employed to demonstrate the signal intensity of 0.5 pmoles of DNA, and was also the precise size of the starting template. The reaction products were run on a 6% denaturing gel, transferred to nylon, and bound with streptavidin-HRP prior to performing enhanced chemiluminescence to reveal the biotinylated products of the reactions.

In all cases, successful invasion and elongation with the biotinylated Tester3bio has occurred as seen by presence of fully elongated products. The products were slightly slower mobility that the control, due to the presence of overhangs on the oligonucleotides. Furthermore, there was evidence for several rounds of invasion/run-ons as the signal intensity was at least as great as the 0.5 pmoles control (we initiated the reaction with only 0.05 pmoles). There was a significant accumulation of a product roughly 37 nucleotides larger than the control. This was predicted to arise from Tester3bio elongating on a strand previously copied from, and including the overhang from, the opposing primer. Two exposures of the same gel are shown.

The inclusion of various different proteins, which are normally involved in DNA metabolism, had varying effects. DNA gyrase, and toposiomerase I (human) decreased the yield of amplification product, and the topoisomerase profoundly reduced the generation of shorter elongation products. Inclusion of E. coli ruvA and ruvB also lead to a general reduction in product formation. E. coli priA increased the amount of product formed, and significantly increased the number of shorter products formed. Inclusion of E. coli dnaB and dnaC810 protein slightly increased the amount of product formed. Note that a significantly stronger signal detected in reactions containing Phospho-1 oligonucleotide in comparison to Tester3bio alone. This suggested that Phospho-1 was able to hybridise with displaced strands and lead to formation of duplex DNA.

Figure 17:
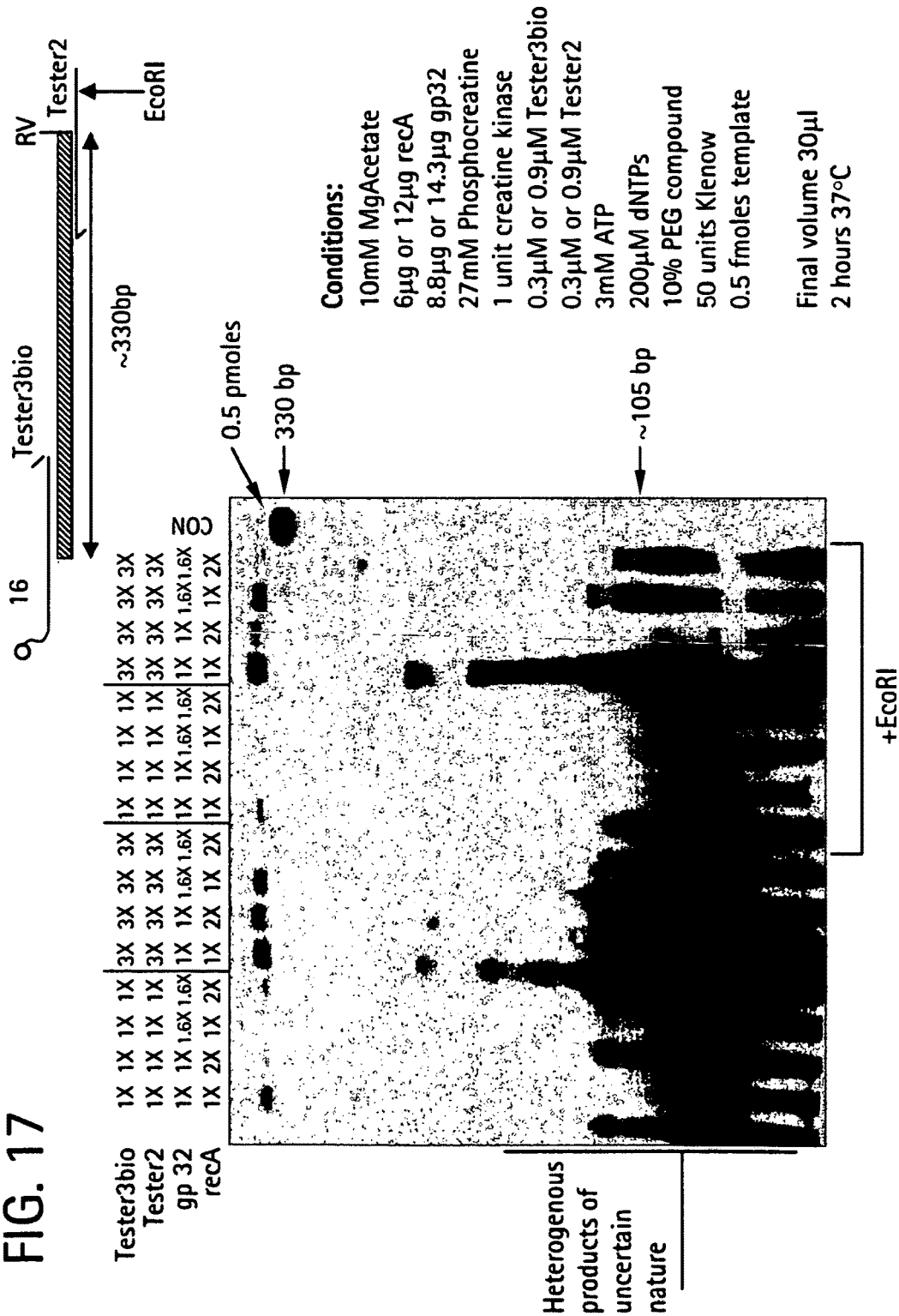
FIG. 17 depicts leading strand RPA and limits of Klenow processivity. Limited amplification of an approximately 300 base pair fragment when only 0.5 fmoles of starting template is utilised with the recA protein, gp32(N), and the Klenow fragment of E. coli. Strong accumulation of shorter products suggests that the poor processivity of Klenow (10-50 nucleotides) may underlie the template concentration dependence of the reaction.

FIG. 17 shows leading strand RPA and Klenow processivity. In this experiment, we have employed pairs of oligonucleotide primers in an effort to establish an amplification reaction in a manner similar to that shown in FIG. 16, except using a further 100-fold dilution of the start template. The reaction solution included 10 mM Mg-acetate, 6 or 12 µg recA, 8.8 or 14.3 µg gp32, 27 mM phosphocreatine, 1 U creatine kinase, 0.3 or 0.9 µM Tester3bio, 0.3 or 0.9 µM Tester2, 3 mM ATP, 200 µM dNTPs, 10% PEG compound, 50 U Klenow, and 0.5 pmoles template. The final volume was 30 µl. Incubation was carried out for 2 hours at 37° C. Shown schematically is the relationship of the oligonucleotides used to an EcoRV fragment from a plasmid carrying the E. coli ruvB gene, which is used as target template. Tester3bio included a 16-nucleotide overhang relative to the starting template, while Tester2 included a 21-nucleotide overhang, is targeted to the other end of the template, and encodes an EcoRI site within the overhang. A control fragment of biotinylated PCR product was employed to demonstrate the signal intensity of 0.5 pmoles of DNA, and was also the precise size of the starting template. The reaction products were run on a 6% denaturing gel, transferred to nylon, and bound with streptavidin-HRP prior to performing enhanced chemiluminescence to reveal the biotinylated products of the reactions.

The concentration of the oligonucleotides, gp32(N) and the recA(C) were varied, and we have also investigated whether the inclusion of EcoRI restriction enzyme, which can cleave part of the additional sequence incorporated by the Tester2 overhang, has any effect on the reaction. In most cases, there was evidence of some limited degree of amplification of the expected size of fragment, but there was principally generation of shorter DNA fragments. We deduced that the relatively poor accumulation of bona fide full length product may occur at these more dilute template concentrations because the poor processivity of the E. coli DNA polymerase I Klenow fragment (10-50 nucleotides) results in most interactions generating short fragments, which is more significant at low target template concentrations.

FIG. 18 shows spacing dependence of RPA primers. As a consequence of earlier results, we attempted to establish whether decreasing the distance between primer pairs would result in an increase in amplification efficiency. To test this, we employed a series of oligonucleotides, Sizer1, 2, 3, and 4, which were positioned at increasing distances away from the 3' end of the Tester3bio oligonucleotide. All Sizer oligonucleotides included the EcoRI overhang indicated in the bottom right side of the figure. The sequence of the target DNA, an EcoRV fragment from a plasmid carrying the E. coli ruvB gene, and the position of the oligonucleotides used are shown. The reaction solution included 10 mM Mg-acetate, 6 µg recA, 8.8 µg gp32, 27 mM phosphocreatine, 1 U creatine kinase, 0.3 µM Tester3bio, 0.3 µM variable oligonucleotide, 3 mM ATP, 200 µM dNTPs, 10% PEG compound, 50 U Klenow, 5 U EcoRI, and 0.5 pmoles template. The final volume was 30 µl. The reaction solution was incubated for 2 hours at 37° C. Other reactions conditions are indicated on the figure.

A control fragment of biotinylated PCR product was employed to demonstrate the signal intensity of 0.5 pmoles of DNA, and was also the precise size of the starting template. The reaction products were run on a 6% denaturing gel, transferred to nylon, and bound with streptavidin-HRP prior to performing enhanced chemiluminescence to reveal the biotinylated products of the reactions. Specific fragments of the expected lengths were efficiently amplified from 0.5 fmoles of starting template when Sizer2, 3, and 4 were employed. The yield of product decreased somewhat however as the length of the product increased. Little or no product of the expected size is produced when Sizer1 was used. Lane 4 was estimated to contain ~$4 \times 10^4$ fold amplification. This primer included the shortest inter-oligonucleotide distance of only 25 nucleotides. This suggested there is a minimal required distance to separate the ends of the oligonucleotides, although other explanations such as poor primer behaviour could also explain the result. Included in the experiment were several samples containing no template DNA. In the case of Sizer2, a faint band of approximately the expected size is observed even in the absence of exogenous DNA. Based on a variety of data we believe that this arises from contamination of our protein preparations with significant quantities of E. coli genomic DNA.

FIG. 19 shows that RPA products are largely double stranded. RPA reaction can generate double-stranded DNA products as evidenced by agarose gel electrophoresis and restriction enzyme cleavage. However, under the conditions used here, there were significant decreases in reaction efficiency if the starting template dropped significantly below 0.5 fmoles. Furthermore, signals observed in the water-only control suggested significant genomic contamination of E. coli DNA. In this experiment we have incubated 0.5 fmoles, or more dilute quantities, of the fragment detailed in FIG. 10 with Tester3bio and Sizer2 under the conditions indicated. The reaction solution included 10 mM Mg-acetate, 6 µg recA, 8.8 µg gp32, 27 mM phosphocreatine, 1 U creatine kinase, 0.3 µM Tester3bio, 0.3 µM Sizer2, 3 mM ATP, 200 µM dNTPs, 10% PEG compound, 50 U Klenow, and 0.5 pmoles template or dilution indicated in figure. The final volume was 30 µl.

We have included a no DNA control, progressive dilution of the template, and investigated initiating the reaction on embedded template (the ClaI fragment detailed on FIGS. 1 and 7), of using PEG 1450, and diluting the Klenow fragment. A fraction (1/10) of the reaction products were run on a 6% denaturing gel, transferred to nylon, and bound with streptavidin-HRP prior to performing enhanced chemiluminescence to reveal the biotinylated products of the reactions (FIG. 19A). A further fraction (3/10) was phenol extracted, precipitated, and run on a 2% agarose gel and stained with ethidium bromide (FIG. 19B). A final fraction (3/10) was cut with BbvC1 and electrophoresed on a 2% agarose gel alongside equivalent uncut DNA (FIG. 19C).

Lane 2 (FIG. 19A) was estimated to contain $5 \times 10^4$ fold amplification, which corresponded to $10^{13}$ molecules of final product. In the presence of 0.5 fmoles of starting template, an extremely robust amplification of the expected size fragment was seen as evidenced by denaturing gel electrophoresis. Furthermore, when part of the sample was electrophoresed on agarose a strong clean band of precisely the correct size for a double-stranded DNA product was observed. This product could be cut by BbvC1 to yield a slightly smaller fragment of the expected size. Dilution of the template by 100-fold or more resulted in a significantly less intense band, and a much larger quantity of fragments shorter than the expected length. This was determined by denaturing gel electrophoresis and by agarose gel electrophoresis. A similar pattern was observed when ClaI cut DNA was used, or if no DNA was used. We believe that when less than a threshold quantity of DNA is used under these conditions, there is a suboptimal amplification reaction, which leads to heterogeneous products, and furthermore that our samples are highly contaminated with E. coli genomic DNA from the single-step purification procedures used in generating our recombinant proteins used here.

Figure 20:
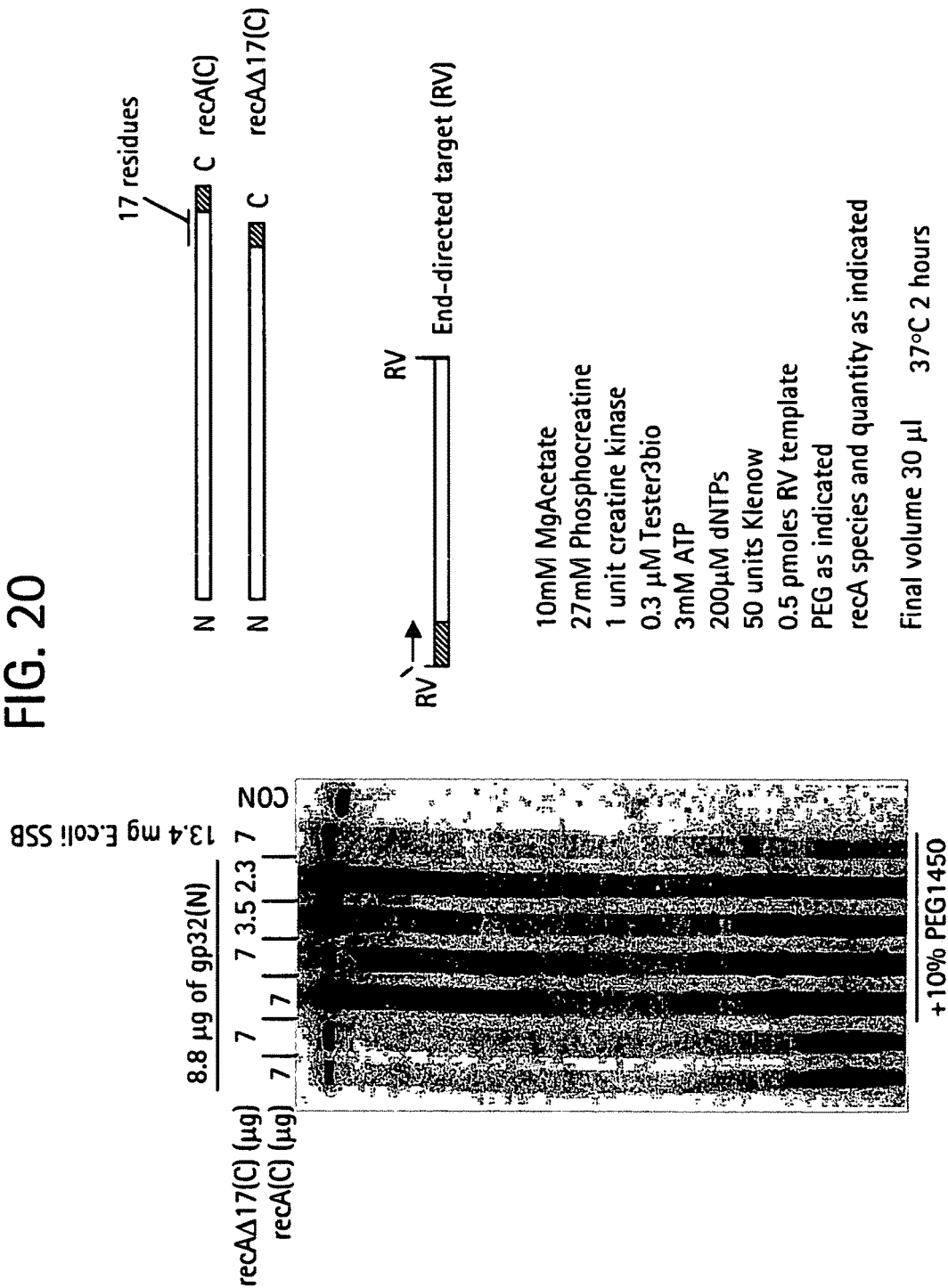
FIG. 20 depicts activity of a recA C-terminal truncation mutant. Mutant recA protein with a deletion of the C-terminal acidic peptide (recA(C)delta) can promote strand exchange and extension in a linear template run-on assay.

FIG. 20 shows activity of a recA C-terminal truncation mutant. RecA proteins with a deletion of the C-terminal acidic peptide (recA(C)A) are active in promoting strand exchange and extension in a linear template run-on assay. However, there was some suggestion that the optimal protein concentration was lower than that with the recA(C) protein. This experiment addresses whether a C terminal truncated form of the E. coli recA protein, described elsewhere, could be used successfully in invasion/extension reactions. Shown is the result of a single-sided run-on assay using either the E. coli recA(C) protein or the E. coli recAA17(C) protein, which lacks the 17 C-terminal acidic residues. The relationship between primers and template and other experimental conditions are indicated. The reaction solution included 10 mM Mg-acetate, 27 mM phosphocreatine, I U creatine kinase, 0.3 µM Tester3bio, 3 mM ATP, 200 µM dNTPs, 50 U Klenow, 0.5 pmoles RV template, and recA species and amount as indicated in figure. PEG was included as shown. The final volume was 30 µl. The solution was incubated for 2 hours at 37° C. Reactions were performed with or without 10% PEG1450, and with the indicated quantities of the respective recombinase. Both recombinases successfully supported invasion/extension, although under the conditions used here there appears to be a different optimum for the amount of protein required.

FIG. 21 shows Modified gp32 proteins. Shown is a schematic representation of T4 gp32 proteins used in this study and the position of various modification and mutations.

FIG. 22 shows activity of gp32 proteins. Significant variations confirm that gp32 cooperativity has a substantial effect on the rate of invasion/extension reactions, and further confirms that gp32(N) displays a significant decrease in cooperativity consistent with interference with the function of the N-terminal B domain. Shown are the results of an experiment in which linear run-ons were generated using as template the EcoRV fragment of a plasmid carrying the E. coli RuvB gene and the Tester3bio oligonucleotide. The reaction solution included 10 mM Mg-acetate, 27 mM phosphocreatine, 100 ng/µl creatine kinase, 400 nM Tester3bio, 3 mM ATP, 200 µM dNTPs, 10 U chicken myokinase, 8 µg C-tag uvsX, 7.5 or 15 µg gp32 (each species), 50 U Klenow, and 0.5 pmoles template; no PEG was included. The final volume was 30 µl. The solution was incubated for 2 hours at 37° C. Reactions contained uvsX(C) and various gp32 forms as indicated. Two concentrations of each gp32 form were used in this experiment. To analyze the reaction products, 2 µl of the total volume (30 µl) was loaded onto the gel.

In all cases, elongated products of the oligonucleotide were generated that extend up to a length consistent with full length run-ons. We note that in this experiment there was a gel artifact which we occasionally observed. We observed a slower mobility shadow of the bands. This was seen in the PCR control fragment lane, also. The smallest quantity of product was formed when using the gp32(C) protein, which was consistent with it permitting only a low level of recombinase-loaded filaments to be present in the reaction. A smaller quantity of product was formed with 15 µg compared with 7.5 µg, consistent with the notion that higher concentrations decreased the efficiency of recombinase loading.

The gp32(C)K3A protein was predicted to be the next most cooperative form. Consistent with this, it produced a limited number of full-length products when 15 µg of protein is used. However, the number of run-ons was greater than that observed with either quantity of gp32(C), indicating that there were more recombinase-loaded filaments in the reaction and a higher rate of invasion/elongation. When 7.5 mg of gp32(C)K3A was used, there was a dramatic change in the quantity of product formed. One explanation is that an increased rate of invasion/elongation in this reaction could lead to the out-titration of the gp32(C)K3A by single-stranded DNA run-offs. Under these conditions, most of the oligonucleotide would become coated with uvsX(C), leading to a high invasion rate and to an inability to stabilise the outgoing strand and coat it with gp32. This would result in shorter truncated products, some of which would be folded back on themselves, self-primed, and formed into a variety of other such products. This suggested that the rate of invasion/elongation of gp32(C)K3A was notably higher for this protein than gp32(C).

By comparing the intensities of the products produced when using 15 µg of each protein, we estimated that reactions containing gp32(C)K3A have an invasion/elongation rate of approximately 10 times that of gp32(C). All of the other gp32 proteins tested in this experiment produced a pattern similar to that seen when gp32(C)K3A was employed and large amounts of product. This was the case even when 15 µg of the relevant protein was employed, suggesting that they all exhibited lower cooperativity than either gp32(C) or gp32(C)K3A. Notably, however, both gp32(N) and gp32(C)R4T produced significantly less product when only 7.5 µg of protein was used when compared with 15 µg. This contrasted to the situation with the other proteins. On this basis, we suggest that gp32(N) and gp32 (C)R4T possess a similar degree of cooperativity. An earlier study has suggested that gp32K3A and gp32R4Q are of similar cooperativity. However, our data would suggest that gp32(C)R4Q lies somewhere between gp32(C)K3A and gp32(C)R4T with regard to its behaviour in supporting invasion/synthesis.

FIG. 23 shows invasion and extension using uvsX. This experiment addresses whether a C terminal truncated form of the bacteriophage T4 uvsX protein could be used successfully in invasion/extension reactions. Shown are the results of single-sided run-on assays using either the uvsX (C) protein or the uvsX.DELTA.21(C) protein which lacks the 21 C-terminal acidic residues. The reaction solution included 10 mM Mg-acetate, 27 mM phosphocreatine, 1 U creatine kinase, 0.4 µM Tester3bio, 3 mM ATP, 200 µM dNTPs, 50 U Klenow, 1 U chicken myokinase, uvsX(C) or uvsXA21(C), 8.8 µg gp32(N), and 0.5 pmoles RV template. The final volume was 30 µl. The solution was incubated for 2 hours at 37° C., and 2 µl or reaction mixture was loaded onto each lane of the gel. The relationship of the template and oligonucleotides and other experimental conditions are indicated in the figure. Reactions were performed with the indicated quantities of the respective recombinase.

Both recombinases successfully supported invasion/extension. However, under the conditions used here, there appears to be a different optimum for the amount of protein required. In the case of uvsX(C), the rate of invasion/extension increased progressively with the concentration of protein within the range tested. However for the uvsXA21 (C) protein, the rate was inhibited at higher concentration and the overall level of product production was lower under these conditions. In contrast to recA-mediated invasion/extension in similar reactions, uvsX(C), appeared to stimulate multiple invasion/extension events without the need for the addition of polyethylene glycol.

FIG. 24 shows RPA using uvsX(C). In this experiment, uvsX(C) has been combined with gp32(N) in the presence of the oligonucleotides Tester3bio and Sizer2. The template DNA in this experiment was the EcoRV digested plasmid carrying the *E. coli* ruvB gene used in Example 1. The reaction solution included 10 mM Mg-acetate, 27 mM phosphocreatine, 100 ng/µl creatine kinase, 400 nM Tester3bio, 400 nM Sizer2, 3 mM ATP, 200 µM dNTPs, 50 U Klenow fragment, 10 U chicken myokinase, 10 µg (1×) or 20 µg (2×) C-tag uvsX, 8.8 µg gp32(N). Optionally, we included 0.2 mM ADPβS, 10 µg *E. coli* topoisomerase I, 10% PEG 1450, and 10 µg uvsXA21(C). Tester3bio recognised one end of an approximately 300 base pair fragment and included a 5' overhang relative to the end of the target. Sizer2 recognised the other strand of this template and was directed toward an embedded sequence such that its 3' end is about three and a half helical turns from the end of Tester3bio.

In the presence of PEG1450, we observed the amplification of the expected fragment within 2 hours. In the cases where amplification occurred, almost the entire of population of oligonucleotides was consumed indicating an amplification of $3-5 \times 10^4$. The reaction components are indicated. Included in some samples are additional components. We found that 200 µM ADP-β-S slightly increased the amount of product generated under these conditions. Conversely under the conditions used here, addition of *E. coli* toposiomerase I inhibited amplification. Under the conditions used, we detected no amplification with uvsXA21(C) protein. However, no PEG1450 was included in these samples, and uvsX(C) did not amplify either under these conditions without PEG1450.

Figure 25:
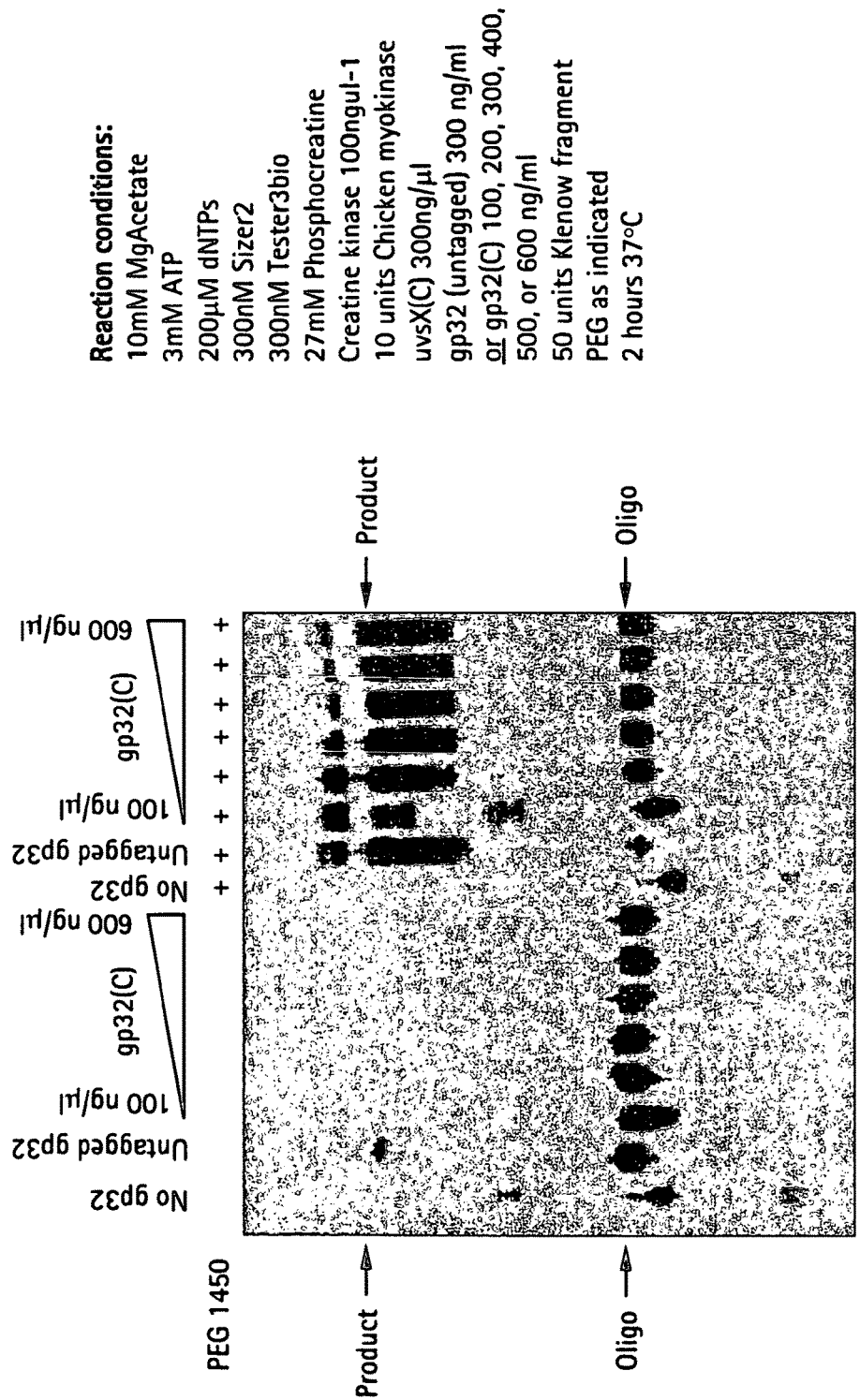
FIG. 25 depicts wild-type versus modified gp32. The modified version of gp32, gp32(C) is qualitatively different to wild-type untagged gp32.

FIG. 25 shows wild-type versus modified gp32. The variant uvsX(C) protein was determined to be qualitatively different to native untagged gp32. The reaction solution included 10 mM Mg-acetate, 27 mM phosphocreatine, 100 ng/µl creatine kinase, 300 nM Tester3bio, 300 nM Sizer2, 3 mM ATP, 200 µM dNTPs, 50 U Klenow fragment, 10 U chicken myokinase, 300 ng/µl uvsX(C), 300 ng/ml gp32 (untagged) or 100, 200, 300, 400, 500, or 600 ng/ml gp32 (C), and PEG as indicated. The reaction was incubated for 2 hours at 37° C. A comparison is shown between amplification reactions performed in the presence of untagged gp32 and a titration of gp32(C), either in the presence or absence of PEG1450. We observed that PEG was required in the reaction for gp32(C) to function, while this is not the case for untagged gp32. However, PEG significantly increased the quantity of product formed during the reaction period in either case. Even in the presence of PEG, untagged gp32 consistently appeared to generate slightly more product than gp32(C) at each point on the titration curve.

Figure 26:
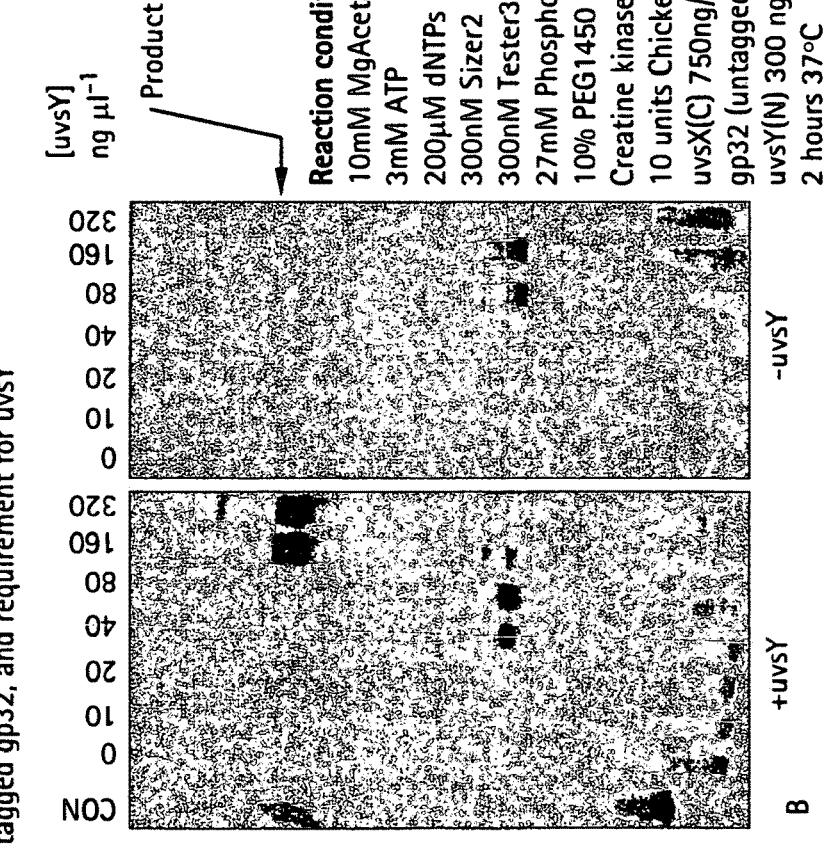
FIG. 26 depicts titration of gp32 and effect of uvsY. Titration of gp32 reveals a requirement for a minimal quantity of gp32, and a requirement for uvsY(N) protein when untagged gp32 is employed.

FIG. 26 shows titration of gp32 and effect of uvsY. Titration of gp32 revealed a requirement for a minimal quantity of gp32, and a requirement for uvsY(N) protein when untagged gp32 was employed. In FIG. 26A, the results of an experiment are shown demonstrating that when untagged gp32 was used, uvsY(N) protein was required for amplification. The reaction solution included 10 mM Mg-acetate, 27 mM phosphocreatine, 100 ng/µl creatine kinase, 300 nM Tester3bio, 300 nM Sizer2, 3 mM ATP, 200 µM dNTPs, 10% PEG1450, 50 U Klenow fragment, 10 U chicken myokinase, 300 ng/µl uvsX(C), 300 ng/µl gp32 (untagged), and uvsY(N) as indicated in the figure. The solution was incubated for 2 hours at 37° C. The uvs(Y) protein operated over a range of concentrations shown here (50 to 300 ng/µl). Other experiments demonstrated that higher quantities inhibited the reaction. Thus, an optimum must be established for any given reaction (probably between 5 and 50 ng/µl).

FIG. 26B shows the results of titrating the untagged gp32 protein in the presence or absence of uvsY(N). The reaction solution included 10 mM Mg-acetate, 27 mM phosphocreatine, 100 ng/µl creatine kinase, 300 nM Tester3bio, 300 nM Sizer2, 3 mM ATP, 200 µM dNTPs, 10% PEG1450, 10 U chicken myokinase, 750 ng/µl uvsX(C), 300 ng/µl gp32 (untagged), and 300 ng/µl uvsY(N). The solution was incubated for 2 hours at 37° C. Once again, there is a requirement for uvsY(N) to achieve amplification. Additionally, this experiment demonstrates a need for a minimal amount of gp32. In this experiment, varying the gp32 concentrations between 80 and 160 ng/µl gp32 resulted in a sharp transition from no amplification to efficient amplification. A simple analysis of known binding site size for gp32, the length of the oligonucleotides, and their concentration, suggested that this rise in concentration would represent a transition from substoichiometric levels of gp32 for the primer, to saturating levels. Consequently, the simplest interpretation is that gp32 saturates the oligonucleotides in order to have excess gp32 in the reaction to collect and stabilise the outgoing strand.

Figure 27:
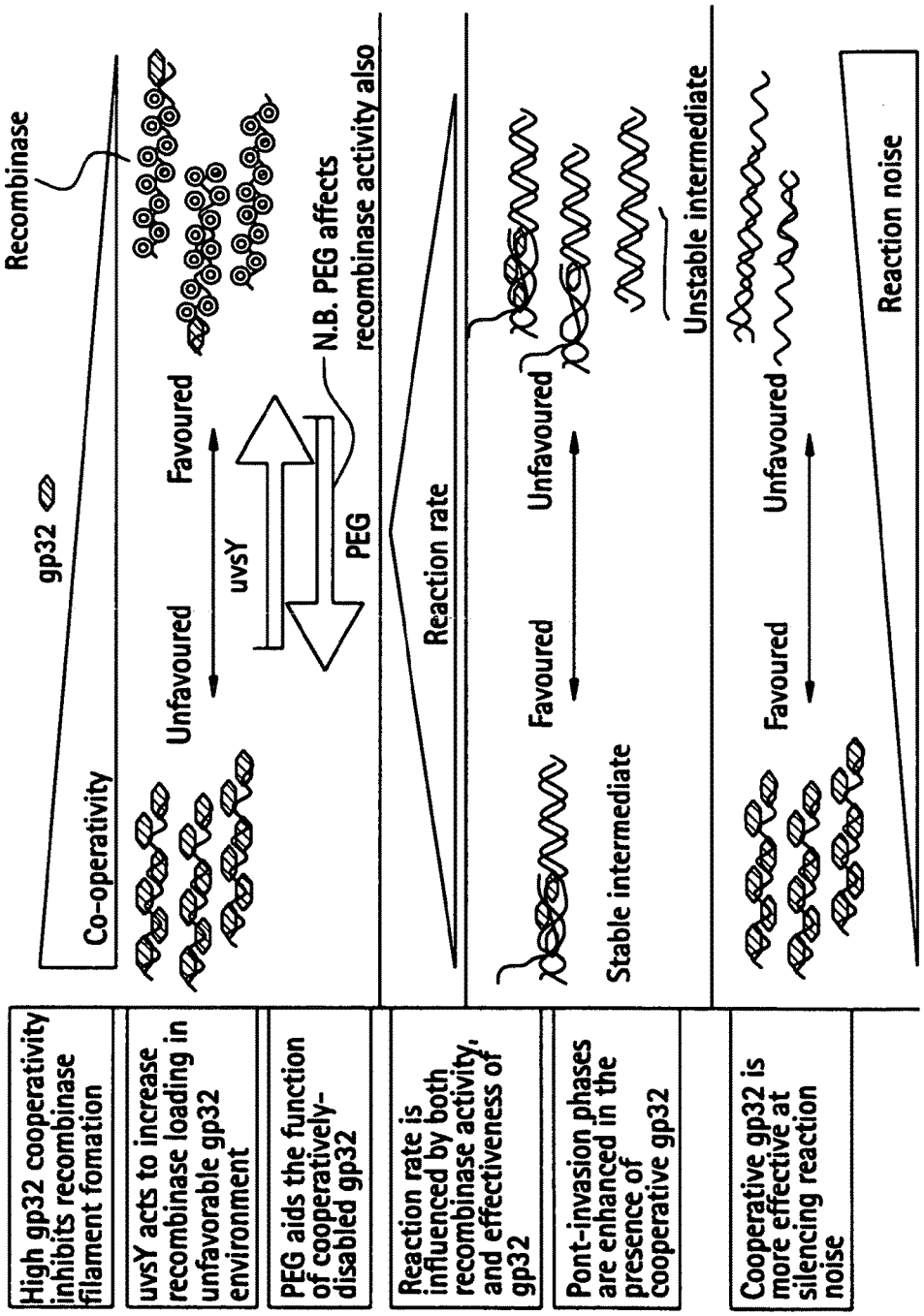
FIG. 27 depicts factors affecting reaction rate and noise. Shown is a schematic representation of the factors affecting reaction behaviour, particularly reaction rate and noise. The predicted effects and interactions of gp32, uvsX, UvsY and PEG are suggested, with the conclusion that an optimal balance between reaction rate and noise must be struck.

FIG. 27 shows factors affecting reaction rate and noise. High gp32 cooperativity inhibits recombinase filament formation (FIG. 27A). In addition, uvsY acts to increase recombinase loading in an unfavorable gp32 environment (FIG. 27B). PEG aids the function of cooperatively-disabled gp32 (FIG. 27C). The reaction rate is influenced by both recombinase activity and effectiveness of gp32 (FIG. 27D). Post-invasion phases are enhanced in the presence of cooperative gp32 (FIG. 27E). Cooperative gp32 is more effective at silencing reaction noise (FIG. 27F).

The predicted effects and interactions of gp32, uvsX, uvsY, and PEG were suggested, with the conclusion that an optimal balance between reaction rate and noise must be reached. The degree of cooperativity of gp32 is indicated across the top of the figure. High cooperativity favoured efficient binding to single-stranded DNA, which prevented significant reaction noise by inhibiting undesirable priming behaviour. High cooperativity also favoured stabilisation of the outgoing strand during recombination and DNA synthesis. Conversely highly cooperative gp32 reduced the abundance of recombinase-loaded searching filaments, and can affect reaction rate considerably.

This behaviour could be partly overcome by including uvsY in the reaction. However, whether this could achieve as high a loading rate as desired is yet to be determined. One could employ modified gp32 proteins that are less cooperative. Also, the cooperativity of gp32 proteins and uvsX proteins can be affected by the inclusion of PEGs. PEG may also have beneficial, or sometimes detrimental, consequences on other components of the reaction such as DNA hybridisation behaviour and polymerase processivity. Optimal rate may be acquired at some position away from either extreme, as indicated, as a balance between recombinase loading and gp32 function may need to be reached.

FIG. 28 shows the effects of PEG. PEG was able to reduce the average length of linear invasion/run-on products in uvsX-mediated linear run-on experiment in the presence of gp32(C). Shown are the results of a linear run-on experiment utilising the Tester3bio oligonucleotide targeted to the end of the approximately 300 base pair EcoRV fragment of E. coli RuvB. This fragment was used throughout the disclosed experiments and is depicted schematically on the right of the figure. Reaction were reconstituted with 8 mg of UvsX(C) in a final reaction volume of 30 ml, in the presence of gp32(C), and in some cases, varying amounts of UvsY(N) or UvsY (C). The reaction solution included 10 mM Mg-acetate, 27 mM phosphocreatine, 1 U creatine kinase, 0.4 µM Tester3bio, 3 mM ATP, 200 µM dNTPs, 50 U Klenow fragment, 1 U chicken myokinase, 8 µg uvsX(C), 7.5 µg gp32(C) or 8.8 µg gp32(N), and 0.5 pmoles template. The final volume was 30 µl. The solution was incubated for 2 hours at 37° C., and 2 µl of the solution was loaded in each lane.

In the absence of PEG, multiple invasion/run-on cycles appear to have occurred on each template, and there was generation of a significant amount full-length product. However, an even greater amount of slightly shorter fragment was produced, which we believe constitute slightly shorter run-ons which may have folded back on themselves and synthesised a short hairpin. We interpreted all bands not full-length as resulting from some form of bona fide invasion/extension reaction that has not achieved full extension. Both UvsY(N) and UvsY(C) stimulate the quantity of product formed to some extent. In the case of no PEG, UvsY(C) seems to be more effective than UvsY(C). This is in contrast to other geometric amplification data we generated, suggesting that only UvsY(N) supported efficient geometric amplification.

Most notably, the inclusion of PEG, in contradiction to findings with E. coli recA, seemed to decrease the overall amount of product on this gel. It also decreased the average length distribution of products. In order to explain this, we suggest that under these conditions the cooperativity of gp32(C), perhaps already at a maximum, cannot be increased by PEG whilst that of UvsX can be. Thus, relatively hyperactive UvsX behaviour results in rapid loading onto the outgoing stand, reinvasion, and efficient 'bubble migration' which chases the newly synthesised strand and displaces it more readily. Consequently, the average product length is significantly reduced.

FIG. 29 shows DNA end directed invasion. The first round of invasion/synthesis using end-targeting and oligonucleotide overhang is illustrated (FIG. 29A). Additional ~10 to 15 residues (5' end) and ~30 residues (3' end) approximate the minimal requirement for strand exchange (FIG. 29B). Invasion occurs, followed by release of the deconstrained outgoing strand, and backfire synthesis (FIG. 29C). Most nucleoprotein filaments that are coated enough to complete strand exchange will catalyze complete and deconstrained release of the outgoing strand (FIG. 29D). Subsequent rounds of invasion/synthesis occur (FIG. 29E). Few or no nucleoprotein filaments can exchange to the end of the target (FIG. 29F). One or no gp32 molecules are provided (FIG. 29G). Following this is recombinase loading (FIG. 29H) and branch migration (FIG. 29I).

This figure describes how targeting oligonucleotides initially possessing an overhang relative to a linear target template might behave during the first and then subsequent attempts to carry out strand exchange. The purpose of this model is to rationalize data suggesting that when such a situation in reconstituted experimentally, there is a significant difference between the first and subsequent invasions. The top of the figure depicts recombinase loaded oligonucleotide filaments, displaying different 5' extents of coverage. The 5 to 3' directional assembly means that most should have coating to the very 3' end. As depicted in the figure, the oligonucleotides all possess a 5' overhang relative to the initial target.

The first invasion event is likely to result in complete release of the outgoing strand as there is a significant likelihood that recombinase will coat the searching oligonucleotide to a further 5' extent than the sequence that will be involved in the strand exchange. Once the outgoing strand is freed, it is topologically unconstrained and can be easily stabilised by single-stranded DNA binding proteins, presumably even those with relatively poor cooperativity. Furthermore, stability is also generated by polymerases extending the 3' end of the duplex DNA to generate the complement to the very 5' end of the targeting oligonucleotide. We refer to this synthesis as backfire synthesis. As a consequence of backfire synthesis any subsequent invasion will be flush with the extended template.

Under these circumstances, most oligonucleotides are not completely coated with recombinase to the their very 5' ends. In some cases, there may be one or more gp32 molecules coating the 5' part of the oligonucleotide. When these oligonucleotides perform strand exchange on the now extended target, the outgoing strand is unlikely to be immediately freed. As a consequence, the event initially resembles the topologically constrained event already depicted in FIG. 6. The model suggests that only if, the cooperativity of the single-stranded DNA binding protein is sufficient will these strained unstable intermediates be able to exist for some limited period. In the bottom part of the figure, we explore what might occur to these unstable intermediates.

In scenario 1, the unexchanged 5' extent of the oligonucleotide undergoes branch migration with the equivalent duplex portion of the target. This could easily lead to complete dissociation of this part of the outgoing strand which would then rapidly rotate to release any stress and be stabilised by single-stranded DNA binding proteins as occurred in the first invasion. These now stable substrates will be ideal and relatively stable assemblies for polymerase elongation. Alternatively, in scenario 2, the single-stranded DNA binding protein disassembles from the outgoing strand and branch migration proceeds in the opposite direction to that in scenario 1, so that the invading DNA is ejected. In scenario 3, the outgoing strand becomes coated with recombinase and re-invades leading to ejection of the oligonucleotide. This process resembles a process described elsewhere as bubble migration. If recombinase loads onto the freed outgoing strand in scenario 1 then bubble migration could also occur. We have experimental data that is most easily reconciled by considering the existence of bubble migration as shown in FIG. 28.

FIG. 30 shows RPA in a complex sample. In this experiment we have examined the sensitivity of RPA, and need for a DNA-end, in an RPA reaction on a complex DNA target. A schematic representation is given of the DNA sequence, which corresponds to part of the human angiotensin converting enzyme (ACE) gene. Three different combinations of primers were used. The experiment used a mixture of uvsX(C), uvsY(N), and gp32(C)K3A. The reaction solution included 10 mM Mg-acetate, 27 mM phosphocreatine, 100 ng/µl creatine kinase; 300 nM Up3 primer; 300 nM Down1, 2, or 3 primer; 3 mM ATP, 200 µM dNTPs, 10% PEG1450, 50 U Klenow fragment, 10 U chicken myokinase, 300 ng/µl uvsX(C), 300 ng/µl gp32(C)K3A, and 50 ng/µl uvsY(N). The final volume was 30 µl. The solution was incubated for 5 hours at 37° C. Reaction products were electrophoretically separated on an acrylamide gel, transferred to a nylon membrane, and probed with a biotinylated oligonucleotide recognising a unique internal sequence.

For the RPA reaction, uncut template (genomic DNA) and cut template were compared, and primer pairs were compared. A fragment of the expected size was detected. In all cases, there was no specific product when no genomic DNA is added to the reaction, but a specific product was generated when DNA (equivalent to roughly 10,000 copies of any sequence) was added. Digestion of the DNA prior to RPA with HpaII resulted in the generation of at least one end overlapping with one of the oligonucleotides, and an increase in signal strength. However, there was not an absolute requirement for HpaII digestion for RPA to occur.

FIG. 31 shows RPA sensitivity. In this experiment, we have examined the sensitivity in an RPA reaction on a complex DNA target. A schematic representation is given of the DNA sequence, which corresponds to part of the human angiotensin converting enzyme (ACE) gene. Three different combinations of primers were used. The experiment used a mixture of uvsX(C), uvsY(N), and gp32(C)K3A. The reaction solution included 10 mM Mg-acetate, 27 mM phosphocreatine, 100 ng/µl creatine kinase; 300 nM Up3 primer; 300 nM Down1, 2, or 3 primer; 3 mM ATP, 200 µM dNTPs, 10% PEG1450, 50 U Klenow fragment, 10 U chicken myokinase, 300 ng/µl uvsX(C), 300 ng/µl gp32(C)K3A, and 50 ng/µl uvsY(N). The final volume was 30 µl. The solution was incubated for 5 hours at 37° C., and probe ACE-hyb was used. Reaction products were electrophoretically separated on an acrylamide gel, transferred to a nylon membrane, and probed with a biotinylated oligonucleotide recognising a unique internal sequence. A fragment of the expected size was detected. In all cases, there was no specific product when no genomic DNA is added to the reaction, but a specific product was generated when sufficient DNA was added. In all cases, 1000 copies were sufficient to generate a significant signal, and in one case we could detect a very faint signal at 100 copies.

FIG. 32 shows RPA sensitivity and template independent artifacts. The results of an experiment are shown in which we have investigated the sensitivity in an RPA reaction on a complex DNA target. A schematic representation is given of the DNA sequence, which corresponds to part of the human angiotensin converting enzyme (ACE) gene. A time course of the amplification was performed taking reaction samples at 1, 2 and 3 hours. Reaction products were detected by virtue of the presence of a biotin residues attached to the 5' end of one of the oligonucleotides used in the amplification. In this way, it was possible to visualize all the reaction products involving this oligonucleotide, including any artifacts that might arise. We tested several different concentrations of the uvsY(N) protein. The reaction solution included 10 mM Mg-acetate, 27 mM phosphocreatine, 100 ng/µl creatine kinase; 300 nM Up3 primer; 300 nM Down1 primer; 3 mM ATP, 200 µM dNTPs, 10% PEG1450, 50 U Klenow fragment, 10 U chicken myokinase, 300 ng/µl uvsX(C), 300 ng/µl gp32(C), and 50 ng/µl uvsY(N). The final volume was 30 µl. The solution was incubated for 5 hours at 37° C. At an uvsY(N) concentration of 50 ng/µl, we detected the correct product directly, albeit faintly, after 3 hours of incubation. During this period there was an accumulation of strong bands of roughly twice the length of the oligonucleotide, which accumulated similarly in the template minus sample. These were most likely to be primer artifacts.

Figure 33:
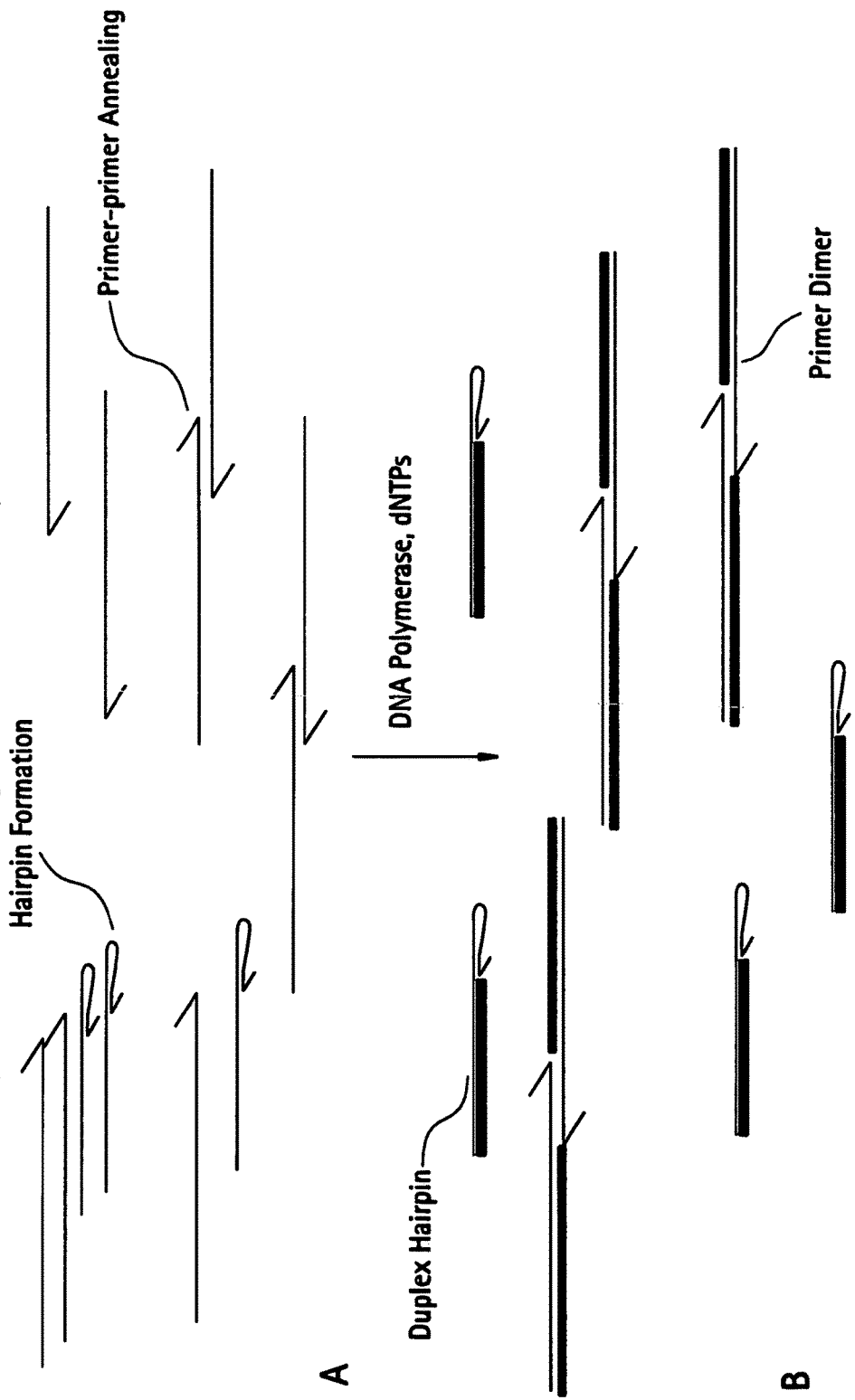
FIG. 33 depicts how primer artifacts may arise. Shown is a schematic representation of the possible mechanism by which primer artifacts may arise.

FIG. 33 shows how primer artifacts may arise. Primer artifacts likely initiate by erroneous self-priming events as depicted here. Primers may form hairpins, as occurs in FIG.

33A, or hybridise to a second primer, as occurs in FIG. 33B. If a polymerase can extend such a hairpin a significant stretch of double-stranded DNA may be formed, as seen in A* and B*. These structures might become targets for other recombinase-loaded filaments, titrate active filaments from bona fide targets, and possibly enter into geometric forms of amplification themselves.

Figure 34:
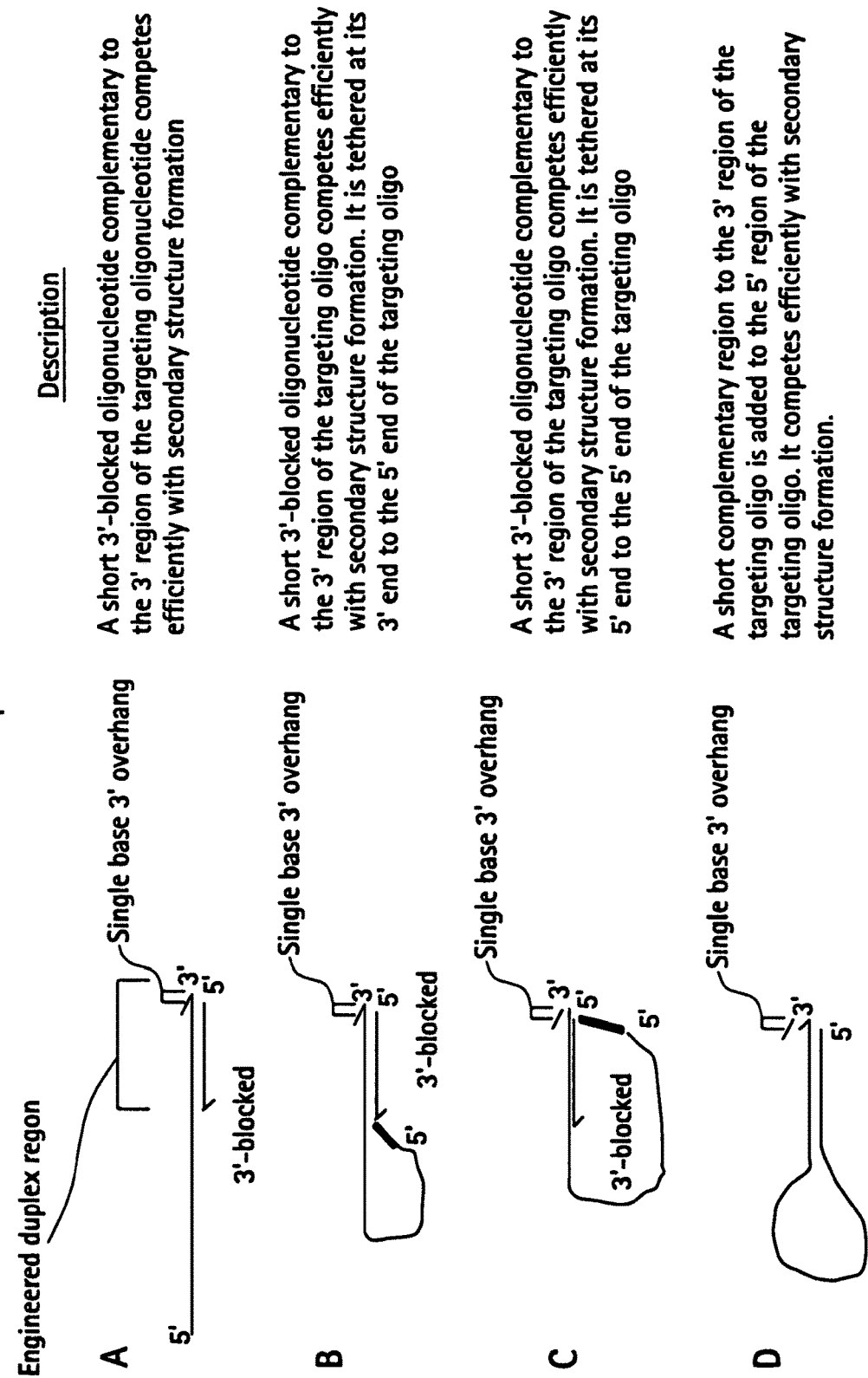
FIG. 34 depicts primer artifact suppression. Shown in schematic are methods to suppress primer artifacts.

FIG. 34 shows primer artifact suppression. Depicted schematically are several strategies to suppress primer artifact noise. In FIG. 34A, a second short, 3'-blocked oligonucleotide complementary to the 3' sequences of the targeting oligonucleotide is included in the reaction to compete for the formation of secondary structure formation that might result in erroneous priming. In FIGS. 34B and 34C, a similar short blocked oligonucleotide is employed as in (A), but in this case a covalent bridge is engineered between the 5' end of the targeting oligonucleotide and the 5', or 3', end of the competing short primer. In this way, the blocked nucleotide is tethered at its 5' end to the 5' end of the targeting oligonucleotide (FIG. 34A-B) In FIG. 34D, a short sequence complementary to the 3' region of the targeting oligonucleotide is added to the 5' region of the targeting oligonucleotide. It competes efficiently with secondary structure formation.

FIG. 35 shows use of hairpin oligonucleotides to stimulate self-priming of displaced strands. Depicted is a scheme showing how oligonucleotides whose design includes a 5' section with perfect complementarity to the 3' section might be used to stimulate amplification through self-priming. At the top of the diagram is shown a target DNA, designated A, which has distinct ends which are targets for one of the two targeting oligonucleotides shown in the upper left and right of the figure. Both of these oligonucleotides possess complementarity between their 5' and 3' regions as indicated by short arrows. The target, A, would likely have been generated by earlier invasion/elongation events involving these oligonucleotides and an initial target lacking the 5'-most regions of these oligonucleotides. On the left or right side of the figure we follow the outcome of invasion/elongation events initiated by targeting by the left or right primers respectively. The outcome is similar in both cases, albeit the final products are arranged slightly differently.

Focusing on the left side of the figure we observe that when target A is subject to invasion and elongation with the left primer the result is formation of a new duplex identical to A and a single-stranded DNA equivalent to the top strand of the initial target, designated B. Due to the presence of the complementarity between the very 3' region and adjacent sequences, B is capable of forming a hairpin which will prime DNA synthesis to generate a largely double-stranded product C. The product C can readily be targeted once again by the left oligonucleotide. However, in this case, no single-stranded displaced strand is formed. Instead, product D is formed with a length that is roughly twice that of the original target. This product is an inverted repeat and contains two sequences that are targets for the left oligonucleotide, and one for the right oligonucleotide located in the middle.

Subsequent invasion/elongation events, and the possible occurrence of hybridisation events between displaced strands, could easily lead to such 'dimeric' species becoming further enlarged, and the formation generally of more complex products. A similar course of events is shown on the right side of the figure, this time initiated by invasion/elongation by the right primer. The final dimeric product, D', is not equivalent to D as the two end sequences are targets for the right primer, and the central region is a target for the left primer. Processes similar or identical to those shown here are likely to occur with some frequency under some conditions even in the absence of the deliberate design of oligonucleotides to promote it, as there is often some limited capacity for self-priming of single-stranded DNAs.

FIG. 36 shows conditions that support the amplification of DNA with little or no primer artifacts. The results of an experiment are shown in which we have investigated the sensitivity of an RPA reaction on a complex DNA target. A schematic representation is given of the DNA sequence, which corresponds to part of the human angiotensin converting enzyme (ACE) gene. Oligonucleotides used are the biotinylated Angio1bio primer and the unbiotinylated Angio3 primer whose sequence is given in the experimental methods. These primers amplified a 132 bp double-stranded DNA fragment. Uncut human genomic DNA was titrated from 45 copies up to 2880 copies. Reaction products were detected by virtue of the presence of a biotin residue attached to the 5' end of one of the oligonucleotides used in the amplification. In this way, it was possible to visualize all the reaction products involving this oligonucleotide, including any artifacts that might arise.

The reaction was incubated for 2 hours at 37° C. in the case of the Klenow exo-, and 2 hours at 42° C. in the case of the Bst polymerase. The reaction included the following: 50 ng/µl uvsY(N), 300 ng/µl gp32(C), 100 ng/µl uvsX(C), 20 mM phosphocreatine, 3 mM ATP, 25 milliunits/µl myokinase, 100 ng/µl creatine kinase, 200 µM dNTPs, 5% w/v PEG compound, 300 nM Angio1bio primer, 300 nM Angio3 primer, 800 ng/µl Klenow exo- or 1.2 units/µl Bst polymerase. The Klenow-mediated amplification was performed in U2 buffer comprising a final composition of 20 mM Tris acetate pH 7.9, 8 mM magnesium acetate, 120 mM potassium acetate. The Bst polymerase-mediated amplification was performed in U1 buffer comprising a final composition of 20 mM Tris acetate pH 7.5, 6 mM magnesium acetate, 100 mM potassium acetate.

Example 13

DNA Amplification for Point-of-Use Applications

Clones and proteins were produced as described in Example 11, above.

DNAs Used in RPA Reactions

Figure 39:
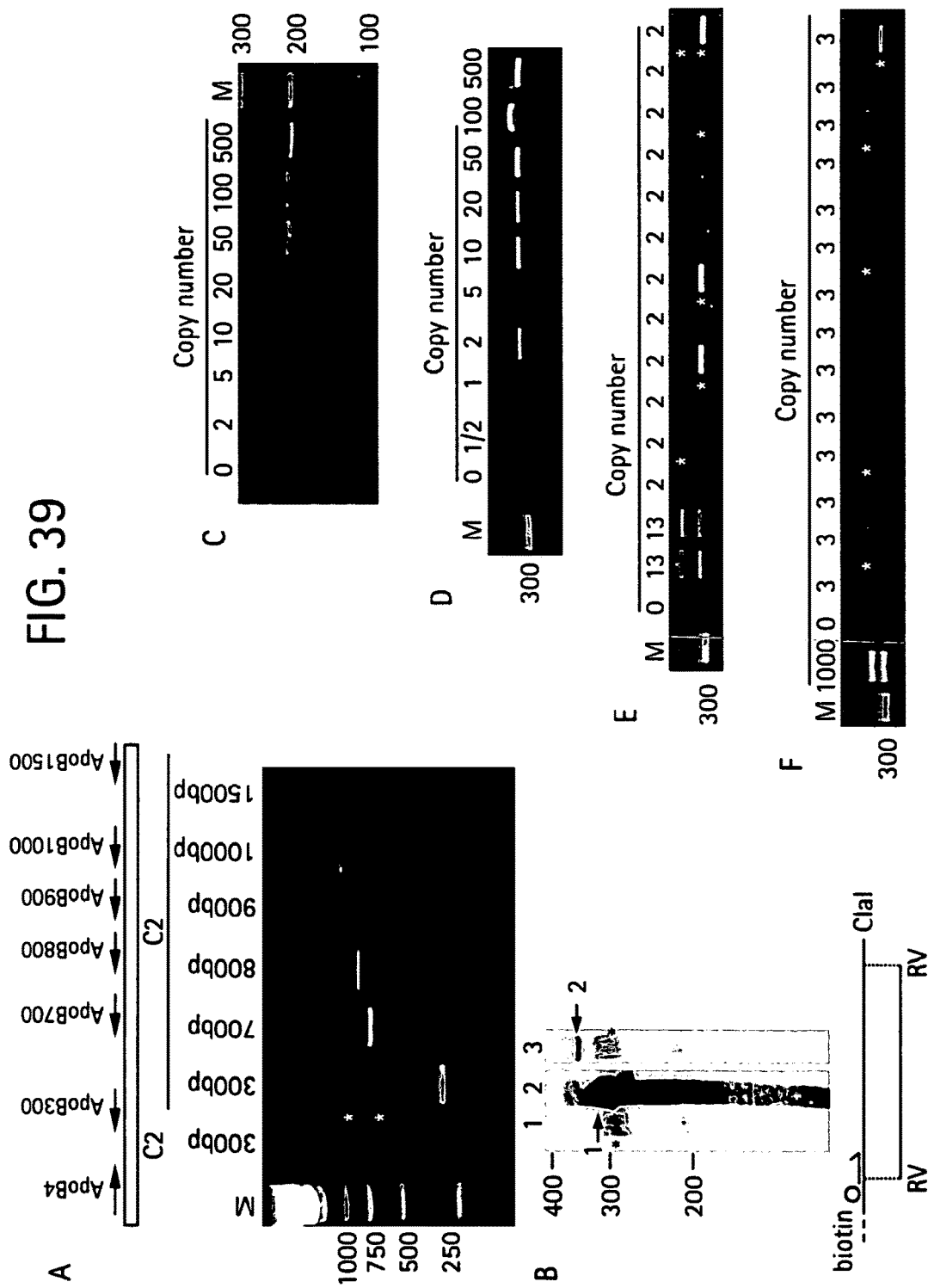
FIG. 39 depicts (A) Size limits of RPA reactions; (B) Elongation efficiencies from embedded or end sequences; (C) Sensitivity of RPA reactions; (D) Human DNA of the indicated copy number amplified with primers ApoB4 and Apo300 generating a 300 bp fragment using conditions C2; (E,F) Human DNA from single individuals amplified with primers D18S51 5' and 3'. Conditions employed were C2 in (E), and C4 in (F).

We have employed several different target DNAs in this study, and a number of oligonucleotides. The sequence of the oligonucleotides is given below, and the template target in the experiment shown in FIG. 39B. The E. coli RuvB gene target was used for linear run-on assay (FIG. 39B). Identical quantities of plasmid template containing this fragment were cut either with EcoRV, releasing a roughly 300 bp fragment, or with ClaI which linearises the DNA. Equal molar quantities of template were used in the run-on experiments (20 nM each template). The sequence of a KpnI/ClaI fragment of this template is given below. The EcoRV fragment is embedded within this sequence, and the sites are highlighted.

```
                                      (SEQ ID NO: 18)
GGTACCACTTTGCCGGAAGATGTAGCAGATCGCGCCATTCGCCCCAAATT

ACTGGAAGAGTATGTTGGTCAGCCGAGGTTCGTTCACAGATGGAGATTTT

CATCAAAGCAGCGAAACTGCGCGGCGATGCCCTCGATCATTTGTTGATTT

TTGGTCCTCCGGGGTTGGGTAAAACTACGCTTGCCAACATTGTCGCCAAT
```

-continued

```
GAAATGGGCGTTAATTTACGCACGACTTCTGGTCCGGTGCTGGAAAAGGC

GGGCGATTTGGCTGCGATGCTCACTAACCTTGAACCGCATGACGTGCTGT

TTATTGATGAGATCCACCGTCTATCGCCAGTTGTTGAAGAAGTGCTGTAC

CCGGCAATGGAAGACTACCAACTGGATATCATGATTGGTGAAGGTCCGGC

GGCACGCTCCATTAAAATTGATTTGCCGCCGTTTACCCTGATTGGTGCAA

CCACGCGCGCAGGTTCGCTGACATCACCGTTGCGCGACCGTTTTGGTATT

GTGCAACGTCTGGAGTTTTATCAGGTGCCGGATCTGCAATATATCGTCAG

TCGCAGCGCACGCTTTATGGGGCTTGAGATGAGTGATGACGGCGCGCTGG

AAGTTGCTCGTCGCGCTCGCGGTACGCCGCGCATTGCCAACCGTCTGCTG

CGTCGAGTGCGTGATTTCGCCGAAGTGAAGCACGATGGCACCATCTCGGC

AGATATCGCTGCTCAGGCGCTGGATATGTTGAATGTCGATGCTGAAGGTT

TCGATTATATGGACCGCAAATTGTTGCTGGCGGTAATCGAT
```

Oligonucleotide Tester3bio sequence. Bases homologous to the target are in bold.

```
                                        (SEQ ID NO: 19)
5'biotin-CTCACTATACCTCAGCATCATGATTGGTGAAGGTCCGGC
GG CAC
```

Human DNAs

We have used human genomic DNAs from several sources. A mixed population male genomic DNA from Promega was utilised. Also, DNA from individual male samples was studied in FIG. 38A. Individual 1 and 2 were father and son. Individual 2 DNA was used in the experiment in FIG. 39E, while DNA for the experiment in FIG. 39F was another male individual. Sequences of oligonucleotides used for amplifying human and *B. subtilis* sequences are as follows:

Corresponding to the Human ApolipoproteinB Locus:

```
ApoB4
                                        (SEQ ID NO: 20)
5' CAGTGTATCTGGAAAGCCTACAGGACACCAAAA 3'

Apo300
                                        (SEQ ID NO: 21)
5' TGCTTTCATACGTTTAGCCCAATCTTGGATAG 3'

Apo700
                                        (SEQ ID NO: 22)
5' TGGTAAACGGAAGTCTGGCAGGGTGATTCTCG 3'

Apo800
                                        (SEQ ID NO: 23)
5' CAATTGTGTGTGAGATGTGGGAAGCTGGAAT 3'

Apo900
                                        (SEQ ID NO: 24)
5' GAGGTGGTTCCATTCCCTATGTCAGCATTTGC 3'

Apo1000
                                        (SEQ ID NO: 25)
5' GGGTTTGAGAGTTGTGCATTTGCTTGAAAAT 3'

Apo1500
                                        (SEQ ID NO: 26)
5' TTGAATTTCAAGTTTAGAAAAGTTGAGGGAGCCAG 3'
```

Corresponding to the Human SRY Locus:

```
SRY3
                                        (SEQ ID NO: 27)
5' AAAGCTGTAACTCTAAGTATCAGTGTGAAAC 3'

SRY4
                                        (SEQ ID NO: 28)
5' GTTGTCCAGTTGCACTTCGCTGCAGAGTACC 3'
```

Corresponding to *B. subtilis* Genomic DNA:

```
BSA1
                                        (SEQ ID NO: 29)
5' TTGGGCACTTGGATATGATGGAACTGGCAC 3'

BSA3
                                        (SEQ ID NO: 30)
5' ACAGAAAGCTATTAAAGCAACTGACGGTGTGG 3'

BSB3
                                        (SEQ ID NO: 31)
5' CCATCTTCAGAGAACGCTTTAACAGCAATCC 3'
```

Human STR Marker Primers:

```
CSF1PO
                                        (SEQ ID NO: 32)
5' GTTGCTAACCACCCTGTGTCTCAGTTTTCCTAC

CSF1PO
                                        (SEQ ID NO: 33)
3' AGACTCTTCCACACACCACTGGCCATCTTCAGC

D7S820
                                        (SEQ ID NO: 34)
5' GAACACTTGTCATAGTTTAGAACGAACTAACG

D7S820
                                        (SEQ ID NO: 35)
3' GAATTATAACGATTCCACATTTATCCTCATTGAC

D13S317
                                        (SEQ ID NO: 36)
5' TTGCTGGACATGGTATCACAGAAGTCTGGGATG

D13S317
                                        (SEQ ID NO: 37)
3' CCATAGGCAGCCCAAAAAGACAGACAGAAAGA

D16S539
                                        (SEQ ID NO: 38)
5' AAACAAAGGCAGATCCCAAGCTCTTCCTCTTCC

D16S539
                                        (SEQ ID NO: 39)
5' ATACCATTTACGTTTGTGTGTGCATCTGTAAGC

D18S51
                                        (SEQ ID NO: 40)
5' GGTGGACATGTTGGCTTCTCTCTGTTCTTAAC

D18S51
                                        (SEQ ID NO: 41)
3' GGTGGCACGTGCCTGTAGTCTCAGCTACTTGC

THO1
                                        (SEQ ID NO: 42)
5' TACACAGGGCTTCCGGTGCAGGTCACAGGGA

THO1
                                        (SEQ ID NO: 43)
3' CCTTCCCAGGCTCTAGCAGCAGCTCATGGTGG
```

-continued

TPDX
(SEQ ID NO: 44)
5' ACTGGCACAGAACAGGCACTTAGGGAACCC

TPDX
(SEQ ID NO: 45)
3' GGAGGAACTGGGAACCACACAGGTTAATTA

Timecourse Experiment:

APOB600
(SEQ ID NO: 46)
GCTCACTGTTCTGCATCTGGTCAATGGTTCTG

APOB300REV
(SEQ ID NO: 47)
CTATCCAAGATTGGGCTAAACGTATGAAAGCA

Shorter Oligonucleotide Experiment:

APOB500
(SEQ ID NO: 48)
ATGGTAAATTCTGGTGTGGAAAACCTGGATGG

APO500-28
(SEQ ID NO: 49)
TAAATTCTGGTGTGGAAAACCTGGATGG

APO500-25
(SEQ ID NO: 50)
ATTCTGGTGTGGAAAACCTGGATGG

APOB300REV
(SEQ ID NO: 51)
CTATCCAAGATTGGGCTAAACGTATGAAAGCA

APOB300REV-28
(SEQ ID NO: 52)
CCAAGATTGGGCTAAACGTATGAAAGCA

APOB300REV-25
(SEQ ID NO: 53)
AGATTGGGCTAAACGTATGAAAGCA

D18S51
(SEQ ID NO: 54)
5' GGTGGACATGTTGGCTTCTCTCTGTTCTTAAC

D18S51
(SEQ ID NO: 55)
5-28 GACATGTTGGCTTCTCTCTGTTCTTAAC

D18S51
(SEQ ID NO: 56)
5-25 ATGTTGGCTTCTCTCTGTTCTTAAC

D18S51
(SEQ ID NO: 57)
3' GGTGGCACGTGCCTGTAGTCTCAGCTACTTGC

D18S51
(SEQ ID NO: 58)
3'-28 GCACGTGCCTGTAGTCTCAGCTACTTGC

D18D51
(SEQ ID NO: 59)
3'-25 CGTGCCTGTAGTCTCAGCTACTTGC

SRY3
(SEQ ID NO: 60)
AAAGCTGTAACTCTAAGTATCAGTGTGAAAC

SRY3-28
(SEQ ID NO: 61)
GCTGTAACTCTAAGTATCAGTGTGAAAC

SRY3-25
(SEQ ID NO: 62)
GTAACTCTAAGTATCAGTGTGAAAC

SRY4
(SEQ ID NO: 63)
GTTGTCCAGTTGCACTTCGCTGCAGAGTACC

SRY4-28
(SEQ ID NO: 64)
GTCCAGTTGCACTTCGCTGCAGAGTACC

SRY4-25
(SEQ ID NO: 65)
CAGTTGCACTTCGCTGCAGAGTACC

Conditions of standard RPA reactions included: 50 mM Tris pH 8.4, 80 mM Potassium acetate, 10 mM Magnesium acetate, 1 mM DTT, 5% PEG compound (Carbowax-20 M), 3 mM ATP, 20 mM Phosphocreatine, 100 ng/µl Creatine kinase, 600 ng/µl gp32; 109 ng/µl, or 125 ng/µl, or 200 ng/µl uvsX; 16 ng/µl, or 25 ng/µl, or 40 ng/µl, or 60 ng/µl uvsY; 20 ng/µl Bsu polymerase, 200 µM dNTPs, and 300 nM each oligonucleotide. Reaction conditions C1-C4 are as above with: C1=109 ng/µl uvsX, 16 ng/µl usvY; C2=125 ng/µl uvsX, 25 ng/µl uvsY; C3=200 ng/µl uvsX, 40 ng/µl uvsY; C4=200 ng/ml uvsX, 60 ng/µl uvsY.

Experimental Results

Figure 37:
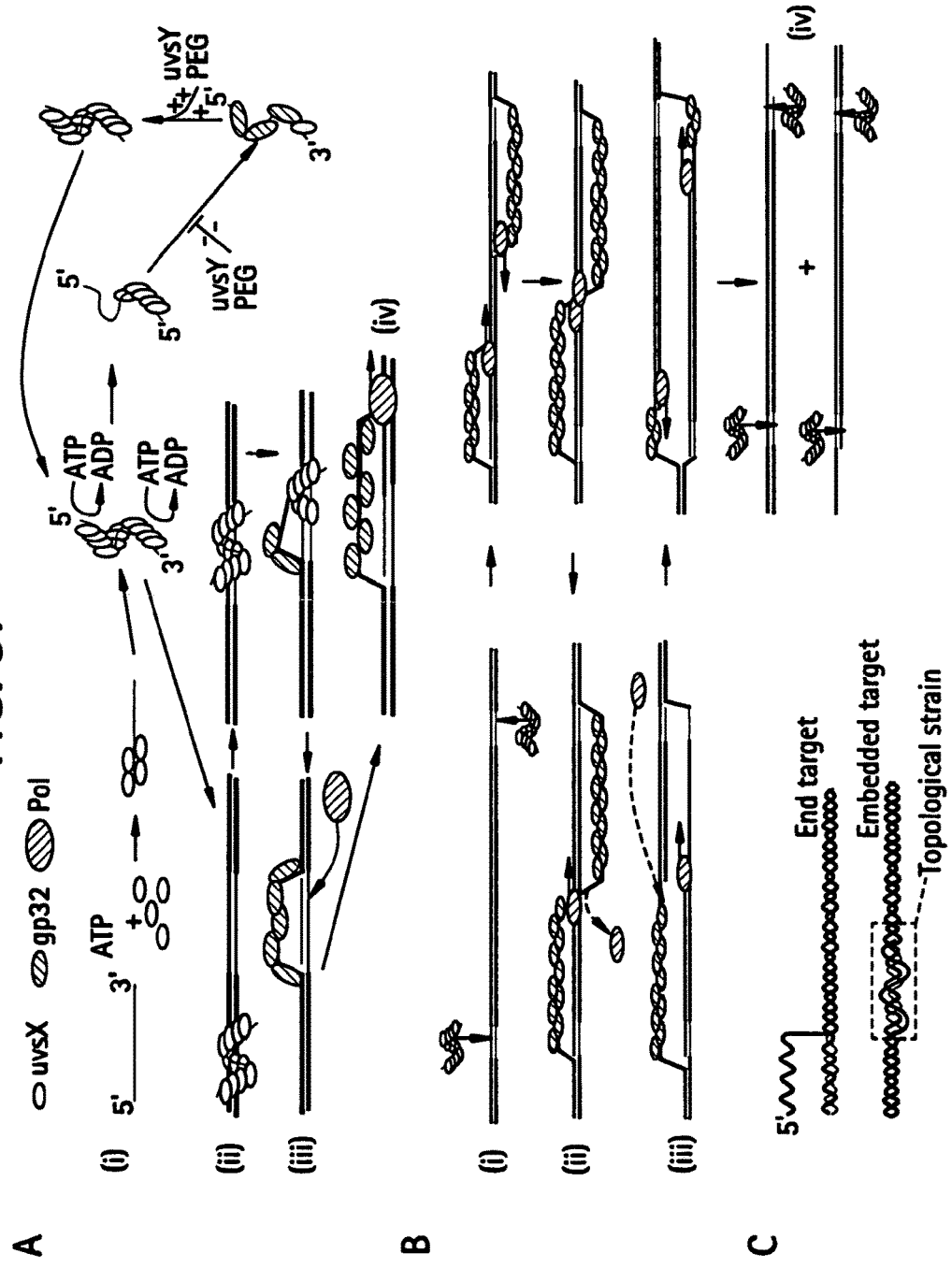
FIG. 37 depicts a schematic representation of RPA method as shown in (A), (B), and (C).

FIG. 37 shows a schematic representation of RPA method. In FIG. 37A(i), Recombinase protein uvsX binds cooperatively to single-stranded oligonucleotides in the presence of ATP. Nucleoprotein filaments actively hydrolyse ATP to ADP. Spontaneous disassembly can lead to competitive binding of single stranded binding protein gp32, this being deterred and reloading aided by uvsY protein and polyethylene glycol. In FIG. 37A(ii), recombinase filaments catalyse strand exchange if homologous DNA is detected. In FIG. 37A(iii), strand exchange matches the searching strand with its complement and displaces a strand then bound by gp32. Recombinase disassembles. In FIG. 37A(iv), polymerases access the structure and extend the oligonucleotide, displacing more of the original strand. In FIG. 37B(i), two opposing targeting nucleoprotein complexes recombine with their respective targets and DNA synthesis is initiated. In FIG. 37B(ii), polymerase complexes encounter one another and one of the polymerases dissociates. In FIG. 37B(iii), the remaining polymerase continues synthesis freeing the two parent strands, a polymerase re-binds to the free 3'-end thus replication of both strands occurs. In FIG. 37B(iv), new targeting events occur. In the second round one targeting primer will displace a free end. In FIG. 37C, comparison of the products of strand exchange at a DNA end or at an embedded DNA sequence.

FIG. 38A shows the results of amplification of STR markers from two individuals (1 and 2, father and son) using primer pairs for seven independent markers. RPA conditions C4 were employed (see above). FIG. 38B=shows titration of reaction components to determine concentrations that support in vitro amplification. Reactions included the primers SRY3 and SRY4 at 0.3 µM (targeting the SRY gene), 80 mM potassium acetate, 50 mM TrisCl pH 8.4, 2 mM DTT, 5% Carbowax-20M, 200 ng/µl uvsX, 60 ng/µl uvsY, 600 ng/µl gp32, 20 ng/µl Bsu polymerase, and 50 copies/µl Y chromosomal DNA, except when a given component was that under investigation. Optimal quantities of gp32, ATP, uvsX, uvsY, PEG, and Bsu polymerase for effective amplification of this particular product were determined. ATP-γ-S and ADP-β-S inhibited the reactions.

FIG. 39A shows the size limits of RPA reactions. Primer ApoB4 was combined with opposing primers capable of generating amplified products of the indicated sizes. Conditions of 125 ng/μl uvsX and 25 ng/μl uvsY (C2) were employed except C1 where 109 ng/μl uvsX and 16 ng/μl uvsY were used; 15 copies/μl human DNA were used (30 μl reactions). Under conditions C2, some hairpin-mediated product duplication occurred converting some of the 300 bp amplicon to 2× and 3× unit length (*) (L. D. Harris, J. D. Griffith, J Mol Biol 206, 19-27 (Mar. 5, 1989)).

FIG. 39B shows elongation efficiencies from embedded or end sequences. A biotinylated primer was incubated with linearized plasmid DNA. Equal quantities (20 nM final) of templates linearized with either ClaI (lane 3) or EcoRV (lanes 1 and 2) were used, the primer either overlapping the cut end, or the target site being embedded (lane 3). Incubation with recombinase targeting components with (lanes 2 and 3) or without (lane 1) Klenow reveals limited elongation from the embedded site (product 1*), and abundant elongation from the end site (product 2*). Electrophoresed products were transferred to nylon and biotin detected by chemiluminescence. The weak common band (~300 bp, lanes 1 and 3) was an artifact arising from this particular protocol.

FIG. 39C shows the sensitivity of RPA reactions. The indicated copy number of *B. subtilis* genomes was amplified with oligonucleotides BsA1 and BsB3, which amplify a 200 bp fragment. Conditions C1 were employed. FIG. 39D shows human DNA of the indicated copy number amplified with primers ApoB4 and Apo300 to generate a 300 bp fragment. Conditions C2 were employed. FIG. 39E, F show results from human DNA from single individuals. The DNA was diluted and samples theoretically containing the indicated copy number were amplified with primers D18S51 5' and 3' which amplify an STR of size ~300-360 bp. At predicted copy numbers of 2 or 3, a number of samples amplified single alleles (*). Conditions employed were C2 in (E), and C4 in (F).

Figure 40:
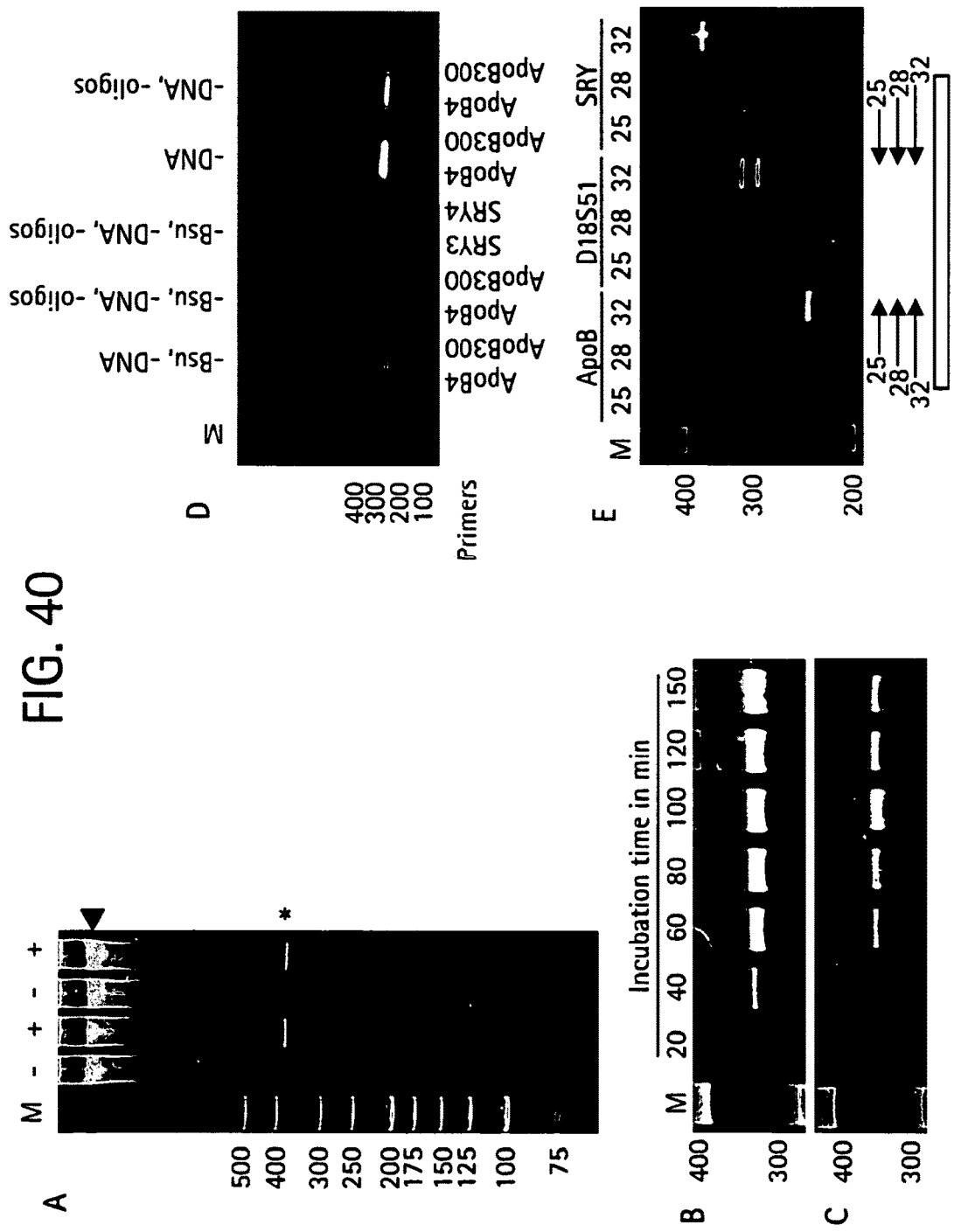
FIG. 40 depicts specificity of RPA reactions for: (A) Primers BsA3 and BsB3, which amplify a 380 bp fragment using conditions C3. An asterisk indicates the position of the expected reaction product, and an arrow indicates the position of the genomic DNA; (B,C) Oligonucleotides Apo600bio and Apo300rev which generate a 345 bp fragment using conditions C4; (D) Mixtures of reaction components assembled in the absence of the indicated components, PEG and buffer. Primers used are indicated. Target DNA was human male genomic DNA at 150 copies/µl; (E) Oligonucleotides targeting three independent loci in human genomic DNA incubated with overlapping primer pairs of 25, 28, or 32 bases as indicated.

FIG. 40 shows specificity of RPA reactions. Primers BsA3 and BsB3, which amplify a 380 bp fragment from *B. subtilis* genomic DNA were incubated with 1 μg of human DNA, with (+) or without (−) addition of 100 copies of *B. subtilis* DNA (FIG. 40A). An asterisk indicates the position of the expected reaction product, and an arrow indicated the position of the genomic DNA. Conditions C3 were employed. To investigate how long it takes RPA to generate detectable reaction products a series of amplification reactions were established with oligonucleotides Apo600bio and Apo300rev generating a 345 bp fragment. A copy number of 60 copies/μl (FIG. 40B) or 6 copies/μl (FIG. 40C) were used. Individual reactions were stopped at the indicated number of minutes and analysed on a gel. Conditions C4 were employed (FIG. 40D).

For long-term storage of reaction components we lyophilised RPA reactions. Mixtures of reaction components were assembled in the absence of the indicated components, PEG and buffer. The material was freeze-dried, and then reconstituted with PEG and buffer plus the additional omitted components. Primers used are indicated. All components apart from PEG and buffer could be lyophilised and successfully reconstituted in a functional reaction. Target DNA was human male genomic DNA at 150 copies/μl (FIG. 40E). Oligonucleotides targeting three independent loci in human genomic DNA were incubated with overlapping primer pairs of 25, 28, or 32 bases as indicated. Only the primers of 32 bases in length successfully amplified targets. Other experiments show that primers of 30 residues are also effective at amplifying target DNAs.

FIG. 41 shows primer noise at low target copy number. Two primers, BsA1 and BsB3 (BsA1-5'TTGGGCACT-TGGATATGATGGAACTGGCAC3' (SEQ ID NO:29), BsB3—5'CCATCTTCAGAGAACGCTTTAACAG-CAATCC3' (SEQ ID NO: 31), which flank a roughly 300 bp fragment of the *Bacillus subtilis* genome were incubated with *B. subtilis* genomic DNA serially diluted with water. Conditions used were 80 mM Potassium acetate, 50 mM Tris.Cl pH 8.4, 2 mM DTT, 5% Carbowax 20M, 200 μM dNTPS, 3 mM ATP, 20 mM Phosphocreatine, 50 ng/μl creatine kinase, 300 nM each oligonucleotide, 800 ng/~1 gp32, 120 ng/μl uvsX, 25 ng/μl uvsY, and 28 ng/μl Bsu polymerase. The reaction was incubated for 90 minutes at 37° C. Products were separated on a 2.5% agarose gel and stained with ethidium bromide. Arrows indicate the expected position of the correct amplicon.

FIG. 42 details the selection of optimal primers by combining a selection of candidate forward and reverse primers and testing the outcome at very low start copy densities.

Several primer pairs were designed to sequences in the *Bacillus subtilis* sporulation locus SpoOB. The position and orientation of these primers is indicated in (B) as the following:

```
J1
                                              SEQ ID NO: 66
ACGGCATTAACAAACGAACTGATTCATCTGCTTGG

J2
                                              SEQ ID NO: 67
ATAACCATTTCTTCAATCATTTCAAAGACACGGTC

K1
                                              SEQ ID NO: 68
TATAGACGCAAAGCACGAATCAAAGCTCTCAAACC

K2
CCTTAATTTCTCCGAGAACTTCATAT-residues 1-26 of
SEQ ID NO: 69

L1
                                              SEQ ID NO: 70
ATATGAAGTTCTCGGAGAAATTAAGGATTTGTCGG

L2
                                              SEQ ID NO: 71
AATCAGCTGTCTGTCAGGATGATCCGTTTGAAGCG-

NEST1
                                              SEQ ID NO: 72
CATTAACAAACGAACTGATTCATCTGCTTGG

NEST2
                                              SEQ ID NO: 73
ACAGATGAAACAGCTTTCTCATCAGTTTCG.
```

These primers were combined as indicated in (A), and incubated for 90 minutes under the following conditions: 80 mM Potassium acetate, 50 mM Tris.Cl pH 8.4, 2 mM DTT, 5% Carbowax 20M, 200 μM dNTPS, 3 mM ATP, 20 mM Phosphocreatine, 50 ng/μl creatine kinase, 300 nM each oligonucleotide, 800 ng/μl gp32, 120 ng/μl uvsX, 25 ng/μl uvsY, and 28 ng/μl Bsu polymerase, .about.2 copies/μl *B. subtilis* genomic DNA (estimated by serial dilution), 37° C. Arrows indicated the position of products determined to be the expected fragment based on size. Some primer pairs give product, but it was accompanied by smearing, or some additional bands. A few combinations fail to give product of the expected size. The primer J1 and K2 give a significant amount of the product of the expected size, and rather cleanly. Interestingly when NEST1 primer, lacking the 4 5'-most bases present in J1, replaces J1 in the equivalent reaction, the reaction is not improved indicating that adding as well as removing bases may improve primer performance even when all tested are over 30 residues in length.

FIG. 43 shows a theoretical consideration of how primer noise initiates.

(A) An oligonucleotide is shown, and above it is an arrow, the head indicating the 3'-end of the oligonucleotide. The sequence was generated arbitrarily, although 4 of the 5 most 3' bases form a palindrome, which might well be avoided in practice. (B) It is assumed that most initial events consist of the 3' end folding transiently onto more 5' sequences to transiently form a Watson-Crick base pair. (C) Occasionally a polymerase successfully elongates this structure to give a long double-stranded hairpin with a turn at one end (labeled H). The sequence and 5'-3' direction of the reverse complement of the original is indicated by a pale arrow. (D) In strategy 1 it is assumed that a second recombinase-coated oligonucleotide of identical sequence targets the homologous double-stranded body of the hairpin, thus unraveling it. Mismatches occur at the 3' region of the invading oligonucleotide because the complement to this section was not correctly generated in step C. If a 4 base pair palindrome had not fortuitously been generated the mismatches would be even more severe than shown here. (E) A polymerase, very occasionally, might extend the mismatched 3' region of this intermediate to generate an inverted repeat with mismatches in the middle. This structure would also resemble the product if two identical primers had formed a brief 3' overlap resulting in formation of a primer dimer. These structures cannot readily enter geometric phase amplification. (F) In strategy 2 the long hairpin formed in (C) is briefly unzipped at one end. This step might be enhanced by recombinase binding to dsDNA because some reports indicate that recA may bind to dsDNA and promote melting of short duplexes. (G) The transiently melted 3'-end (reverse complement to the original 5' end of the oligonucleotide) folds back in a similar manner to (B) and forms a structure capable of elongation. (H) Polymerase elongation creates a large hairpin. In this case one end contains an identical duplex sequence to the parent oligonucleotide. (I) Another parent oligonucleotide invades the perfect duplex target. (J) Polymerase elongation of (I) generates a large inverted repeat with the indicated structure. Both ends contain perfect primer target sites and so this structure can amplify exponentially. Interestingly, the inverted repeat structure means that if an invasion and elongation occurs from one end, the displaced strand will rapidly tend to fold back onto itself to form the structure shown in (H). This product will require another recombination event to become structure (J), and thus it may be that higher recombination activity particularly benefits noise amplification, and is strongly impeded by lower recombination activity.

FIG. 44 shows several oligonucleotide design strategies to improve signal to noise in RPA reactions Shown are three general strategies to improve signal to noise ratios in RPA reactions by facets of oligonucleotide design. (1) Progressively shortened oligonucleotides may be tested. The assumption is that shortening of an oligonucleotide progressively from the 5' end leads to a drop in activity of the respective nucleoprotein filament, and that this influences the doubling time of noisy artifacts more rapidly than that of target. Low activity nucleoprotein filaments may also be combined effectively with more active ones in some cases. (2) Locked nucleic acids, or other modified sugars, may be included in the primers with consequent effect on amplification behaviour. The structure of a locked nucleic acid (LNA) sugar is indicated. (3) Oligonucleotides behaviour may be improved by the addition of 5' residues, possibly unrelated to the target, which suppress noise via mechanisms such as deterring snapback priming, or by altering nucleoprotein recombination activity. Sequences may be homopolymer stretches, or otherwise. Ideal sequences may be determined empirically.

FIG. 45 shows the consequences of reducing primer length (A) Schematic description of experimental design. Pairs of oligonucleotides were synthesized to three human targets, and sets of primers were made in which the 5'-most residues were progressively deleted (full length primers have been described above: D18S51 5' GGTGGACATGTTGGCT-TCTCTCTGTTCTTAAC (SEQ ID NO:54), D18S51 3' GGTGGCACGTGCCTGTAGTCTCAGCTACTTGC (SEQ ID NO:57), SRY3 5' AAAGCTGTAACTCTAAGTATCA-GTGTGAAAC 3' (SEQ ID NO:27), SRY4 5' GTTGTCCA-GTTGCACTTCGCTGCAGAGTACC 3'(SEQ ID NO:28), APOB500 ATGGTAAATTCTGGTGTGGAAAACCTG-GATGG (SEQ ID NO:48), APOB300REV CTATC-CAAGATTGGGCTAAACGTATGAAAGCA (SEQ ID NO:51). Shorter primers were made by deleting 5'-most bases to give the final indicated length). Primer pairs of identical length were combined in amplification reactions in the fashion indicated. (B) Amplification reactions were performed on human genomic DNA, present in the start reaction at 50 copies/µl. The three targets, an STR marker D18S51II, part of the human SRY gene, and the human Apolipoprotein B locus, were amplified with pairs of oligonucleotides. The oligonucleotides were progressively truncated from the 5' end in the manner as described in (A), and the length of both primers in the primer pairs used is indicated above the respective lane. It is evident that there is a fairly precipitous drop in amplification behaviour as oligonucleotides are shortened from just over to just under 30 residues. Consequently comparing oligonucleotides with length variation of just over to just under 30 residues is generally likely to reveal optimal length to get sufficient specific amplification, but very little or no background. For example two 29-mers were sufficient to amplify the D18S51 II locus, and do so cleanly. Amplification conditions were: 50 mM Tris.Cl pH 8.3, 90 mM Magnesium acetate, 2 mM DTT, 80 mM Potassium acetate, 200 µM dNTPs, 600 ng/µl gp32, 200 ng/µl uvsX, 60 ng/µl uvsY, 300 nM primers, 20 ng/µl Bsu polymerase, 50 copies/µl genomic DNA, 90 minutes at 37° C.

FIG. 46 shows how a 3' LNA residues alter amplification behavior in RPA

Amplification of a part of the human ACE locus is shown using combination of regular oligonucleotides and counterparts in which the 3'-most residue has an LNA sugar. (A) Schematic representation of the relationship of oligonucleotide primers to one another. LNA1 and DNA1 are identical except that LNA1 contains a LNA sugar at the most 3' position. Likewise LNA2 and DNA2 differ similarly. (sequence of LNA/DNA1 is: GCTCCTTGGACTGGTAGAT-GTCACACTTGTG-SEQ ID 74, sequence of LNA/DNA2 is GCCTTGGCTCTGCTGTGCGCATGTGACTTAGC-SEQ ID 75). (B) RPA reactions were assembled with the indicated oligonucleotide primer combinations. Product levels are significantly reduced when both oligonucleotides contain a 3' LNA under standard reaction conditions. However substitution of only one oligonucleotide does not suppress the reaction too greatly (lanes 2 and 3). Note that the background pattern in lane 3 resembles that in lane 4, while in 2 it is largely absent. This suggests that the background derives principally from the activities of a single primer species. Amplification conditions were: 50 mM Tris.Cl pH 8.3, 90 mM Magnesium acetate, 2 mM DTT, 80 mM Potassium acetate, 200 µM dNTPs, 800 ng/µl gp32, 200 ng/µl uvsX, 60 ng/µl uvsY, 300 nM primers, 20 ng/µl Bsu polymerase, 50 copies/µl genomic DNA, 120 minutes at 37° C. (C) Increasing the levels of polymerase result in restoration of robust activity when two LNA-modified oligonucleotides are used. LNA1 and LNA2, or DNA1 and DNA2, were combined in the presence of the indicated concentrations of polymerase. Notably the DNA primers displayed high activity at the lowest used concentration, and if anything the products looked less good as polymerase concentration was increased. Short products, 50-100 base pairs, are notably also seen. Conversely the LNA primers were only optimally active at higher polymerase concentrations. Less small products were seen, and those seen other than the expected size are likely product related (see below). Amplification conditions were: 50 mM Tris.Cl pH 8.3, 90 mM Magnesium acetate, 2 mM DTT, 80 mM Potassium acetate, 200 µM dNTPs, 800 ng/µl gp32, 200 ng/µl uvsX, 60 ng/µl uvsY, 300 nM primers, 43 to 1400 ng/µl Bsu polymerase, 100 copies/µl genomic DNA, 120 minutes at 37° C. (D) LNA-modified oligonucleotides give little, if any, background when no target is present, but efficiently amplify bona fide product to high levels when reaction conditions are optimized. A polymerase concentration of 200 ng/µl Bsu polymerase was employed. Reactions were carried out with DNA primers pairs, or LNA primer pairs, in the presence or absence of target. A faint band of the expected size was found in the negative controls indicating a contamination problem. Nevertheless both primer pairs amplified efficiently in the presence of target, but in its absence the DNA pair gave significant noisy smear, while the LNA pair gave no other product than the slight contamination. This indicates that the LNA primer pair may be able to cleanly distinguish between the presence and absence of target in the sample, while the DNA primers generate primer-derived products in the absence of target. Amplification conditions were: 50 mM Tris.Cl pH 8.3, 90 mM Magnesium acetate, 2 mM DTT, 80 mM Potassium acetate, 200 µM dNTPs, 800 ng/µl gp32, 200 ng/µl uvsX, 60 ng/µl uvsY, 300 nM primers, 200 ng/µl Bsu polymerase, 50 copies/µl genomic DNA, 120 minutes at 37° C.

FIG. 47 shows that adding homopolymeric stretches to the 5' ends of primers may alter nucleoprotein activity.

(A) The sequence of six oligonucleotides used in the experiment is shown. The J1 and K2 oligonucleotide target the *B. subtilis* SpoOB locus (SEQ IDs 66 and 69 respectively), and the other listed oligonucleotides are derivatives of them, carrying a homopolymeric stretch of cytosines, or guanosines as indicated. These oligonucleotides can be incubated in a pairwise fashion to assess which pair most effectively amplifies the target. (B) The results of incubating the six primers alone, or in all possible combinations, is shown. Reactions were incubated at 37° C. for 2 hours. Reaction conditions were 50 mM Tris.Cl pH 8.4, 2 mM DTT, 5% Carbowax 20M, 80 mM Potassium acetate, 200 µM dNTPS, 3 mM ATP, 20 mM Phosphocreatine, 50 ng/µl creatine kinase, 300 nM each relevant oligonucleotide, 800 ng/µl gp32, 120 ng/µl uvsX, 25 ng/µl uvsY, and 28 ng/µl Bsu polymerase, .about.1 copy/µl *B. subtilis* genomic DNA (estimated by serial dilution) (20 µl reaction volume). Optimal primers pairs were J1+K2, and then J1C+K2C. In general a homopolymeric Cytosine stretch appeared to make nucleoprotein filaments more active, and a Guanosine stretch less active.

Figure 48:
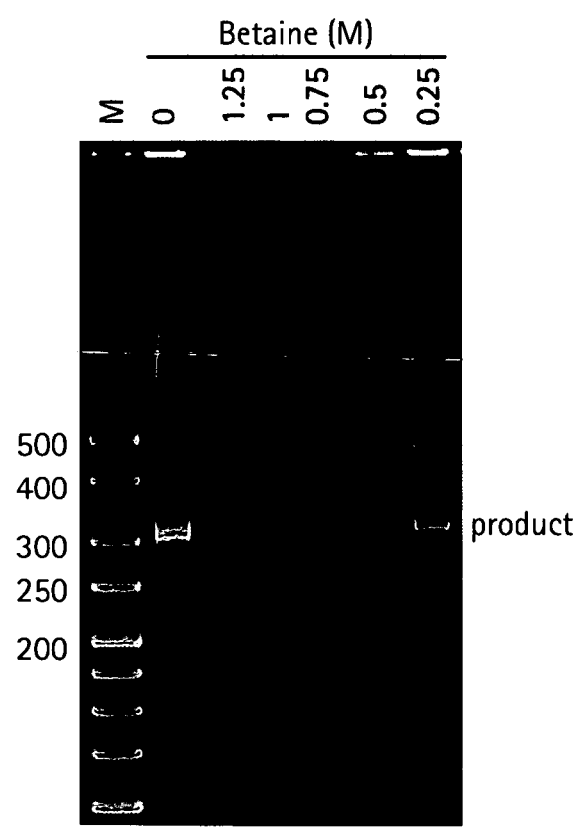
FIG. 48 Betaine reduces levels of product and noise.

FIG. 48 shows the effects of betaine on RPA reactions

RPA reactions were established in which an increasing concentration of betaine was present in each reaction. Betaine concentration of 0.5M, or greater, in this experiment reduced the degree of amplification. At 0.75M the expected product band was still clearly visible, however the most of the smear present in some samples had been prevented. We believe that the reduction in smear far outweighs the reduction in product consistent with the possibility that levels of betaine can be employed that improve signal to noise ratios. Amplification conditions were: 50 mM Tris.Cl pH 8.3, 90 mM Magnesium acetate, 2 mM DTT, 80 mM Potassium acetate, 200 µM dNTPs, 600 ng/µl gp32, 200 ng/µl uvsX, 60 ng/µl uvsY, 300 nM of primers ApoB4 and Apo300 (SEQ IDs 20 and 21), 40 ng/µl Bsu polymerase, 2.5 copies/µl genomic DNA, 120 minutes at 37° C.

Figure 49:
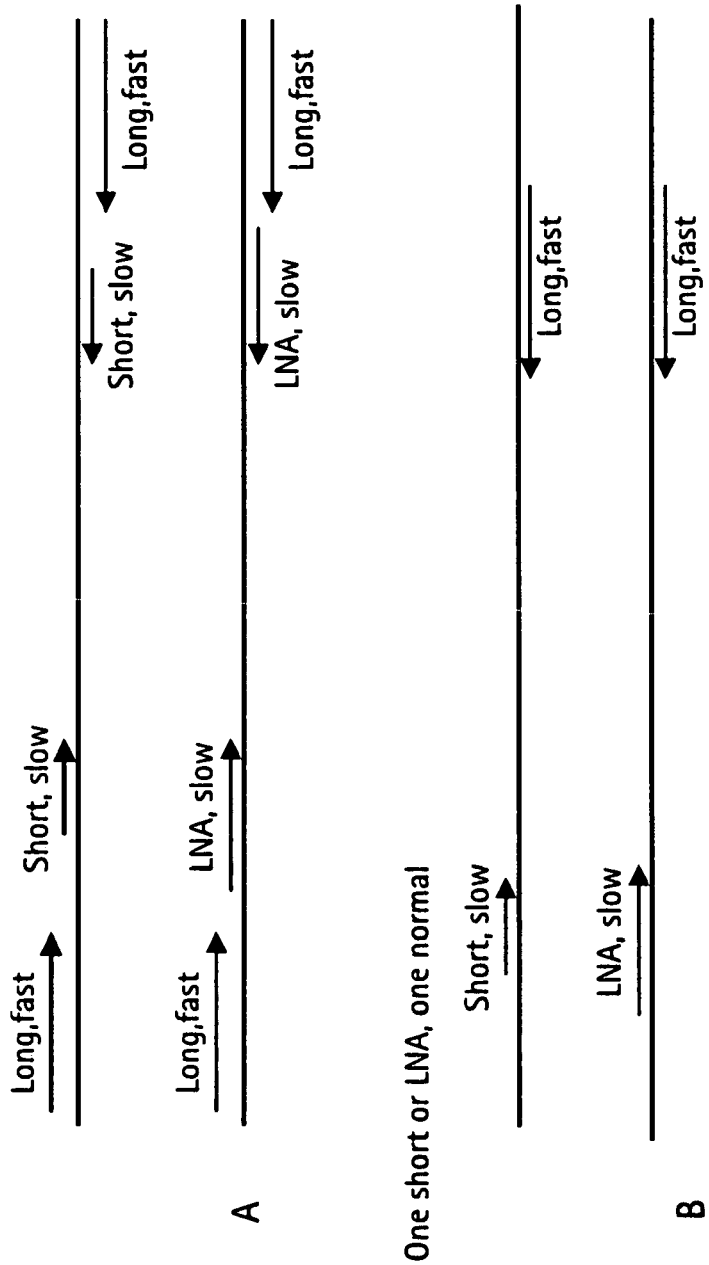
FIG. 49 Combination strategies in which nucleoprotein filaments with differential activities are combined.

FIG. 49 shows combination strategies involving oligonucleotides with different nucleoprotein activities (A) Single reaction nesting strategies are outlined. An outer pair of active nucleoprotein filaments rapidly amplifies DNA, although these primers may also be fairly noisy. The outer primer pair may be maintained at relatively low concentration, low enough to be unable to achieve gel-detectable levels of product. The inner oligonucleotides are less active, but much cleaner. These inner oligonucleotides are maintained at high levels. Activity may be tuned by altering length, composition, and backbone character as detailed in this disclosure. The outer primers quickly enrich the target in the sample, for example through a million-fold amplification. The inner primers, being slow but clean, generate little/no noise, but are less sensitive. The enrichment of target by the outer primers is sufficient to permit robust product accumulation by action of the slow inner primers in an appropriate timeframe. (B) Amplification schemes are shown in which an active primer is combined with a less active primer. While the active primer may engage in noise at low target concentrations, the slower oligonucleotide does not engage in artifacts, and so if association of the primers is tested at the end of the reaction this can cleanly determine whether target was presence or absent in the sample.

FIG. 50 describes several detection protocols. Three simple strategies are shown schematically by which amplification of a target might be assessed without a need for gel electrophoresis. In all cases a primer is utilized that can be attached to a solid phase to permit its separation from bulk reactants, and which can be washed. In the figure a biotin residue on one of the primers represents this immobilizable primer, however other attachment chemistries could be used. (1) One primer is immobilizable, and the other contains a label of some description, for example an enzyme. (2) One of the amplification primers is labeled in some way, and the immobilizable primer is a third primer, which recognizes sequences within the main amplicons. This third primer may be present in the reaction environment during the main amplification, but may be for example designed to be quiet (e.g. by being short), or could be added only at the end of the reaction. (3) A third primer is employed. In this case however the immobilizable probe is related to one of the amplification primers, but contains additional 5' residues that permit it to stably capture amplicons at the end of the reaction, as polymerase extension of the 3'-end of the complement in the amplicon (i.e. 'backfire' synthesis) creates a stable duplex not subject to branch migration if reaction proteins are washed away.

Figure 51:
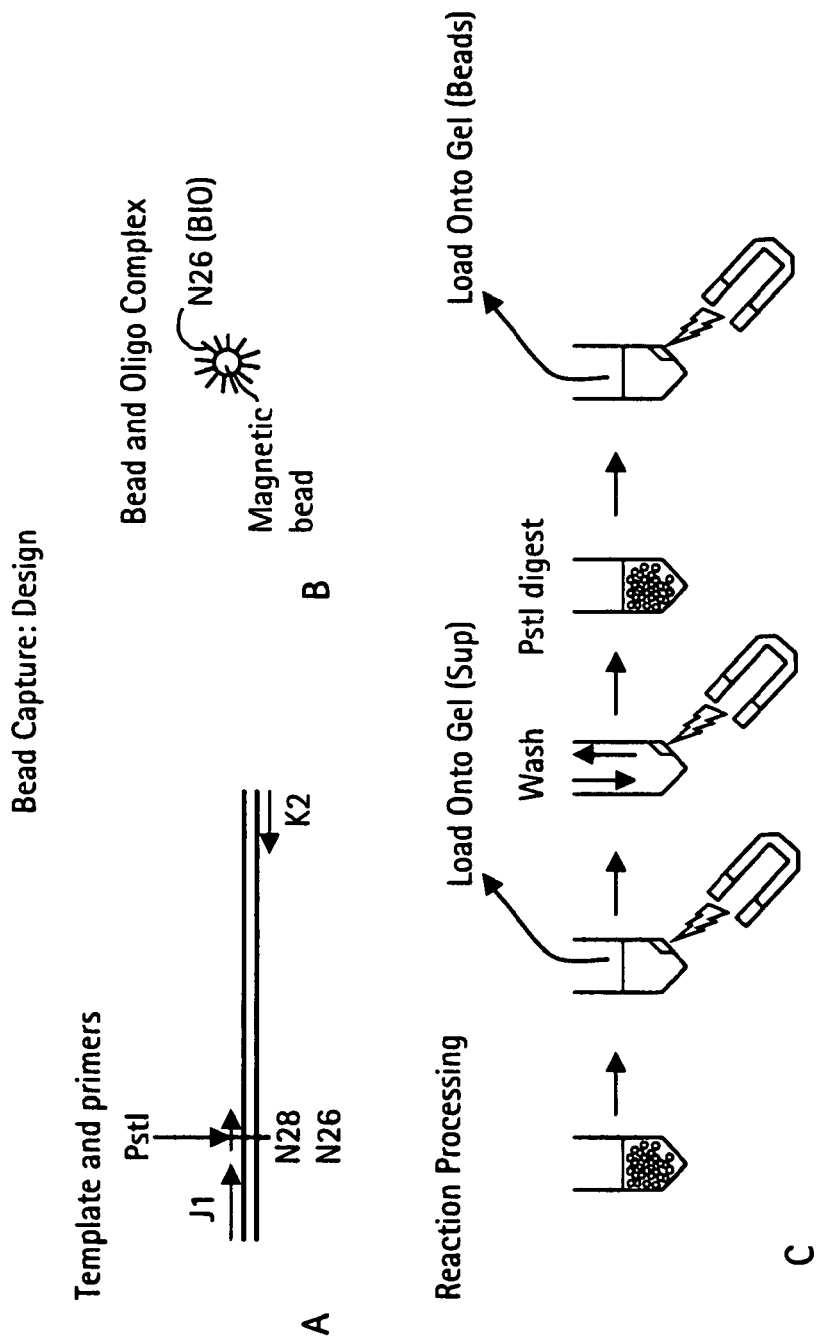
FIG. 51 Bead capture I. Schematic of experimental strategy in which a third probe enriches bona fide products derived from the target.

FIG. 51 shows a third probe enrichment strategy: Bead capture Part I. Schematic of experimental strategy in which a third probe enriches bona fide products derived from the target (A) Schematic representation of the relationship between primers. A PstI restriction enzyme site is indicated, located in the middle of NEST3-28 (GGATGAATAAGCTGCA-GCTGATTAAAGG-SEQ ID 76) and NEST3-26 (AT-GAATAAGCTGCAGCTGATTAAAGG-SEQ ID 77) primers which are homologous to an amplified sequence generated by primer J1 and K2 (SEQ IDs 66 and 69 respectively above). (B) Illustration of the immobilization of a 5'-biotinylated version of N3-26 which is bound to streptavidin-coated magnetic particles. (C) Scheme for capture experiment. An amplification reaction is established in which oligonucleotides J1 and K2 are combined in solution phase with the N3-26 primer immobilized on a bead. The reaction is incubated for 90 minutes, and every 20 minutes the beads are dispersed by flicking (they settle only very slowly in the 5% PEG reaction solution). At the end of the incubation period the beads are concentrated using a magnet, and the supernatant is removed for analysis. The beads are washed twice quickly with water, and then incubated for 30 minutes at 37° C. with excess PstI enzyme in appropriate buffer. Once again the supernatant is removed and analysed.

FIG. 52 shows a third probe enrichment strategy: Bead capture II. Experimental results demonstrating that a low activity nucleoprotein filament immobilized on a solid support can participate as a third primer and separate target amplicons from primer noise.

(A) Schematic representation of the relationship between primers. A PstI restriction enzyme site is indicated, located in the middle of N3-28 and N3-26 primers. (B) Amplification of *B. subtilis* DNA has been performed in the presence (lower panel) or absence (upper panel) of target DNA at 2 copies/µl. Lane 1 contains size ladder. The primers J1 and K2 efficiently amplify their target in the presence of few copies of target genomic DNA (Lower panel, lane 2), however in the absence of target in the sample generate a smear as evidenced in the upper panel lane 2. Oligonucleotides N3-28 and N3-26 are homologous to sequences slightly 3', and the same sense, to J1. N3-28 is a 28-mer, and N3-26 is a 26-mer lacking the two 5'-most bases from N3-28. Co-incubation of N3-28 or N3-26 with J1 and K2 primers results in the generation of two main products corresponding to the J1/K2 product, and the expected N3-28/K2 or N3-26/K2 product (Lower panel, lanes 3 and 4). When N3-28 is incubated alone it generates some smear, but N3-26 incubated alone does not. We deduce that N3-26 is a 'quiet' olignucleotide and may rely significantly on hybridization to displaced strands from the elongation of more active primers in order to generate products. (C) The results of an experiment carried out as detailed schematically in FIG. 51, and using start target density of 30 copies/µl. Lane 1, size marker. Lane 2 and 3, products of an entirely liquid phase reaction (no immobilization of N3-26) performed without (lane 2) or with (lane 3) target. This is effectively equivalent to lanes 4 of the upper and lower panels of (A). Lanes 4 and 5 contain the first supernatant removed after the amplification incubation, without and with target respectively. As expected there is product in the target containing reaction, and the smaller product derived from use of the N3-26 primer (immobilized on the bead) is not seen. Also there is a smear, as expected, in the targetless sample. Lanes 6 and 7 contain the supernatant following PstI digestion of the washed beads. Interestingly the smear in the non-target sample is not present, however in the target sample there is DNA. The products released from the beads appear to comprise the expected N3-26/K2 product, slightly faster mobility than in lane 3 due to clipping by PstI, as well uncut J1/K2 product that has co-purified. It is perhaps unsurprising that some J1/K2 product co-purifies because hybrids may well have formed between such products and the bead-immobilized products and oligonucleotides. It is, however, surprising that this material has not apparently been cut by PstI enzyme. The reason for this strange observation is not known, but could indicate that these products were present in hybrids that were resistant to digestion, or lead to nicking of only one strand of these products.

FIG. 53 shows that Trehalose stabilizes lyophilizates to permit all components except buffered sample to remain active for at least 10 days at room temperature.

RPA reactions were assembled using primers specific for the human Apolipoprotein B locus. In general final reaction composition was 55 mM Tris.Cl pH 8.4, 1 mM DTT, 80 mM Potassium acetate, 5% Carbowax 20M, 200 µM dNTPS, 3 mM ATP, 20 mM Phosphocreatine, 100 ng/µl creatine kinase, 300 nM ApoB4 and Apo300 oligonucleotide (SEQ ID 20 and 21 respectively), 600 ng/µl gp32, 200 ng/µl uvsX, 60 ng/µl uvsY, and 17 ng/µl Bsu polymerase, ~160 copies/µl Human genomic DNA. However, the 55 mM Tris.Cl pH 8.4 and 80 mM Potassium acetate were not included in the lyophilizate, but added back with the DNA sample during reconstitution. Furthermore certain components were also omitted from the lyophilizates detailed as follows. Condition A, no trehalose used, Carbowax added with sample DNA (not in lyophilizate), polymerase added with sample DNA. Condition B, 50 mM Trehalose included in lyophilizate, Carbowax added with sample DNA, polymerase added with sample DNA. Condition C, 50 mM trehalose in lyophilizate, polymerase added with sample. Condition D, 50 mM trehalose in lyophilizate, only buffered sample DNA added for reconstitution. After 3, 6, or 10 days storage on the bench at room temperature, and with no special storage conditions (e.g. use of desiccants etc.) the activity of the lyophilizates were tested by adding the missing reagents to the dry pellet in a final volume of 50 µl. Reaction condition D in each case lacked only the sample DNA in reaction buffer (55 mM Tris.Cl and 80 mM Potassium acetate). Only if trehalose was present in the lyophilizate were reactions stable, but in those cases the reactions remained stable for at least 10 days. Longer periods were not investigated due to running out of test material, but may be possible.

Example 14

RPA Reactions can be Monitored in Real Time to Allow Assessment of Start Target Copy Number FIG. 54 shows how SYBR gold and SYBR green fluorescent dyes were assessed for their compatibilities in RPA reactions, and their reaction-monitoring properties. (A) Arrangement of the primers ApoB4 and Apo300 (SEQ IDs 20 and 21 respectively) which flank a fragment of the human Apolipoprotein B locus. (B) SYBR gold can be included in RPA reactions at dilutions of 1:50,000 or greater without complete inhibition of the reaction. Reactions were composed of 50 mM Tris pH 8.4, 80 mM Potassium acetate, 200 µM dATP, dCTP, dGTP, and dTTP, 50 ng/µl creatine kinase, 1.5 mM ATP, 10 mM Magnesium acetate, 2 mM DTT, 30 mM phosphocreatine, 300 nM ApoB4 primer, 300 nM ApoB300 primer, 5% Carbowax 20M, 360 ng/µl gp32, 86 ng/µl uvsX, 15 ng/µl uvsY, 35 ng/µl Bsu polymerase. SYBR gold at the indicated dilution was included in the reaction. (C)RPA reactions were established in a 96-well plate, each with a final volume of 50 µl. A mastermix of components lacking only the target DNA and the SYBR gold dye was established on ice. Five different dilutions of SYBR gold were tested, with final dilutions from stock of 1:50,000, 1:60,000, 1:70,000, 1:80,000, and 1:100,000. For each dilution starting target copy densities of 2 and 20 copies per microliter were investigated (human genomic DNA diluted in TE to the expected copy density). Once reactions had been thoroughly mixed on ice, the plate was transferred to the pre-warmed plate (37° C.) of a BIO-TEK FLX 800 fluorescent microplate reader. Readings were collected every 1 minute, and 300 ng of human genomic DNA diluted in 50 µl of water was used as a sensitivity standard for the device. Data was transferred to Microsoft Excel and relative fluorescence (arbitrary) was plotted against incubation time for each reaction. (D) An experiment was established as in (C) except that SYBR green rather than SYBR gold was assayed.

FIG. 55 shows that real time RPA demonstrates quantitative behaviour over four order of magnitude using SYBR green. FIG. 55 (A) Arrangement of primers used in this analysis. (B) RPA reactions were established in 96-well microwell plates, with a final volume of 50 µl per reaction volume, using primers specific or the *B. subtilis* SpoOB locus J1 and K2 (J1-5'-ACGGCATTAACAAACGAACT-GATTCATCTGCTTGG-3' SEQ ID 66, K2-5'-CCT-TAATTTCTCCGAGAACTTCATATTCAAGCGTC-3' SEQ ID 69). A defined number of copies of *Bacillus subtilis* genomic DNA was pipetted into wells in to the 96-well plate, and stored on ice. A reaction mastermix was mixed on ice, and then aliquoted in the wells containing DNA and mixed well. The reactions were then transferred to the pre-warmed plate of a BIO-TEK FLX 800 fluorescent microplate reader (set at 38° C.). The reaction composition was 50 mM Tris pH 8.4, 80 mM Potassium acetate, 10 mM Magnesium acetate, 2 mM DTT, 200 µM dATP, dCTP, dGTP, and dTTP, 50 ng/µl creatine kinase, 1.5 mM ATP, 30 mM phosphocreatine, 300 nM BsJ1 primer, 300 nM BsK2 primer, 5% Carbowax 20M, 360 ng/µl gp32, 86 ng/µl uvsX, 15 ng/µl uvsY, 35 ng/µl Bsu polymerase, and 1:50,000 dilution of the DMSO stock of SYBR green from molecular probes. The results of two equivalent experiments is shown in (B) and (C). After reactions had finished 7 µl of the reactions was diluted with 1× sucrose loading buffer and separated on a 2% agarose gel (D, E). Note that when the highest concentration of target was used fluorescence became detectable earliest as expected, but failed to show an enduring exponential rise. This may arise due to consumption of reaction reagents (gp32 was used at lower than typical concentrations in this experiment), or to an inhibitor build-up, or otherwise. Later experiments suggest this may arise due to gp32/uvsX undertitration. See below. Also, there some evidence of product contamination in (B) suggested by the faint presence of the expected band in the endpoint analysis gel (D).

FIG. 56 shows that RPA reactions can kinetically assess of *B. subtilis* genomic DNA copy number of at least 5 orders of magnitude. RPA reactions was established using *Bacillus subtilis* primers J1 and K2 as in FIG. 55. However the quantity of protein reagents was increased as follows: gp32 was used at 600 ng/µl, uvsX was used at 140 ng/µl, uvsY was used at 35 ng/µl, and ATP was at 3 mM. Reaction volumes were increased to 100 µl final volume, and a greater range of genomic DNA concentrations was used (from 0 µl to 100,000 copies/µl). No early trailing of higher copy number samples was observed, and we believe this reflects that earlier experiments had somewhat undertitrated gp32 and uvsX. After reactions had finished 7 µl of the reactions was diluted with 1× sucrose loading buffer and separated on a 2% agarose gel.

FIG. 57 shows that real time RPA demonstrates quantitative response to variation in human genomic DNA copy number. FIG. 57 (A) Arrangement of ApoB4 and Apo300 primers which amplify a human DNA sequence. (ApoB4—5'-CAGTGTATCTGGAAAGCCTACAGGACAC-CAAAA3' SED ID 20, Apo300—5'-TGCTTTCATACGTT-TAGCCCAATCTTGGATAG3' SEQ ID 21). (B) RPA reactions were established in 96-well microwell plates, with a final volume of 100 µl per reaction volume. A defined number of copies of human genomic DNA was pipetted into wells in to the 96-well plate, and stored on ice. A reaction mastermix was mixed on ice, and then aliquoted in the wells containing DNA and mixed well. The reactions were then transferred to the pre-warmed plate of BIOTEK FLX 800 fluorescent microplate reader. The reaction composition was 50 mM Tris pH 8.4, 80 mM Potassium acetate, 10 mM Magnesium acetate, 2 mM DTT, 200 µM dATP, dCTP, dGTP, and dTTP, 50 ng/µl creatine kinase, 1.5 mM ATP, 30 mM phosphocreatine, 300 nM ApoB4 primer, 300 nM Apo300 primer, 5% Carbowax 20M, 360 ng/µl gp32, 86 ng/µl uvsX, 15 ng/µl uvsY, 35 ng/µl Bsu polymerase, and 1:50,000 dilution of the DMSO stock of SYBR green from molecular probes. Note that, as in Example 2 (C), the highest concentration of target generated a curve which trailed off unexpectedly early. As with FIG. 55 these experiments were performed under conditions of uvsX, uvsY, gp32, ATP and dNTP concentrations that may require finessing to ensure robust detectable exponential phase at higher target concentrations. This is supported by (C), in which a similar experiment was performed to that in (B), except that concentrations of certain reagents were as follows: gp32 was used at 600 ng/µl, uvsX was used at 140 ng/µl, uvsY was used at 35 ng/µl, ATP was at 3 mM. After reactions had finished 7 µl of the reactions was diluted with 1× sucrose loading buffer and separated on a 2% agarose gel.

Example 15

Asymmetric Primer RPA Using a 3'LNA-capped Primer

As an example of amplification of a target DNA using the asymmetric primer RPA method, standard RPA conditions are employed with two differences. First, one primer is a 3'LNA-capped primer. Secondly, an additional polymerase, phi29, is used, which is unable to initiate synthesis from recombinase intermediates.

Thus amplification conditions are as follows:
50 mM Tris.Cl pH 7.85
10 mM Magnesium acetate
2 mM Dithiothreitol
80 mM Potassium acetate
5% PEG compound (Carbowax 20M)
15 mM Phosphocreatine
3 mM ATP
200 µM dNTPs
12 ng/µl creatine kinase
0.3 µM oligonucleotide 1, 3'LNA-capped
0.3 µM oligonucleotide 2
350 ng/µl T4 gp32

100 ng/µl T4 uvsX
20 ng/µl T4 uvsY
20 ng/µl Bsu polymerase
20 ng/µl phi29 polymerase (exo-, or exo-attenuated)
Incubation at 33-40° C. for 30 minutes to 2 hours Example 16

Initiation of Real-time RPA with Deprotection of Caged ATP

As an example of the use of ATP pulsed RPA to quantify input template DNA reactions are assembled as standard RPA reactions with several differences. Firstly, caged-ATP is used instead of ATP. Secondly, a double-stranded DNA detection reagent, SYBR green, is used to quantify RPA products. Primers are designed such that short (<200 bp) reaction products are generated, to ensure complete synthesis with each pulse of ATP.

Thus amplification conditions are as follows:
50 mM Tris.Cl pH 7.85
10 mM Magnesium acetate
2 mM Dithiothreitol
80 mM Potassium acetate
5% PEG compound (Carbowax 20M)
3 mM caged-ATP
1:50,000 dilution of SYBR-green I commercial stock (Molecular Probes)
200 1M dNTPs
0.3 µM oligonucleotide 1
0.3 µM oligonucleotide 2
600 ng/µl T4 gp32
150 ng/µl T4 uvsX
25 ng/µl T4 uvsY
20 ng/µl Bsu polymerase
Incubation at 33-40° C.

Prior to each cycle of ATP uncaging, SYBR-green I fluorescence (494 nm Excitation Max-521 nm Emission Max) is measured in the sample. The detected fluorescence will be the basis of quantification. Every minute a short pulse of 365 nm light is applied to uncage ATP, leading to a burst of recombinase activity. Fluorescence measured at each cycle is then compared to an input template standard and the quantity of input sample template can be determined.

Example 17

Describes the Use of Caged ATP to Control the Initiation of RPA in a Polony Analysis As an example of RPA-based polony analysis polyacylamide gels are generated on microscope slides as described by Church and colleagues [Mitra R, Church G (1999) In situ localized amplification and contact replication of many individual DNA molecules. Nucl Acids Res 27(24): e34i-vi.]. In this analysis distinct polymorphic products are detected after an initial amplification by single-base extension using fluorescent nucleotides and polymorphic-target specific primers. One difference between this configuration and normal polony analysis is that it may not be necessary to use the 5'acrydite modified primers, as RPA performed at a low constant temperature and for significantly shorter times (normally PCR-based polony reactions would take 3-7 hours). In this example, both 5'acrydite modified primers as well as normal primers are used.

In place of the PCR "diffuse-in" mix, an RPA "diffuse-in" mix is used and comprises the following:

50 mM Tris.Cl pH 7.85
10 mM Magnesium acetate
2 mM Dithiothreitol
80 mM Potassium acetate
5% PEG compound (Carbowax 20M)
15 mM Phosphocreatine (included depending upon configuration)
200 µM dNTPs
* 3 mM caged-ATP (included depending upon configuration)
12 ng/µl creatine kinase (included depending upon configuration)
0.3 µM oligonucleotide 1
0.3 µM oligonucleotide 2
350 ng/µl T4 gp32
100 ng/µl T4 uvsX
20 ng/µl T4 uvsY
20 ng/µl Bsu polymerase The reaction is then initiated either by diffusing in ATP, or activating caged-ATP included in the original "diffuse-in" mix. Polonies are generated after incubation at 33-40° C. for 30 minutes to 2 hours After amplification, a new polymorphic-target primer is diffused in along with fluorescently labelled nucleotides, and the reaction is re-started with an additional pulse of ATP, either applied manually, or by photolysis. Incorporated fluorescence can then be quantified using fluorescence microscopy.

Example 18

Non Gel-based Determination of Polymorphic Repeat Number in an Amplicon Using Recombinase-Mediated Hybrid Formation Between Single-Stranded Amplified DNA and Duplex Probes In this example an STR is amplified by flanking oligonucleotide primers. The STR is the marker known as TPOX and commonly used in both US and European standard STR marker sets used for forensic analysis. The marker is amplified by flanking primers with the sequence for primer 1 of 5'-ACTGGCACAGAACAGGCACTTAGGGAACCC-3' (SEQ ID NO: 44), and primer 2 5'-GGAG-GAACTGGGAACCACACAGGTTAATTA-3' (SEQ ID NO: 45). The marker has a repeat of 4 nucleotides, AATG, which vary between 5 and 14 repeats.

Amplification conditions are as follows:
50 mM Tris.Cl pH 7.85
10 mM Magnesium acetate
2 mM Dithiothreitol
80 mM Potassium acetate
5% PEG compound (Carbowax 20M)
15 mM Phosphocreatine
3 mM ATP
200 µM dNTPs
12 ng/µl creatine kinase
0.3 µM oligonucleotide 1,5'-fluorescein-labeled
0.05 µM oligonucleotide 2
600 ng/µl T4 gp32
150 ng/µl T4 uvsX
35 ng/µl T4 uvsY
20 ng/µl Bsu polymerase
Incubation at 33-40° C. for 30 minutes to 2 hours The amplification reaction generates a quantity of single-stranded DNA due to primer imbalance, and this single-stranded DNA is fluorescently labeled. At the end of the amplification reaction the reaction mixture is contacted directly to an array of spatially immobilized double-stranded probes. Each probe corresponds to one of the known polymorphic forms of the DNA under study, and is the same length as the amplicon that would be made if this form exists in the sample.

Recombinase loads onto the amplified single-stranded sample DNA to form homology-searching filaments. These filaments will be able to target the double-stranded probes immobilized on the array support surface. When a recombination event occurs between the recombinase-coated amplification product and the probes it will lead to the amplification product becoming productively Watson-Crick base-paired with its complement in the probe, while the originally paired equivalent strand is displaced and freed into solution. Ideally completion of such recombination events will be inhibited if the event initiates between a sample DNA and an imperfectly matched probe leading to enrichment of only perfect hybrids.

The reaction is dynamic such that hybrids formed between probe and sample may themselves become targets for other targeting DNAs. This dynamic behavior coupled to a lower efficiency of completion of recombination of imperfectly formed hybrids should lead to an enrichment of the perfect hybrids in the population of probe/sample mixtures. This is further enhanced by the addition of either a helicase such as $E.\ coli$ PriA (2-20 ng/µl), $E.\ coli$ DnaB (5-50 ng/µl), $E.\ coli$ RuvAB (5-50 ng/µl), T4 phage dda helicase (5-50 ng/µl), T4 phage gp41 (5-50 ng/µl) or an appropriate nuclease. These agents utilize, or enhance, disruptions in the helix, which exist due to mismatches and lead to such imperfect hybrids being less stable than perfect hybrids.

After a suitable incubation period, such as 10-30 minutes at 28-40° C., the reaction is terminated if necessary, for example by the addition of EDTA or chaotropic agents such as urea or guanidine hydrochloride, although no such termination may be necessary. Productive interactions between probe and sample are then measured by exposing the array to light of an appropriate wavelength, and recording fluorescence using appropriate filters and camera.

Example 19 Shows a Non Gel-based Determination of Polymorphic Repeat Number in an Amplicon Using Recombinase-Mediated Hybrid Formation Between Duplex Amplified DNA and Single-stranded Probes As above this example would involve amplification of the TPOX STR marker used in forensics. The amplification conditions would be the same as for Example 18 except that the ratio of amplification primers would be 1:1, with both used at a concentration of 0.3 µM. The amplification reaction is then contacted to an array of single-stranded probes corresponding to the known possible polymorphic forms of the DNA under study. With this format the recombinase loads preferentially onto the probes which then search and form hybrids with the double-stranded sample DNAs. As in Example 18 hybrids will ideally become enriched if they are perfect, and similarly the inclusion of agents such as helicases (e.g. PriA, recG, DnaB, RuvAB, gp41, or dda) or appropriate nucleases can accelerate and improve this enrichment. After a suitable incubation period, with or without arrest of the reaction as necessary, interactions are visualized as described in Example 18.

Example 20 Shows a Non Gel-based Determination of Polymorphic Repeat Number in an Amplicon Using Recombinase-mediated Hybrid Formation and Nuclease Processing of Heterologies to Release a Label from an Immobilization Point In this example the amplification reaction and hybrid formation between probe and sample are performed as described in Example 1, except that the amplification primers need not contain a label. The probe instead of the sample is labeled at one end. After an appropriate incubation period, as described for Examples 18 and 19, arrays are treated with an appropriate nuclease, which will cleave imperfect DNA duplexes. As such cuts are made in the backbone of imperfect hybrids and the label is thus freed from an immobilization point. Additionally a DNA polymerase may be included such that if a nick is introduced by the nuclease, and the polymerase is strand displacing then it acts to synthesize in a strand-displacing manner and thus remove the labeled strand accordingly. The array can be then quantified as described in Example 18.

Example 21 Shows a Non Gel-based Determination of Polymorphic Repeat Number in an Amplicon Using Recombinase-mediated Hybrid Formation and Nuclease Processing of Heterologies Followed by DNA Synthesis Labeling In this example amplification and hybrid formation are as for either Example 18 or Example 19 except that the amplification primers are not necessarily labeled. During the hybrid formation phase a nuclease is included that nicks at bubbles or helix disturbances and the inclusion in the reaction of labeled nucleotides and a strand displacing polymerase leads to imperfect hybrids being processed to a perfect hybrid form which includes modified labeled bases that can then be visualized.

Example 22 Shows the Use of a Helicase to Disrupt Imperfect Hybrids in a Dynamic Recombination System Environment In this example amplification and hybrid formation is done as for either Example 18 or Example 19 except that the amplification primers are not necessarily labeled. The probe or sample DNA should however contain a label. The probe or sample DNA is immobilized at one end to a solid support or bead through a high affinity non-covalent interaction such as a biotin-streptavidin interaction. During the hybrid-forming phase a helicase such as the T4 dda helicase, or combination of helicases such as PriA and dda helicases, or other mixtures are include to target imperfect hybrids and unwind them, effectively accelerating the dissociation of high affinity non-covalent interaction by physical disruption. After a suitable incubation period the association between the labeled nucleic acid and the solid support is measured positive signal indicating that perfect hybrids have formed.

FIG. 58 shows in principal how imperfect hybrids will possess bubbles which permit enhanced overall duplex disruption in a dynamic recombination environment A double-stranded amplicon shown in A containing 8 repeats of a short tandem repeat and flanked by unique sequences used for amplification is targeted in B by single-stranded probe oligonucleotides containing varying numbers of the repeat unit. The hybridization is driven by recombinase (not shown here). In C the resultant double-stranded hybrids are shown, some of which contain bubbles caused by non-identical repeat numbers between hybrids. These bubbles are larger as the number of repeats different grows in number, and thus such hybrids become better targets for recombinase, or other DNA processing enzymes.

FIG. 59 shows the possible outcome of a hybridization reaction as described in Example 18, of FIG. 58, is shown. A sample DNA containing 8 repeats is incubated with an array of probes corresponding to different repeat numbers. Over time hybrids are enriched for perfect repeat numbers, and less so but to a small extent those that differ only by one or two repeats.

Figure 60:
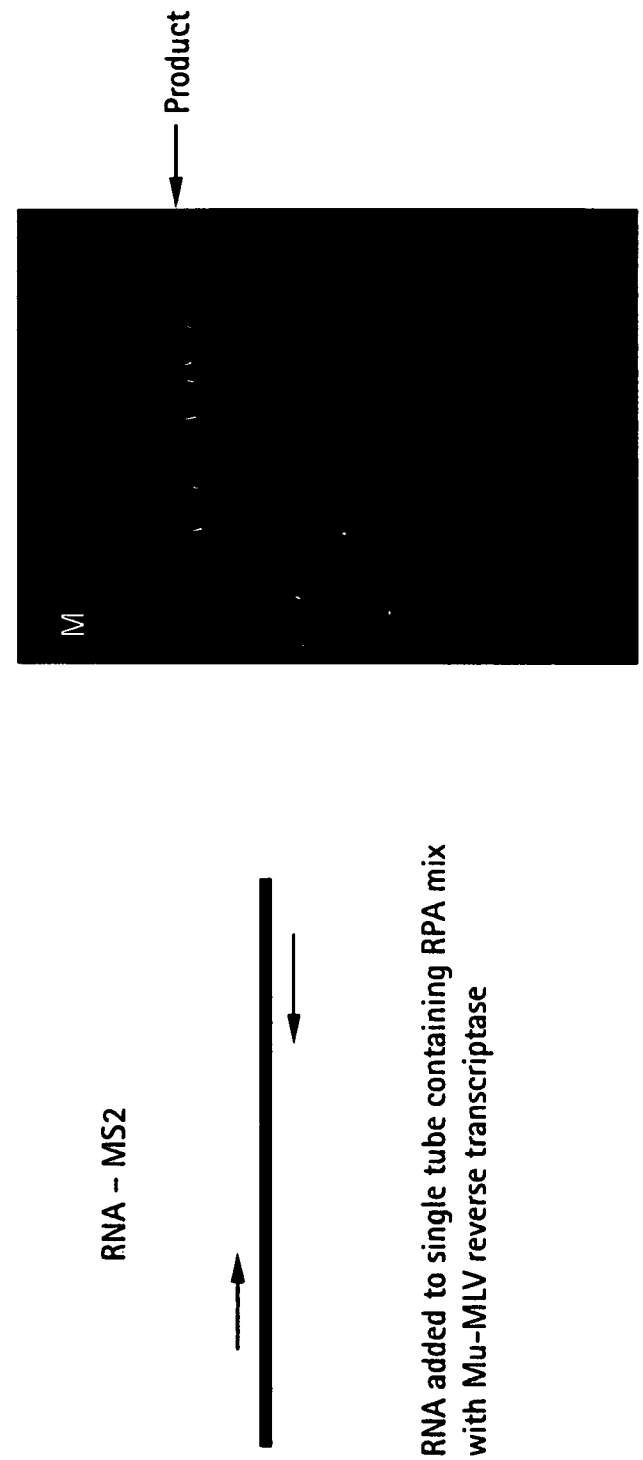
FIG. 60 Single tube reverse transcription RPA (RT-RPA) shows high sensitivity without significant optimisation FIG. 61 dUTP can be included in RPA reactions to wholly or partially replace dTTP thus providing a mechanism to develop effective carry-over contamination control.

FIG. 60 shows how easily RPA reactions can be performed to assess the presence of specific RNA species by including an enzyme capable of reverse transcription in the reaction.

Defined copy numbers of viral MS2 RNA (from a commercial source) were incubated in RPA reactions which included reverse transcriptase as indicated. Two primers were employed which recognised the MS2 sequence as indicated, more specifically these primers were:

```
MS2up2
                                        SEQ ID 78
TTCCGACTGCGAGCTTATTGTTAAGGCAATG

MS2down2
                                        SEQ ID 79
CTTAAGTAAGCAATTGCTGTAAAGTCGTCAC
```

Reaction conditions were standard except for increased concentration of dNTPs (500 µM), an increase in DTT, the inclusion of RNase inhibitor, and the inclusion of reverse transcriptase where indicated. Conditions were:

50 mM Tris.Cl pH 8.5
10 mM Magnesium acetate
1 0 mM Dithiothreitol
80 mM Potassium acetate
5% PEG compound (Carbowax 20M)
15 mM Phosphocreatine
3 mM ATP
500 µM dNTPs
100 ng/µl creatine kinase
0.3 µM MS2UP
0.3 µM MS2DOWN
800 ng/µl T4 gp32
120 ng/µl T4 uvsX
30 ng/µl T4 uvsY
70 ng/ll Bsu polymerase
0.13 Units/µl RNase inhibitor
MuMLV (RNase H containing) reverse transcriptase 10 units/µl (Promega)

Reactions products were phenol extracted, precipitated and separated on a non-denaturing acrylamide gel before staining with SYBR-gold. RNA concentrations as low as 100 copies per microliter can be readily detected in this format without further optimization.

Figure 61:
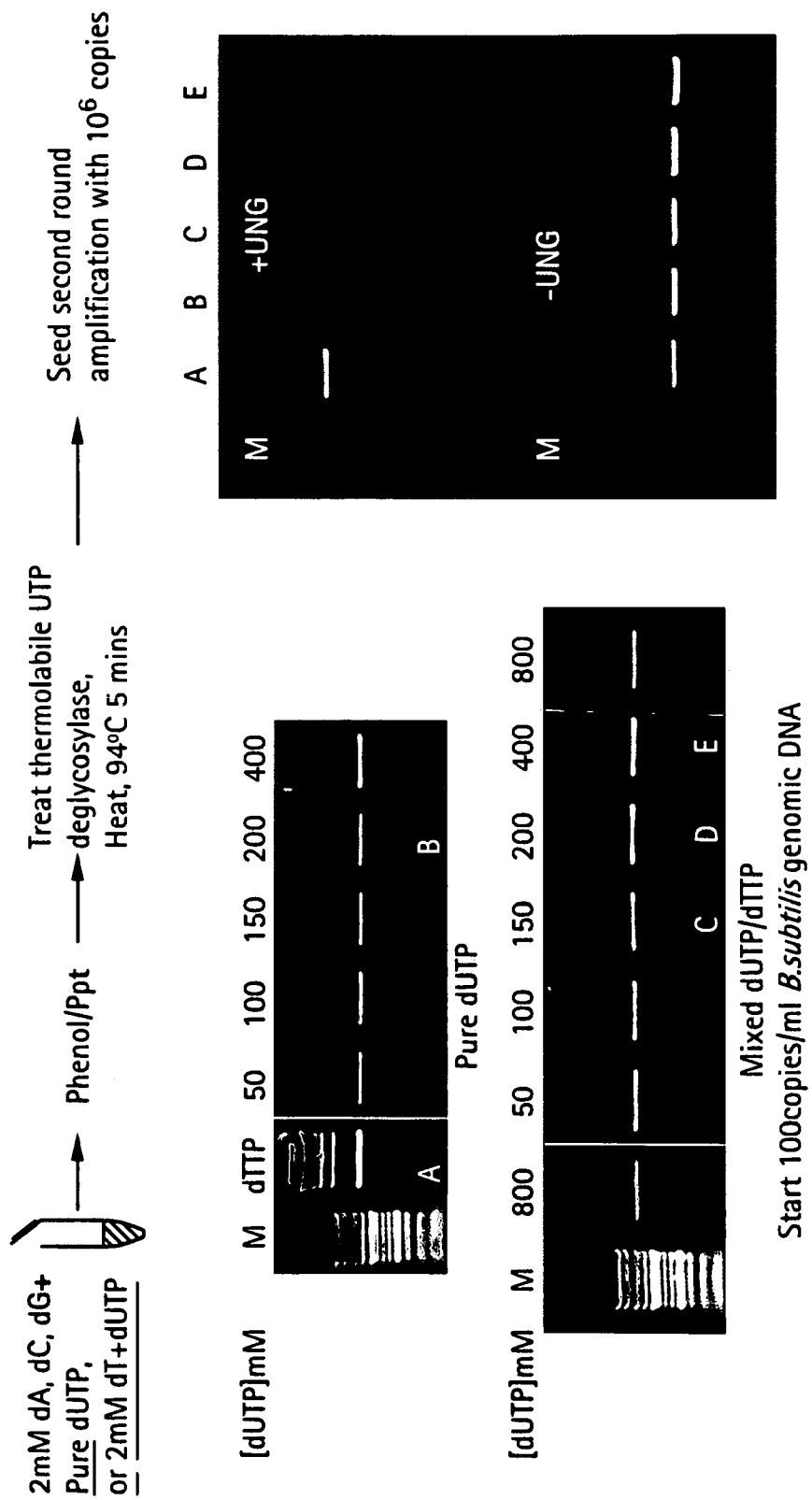

FIG. 61 shows that dUTP can be used to partially or completely replace dTTP in RPA reactions, thus offering a strategy to control carry-over contamination.

RPA reactions were established using the following conditions:

50 mM Tris.Cl pH 8.5
10 mM Magnesium acetate
2 mM Dithiothreitol
100 mM Potassium acetate
5% PEG compound (Carbowax 20M)
15 mM Phosphocreatine
3 mM ATP
200 µM dNTPs (dA, dC & dG)
100 ng/µl creatine kinase
0.3 µM J1 primer for *B. subtilis* DNA (SEQ ID 66)
0.3 µM K2 primer for *B. subtilis* DNA (SEQ ID 69)
630 ng/µl T4 gp32
140 ng/µl T4 uvsX
35 ng/µl T4 uvsY
20 ng/µl Bsu polymerase
100 copies/µl *B. subtilis* genomic DNA The product of reactions was separated on a 2% agarose gel and stained with ethidium bromide. As indicated in the left-most panels, dUTP or dTTP was employed in different reactions. More specifically the upper left-most lane contained 200 µM dTTP, and was therefore typical of a standard RPA reaction. The following six lanes also contained 200 µM dTTP, but in this case dUTP was also present at the indicated concentrations. The last six lanes of the lower left-most panel contain the products of RPA reactions in which no dTTP was included, and the indicated concentration (50-800 µM dUTP) of dUTP was used. In all cases amplification of the expected fragment occurred, but notably the presence of dUTP decreased the quantity of amplicon generated, and inhibited the doubling-up' phenomenon often seen in which snap-back synthesis has occurred.

The right-most panel indicates the results of using as starting material products generated from the first reactions in the left-most panel following processing as indicated in the schematic. More specifically the reactions shown as A, B, C, D and E in the left-most panels were processed as follows. Based on staining intensity and estimation of DNA content, an estimated $10^6$ molecules of each product were incubated for 20 minutes with 1 µl of a commercial preparation (Roche) of heat-labile dUTP-deglycosylase, a similar amount was left untreated, and then finally all samples were heated to 94° C. for 10 minutes. This enzyme was quality-controlled by the manufacturer to effectively combat carry-over contamination from $10^5$ molecules, thus we imposed a stringent challenge in this case. The samples were then used to seed an RPA reaction configured under normal RPA conditions with 200 µM of each dATP, dCTP, dGTP, and dTTP (see conditions above). As indicated samples untreated with dUTP-deglycosylase were excellent start templates, while those that had been treated were extremely poor unless no dUTP had been initially employed. In particular even the mixed blends were effective.

Figure 62:
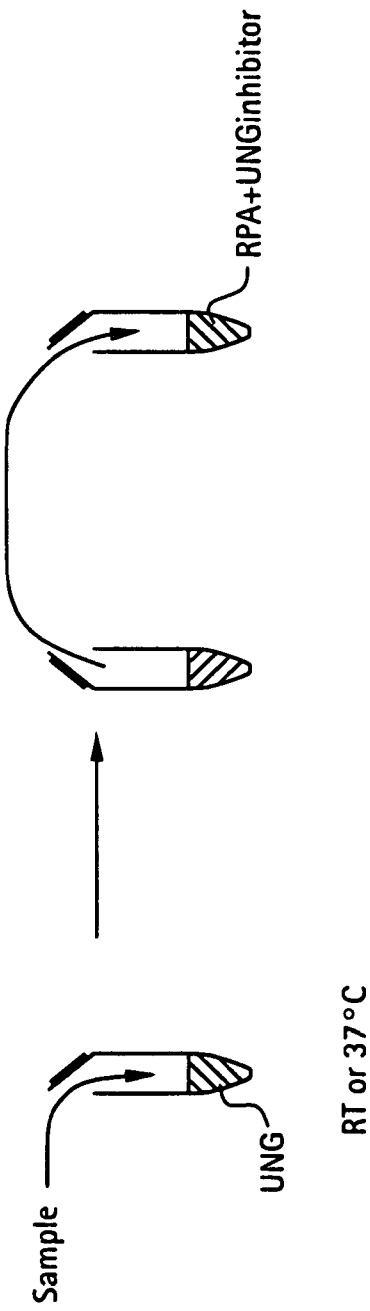
FIG. 62 A strategy for controlling carry-over contamination in RPA reactions.

FIG. 62 shows how one might combat carry-over contamination in the RPA system.

The capacity to employ dUTP in RPA reactions could be used to prevent carry-over contamination according to the depicted scheme. RPA reactions would be performed with pure dUTP, or mixes of dTTP and dUTP as shown in FIG. 61. Prior to, or at the initiation of an RPA reaction, *E. coli* Uracil deglycosylase (UDG) or similar would be incubated with the sample and would attack carry-over material. Then after several minutes, or at the start of the reaction, an UDG inhibitor would be added. A specific inhibitor of *E. coli* UDG is known as is referred to as Uracil Gygosylase Inhibitor (UGI) and is a 9.5 kD peptide from *Bacillus subtilis*, and is commercially available.

Figure 63:
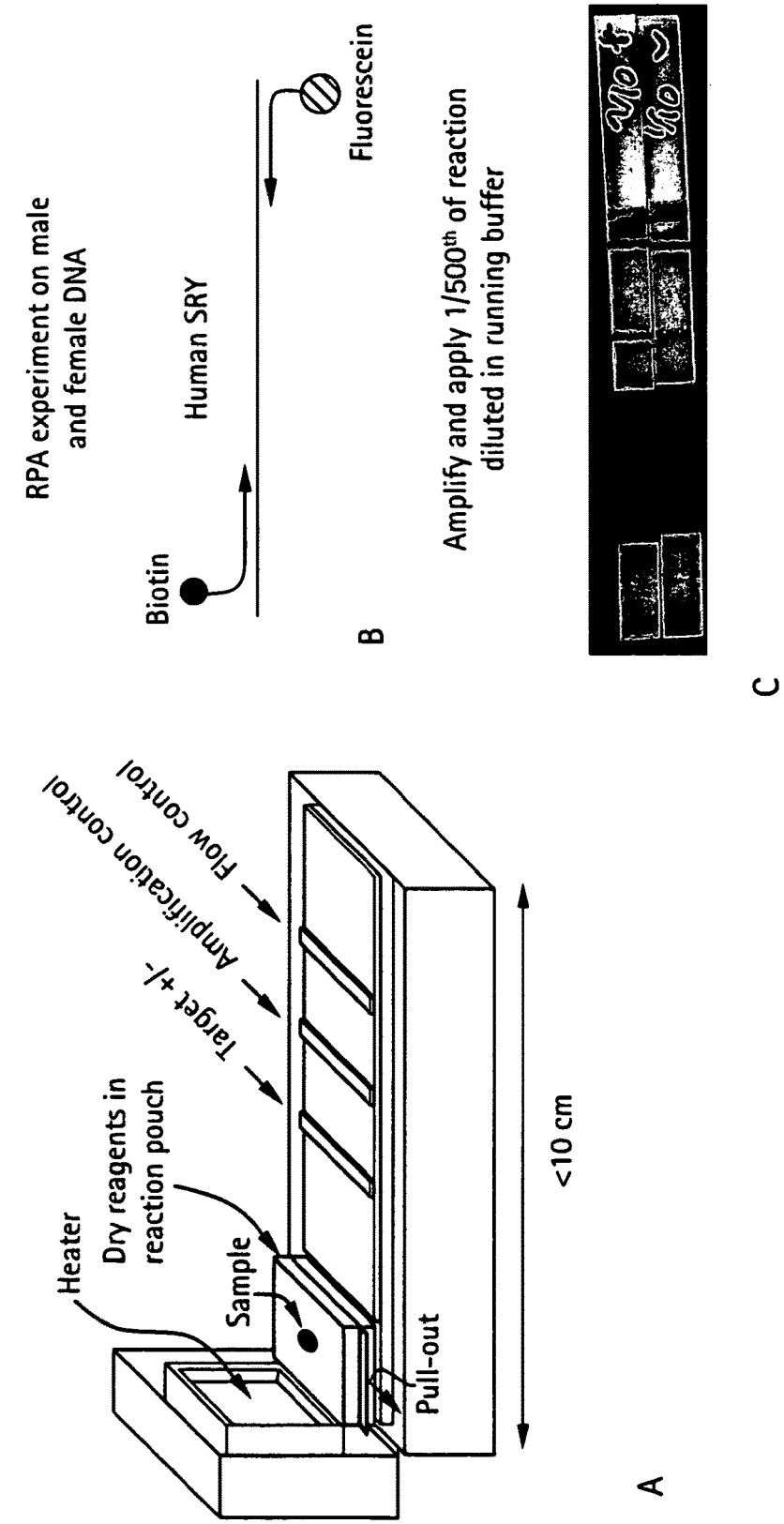
FIG. 63 Format of a stand-alone RPA assay to determine the presence of a specific nucleic acid comprising disposable amplification pouch and lateral flow strip to detect successful amplification.

FIG. 63 shows how a simple integrated disposable system can be configured to permit rapid point-of-use testing for the presence of specific DNA sequences in a sample. In (A) a schematic description is given of a disposable RPA reaction/ lateral flow strip that might be placed into a cheap heater than can deliver roughly 30-39° C. in the vicinity of a reaction pouch containing dried RPA reagents. It is assumed that processed/lysed sample would be used to rehydrate the contents of the pouch in an appropriate volume, and then the pouch would be incubated at appropriate temperature for 15-60 minutes, as necessary. Subsequently part or all of the sample would be transferred to the sample pad of a lateral flow strip, configured in a manner that only if the correct amplicons have formed will a visible line form at a specific position on the strip. In (B) is shown the arrangement of two oligonucleotide primers used for an RPA reaction performed on male and female DNA respectively. The oligonucleotides SRY3 and SRY4 were used, and one contained a 5'-fluorescein moiety, and the other a 5'-biotin moiety. At the end of the reaction 1/500 of a 50 µl reaction was mixed with 'running buffer' (Milenia, germany) and applied to a commercially-available lateral flow strip (Milenia, germany) such that only products in which the fluorescein and biotin were co-associated (i.e. in an amplification product) would lead to the accumulation of visible gold particles on the detection line. In (C) the result of this experiment is shown. Only the reaction performed in male DNA generates the signal line, and the efficacy of the amplification reaction was separately validated on agarose gels (data not shown).

Figure 64:
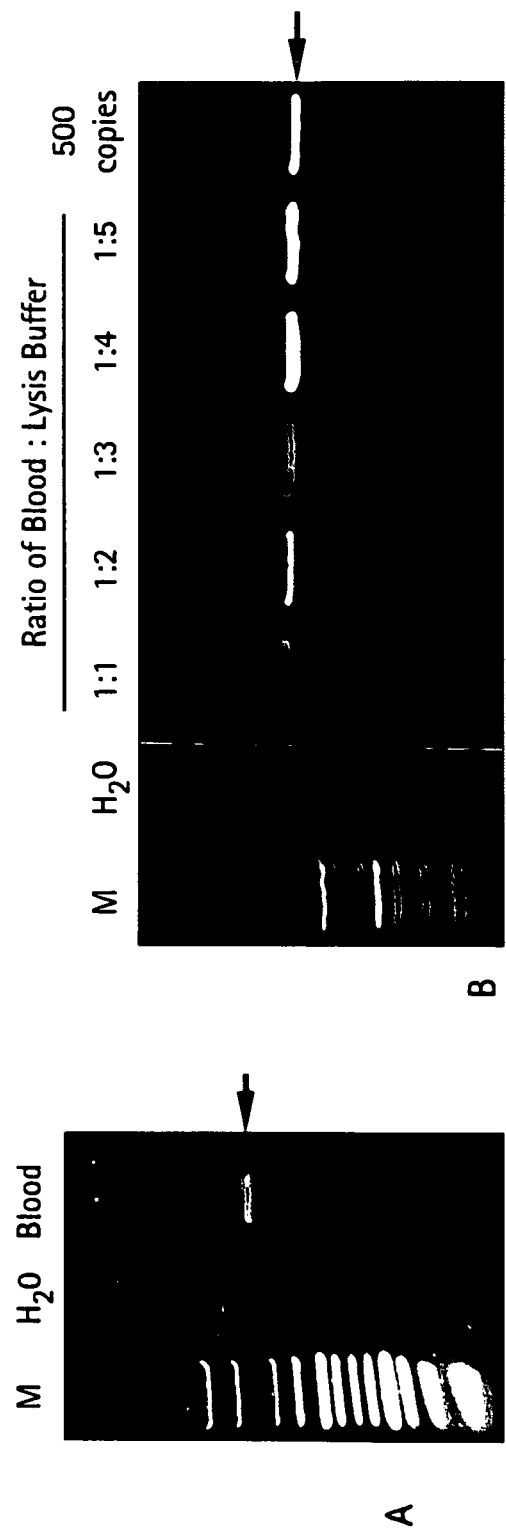
FIG. 64 Compatibility of RPA with crude lysates of human blood indicate the possibility that sophisticated sample preparations may be obviated for many samples.

FIG. 64 shows that RPA reactions are not inhibited by the presence of materials in blood providing appropriate ratios of reagents are employed.

The ability to amplify a genomic DNA fragment from whole and lysed blood added directly to RPA reactions was investigated. RPA reactions were configured as follows:
  50 mM Tris.Cl pH 8.5
  10 mM Magnesium acetate
  2 mM Dithiothreitol
  80 mM Potassium acetate
  5% PEG compound (Carbowax 20M)
  25 mM Phosphocreatine
  3 mM ATP
  200 µM dNTPs
  100 ng/µl creatine kinase
  0.3 µM oligonucleotide ApoB4 (SEQ ID 20)
  0.3 µM oligonucleotide ApoB300 (SEQ ID 21)
  420 ng/µl T4 gp32
  140 ng/µl T4 uvsX
  35 ng/µl T4 uvsY
  20 ng/µl Bsu polymerase In (A), either 1 µl of water or 1 µl of fresh whole human blood was added to an RPA reaction. Products were separated on a 2% agarose gel, and an arrow indicates the position of the expected amplicon. Non-specific 'primer' artifacts were present in water control, and in the sample, and presumably arise as a consequence of absent or very low copies of target. We deduce that very few copies of genomic DNA were available for amplification in the blood sample amplification. In (B) samples were analysed in which 1 µl of blood had first been mixed with either 1 µl, 2 µl, 3 µl, 4 µl, or 5 µl of a lysis solution comprising 10 mMlTris, 1 mM EDTA, 120 mM NaOH, 0.1% SDS (as indicated). In each case 1 µl of the respective lysate was used to start an RPA reaction (thus those lysed with more buffer contained less blood sample per amplification). Also shown are samples from the same experiment in which water only (lane 1), or purified DNA equivalent to 500 copies of target (Promega) (lane 7) were used to seed the amplification reaction. When 4 µl or 5 µl of lysis buffer were used, lysis of the red blood cells was clearly visible and the solution became viscous. We note that these samples became excellent start materials for RPA reactions, presumably releasing most of the DNA as accessible templates.

Figure 65:
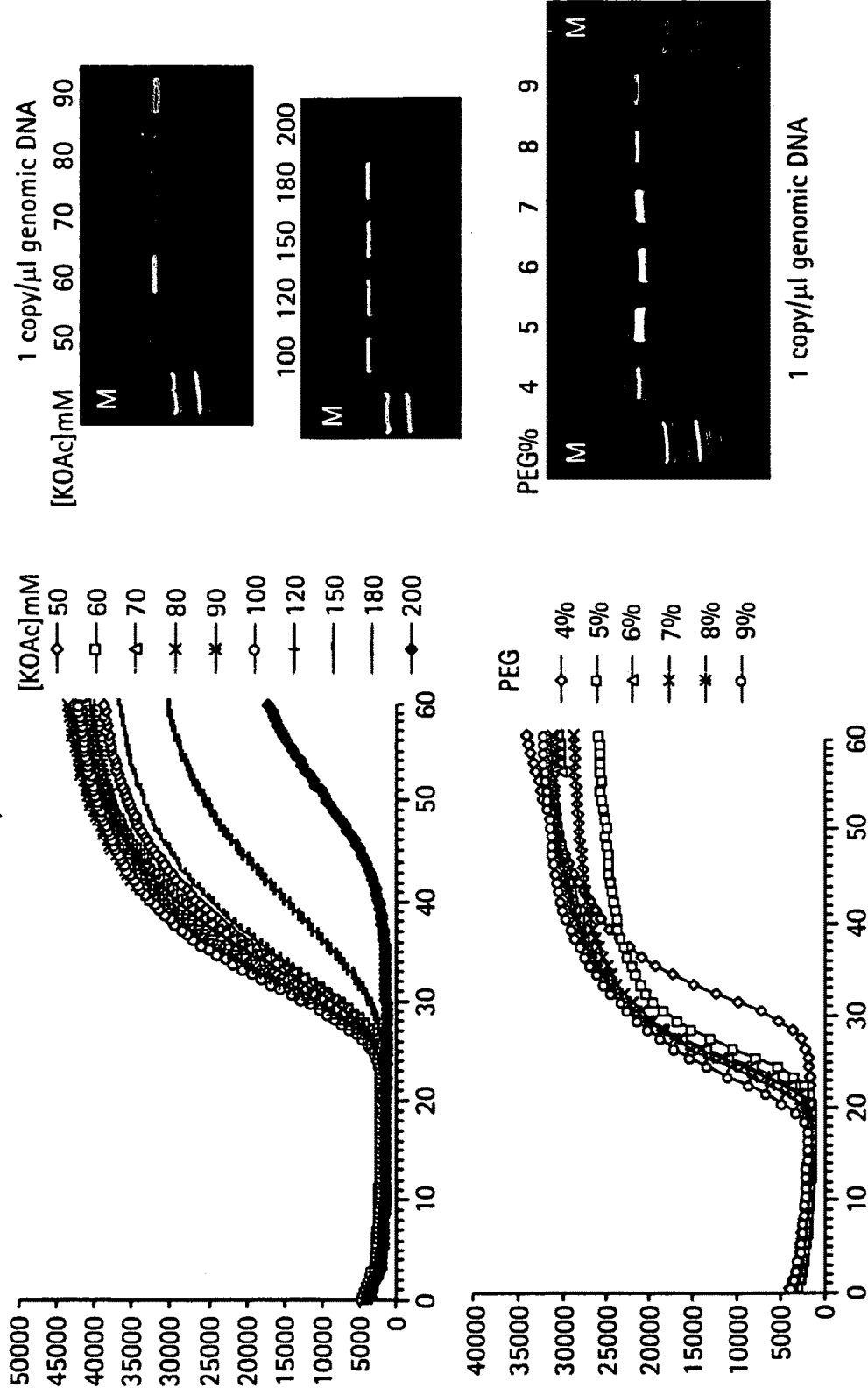
FIG. 65 Utility of real-time RPA analysis in optimising reaction environment; salt and PEG concentrations.

FIG. 65 shows how real-time monitoring of RPA reactions can be employed to optimise reactions.

In this case RPA reactions were established using the primer pair J1 and K2 mentioned above, and template consisting of *Bacillus subtilis* genomic DNA (start density 1 copy per microliter). Either Potassium acetate concentration, or PEG compound concentration, was varied. Other conditions were, unless specified otherwise:
  50 mM Tris.Cl pH 8.5
  10 mM Magnesium acetate
  2 mM Dithiothreitol
  80 mM Potassium acetate (or as indicated)
  5% PEG compound (Carbowax 20M)(or as indicated)
  25 mM Phosphocreatine
  3 mM ATP
  200 µM dNTPs
  100 ng/µl creatine kinase
  0.3 µM oligonucleotide J1 primer (SEQ ID 66)
  0.3 µM oligonucleotide K2 (SEQ ID 69)
  620 ng/µl T4 gp32
  140 ng/µl T4 uvsX
  35 ng/µl T4 uvsY
  1:50,000 dilution form stock of SYBR green (Invitrogen)
  20 ng/µl Bsu polymerase. At the end of the reaction a portion of the reactants were mixed with sucrose loading buffer and separated on an agarose gel, and then stained with ethidium bromide. We note that high salt slows the reaction, but there is a broad range of salt concentrations that work well. We also note that increasing PEG concentrations from 4% to 9% resulted in ever faster reaction behaviour, however the appearance of products in the gel system was adversely affected by higher PEG concentrations. We surmise that the smeary appearance of high PEG concentration samples may arise from ongoing networks of DNA generated by very high recombination activity. While this may be undesirable for gel analysis, it may be perfectly adequate for real-time analysis using fluorescence.

Figure 66:
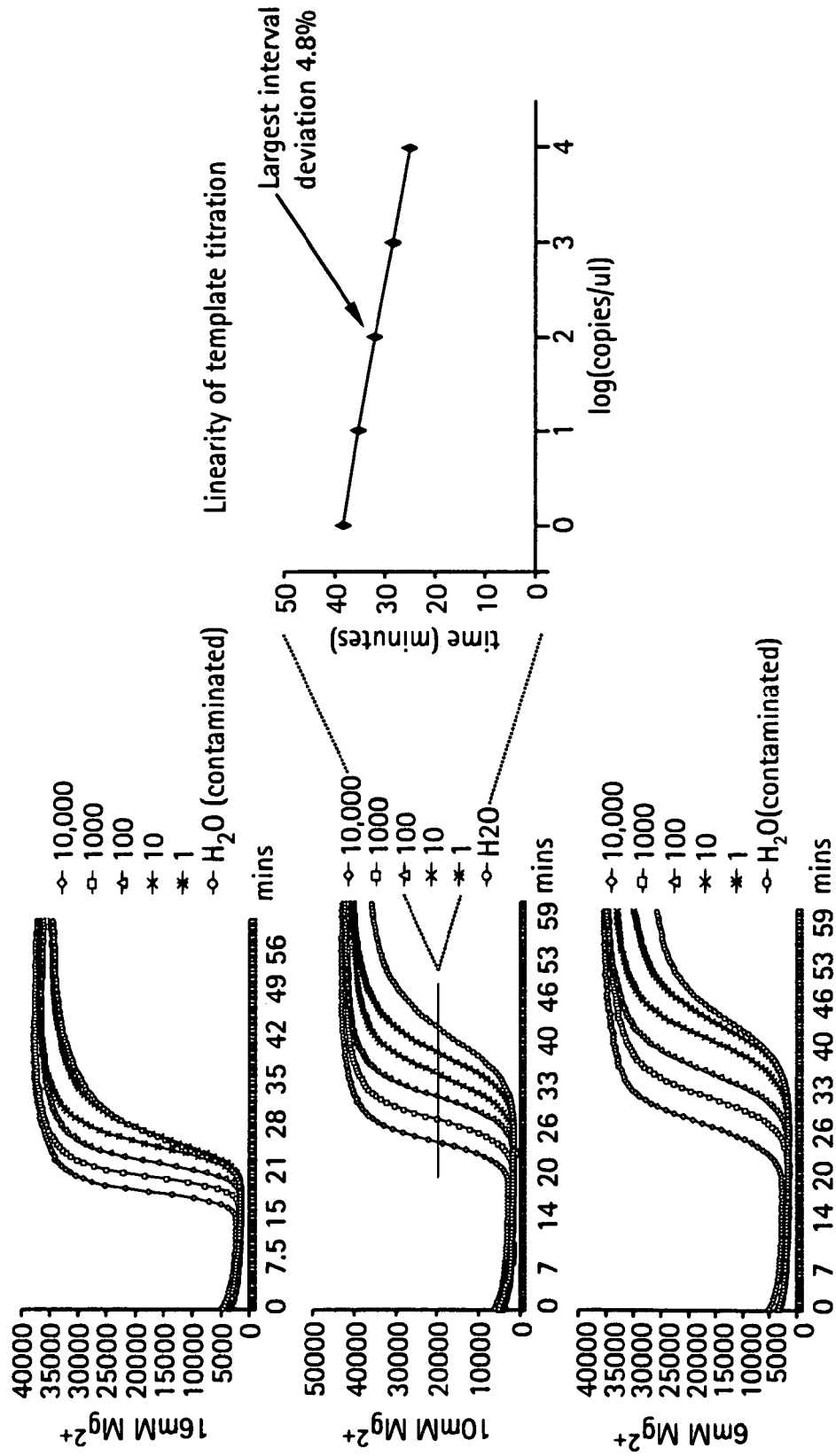
FIG. 66 Utility of real-time RPA analysis in optimising reaction environment; Magnesium concentrations.

FIG. 66 shows how RPA reactions are affected by Magnesium concentration.

Real-time RPA reactions were established as follows:
  50 mM Tris.Cl pH 8.5
  6, 10, or 16 mM Magnesium acetate as indicated
  2 mM Dithiothreitol
  80 mM Potassium acetate
  5% PEG compound (Carbowax 20M)
  25 mM Phosphocreatine
  3 mM ATP
  200 µM dNTPs
  100 ng/µl creatine kinase
  0.3 µM oligonucleotide J1 primer (SEQ ID 66)
  0.3 µM oligonucleotide K2 primer (SEQ ID 69)
  600 ng/µl T4 gp32
  120 ng/µl T4 uvsX
  30 ng/µl T4 uvsY
  20 ng/µl Bsu polymerase
  1:50,000 dilution from stock of SYBR green (Invitrogen)

The start density of target DNA, *Bacillus subtilis* genomic DNA, in copies per microliter is indicated. In the 6 mM and 16 mM Magnesium acetate samples some carry-over contamination was evident when samples at end-point were checked on agarose gels, and this may in part explain the poor resolution between zero and 1 copy per microliter start density. Note that RPA is effective at all tested Magnesium concentrations, but is much faster as the Magnesium concentration rises. End-products from these higher Magnesium samples still appear of high quality (data not shown). This indicates that in order to achieve maximal reaction rates, Magnesium concentrations significantly higher than 10 mM (used as a standard through most of this document) may be usefully employed.

FIG. 67 shows that different primer pairs/amplicons show different amplification kinetics. Reaction time dependence varies between oligonucleotide primers, and analysis indicates a possible sequence-bias underlying this phenomenon.

Two different timecourses were performed using different primer pairs. Conditions were not identical between these reactions, nevertheless the level of variation indicated is typical of the range of behaviours that we have observed between primer pairs in our hands and is included as just one typical example of rates that are observed (CSF primers used at 125 ng/µl UvsX, 45 ng/µl uvsY; Apo primers used at 200 ng/µl UvsX, 60 ng/µl uvsY). Primer sequences are shown. Primers CSF5'(SEQ ID 32) and CSF3' (SEQ ID 33)(targeting the human STR locus CSF1PO) are really an exceptional primer pair insofar as they demonstrated particularly rapid product accumulation kinetics, the fastest we have as yet determined. Primers ApoB600 (SEQ ID 46) and ApoB300rev (SEQ ID 47), targeting part of the human Apoliprotein B locus, demonstrate slower amplification kinetics. In this experiment this latter pair generated a similar amount of material after 40 minutes as occurred after only 20 minutes with the CSF primers. Based on this, and other, data we conclude that typical doubling times vary, on the average, between about 30 seconds and 1 minute for most primer pairs of 30-35 residues in RPA. CSF primers were also notably dominant in multiplex experiments (data not shown), consistent with the notion that they were particularly efficient and fast. Composition analysis of the primers, comparing both CSF primers with, in this case, the Apo primers used here, highlights that guanosine content is low in both CSF primers, while average in the Apo primers, and cytosine content is one third or more for both CSF primers, while one quarter or less for the Apo primers. This suggested to us a possible composition origin for rate variability. Reactions were performed under similar conditions apart from the aforementioned differences in UvsX and UvsY, and slightly variant dNTP concentrations:

50 mM Tris pH 8.4
80 mM Potassium acetate
10 mM Magnesium acetate
2 mM DTT
5% PEG compound (Carbowax-20M)
3 mM ATP
20 mM Phosphocreatine
100 ng/.quadrature.l creatine kinase
600 ng/ml gp32
200 .quadrature.M dNTPs for Apo primer, 1000M dNTPs for CSF primers
300 nM each oligonucleotide FIG. 68 shows that appended 5' homopolymeric stretches influence reaction behaviour—cytosine increases activity and guanosine decreases it.

Primers were as indicated. J1 and K2 (SEQ IDs 66 and 69) are homologous to part of the *Bacillus subtilis* SpoOB locus. Reaction conditions were:

50 mM Tris pH 8.4
80 mM Potassium acetate
10 mM Magnesium acetate
2 mM DTT
5% PEG compound (Carbowax-20M)
3 mM ATP
30 mM Phosphocreatine
100 ng/µl creatine kinase
420 ng/µl gp32
140 ng/µl UvsX
35 ng/µl UvsY
2000M dNTPs
300 nM each oligonucleotide
35 ng/µl Bsu polymerase
25 copies/µl *B. subtilis* genomic DNA
1:50,000 dilution from stock of SYBR green (Molecular probes)
Reaction volumes 50 µl, 37° C.

Primers J1(C), K(C), J1(G), and K2(G) were equivalent to J1 and K2, but possessing appended stretches of cytosine or guanosine, as indicated. Reactions were established on ice in a microtitre plate, and then transferred to the heated stage of a fluorometer (FLX800). After 90 minutes the reactions were diluted with 1× sucrose loading buffer to twice the original reaction volume, and then 20 µl of this was run directly on a 2% agarose gel. Reactions either contained target DNA, or no target. We observed that appending cytosine residues to the primers resulted in faster amplification rate, while appending guanosines resulted in defective amplification. Cytosine-appended primers also amplified 'noise' very rapidly.

FIG. 69 shows that appended 5' sequences consisting of Thymine and Cytosine residues demonstrate significant variation in amplification behaviour.

Primers were as indicated. J1 and K2 (SEQ IDs 66 and 69) are homologous to part of the *Bacillus subtilis* SpoOB locus. Reaction conditions were:

50 mM Tris pH 8.4
80 mM Potassium acetate
10 mM Magnesium acetate
2 mM DTT 5% PEG compound (Carbowax-20M)
3 mM ATP
30 mM Phosphocreatine
100 ng/µl creatine kinase
420 ng/µl gp32
140 ng/µl UvsX
35 ng/µl UvsY
200 µM dNTPs
300 nM each oligonucleotide
35 ng/µl Bsu polymerase
20 copies/µl *B. subtilis* genomic DNA
1:50,000 dilution from stock of SYBR green (Molecular probes)
Reaction volumes 50 µl, 37° C.

Amplification reactions were assessed in real-time employing SYBR green dye as described in FIG. 66. Conditions were similar, except that only 20 copies/µl of start target template were employed, and the primer sequences varied. Endpoint analysis was made by running products generated at 60 minutes on a 2% agarose gel after dilution as described for FIG. 68. Reactions containing homopolymeric thymidine stretches, or very thymidine-rich stretches, amplified somewhat poorly. Typically less DNA was generated, and there was some indication that asymmetry of amplification was occurring substantially. In general this data was consistent with cytosine residues being preferred in the 5' sequences, and that other hard-to-determine phenomena were occurring, possibly some effects of preferred recombinase 'phasing'.

FIG. 70 shows more detailed study of the effects of 5' appended sequences.

We investigated yet more primers derived from the J1 and K2 primers (SEQ IDs 66 and 69), mostly containing additional pyrimidine residues, but one pair containing a very 5' guanosine residue. Some primers (6 and 12 in this series) contained 5' pyrimidines, but were shortened to a total of 33 residues by removing bases at the 5' (J1) or 3' ends (K2) respectively. These primers thus shared less than 30 residues of homology with the genomic target. Primers were incubated under similar conditions to those used in FIGS. 69 and 70. The main differences were that 630 ng/ml of gp32 were employed, and only 1 copy per microliter of target genomic DNA was used. Furthermore, in these experiments we also examined the rate of amplification occurring in reactions containing only single primers. In those reactions containing primer pairs, pairs were examined containing one oligonucleotide that is a J1 derivative, and one that is a K2 derivative. Pairs were used in which derivatives were containing similar 5' modifications. Notably single primer amplification rates were quite similar to two primer amplification rates at this low target density, indicating that primer noise tends to initiate as a competitive effect at about this very low target density. Oddly, primers 8 and 9, differing in only one cytosine residues, showed profoundly different amplification behaviour. This may indicate a that a minimal stretch of cytosines is required for high rate activity, or that some specific phasing effect is in evidence.

FIG. 71 shows several strategies by which the specificity of sequence detection might be improved by the use of 'third probes', and how they might be configured to function with fluorophore/quencher pairs.

The presence of a specific DNA sequence can be detected by use of a third oligonucleotide probe which is blocked at the 3' end, and hence does not engage in noisy amplification (at least without subsequent processing). Such third probes may form hybrids with the amplicon specifically, and in such a duplex environment become the substrates for DNA processing enzymes which cleave the probe, thus separating the fluorophore and quencher. Given the nature of the recombinase environment, fluorophore and quencher will be separated by no more than about 10-12 nucleotides. A selection of candidate nuclease is listed, and modified bases that would be included in the probes, or the backbone nature of the probe for each nuclease, are indicated.

Figure 72:
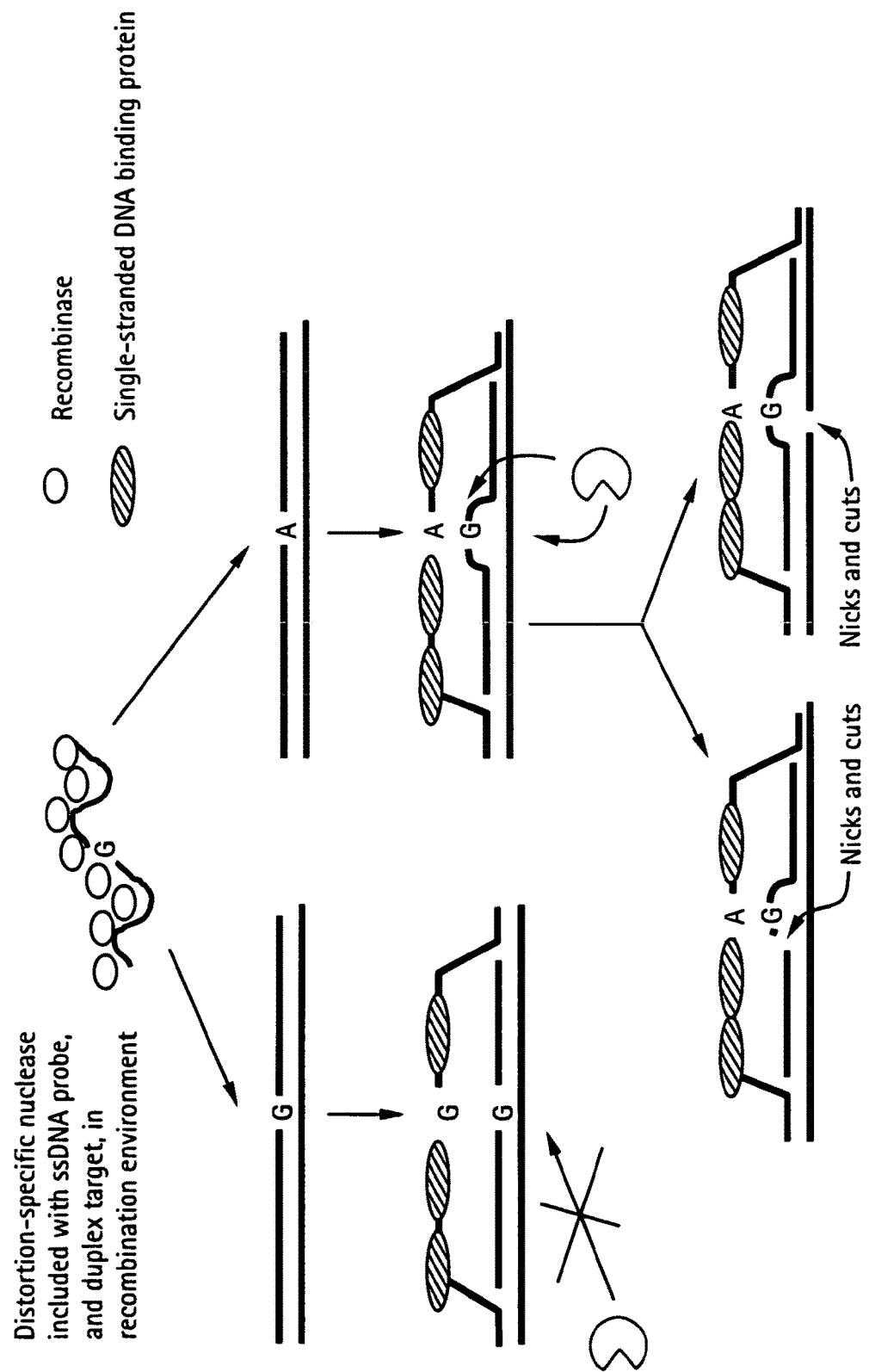
FIG. 72 Enzymes that recognise abnormal features such as helix distortions and damaged bases/abasic sites may be employed to process probe/target hybrids.

FIG. 72 shows how a helix-distorting or base-specific nuclease can be employed to detect specific sequenced including polymorphisms.

A single-stranded DNA is shown which has been coated with recombinase to form a homology-searching nucleoprotein filament. Arrows indicate the interaction of such a structure will homologous duplexes, either identical to the probe with regard to a single nucleotide polymorphism (SNP), or different (A instead of G). In both cases a strand exchange occurs successfully, and the outgoing strand is stabilised by single-stranded DNA binding protein. The resulting new duplexes are either perfectly complementary, or contain a base mismatch, which will cause a local distortion of the helix. In the presence of a suitable structure-specific nuclease the probe/template containing the distortion is specifically cleaved, either as nicks possibly on either strand, or as a double-strand break, depending on the nuclease. In other formats a similar approach could be used to detect the presence or absence of a specific sequence, regardless or not of polymorphic state, by including modified bases in the probe, such as 8-oxoguanine. In this case a base-removing and abasic-site-cleaving enzyme specific for 8-oxoguanine and duplex environments could be employed, such as *E. coli* Fpg protein (8-oxoguanine DNA glycosylase). In either case probe molecules might contain both a fluorophore and a quencher which are separated on cleavage.

FIG. 73 shows how dual-labeled fluorescent oligonucleotides show differential properties in an RPA environment compared to an environment lacking saturating recombinase and single-stranded DNA binding proteins.

Upper left, three probes are shown which were used in an experiment to investigate the fluorescent properties of those oligonucleotides in the presence or absence of proteins used in RPA environments. Conditions were as follows:

50 mM Tris pH 8.4
80 mM Potassium acetate
1 0 mM Magnesium acetate
2 mM DTT
5% PEG compound (Carbowax-20M)
3 mM ATP
30 mM Phosphocreatine
100 ng/µl creatine kinase
200 µM dNTPs
120 nM each oligonucleotide as indicated
Optional:
630 ng/µl gp32
140 ng/µl UvsX
35 ng/µl UvsY We observe that the FAM only containing oligonucleotide is slightly quenched in the presence of DNA binding proteins, likely indicating some quenching of fluorescence by protein bound close to the fluorophore. In marked contrast, however, the oligonucleotides containing both fluorophore and quencher show a reverse phenomenon, and this is markedly different depending on whether they are 10 or 15 residues in length. More specifically both latter probes were significantly quenched in the absence of proteins, consistent with the idea that formation of a random coil would ensure efficient quenching regardless of length. However in the presence of proteins this quenching is reduced. In particular the quenching for the 15-mer is almost abolished, and it assumes a fluorescence close to that level of the FAM only containing oligonucleotide in the presence of proteins. Conversely the 10-mer is little-affected and remains highly quenched. This reduction in quenching for the 5-mer is most easily explained by the suggestion that in the presence of DNA binding proteins the probe is stretched out into a fairly rigid rod. For example UvsX and recA stretch single and double-stranded DNA to about 1.5 times the equivalent length of B-form DNA, and similar extension is described for gp32. Thus, and in contrast to free solution behaviour, fluorophore and quencher are highly separated in an RPA environment, even more so than in a DNA duplex, and are likely to become more quenched on hybridization (although not investigated in this experiment). A schematic is provided on the right-hand side indicating what the states of the 10-mer and 15-mer probe may be in the absence or presence of a recombinase environment, and potentially when hybridized to duplex DNA. Fluorophore and quencher are shown with a larger excitation' radius, which when overlapping would lead to efficient fluorescence resonance energy transfer, and a concomitant decrease in fluorescence emission.

Figure 74:
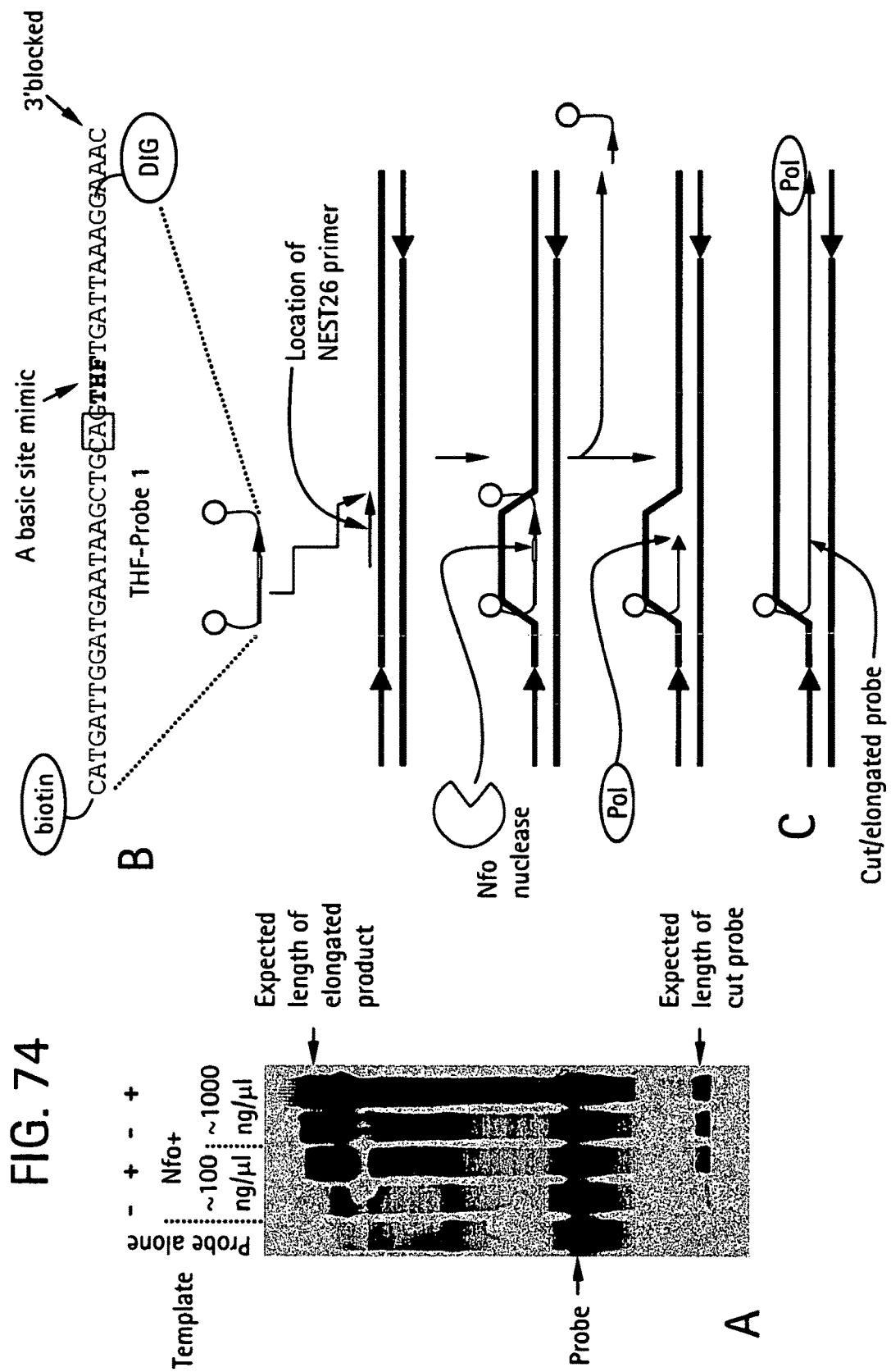
FIG. 74 A probe (SEQ ID NO: 80) containing a tetrahydrofuranyl residue is efficiently cut and extended in an RPA environment containing amplified target, the *E. coli* Nfo enzyme, and polymerase.

FIG. 74 shows that an amplicon-probe containing a tetrahydrofuranyl residue becomes a substrate for the *E. coli* Nfo enzyme in an RPA amplification reaction, is cleaved, and that the cleavage product can be elongated.

RPA reactions were established using the *B. subtilis* genomic DNA specific primers J1 and K2 (SEQ ID NO:66 and SEQ ID NO:69), the nested primer NEST26 (SEQ ID NO:77) and the biotin and Digoxygenin labeled probe THF-Probe 1 (5'-BIOTIN-CATGATTGGATGAATAAGCT-GCAG-tetrahydrofuran-TGATTAAAGGAAAC-DIG-3' SEQ ID NO:80), which also contains a Tetrahydrofuranyl residue within the probe body. This probe is specific for the fragment amplified by J1 and K2 primers, and overlaps the sequence of the NEST26 primer (all these primers are discussed elsewhere). NEST26, a primer which generates no noise on its own, was included so that a smaller nested product might be generated one of whose ends would be the target for the probe, just in case the probe was highly unstable in the topologically constrained environment which will result from probe invasion into duplex J1/K2 amplicon. Reactions had the following conditions:

50 mM Tris pH 7.9
80 mM Potassium acetate
10 mM Magnesium acetate
2 mM DTT
5% PEG compound (Carbowax-20M)
3 mM ATP
25 mM Phosphocreatine
100 ng/µl creatine kinase
600 ng/µl gp32
120 ng/µl UvsX
30 ng/µl UvsY
100 µM dNTPs
200 nM of J1 primer, K2 primer, and NEST26 primer
100 nM Probe
30 ng/µl Bsu polymerase
1000 copies/µl B. subtilis genomic DNA, or water controls as indicated Amplification reactions were phenol extracted, precipitated, and separated on a 16.5% denaturing Urea-PAGE. Separated products were transferred to nylon membrane and products were detected using a Streptavidin-HRP conjugate. As the 5' end of the probe was biotinylated, this permitted the detection of uncut, cut and elongated probes. (A) Detection of free, and processed probes. Note that in the presence of an RPA environment capable of amplifying the target fragment, the probe was elongated preferentially elongated. The size of the elongated probe is consistent with elongation to the end of the J1/K2 amplification product, and this can occur because Nfo cleavage activity generates a 3'-hydroxyl, thus 'unblocking' the probe and permitting synthetic extension. More elongation was seen when a higher concentration of Nfo enzyme was employed. In (B) the structure of the probe used in this experiment is shown. It comprises a sequence homologous to part of the amplicons generated by J1 and K2 primers, but contains a tetrahydrofuranyl residue and is labeled at the 5' end with biotin, and at the 3' end (and thus blocked) with digoxygenin. In (C) a schematic representation is given of the sequences of events thought to underlie the generation of elongated product via interaction of the probe with the desired amplicon, cleavage and subsequent polymerase elongation of the free 3' end. In this experiment apparent activity in reactions lacking start template is believed to arise from carry-over contamination of the amplicon from previous laboratory experiments, a phenomenon that has become problematic in our laboratory due to the very high sensitivity of RPA. Supporting evidence is provided in the subsequent figure.

Figure 75:
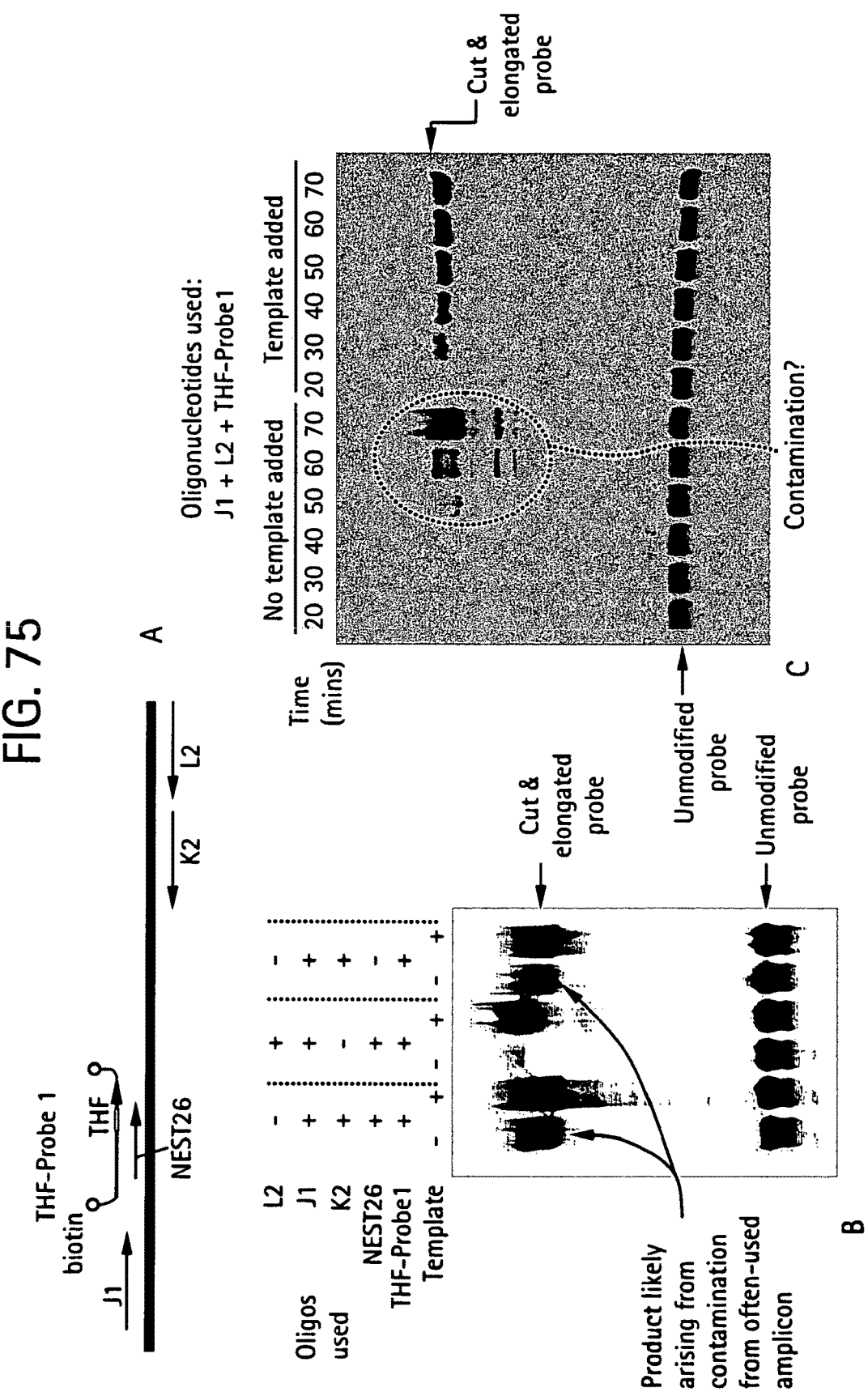
FIG. 75 A probe containing a tetrahydrofuranyl residue in efficiently, rapidly, and specifically cut and extended in an RPA environment containing amplified target, the *E. coli* Nfo enzyme, and polymerase.

FIG. 75 shows that an amplicon-probe containing a tetrahydrofuranyl residue becomes a substrate for the E. coli Nfo enzyme in an RPA amplification reaction, is cleaved, and that the cleavage product can be elongated In these experiments evidence is presented that the cleavage and extension of a tetrahydrofuranyl residue-containing amplicon-specific probe is specific and dependant upon the presence of that target sequences in the reaction, and also that having a free end overlapping the probe target (to prevent topological strain of the probe/target recombination intermediate) is not necessary. In (A) the reaction setup is depicted schematically. The Bacillus subtilis locus targeted by the primers J1, K2, L2, NEST26, (SEQ ID'S 66, 69, 71 AND 77) and the probe are depicted (the actual sequence is shown in FIG. 42B). Usually the primers J1 and K2 are routinely used to amplify this locus and thus the principal laboratory contaminant is the fragment generated by these two primers. Thus we have also combined J1 with L2 in some experiments, this fragment not being subject to amplification from carry-over contamination from the former amplicon. In (B) are shown the results of an experiment in which RPA reactions were configured to amplify either the J1/K2 product, or the J1/L2 product, in the presence of added start template (genomic DNA) or without. Included in the reaction are the probe and the E. coli Nfo protein. In more detail the following conditions were used:

50 mM Tris pH 7.9
80 mM Potassium acetate
10 mM Magnesium acetate
2 mM DTT
5% PEG compound (Carbowax-20M)
3 mM ATP
25 mM Phosphocreatine
100 ng/µl creatine kinase
600 ng/µl gp32
120 ng/µl UvsX
30 ng/µl UvsY
100 µM dNTPs
200 nM of J1 primer, 200 nM K2 OR L2 primer, and 200 nM NEST26 primer (lanes 1-4), in lanes 5 and 6 J1 and L2 primers were at 300 nM and NEST26 was not used
120 nM Probe
30 ng/µl Bsu polymerase
1000 copies/µl B. subtilis genomic DNA, or water controls as indicated Amplification reactions were phenol extracted, precipitated, and separated on a 16.5% denaturing Urea-PAGE gel. Separated products were transferred to nylon membrane and products were detected using a Streptavidin-HRP conjugate. As the 5' end of the probe was biotinylated, this permitted the detection of uncut, cut and elongated probes. (A) Detection of probes, free and processed. Note that in the presence of an RPA environment capable of amplifying the target fragment, the probe was elongated preferentially elongated. Also note that while significant elongation occurs in the absence of the added target for the J1/K2 primer pair (due we believe to contamination), when the J1/L2 primers pair is used this does not occur (a very faint band is, we believe, a sample cross-loading artifact). Consequently we deduce that probe cutting/elongation is a specific event. Furthermore the significant signals in the no-template J1/K2 samples suggests that the system is highly responsive to even very small numbers of targets, as is presumably arising from the carry-over contamination. In (C) is shown the results of a similar experiment in which the J1 and L2 primers were used in combination with the probe on either no target DNA, or on a sample with target DNA at 1000 copies per microliter (genomic DNA). Oligonucleotide concentrations are as follows: J1 and L2 at 240 nM, probe at just 12 nM, and ~1000 ng per microliter of Nfo enzyme were used. Other conditions are as described for the experiment in part (B). Samples were removed at the indicated times and stopped. Samples were phenol extracted, precipitated, and run on a denaturing gel as already described, transferred to nylon membrane, and detected as described above. We note that cleavage/elongation products can be detected by 30 minutes even when the probe is as low as 12 nM. This suggests that the kinetics of Nfo action under these conditions is sufficiently fast to monitor reactions excellently in real-time.

Figure 76:
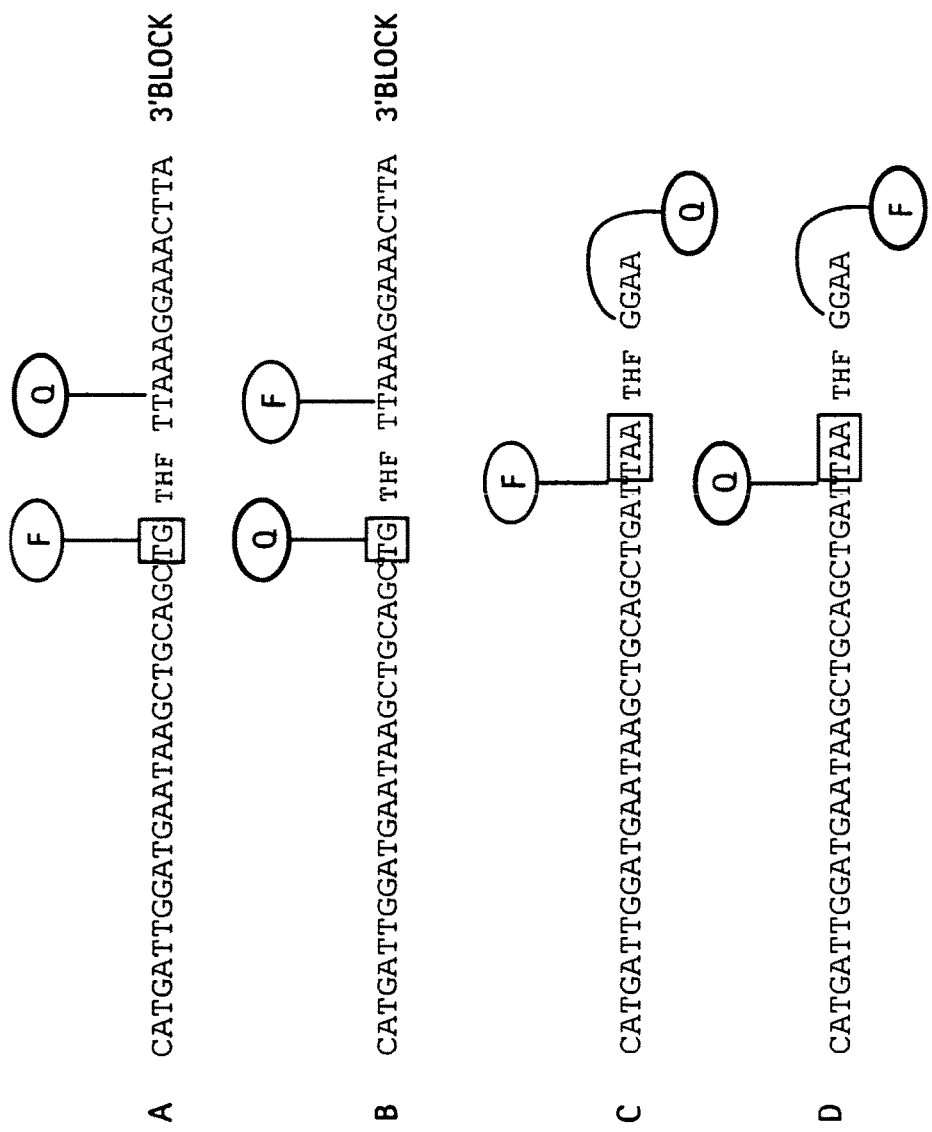
FIG. 76 Examples of probe (SEQ ID NOS 120, 120, 121 and 121, respectively, in order of appearance) design for real-time RPA studies using the *E. coli* Nfo enzyme.

FIG. 76 shows the general structure of several possible sorts of probe that might be used for real-time analysis of RPA reactions.

By combining the data suggesting that dual-labeled probes for use in RPA would require relatively short separation distances to permit quenching with our knowledge of the efficient action of the *E. coli* Nfo protein on processing intermediates between THF-residue containing probes and duplex targets, we suggest several probe structures. In (A) and (B) we show probes in which both a fluorophore and quencher are present internally (through base modifications), and between them is positioned a THF residue. The separation of the fluorophore and quencher is less than 10-12 residues to ensure efficient FRET between the groups. The probe is blocked at the 3' end with a suitable group. Cleavage by the Nfo enzyme at the THF residue will eliminate covalent association of the fluorophore and quencher, ultimately leading to an increase in solution fluorescence. In (C) and (D) and alternative arrangement is depicted. In this case either fluorophore or quencher is positioned at the 3'terminus of the probe, thus blocking elongation. The other light-absorbing moiety is attached via and internal linkage slightly more 5'. The THF residue is positioned between these 2 groups, and the 2 light-absorbing groups are separated by no more than 10-12 residues to ensure good FRET even when stretched by DNA binding proteins.

Discussion

There is a long-standing need for in vitro methods to amplify specific DNA sequences. Since the late 1980's the polymerase chain reaction (PCR) method has principally met this need (R. K. Saiki et al., Science 239, 487-91 (Jan. 29, 1988)). The requirement for thermal cycling equipment, however, poses a significant barrier to the use of PCR outside of a laboratory setting. As described herein, we have developed a method called RPA, which obviates the need for thermal melting of template DNAs. RPA combines components of the bacteriophage T4 recombination/replication system in vitro under critical defined conditions to mediate the hybridisation of oligonucleotide primers to template DNAs. Specifically, the bacteriophage T4 recombinase uvsX, single-stranded DNA binding (SSB) protein gp32, and recombinase loading factor uvsY together with molecular crowding agents, allow high fidelity in vitro recombinase-mediated DNA targeting. When this targeting system is combined with strand displacement DNA synthesis mediated by enzymes of the *E. coli* or *B. subtilis* Pol I class, efficient exponential DNA amplification is achieved.

Any oligonucleotide sequence may be coated by recombinase to form homology searching filaments (FIG. 37) giving RPA a broad utility allowing amplification of virtually any DNA sequence. This feature has been one of the major advantages of PCR over other in vitro DNA amplification methods (G. T. Walker, M. C. Little, J. G. Nadeau, D. D. Shank, Proc Natl Acad Sci USA 89, 392-6 (Jan. 1, 1992); D. Y. Zhang, M. Brandwein, T. Hsuih, H. B. L1, Mol Diagn 6, 141-50 (June, 2001); M. Vincent, Y. Xu, H. Kong, EMBO Rep 5, 795-800 (August, 2004); J. Compton, Nature 350, 91-2 (Mar. 7, 1991)). Resembling their in vivo role, homology-searching filaments scan duplex DNA for sequences complementary to that of the oligonucleotide (T. Yonesaki, Y. Ryo, T. Minagawa, H. Takahashi, Eur J Biochem 148, 127-34 (Apr. 1, 1985); T. Shibata, C. DasGupta, R. P. Cunningham, C. M. Radding, Proc Natl Acad Sci USA 76, 1638-42 (April, 1979)). On finding a match, the recombinase catalyses several reactions: the primer is paired with its complement, the similar 'outgoing' strand is displaced, and the recombinase dissociates. This establishes a 'D-loop' structure accessible to other reaction components. Exchange events occurring away from a free DNA end generate topologically strained joints, as the outgoing strand is attached on both sides of the exchanged region (FIG. 37C).

Embedded sequences generate topologically constrained intermediates that are unstable. Joints formed at DNA ends permit free rotation of the displaced strand (P. W. Riddles, I. R. Lehman, J Biol Chem 260, 165-9 (Jan. 10, 1985)). Because these two structures have different stabilities elongation of initial strand invasion events are less efficient than subsequent ones (FIG. 39B). The free 3' end of the oligonucleotide primes synthesis by a strand-displacing DNA polymerase such as the Klenow fragment of *E. coli*, or the *Bacillus subtilis* DNA polymerase I (Bsu). The synthetic and strand-displacing activities of the polymerase result in the production of a double-stranded DNA and a displaced single strand. This displaced strand is replicated either by direct hybridisation and elongation of the second oligonucleotide, or by strand displacement synthesis if an invasion event had already occurred from the opposite end. The generation of two complete daughter duplexes completes one round of RPA. Invasions continue to act on products of previous synthesis reactions with the endtargeted products eventually dominating the reaction.

In developing the method of the invention, we have found that several important conditions are important for optimal RPA to occur. First, there needs to be saturating quantities of nucleic acid melting proteins present in the reaction especially a SSB such as gp32. Second, there needs to be a sufficient quantity of recombinase-loaded primer to achieve an acceptable invasion/strand-exchange rate. Finally, the recombinase/single-stranded DNA primer filaments need to be dynamic and capable of disassembly. There are competing biochemical activities of the reaction components. For example, in a typical in vitro situation recombinases are usually out-competed by saturating amounts of SSBs such as gp32.

To overcome this problem, others have used nonhydrolyzable ATP analogues such as ATP-γ-S, which stabilises the recombinase/single-stranded primer DNA interaction (S. C. Kowalczykowski, J. Clow, R. Somani, A. Varghese, J Mol Biol 193, 81-95 (Jan. 5, 1987); A. L. Eggler, S. L. Lusetti, M. M. Cox, J Biol Chem 278, 16389-96 (May 2, 2003); T. Shibata, C. DasGupta, R. P. Cunningham, C. M. Radding, Proc Natl Acad Sci USA 77, 2606-10 (May, 1980)). Non-hydrolysable ATP analogues are, however, incompatible with the dynamic activity of recombinase/single-stranded DNA primer filaments needed to complete strand-exchange reactions and allow polymerases access to the D-loops (L. Xu, K. J. Marians, J Biol Chem 277, 14321-8 (Apr. 19, 2002); P. W. Riddles, I. R. Lehman, J Biol Chem 260, 170-3 (Jan. 10, 1985); N. Armes, D. Stemple, in patent application PCT WO 03/072805 (ASM Scientific, Inc., USA, 2003)) (FIG. 38).

There are other ways the recombinase/single-stranded primer DNA interaction could be stabilised. For example, another bacteriophage T4 protein called uvsY is known to aid loading of uvsX onto gp32-coated DNA (L. D. Harris, J. D. Griffith, J Mol Biol 206, 19-27 (Mar. 5, 1989)). In addition, molecular crowding agents are also known to facilitate loading and stabilisation of the *E. coli* recA recombinase protein (P. E. Layery, S. C. Kowalczykowski, J Biol Chem 267, 9307-14 (May 5, 1992)). We therefore tested whether uvsY and molecular crowding agents might alleviate the unfavourable competition between uvsX and gp32 in a dynamic, ATP-dependent system.

Figure 38:
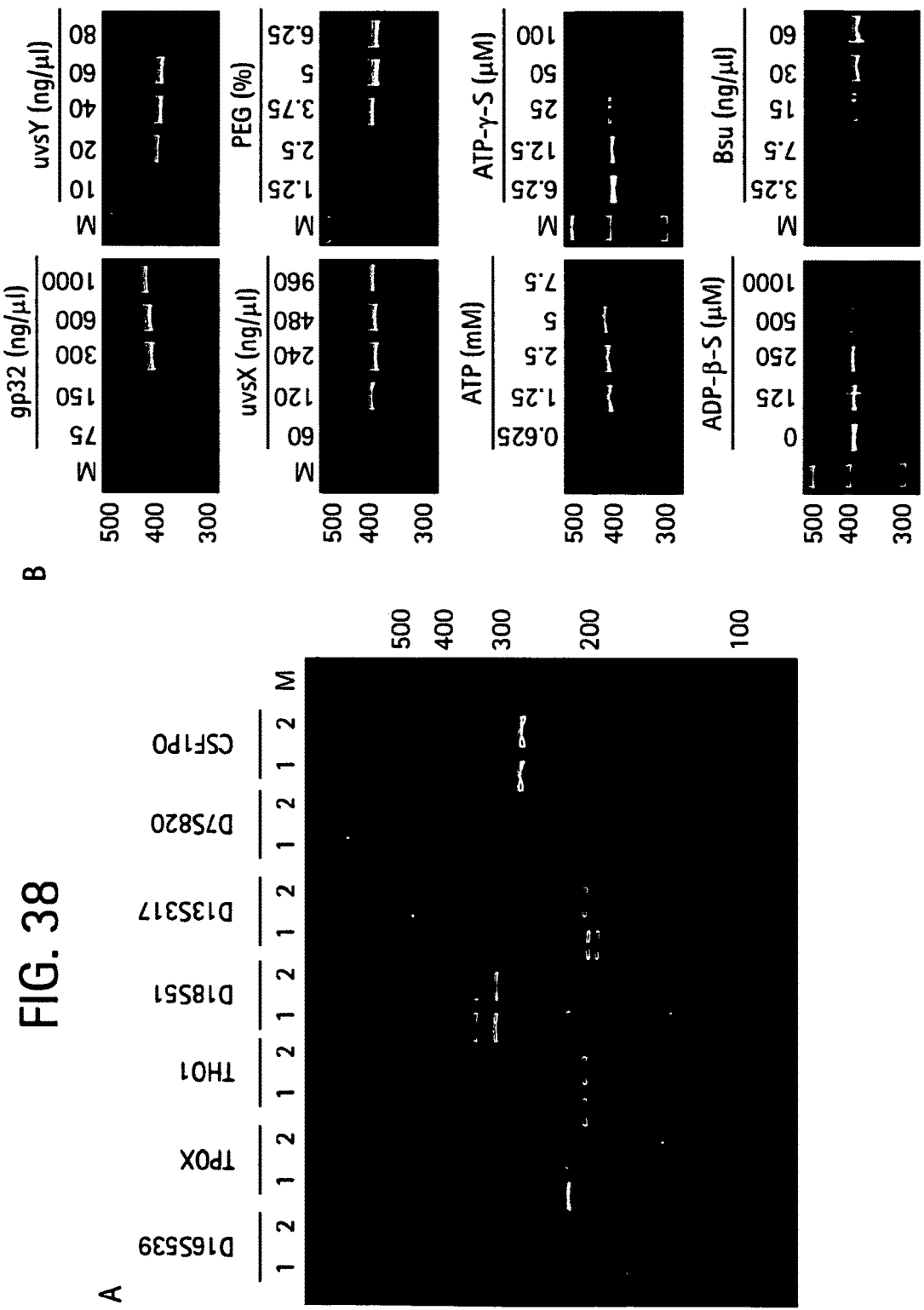
FIG. 38 depicts (A) STR markers from two individuals (1 and 2, father and son) amplified with primer pairs for seven independent markers using RPA conditions C4; (B) Titration of reaction components to determine concentrations that support in vitro amplification.

Titration of reaction components reveals that defined quantities of T4 gp32, T4 uvsX, T4 uvsY, ATP, and PEG are required for DNA amplification (FIG. 38). Indeed the T4 uvsY recombinase mediator protein and PEG-compound (Carbowax 20M) are required to achieve detectable amplification. At reduced concentrations of gp32, amplification efficiency is impaired generating smearing and laddering of reaction products. The recombinase uvsX protein is important for RPA and the reaction rate is accelerated at higher concentrations, although this can also increase artifacts (FIG. 39A). ATP is important for the reaction, and we have found that an ATP regeneration system is needed to reach detectable levels of product for most reactions. Conversely, ATP-γ-S is a powerful inhibitor of amplification.

To be a useful tool for routine DNA amplification applications such as diagnostic testing, RPA should be sensitive and specific, applicable to diverse sequence targets and be capable of amplifying fragments of sufficient size. We first investigated the size of products that could be generated. Amplified products up to 1000 base pairs in size could be amplified using standard reaction conditions (FIG. 38A). Larger amplified products may also be generated using RPA.

We tested the sensitivity of RPA under the most stringent conditions, using a single-step RPA reaction, without nesting, and detecting products by conventional ethidium bromide staining of agarose gels. With several independent primer/target sets we routinely detected less than 10 copies of starting duplex template. We observed variability between experiments at lowest detectable copy number but all attempts were successful at detecting less than 10 copies. With proper sample handling, RPA may be used to amplify from single molecules to detectable levels in a single reaction. To explore this possibility, we amplified a polymorphic simple tandem repeat (STR) marker from human DNA diluted until only a few copies should remain. We generated a number of amplified products corresponding to both possible separate alleles present in the sample DNA (FIG. 39E,F). This allele separation effect suggests that RPA has single molecule sensitivity and thus surpasses the sensitivity of many other DNA amplification methods.

Analysis of the amount of amplified product shows that RPA will routinely amplify DNA samples by $10^{11-12}$-fold from small quantities of starting template. Final product levels are typically in the range of 10-250 nM, generating more than sufficient quantities of DNA for even the least sensitive detection protocols. To assess specificity of amplification reactions we have analysed many primer pairs, most directed to human DNA sequences. For every primer/template set, we have tested the predicted product sizes, restriction enzyme digestion patterns, or product DNA sequence to show that amplification is specific. We have not observed amplification of non-target sequences from sample DNA to the best interpretation of our data. Artifacts we have observed are product or primer related (FIG. 39A).

Often in diagnostic settings, specificity problems arise from the large amounts of nontarget DNA present in a sample. For example, in pathogen detection, human DNA from blood samples can interfere with detection of pathogen DNA. We therefore sought to detect trace quantities of target DNA in a large mass of unrelated DNA. We found that RPA was able to amplify a target to detectable levels from 100 copies of *Bacillus subtilis* DNA in the presence of 1 μg of human DNA (i.e., $10^8$-fold less *B. subtilis* DNA than human DNA by mass). With such a large mass of sample DNA we found we had to increase levels of uvsX and uvsY compared to equivalent reactions without excess competitor DNA to achieve an acceptable reaction rate. This is perhaps due to out-titration of the homology-searching components.

In time-course experiments with several different primer/template sets, we found that amplification rate was partially dependent on product length. For fragments in the range 150-400 base pairs, however, fairly similar rates were observed, allowing amplification from hundreds to thousands of starting copies to gel detectable levels (~$10^{12}$ copies) in as little as 20 minutes). We estimate that we have been able to reduce average cycle' times to as little as 30 seconds on average for such fragments. Using optimally short target sequences and sensitive detection method, we expect that a diagnostic amplification/detection assay could be performed well within an hour. Our studies show that for a large number of arbitrary DNA targets in complex samples high-quality primer pairs can be easily designed. We have addressed minimal oligonucleotide length and found that while oligonucleotides of less than 30 nucleotides do not amplify DNA effectively, those of 30-35 nucleotides in length are excellent primers and are short enough for easy synthesis (FIG. 40).

As demonstrated herein, RPA is an excellent general method to amplify specific DNA sequences. We have shown that RPA reactions can be monitored in real-time using minor groove binding dyes and demonstrate an excellent capacity to assess start target copy number. Furthermore multiple targets can be co-amplified, and sequence-specific real-time sensors ('third probes') can be readily included in the reaction environment. We have identified and demonstrated that DNA repair enzymes such as fpg, Nth and particularly Nfo operate in RPA reactions and can be combined with suitable probes to permit real-time assessment of reaction behaviour in a sequence-specific manner. We show that fluorescence-based probe systems show markedly different properties in the RPA environment to conventional PCR reaction environments, or similar. Finally our initial experiments indicate that it is easy to lyophilise the components of the RPA reaction for convenient storage and reconstitution (FIG. 40). This method, which operates robustly at constant low temperature, can be lyophilised for easy storage and requires no thermal cycling or melting for high sensitivity, nor other complex handling, and can be readily monitored in real-time, offers a significant breakthrough in the development of DNA diagnostic, forensic and other point-of-use applications. Once integrated with portable sample DNA extraction and product detection systems, RPA should enable easy-to-use clinical or domestic testing kits for a variety of pathogens (e.g., Chlamydia or MRSA) as well as field kits for other applications.

The details of one or more embodiments of the invention have been set forth in the accompanying description above. Although any methods and materials similar or equivalent to those described herein can be used in the practice or testing of the present invention, the preferred methods and materials are now described. Other features, objects, and advantages of the invention will be apparent from the description and from the claims.

In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. Unless expressly stated otherwise, the techniques employed or contemplated herein are standard methodologies well known to one of ordinary skill in the art. All patents, patent applications and publications cited in this specification are hereby incorporated by reference herein.

We claim:

1. A recombinase polymerase amplification (RPA) method of detecting target DNA in a biological sample, comprising;
   (a) contacting the biological sample with a lytic agent to form a lysed sample;
   (b) forming a mixture comprising components of a recombinase polymerase amplification (RPA) reaction and a portion of the lysed sample, wherein the components of the RPA reaction comprise a recombinase, a polymerase, a crowding agent, a first nucleic acid primer, and a second nucleic acid primer;
   (c) maintaining the mixture under conditions to amplify a target nucleic acid in the sample;
   (d) determining the presence or amount of target nucleic acid, thereby detecting the presence or absence of a target nucleic acid.

2. The method of claim 1, wherein the lysed sample is added to the mixture without separation or purification of the target nucleic acid from the lysed sample.

3. The method of claim 1, wherein the biological sample is blood.

4. The method of claim 1, wherein the target nucleic acid is genomic DNA.

5. The method of claim 1 wherein the recombinase is selected from UvsX, RecA, and combinations thereof.

6. The method of claim 1, wherein the polymerase includes at least one DNA polymerase which lacks 3'-5' exonuclease activity.

7. The method of claim 1, wherein the polymerase comprises a DNA polymerase with strand displacing properties.

8. The method of claim 1, wherein the crowding agent is present at a concentration between 1 to 12% of a weight or a volume of the mixture.

9. The method of claim 1, wherein the crowding agent is selected from polyethylene glycols, dextran, ficoll and a combination thereof.

10. The method of claim 9 wherein the crowding agent comprises polyethylene glycol at a concentration between 1 to 12% of a weight or a volume of the mixture.

11. The method of claim 10, wherein said polyethylene glycol is selected from PEG1450, PEG3000, PEG8000, PEG10000, PEG compound (molecular weight 15,000 to 20,000), and combinations thereof.

12. The method of claim 1, wherein the first and second nucleic acid primers are selected from DNA, RNA, PNA, LNA, morpholino backbone nucleic acid, phosphorothioate backbone nucleic acid, and a combination thereof.

13. The method of claim 1 wherein the mixture further comprises at least one recombinase loading protein.

14. The method of claim 13, wherein the recombinase loading protein is selected from T4 uvsY, E. coli recO, E. coli recR and combinations thereof.

15. The method of claim 1 wherein the recombinase is temperature-sensitive.

16. The method of claim 1, the mixture further comprising at least one single stranded DNA binding protein.

17. The method of claim 16, wherein said single stranded DNA binding protein is E. coli SSB, and/or T4 gp32.

18. The method of claim 1, wherein the first nucleic acid primer and/or the second nucleic acid primer comprises a 3' blocking group.

19. The method of claim 1, the mixture further comprising trehalose.

* * * * *